US012577267B2

(12) United States Patent
Iyer et al.

(10) Patent No.: US 12,577,267 B2
(45) Date of Patent: Mar. 17, 2026

(54) PYRIMIDINE COMPOUNDS FOR USE AS MAP4K1 INHIBITORS

(71) Applicant: GLENMARK SPECIALITY S.A., Neuchatel (CH)

(72) Inventors: Pravin Iyer, Navi Mumbai (IN); Sanjib Das, Navi Mumbai (IN); Murugan Chinnapattu, Navi Mumbai (IN); Sachin Chaudhari, Navi Mumbai (IN); Jagmohan Saini, Navi Mumbai (IN); Sravan Mandadi, Navi Mumbai (IN); Nagaraj Gowda, Navi Mumbai (IN); Dnyaneshwar Dahale, Navi Mumbai (IN); Sandip Patil, Navi Mumbai (IN); Nanasaheb Kadlag, Navi Mumbai (IN); Chandrasekhar Misra, Navi Mumbai (IN); Priyanka Pangare, Navi Mumbai (IN)

(73) Assignee: Glenmark Speciality S.A., La Chaux-de-Fonds (CH)

( * ) Notice: Subject to any disclaimer, the term of this patent is extended or adjusted under 35 U.S.C. 154(b) by 669 days.

(21) Appl. No.: 17/912,729

(22) PCT Filed: Jul. 6, 2022

(86) PCT No.: PCT/IB2022/056248
§ 371 (c)(1),
(2) Date: Sep. 19, 2022

(87) PCT Pub. No.: WO2023/281417
PCT Pub. Date: Jan. 12, 2023

(65) Prior Publication Data

US 2023/0227483 A1 Jul. 20, 2023

(30) Foreign Application Priority Data

Jul. 6, 2021 (IN) ............................ 202121030204

(51) Int. Cl.
*C07F 9/6558* (2006.01)
*A61P 35/00* (2006.01)
*C07F 9/6561* (2006.01)
*A61K 31/675* (2006.01)

(52) U.S. Cl.
CPC .......... *C07F 9/65583* (2013.01); *A61P 35/00* (2018.01); *C07F 9/6561* (2013.01); *C07B 2200/05* (2013.01)

(58) Field of Classification Search
CPC ................ C07F 9/65583; C07F 9/6561; C07F 9/65586; A61P 35/00; C07B 2200/05; A61K 31/675
See application file for complete search history.

(56) References Cited

U.S. PATENT DOCUMENTS 11,180,482 B2 * 11/2021 Huang .................... A61P 35/00
2024/0270698 A2 * 8/2024 Kim ...................... C07F 9/6561

FOREIGN PATENT DOCUMENTS

WO 2018/102366 A1 6/2018
WO 2021/125803 A1 6/2021

OTHER PUBLICATIONS

Cecil Textbook of Medicine, 1997, 20th Ed, pp. 1004-1010 (Year: 1997).*
Wu Q, Qian W, Sun X, Jiang S. Small-molecule inhibitors, immune checkpoint inhibitors, and more: FDA-approved novel therapeutic drugs for solid tumors from 1991 to 2021. J Hematol Oncol. Oct. 8, 2022;15(1):143. doi: 10.1186/s13045-022-01362-9. PMID: 36209184; PMCID: PMC9548212. (Year: 2022).*
International Search Report dated Aug. 25, 2022, for corresponding International Patent Application No. PCT/IB2022/056248.
Written Opinion dated Aug. 25, 2022, for corresponding International Patent Application No. PCT/IB2022/056248.
Burakoff et al.; "HPK1 as a Novel Target for Cancer Immunotherapy; Immunologic Research", 54(1), (2012).
Zhang, et al.; Inhibited Expression of Hematopoietic Progenitor Kinase 1 Associated With Loss of Jumonji Domain Containing 3 Promoter Binding Contributes to Autoimmunity in Systemic Lupus Erythematosus:; Journal of Autoimmunity 37:(2011).
Hui, et al.; "p38 Alpha Suppresses Normal And Cancer Cell Proliferation By Antagonizing The JNK-c-Jun Pathway"; Nature Genetics, vol. 39, No. 6, Jun. 2007.

* cited by examiner

*Primary Examiner* — Bruck Kifle
*Assistant Examiner* — Kevin S Martin
(74) *Attorney, Agent, or Firm* — Benjamin Aaron Adler

(57) ABSTRACT

The present disclosure is directed to compounds of formula (I) and pharmaceutically acceptable salts thereof, which are useful as MAP4K1 inhibitors, processes for their preparation, pharmaceutical compositions comprising the compounds, and the use of the compounds or the compositions in the treatment or prevention of various diseases, conditions and/or disorders mediated by MAP4K1.

(I)

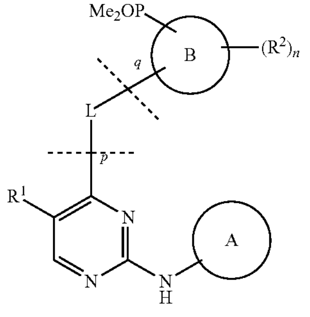

30 Claims, 1 Drawing Sheet

PYRIMIDINE COMPOUNDS FOR USE AS MAP4K1 INHIBITORS

RELATED APPLICATIONS

This application is a National Stage Application under 35 U.S.C. § 371 of PCT International Application No. PCT/IB2022/056248, filed on Jul. 6, 2022, which claims priority from the Indian Provisional Application No. 202121030204 filed on Jul. 6, 2021, all of which are herein incorporated by reference in their entireties.

TECHNICAL FIELD

The present patent application is directed to pyrimidine phospho compounds which are useful as MAP4K1 inhibitors.

BACKGROUND OF THE INVENTION

Protein kinases represent a large family of proteins which play a variety of crucial roles in the regulation of a wide range of cellular processes. Such kinases include Akt, Axl, Aurora A, Aurora B, DYRK2, EPHAa2, FGFR3, FLT-3, VEGFr3, IGFLr, IKK2, JNK3, VEGFr2, MEK1, MET, P70s6K, Plk1, RSK1, Src, TrkA, Zap70, cKit, bRaf, EGFR, Jak2, PI3K, NPM-Alk, c-Abl, BTK, FAK, PDGFR, TAK1, LimK, Flt1, PDK1, Erk and RON. Inhibition of various protein kinases, especially selective inhibition, has become an important strategy in treating many diseases and disorders.

MAP4K1 is a serine/threonine kinase of the Ste20 family. MAP4K enzymes (MAP kinase kinases) are generally involved at the highest level of a largely linear kinase activation pathway. A MAP4K will phosphorylate and activate a particular substrate which is a MAP3K (a MAP kinase kinase). A MAP3K in turn phosphorylates and activates a MAP2K (a MAP kinase kinase). A MAP2K in turn phosphorylates and activates a MAPK (MAP kinase). The MAP kinase is the final effector of the pathway and it in turn phosphorylates a substrate to control key cellular processes such as cell proliferation, cell differentiation, gene expression, transcription regulation, and apoptosis. The substrate of MAPK is generally a nuclear protein, such as nuclear factor kappa-B (NF-κB). Activation of the MAPK by its phosphorylation by an MAP2K results in translocation of this final enzyme in the cascade into the nucleus.

MAP4K1, also known as HPK1, is primarily expressed in the immune system's Tcells and B cells, which are critical in regulation of the immune system. Overstimulation of T cell and B cell activation pathways can result in auto-immune diseases, while understimulation of these pathways can result in immune dysfunction, susceptibility to viral and bacterial infection and increased susceptibility to cancer. MAP4K1 is activated by its interaction with activated T cell receptors (TCRs) and B cell receptors (BCRs), so MAP4K1 activation serves to convey the cellular activation signal from the surface of a T or B cell to the effector proteins in the nucleus.

There is also evidence that MAP4K1 can be activated via the TGF-β receptor, the erythropoietin receptor and the FAS protein (which is involved in apoptosis signaling). MAP4K1 activation ultimately results in activation of several identified nuclear effector proteins, including those involved in the NF-κ1, AP-1, ERK2, and Fos signaling pathways.

MAP4K1 is considered a negative regulator of T cell receptor (TCR) activation signals, and it is one of the effector molecules that mediates immunosuppression of T cell responses upon exposure to prostaglandin E2 (PGE2). Studies have shown that MAPK1 activity dampens the strength of the T cell receptor signal transduction cascade, and thus, targeted genetic disruption of MAP4K1 results in strengthened TCR activation signals.

One particularly important pathway that MAP4K1 appears to be involved with is the JNK pathway. MAP4K1 regulates the MAP3K's MEKK1, TAK1 and MLK3. These in turn regulate the MAP2K's MKK4 and MKK7. These in turn regulate the MAPK JNK. JNK then regulates important transcription factors and other proteins, including p53, SMAD4, NFAT-2, NFAT-4, ELK1, ATF2, HSF1, c-Jun, and JunD. JNK has been implicated in apoptosis, neurodegeneration, cell differentiation and proliferation, inflammatory conditions and cytokine production.

The JNK signal transduction pathway is activated in response to environmental stress and by the engagement of several classes of cell surface receptors, including cytokine receptors, serpentine receptors and receptor tyrosine kinases. In mammalian cells, the JNK pathway has been implicated in biological processes such as oncogenic transformation and mediating adaptive responses to environmental stress. JNK has also been associated with modulating immune responses, including maturation and differentiation of immune cells, as well as effecting programmed cell death in cells identified for destruction by the immune system. Among several neurological disorders, INK signaling is particularly implicated in ischemic stroke and Parkinson's disease, but also in other diseases as mentioned further below.

It is noteworthy that the MAPK p38alpha was shown to inhibit cell proliferation by antagonizing the JNK-c-Jun-pathway. p38alpha appears to be active in suppression of proliferation in both normal cells and cancer cells, and this strongly suggests the involvement of INK in hyperproliferative diseases (see, e.g., Hui et al., *Nature Genetics*, Vol. 39, No. 6, June 2007). JNK signaling has also been implicated in diseases such as excitotoxicity of hippocampal neurons, liver ischemia, reperfusion, neurodegenerative diseases, hearing loss, deafness, neural tube birth defects, cancer, chronic inflammatory diseases, obesity, diabetes, in particular, insulin-resistant diabetes, and it has been proposed that selective JNK inhibitors are needed for treatment of various diseases with a high degree of specificity and lack of toxicity.

Because MAP4K1 is an upstream regulator of JNK, effective inhibitors of MAP4K1 would be useful in treating the same diseases which have been suggested or implicated for JNK inhibitors, especially where such disease or dysfunction is manifested in hematopoietic cells such as T cells and B cells.

Targeted disruption of MAP4K1 (HPK1) alleles has been shown to confer T cells with an elevated Th1 cytokine production in response to TCR engagement. Burakoff et al., *Immunologic Research,* 54(1): 262-265 (2012). HPK1−/− T cells were found to proliferate more rapidly than the haplotype-matched wild-type counterpart and were resistant to prostaglandin E2 (PGE2)-mediated suppression. Most strikingly, mice that received adoptive transfer of HPK1−/− T cells became resistant to lung tumor growth. Also, the loss of HPK1 from dendritic cells (DCs) endowed them with superior antigen presentation ability, enabling HPK1−/− DCs to elicit a more potent anti-tumor immune response when used as cancer vaccine. It was considered probable that blocking the MAP4K1 kinase activity with a small molecule inhibitor may activate the superior antitumor activity of both cell types, resulting in a synergistic amplification of anti-tumor potential. Given that MAP4K1 is not expressed in any major organs, it is less likely that a selective inhibitor of MAP4K1 would cause any serious side effects.

The relationship between MAP4K1 and PGE2 is particularly noteworthy because PGE2 is the predominant eicosanoid product released by cancer cells, including lung, colon and breast cancer cells. Tumor-produced PGE2 is known to contribute significantly to tumor-mediated immune suppression.

Zhang et al., *J. Autoimmunity,* 37:180-189 (2011), described diminished HPK1 expression in CD4 T cells of lupus patients due to the selective loss of JMJD3 histone demethylase binding to the HPK1 locus. This suggests that HPK1 is one of the key molecules involved in the maintenance of peripheral tolerance. Peripheral tolerance is one of the major obstacles to the development of effective anti-tumor immunity.

Several small molecule inhibitors of MAP4K1 have been reported, but they do not inhibit MAP4K1 selectively, or even preferentially. Such inhibitors include staurosporine, bosutinib, sunitinib, lestaurtinib, crizotinib, foretinib, dovitinib and KW-2449. Staurosporine, for example, broadly inhibits a wide range of protein kinases across both the serine/threonine and tyrosine kinase families. Bosutinib is primarily an inhibitor of the tyrosine kinase BCR-Abl, with additional activity against the Src family tyrosine kinases. Sunitinib is a broad inhibitor of tyrosine kinases. Lestaurtinib is primarily an inhibitor of the FLT, JAK and TRK family tyrosine kinases. Crizotinib is primarily an inhibitor of the c-met and ALK tyrosine kinases. Foretinib was under study as an inhibitor of the c-Met and VEGFR tyrosine kinases. Dovitinib is primarily an inhibitor of the FGFR receptor tyrosine kinase. KW-2449 is an experimental inhibitor primarily of the FLT3 tyrosine kinase.

Sunitinib inhibits MAP4K1 at nanomolar concentrations, but it is a broad-spectrum receptor tyrosine kinase inhibitor. Treating T-cells with sunitinib results in enhanced cytokine product similar to that observed with HPK1−/− T cells, which suggests that in T cells a selective MAP4K1 inhibitor could produce the same enhanced immune response phenotype.

Currently, there is a largely unmet need for an effective way of treating disease and disorders associated disrupted protein kinase signaling. Autoimmune diseases, inflammatory diseases, neurological and neurodegenerative diseases, cancer, cardiovascular diseases, allergies and asthma, are all diseases and disorder which can be affected by dysfunctional protein kinase signaling. Improved therapeutic compounds, compositions and methods for the treatment for these disease and disorders are urgently required. MAP4K1 inhibition is an especially attractive target for cancer immunotherapy.

The major challenge currently faced in the field is the lack of MAP4K1 specific inhibitors. The present disclosure provides novel, highly effective small-molecule inhibitors of MAP4K1.

SUMMARY OF THE INVENTION

In one aspect, the present invention relates to compound of formula (I)

(I)

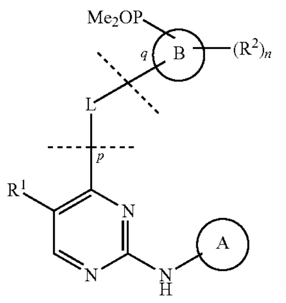

or a tautomer thereof, stereoisomer thereof, or a pharmaceutically acceptable salt thereof, wherein $R^1$ is selected from chloro and —$CONH_2$;

L is selected from

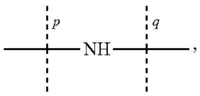

,

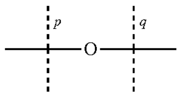

and

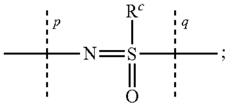

;

p and q are the point of attachments;

$R^c$ is selected from $C_{1-8}$alkyl;

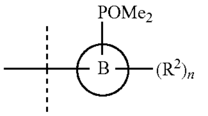

is selected from

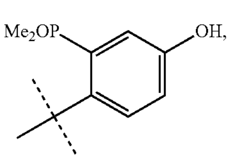

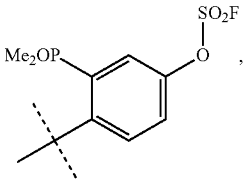

,

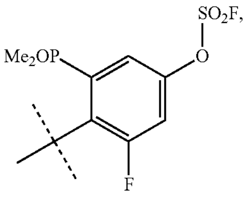

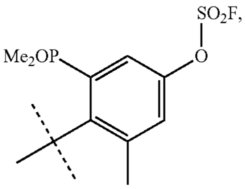

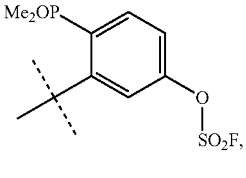

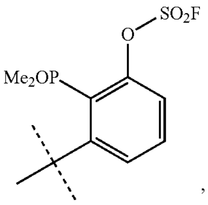

,

-continued
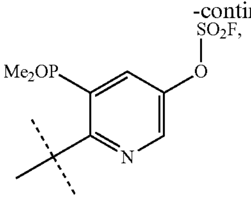
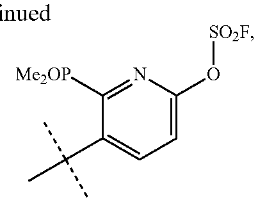
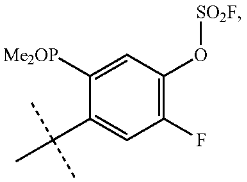
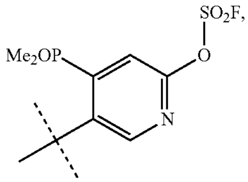
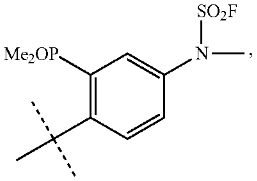
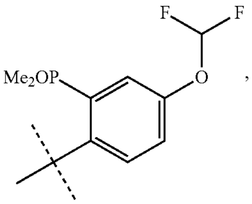
,
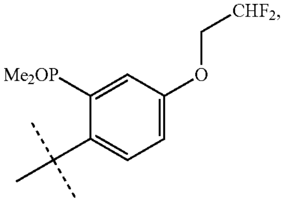
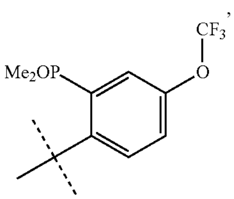
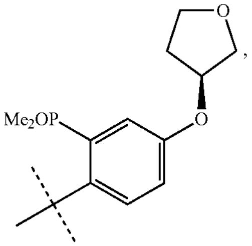
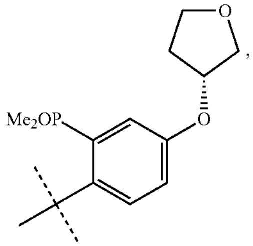
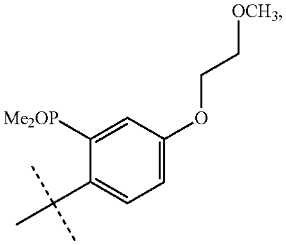
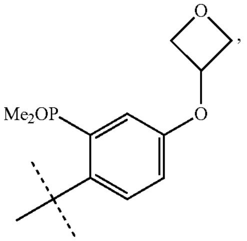
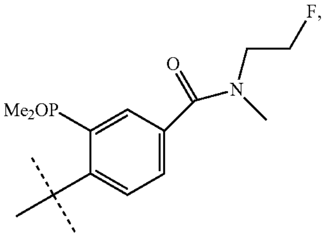
-continued
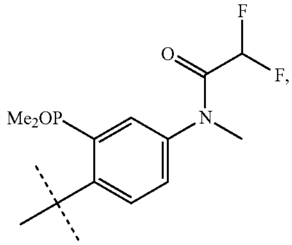
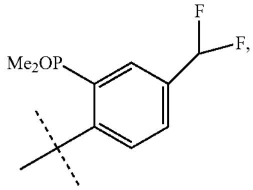
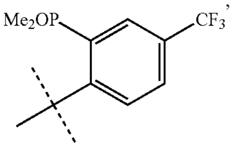
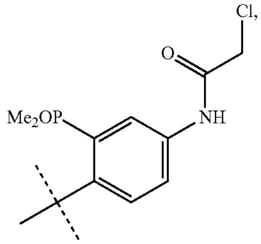
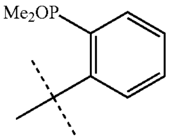
and
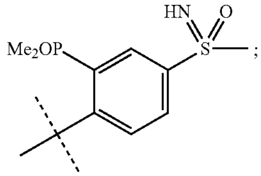
Ring A is selected from
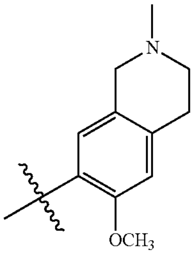
,
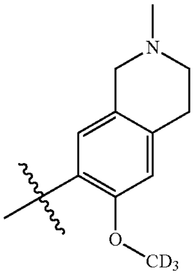
,
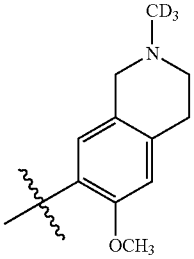
,
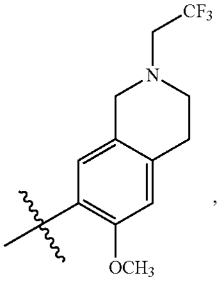
, -continued
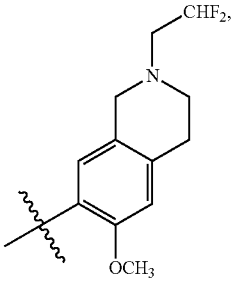
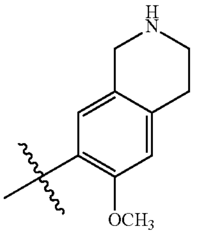
,
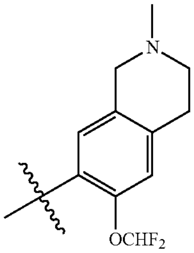
,
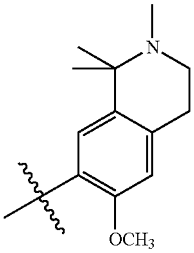
,
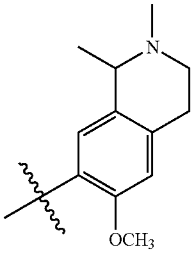
,
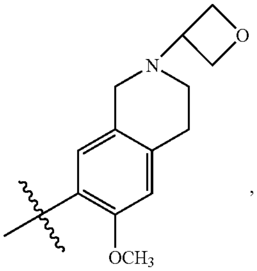
,
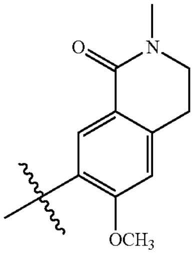
,
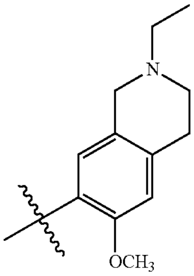
,
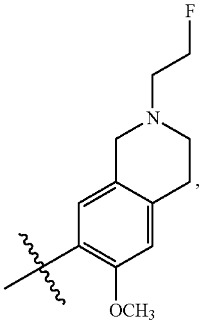
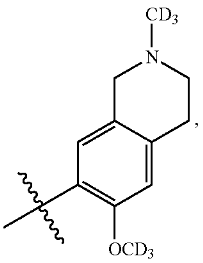
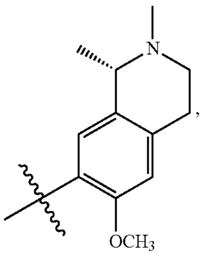
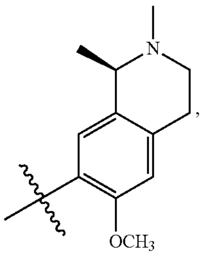
-continued
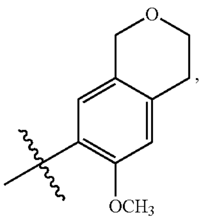
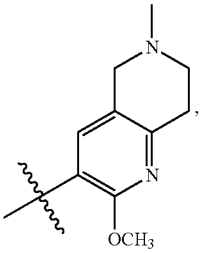
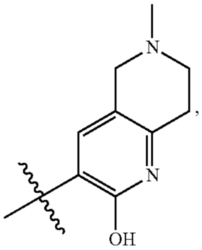
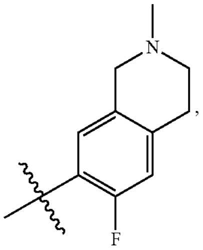
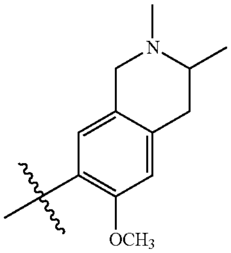
,
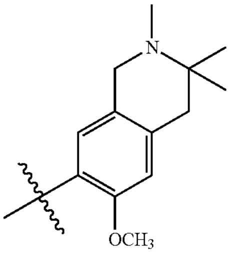
,
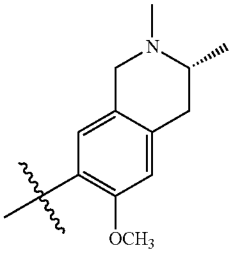
,
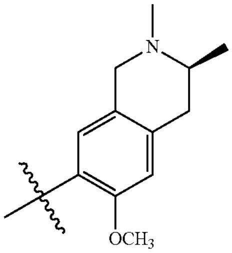
,
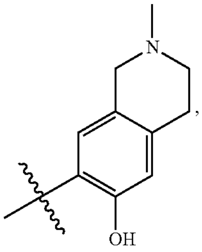
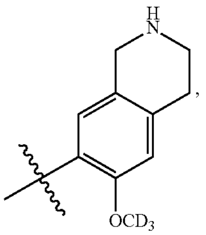
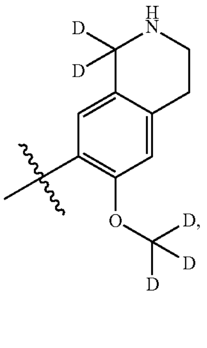
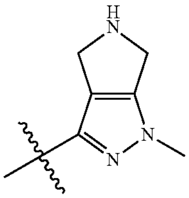
, -continued

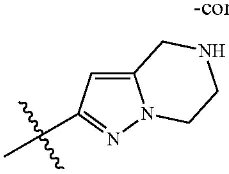

and

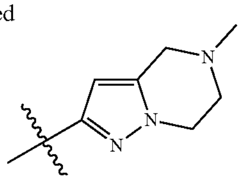

.

The compounds of formula (I) may involve one or more embodiments. It is to be understood that the embodiments below are illustrative of the present invention and are not intended to limit the claims to the specific embodiments exemplified. It is also to be understood that the embodiments defined herein may be used independently or in conjunction with any definition, any other embodiment defined herein. Thus the invention contemplates all possible combinations and permutations of the various independently described embodiments. For example, the invention provides compounds of formula (I) as defined above wherein $R^1$ is chloro (according to an embodiment defined below), $R^1$ is —$CONH_2$ (according to another embodiment defined below) and $R^c$ is methyl (according to yet another embodiment defined below).

According to one embodiment, specifically provided are compounds of formula (I), in which $R^1$ is chloro.

According to another embodiment, specifically provided are compounds of formula (I), in which $R^1$ is —$CONH_2$.

According to yet another embodiment, specifically provided are compounds of formula (I), in which

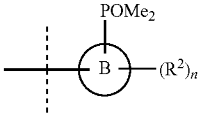

is

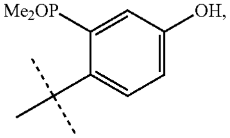

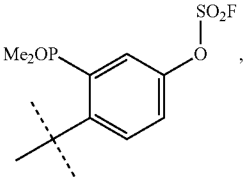

,

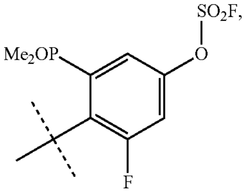

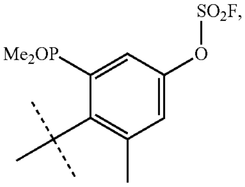

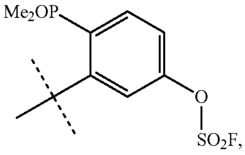

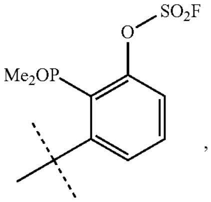

,

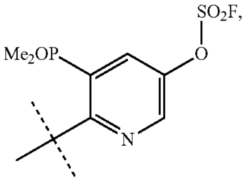

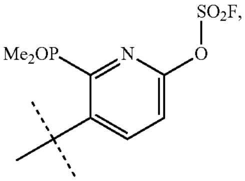

-continued

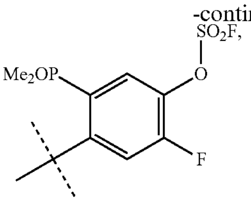

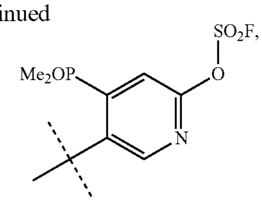

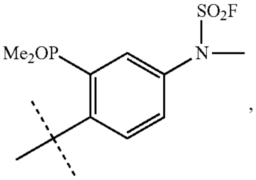

,

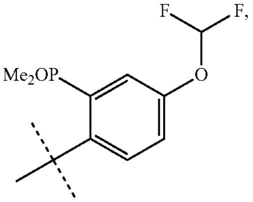

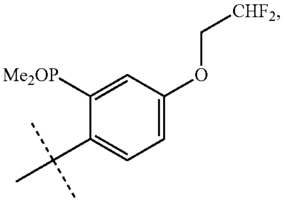

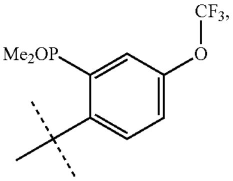

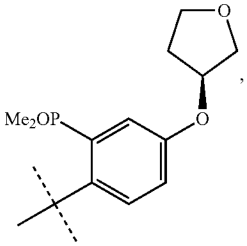

,

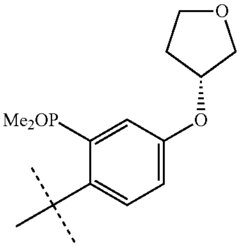

,

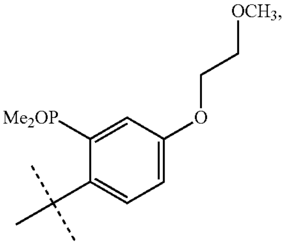

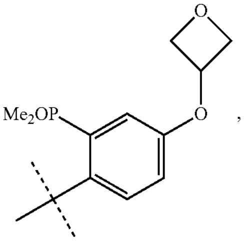

,

-continued

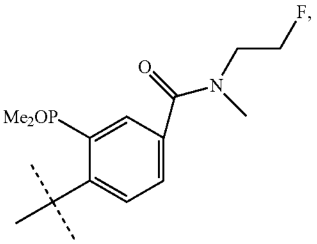

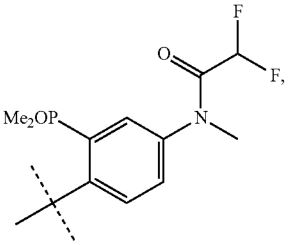

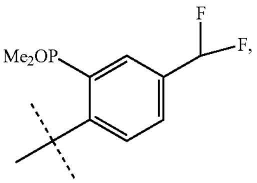

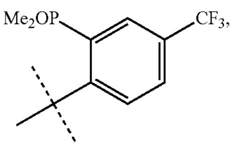

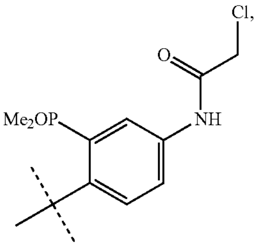

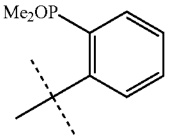

or

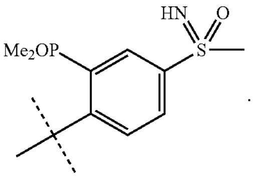

.

According to yet another embodiment, specifically provided are compounds of formula (I), in which L is

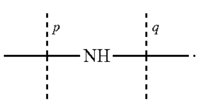

According to yet another embodiment, specifically provided are compounds of formula (I), in which L is

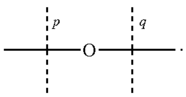

According to yet another embodiment, specifically provided are compounds of formula (I), in which L is

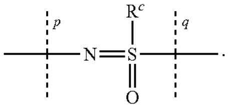

In this embodiment $R^c$ is methyl.

According to yet another embodiment, specifically provided are compounds of formula (I), in which L is

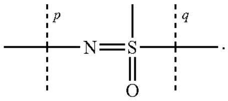

According to yet another embodiment, specifically provided are compounds of formula (I) in which ring A is

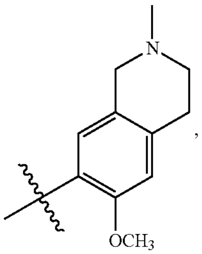

,

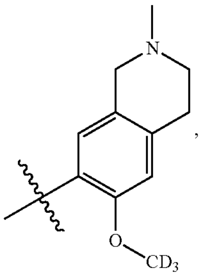

,

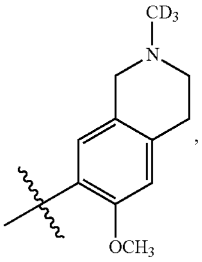

,

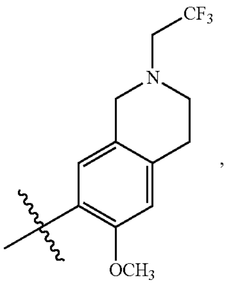

,

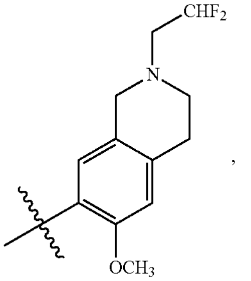

,

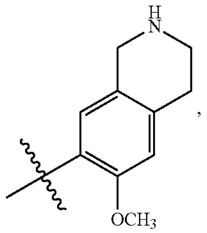

,

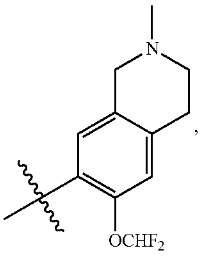

,

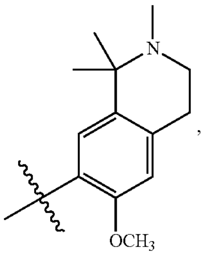

,

-continued
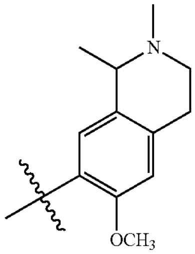,
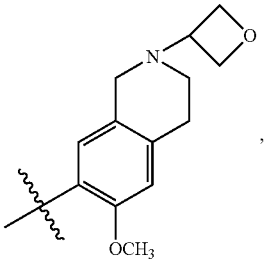,
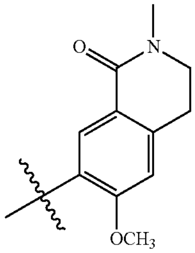,
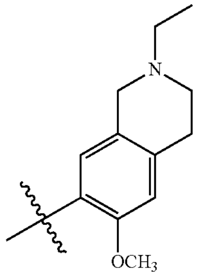,
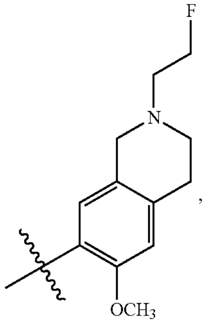,
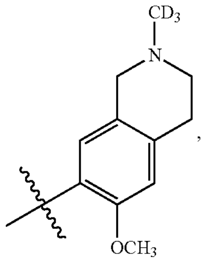,
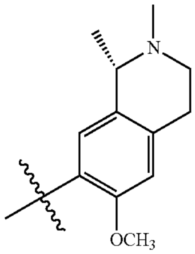,
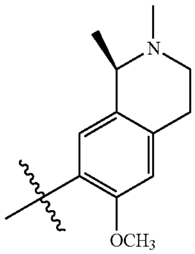,
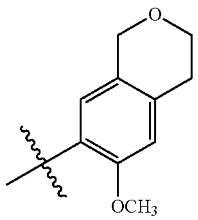,
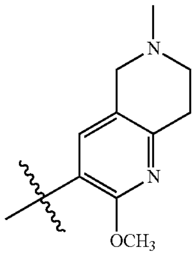,
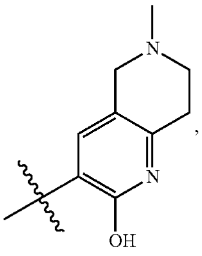,
-continued
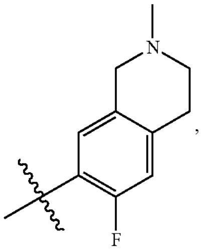,
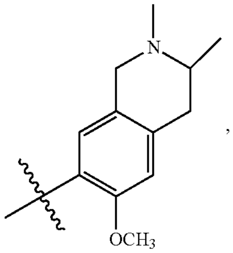,
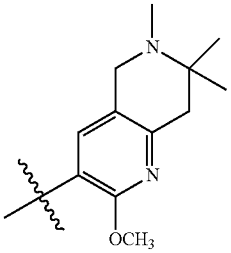,
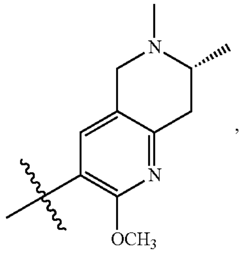,
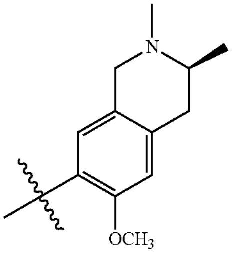,
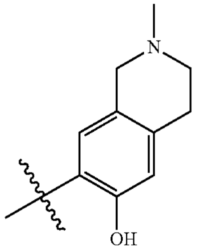,
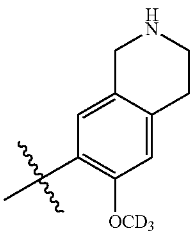,
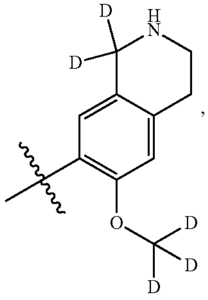,
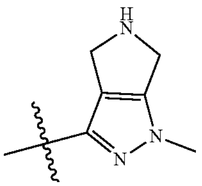,
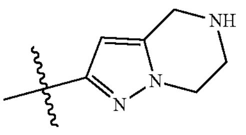 or
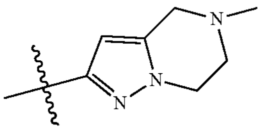.
According to yet another embodiment, specifically provided are compounds of formula (I), in which
$R^1$ is chloro;
L is
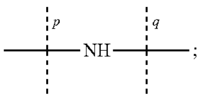; 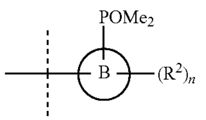 is -continued

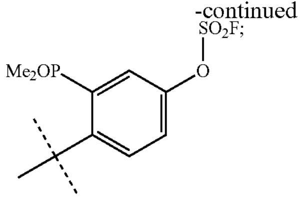

and
ring A is

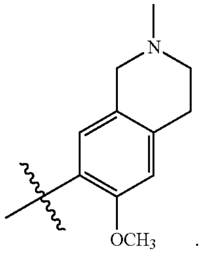 [SMILES: *c1cc2c(cc1OC)CCN(C)C2]

According to yet another embodiment, specifically provided are compounds of formula (I), in which
$R^1$ is chloro;
L is

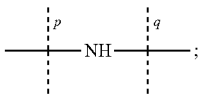

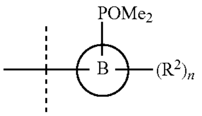 is

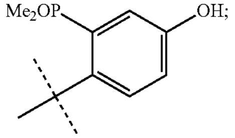

and
ring A is

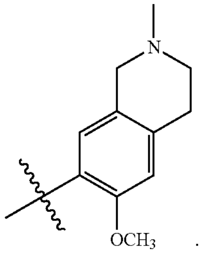 [SMILES: *c1cc2c(cc1OC)CCN(C)C2]

According to yet another embodiment, specifically provided are compounds of formula (I), in which
$R^1$ is chloro;
L is

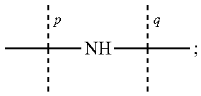

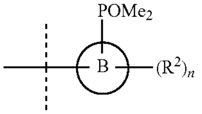 is

-continued

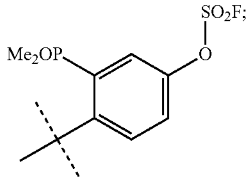

and ring A is

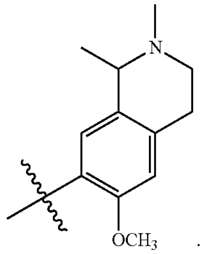 [SMILES: *c1cc2c(cc1OC)CCN(C)C2C]

According to yet another embodiment, specifically provided are compounds of formula (I), in which
$R^1$ is chloro;

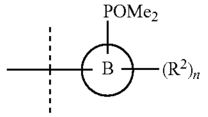 is

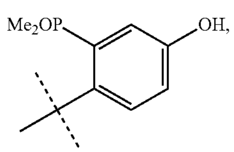

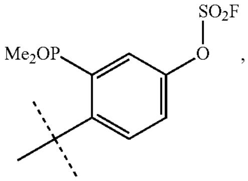 ,

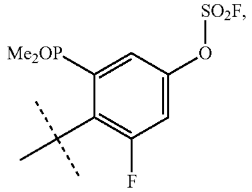

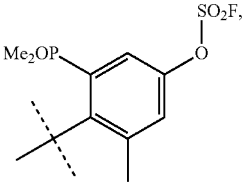

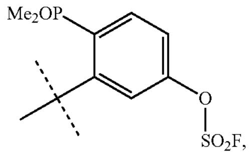

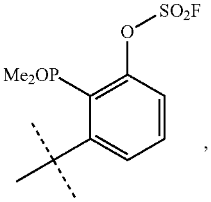 ,

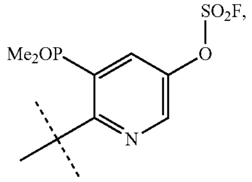

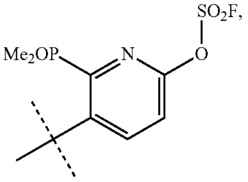

-continued
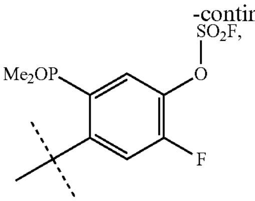
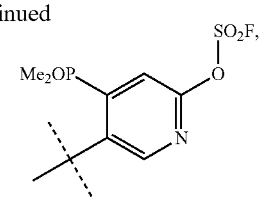
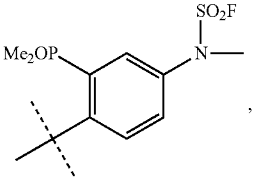
,
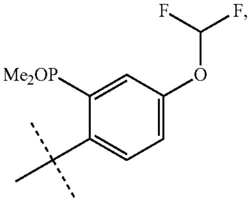
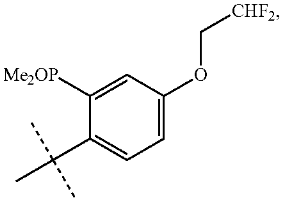
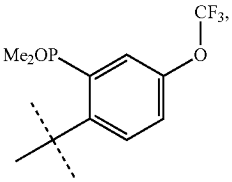
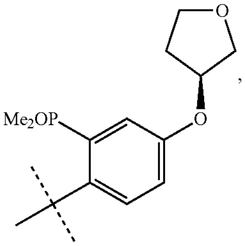
,
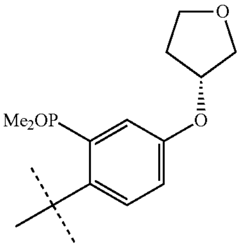
,
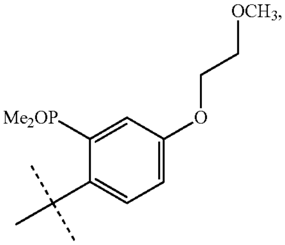
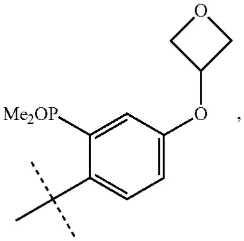
,
-continued
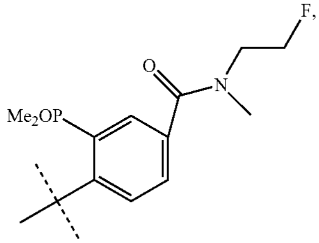
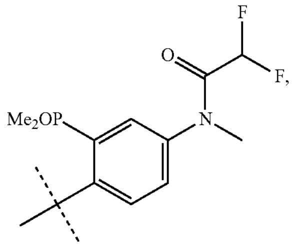
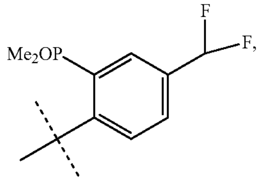
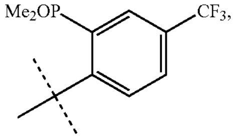
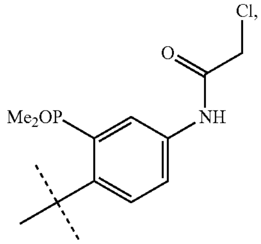
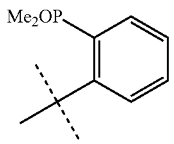
or
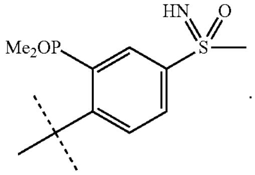
.
L is
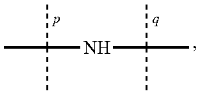
,
and
ring A is
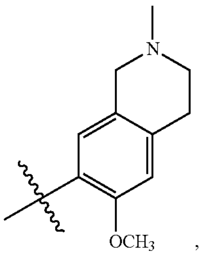
,
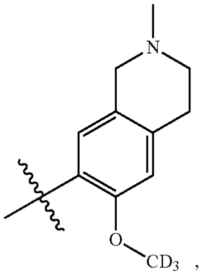
, -continued
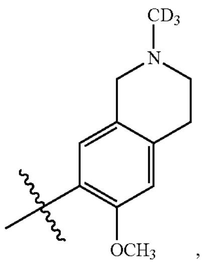 ,
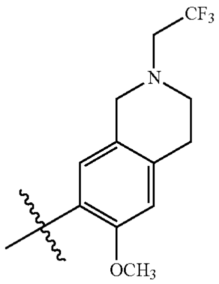 ,
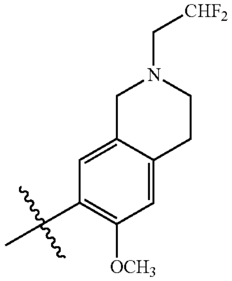 ,
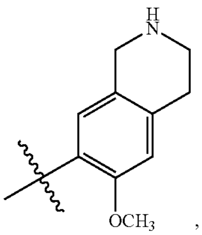 ,
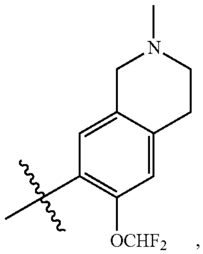 ,
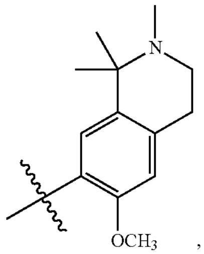 ,
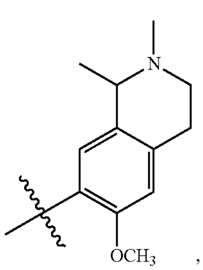 ,
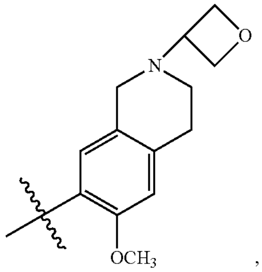 ,
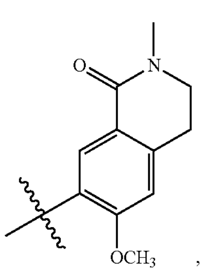 ,
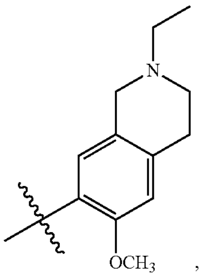 ,
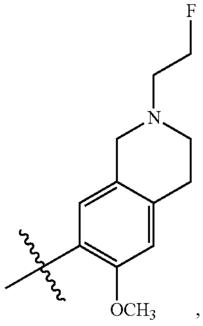 ,
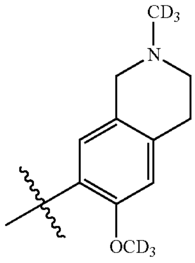 ,
-continued
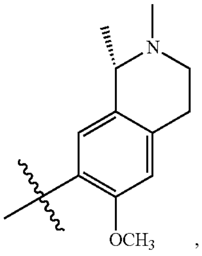 ,
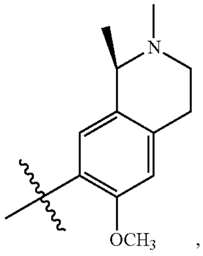 ,
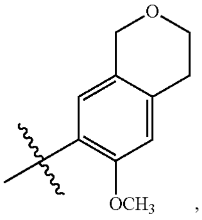 ,
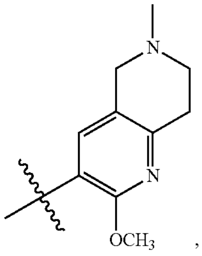 ,
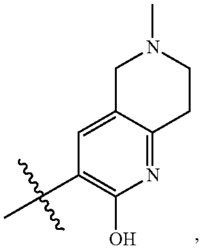 ,
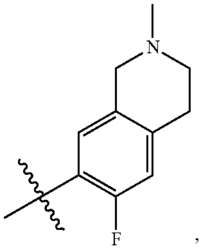 ,
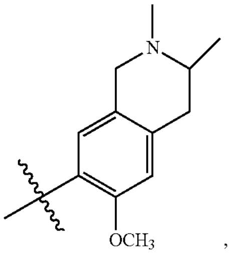 ,
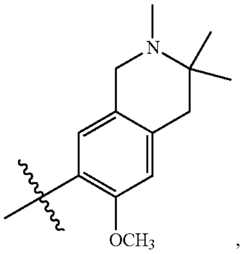 ,
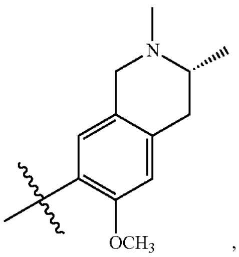 ,
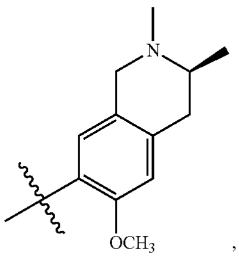 ,
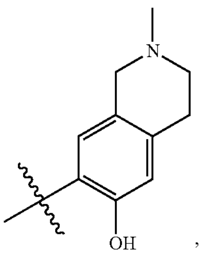 ,
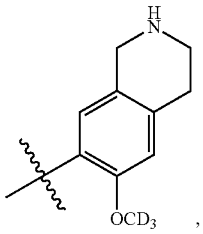 , -continued

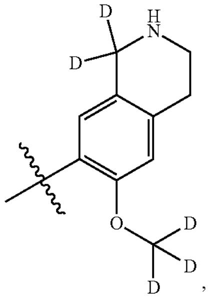

,

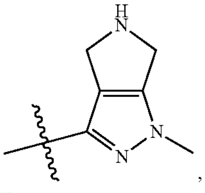

,

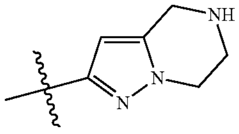

or

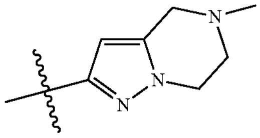

;

According to an embodiment, specifically provided are compounds of formula (I) with an $IC_{50}$ value of less than 500 nM, preferably less than 100 nM, more preferably less than 50 nM, with respect to MAP4K1 inhibition.

Compounds of the present invention include the compounds in Examples 1-61. It should be understood that the formula (I) structurally encompasses all geometrical isomers, stereoisomers, enantiomers and diastereomers, N-oxides, and pharmaceutically acceptable salts that may be contemplated from the chemical structure of the genera described herein.

The present application also provides a pharmaceutical composition that includes at least one compound described herein and at least one pharmaceutically acceptable excipient (such as a pharmaceutically acceptable carrier or diluent). Preferably, the pharmaceutical composition comprises a therapeutically effective amount of at least one compound described herein. The compounds described herein may be associated with a pharmaceutically acceptable excipient (such as a carrier or a diluent) or be diluted by a carrier, or enclosed within a carrier which can be in the form of a tablet, capsule, sachet or other container.

Pharmaceutical compositions comprising Compounds of the Invention may be prepared using conventional diluents or excipients and techniques known in the art.

DETAILED DESCRIPTION OF THE INVENTION

Definitions

Figure 1:
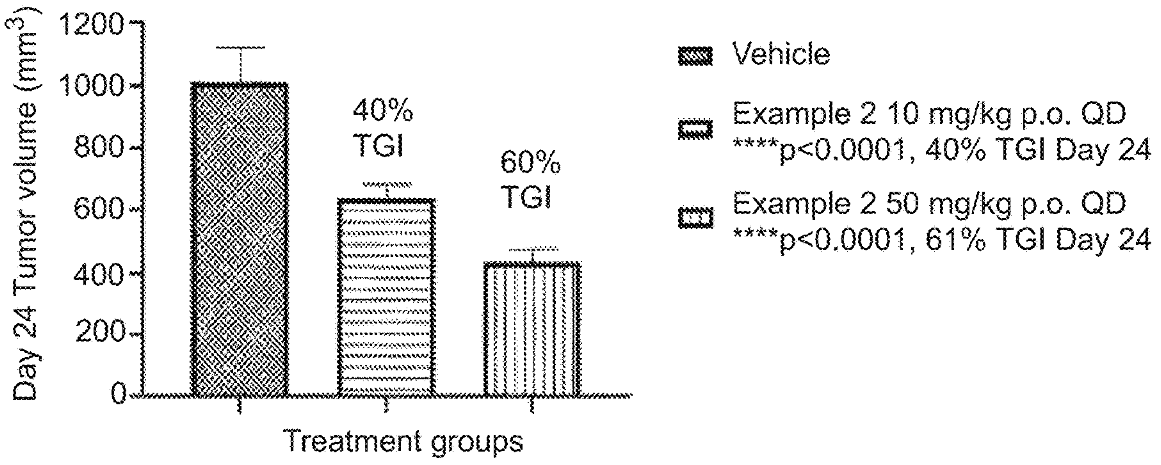
FIG. 1 shows Tumor Growth Inhibition by Example 2 in a CT26 tumor model.

The terms “halogen” or “halo” means fluorine (fluoro), chlorine (chloro), bromine (bromo), or iodine (iodo).

The term “alkyl” refers to a hydrocarbon chain radical that includes solely carbon and hydrogen atoms in the backbone, containing no unsaturation, having from one to eight carbon atoms (i.e. $C_{1-8}$alkyl), and which is attached to the rest of the molecule by a single bond, such as, but not limited to, methyl, ethyl, n-propyl, 1-methylethyl (isopropyl), n-butyl, n-pentyl, and 1,1-dimethylethyl (t-butyl). The term “$C_{1-6}$alkyl” refers to an alkyl chain having 1 to 6 carbon atoms. The term “$C_{1-4}$alkyl” refers to an alkyl chain having 1 to 4 carbon atoms. Unless set forth or recited to the contrary, all alkyl groups described or claimed herein may be straight chain or branched.

The term “haloalkyl” refers to at least one halo group (selected from F, Cl, Br or I), linked to an alkyl group as defined above (i.e. halo$C_{1-8}$alkyl). Examples of such haloalkyl moiety include, but are not limited to, trifluoromethyl, difluoromethyl and fluoromethyl groups. The term “halo$C_{1-4}$alkyl” refers to at least one halo group linked an alkyl chain having 1 to 4 carbon atoms. Unless set forth or recited to the contrary, all haloalkyl groups described herein may be straight chain or branched.

The term “deuterated $C_{1-8}$alkyl” refers to a $C_{1-8}$alkyl group as defined above wherein one to three hydrogen atoms on carbon atoms is/are replaced by one or more deuterium atoms.

The term “alkoxy” denotes an alkyl group attached via an oxygen linkage to the rest of the molecule (i.e. $C_{1-8}$ alkoxy). Representative examples of such groups are $—OCH_3$ and $—OC_2H_5$.

Unless set forth or recited to the contrary, all alkoxy groups described or claimed herein may be straight chain or branched.

The term “haloalkoxy” refers to an alkoxy group substituted with one or more halogen atoms (i.e. halo$C_{1-8}$alkoxy). Examples of “haloalkoxy” include but are not limited to fluoromethoxy, difluoromethoxy, trifluoromethoxy, 2,2,2-trifluoroethoxy, pentafluoroethoxy, pentachloroethoxy, chloromethoxy, dichlorormethoxy, trichloromethoxy and 1-bromoethoxy.

Unless set forth or recited to the contrary, all haloalkoxy groups described herein may be straight chain or branched.

The term “alkoxyalkyl” or “alkyloxyalkyl” refers to an alkoxy or alkyloxy group as defined above directly bonded to an alkyl group as defined above (i.e. $C_{1-8}$alkoxy$C_{1-8}$alkyl or $C_{1-8}$alkyloxy$C_{1-8}$alkyl). Example of such alkoxyalkyl moiety includes, but are not limited to, $—CH_2OCH_3$ (methoxymethyl) and $—CH_2OC_2H_5$ (ethoxymethyl). Unless set forth or recited to the contrary, all alkoxyalkyl groups described herein may be straight chain or branched.

The term “deuterated $C_{1-8}$alkoxy” refers to a $C_{1-8}$alkoxy group as defined above wherein one to three hydrogen atoms on carbon atoms is/are replaced by one or more deuterium atoms.

The term “hydroxy$C_{1-8}$alkyl” refers to a $C_{1-8}$alkyl group as defined above wherein one to three hydrogen atoms on different carbon atoms is/are replaced by hydroxyl groups (i.e. hydroxy$C_{1-4}$alkyl). Examples of hydroxy$C_{1-4}$alkyl moieties include, but are not limited to $—CH_2OH$ and $—C_2H_4OH$.

The term “cycloalkyl” denotes a non-aromatic mono or multicyclic ring system of 3 to about 12 carbon atoms, (i.e. $C_{3-12}$cycloalkyl). Examples of monocyclic cycloalkyl include but are not limited to cyclopropyl, cyclobutyl, cyclopentyl, and cyclohexyl. Examples of multicyclic cycloalkyl groups include, but are not limited to, perhydronapthyl, adamantyl and norbornyl groups, bridged cyclic groups or spirobicyclic groups, e.g., spiro(4,4)non-2-yl. The term “$C_{3-6}$cycloalkyl” refers to the cyclic ring having 3 to 6 carbon atoms. Examples of "$C_{3-6}$ cycloalkyl" include but are not limited to cyclopropyl, cyclobutyl, cyclopentyl, or cyclohexyl.

The term "cycloalkylalkyl" refers to a cyclic ring-containing radical having 3 to about 6 carbon atoms directly attached to an alkyl group (i.e. $C_{3-6}$cycloalkyl$C_{1-8}$alkyl). The cycloalkylalkyl group may be attached to the main structure at any carbon atom in the alkyl group that results in the creation of a stable structure. Non-limiting examples of such groups include cyclopropylmethyl, cyclobutylethyl, and cyclopentylethyl.

The term "aryl" refers to an aromatic radical having 6 to 14 carbon atoms (i.e. $C_{6-14}$aryl), including monocyclic, bicyclic and tricyclic aromatic systems, such as phenyl, naphthyl, tetrahydronapthyl, indanyl, and biphenyl.

The term "heterocyclic ring" or "heterocyclyl" unless otherwise specified refers to substituted or unsubstituted non-aromatic 3 to 15 membered ring radical (i.e. 3 to 15 membered heterocyclyl) which consists of carbon atoms and from one to five hetero atoms selected from nitrogen, phosphorus, oxygen and sulfur. The heterocyclic ring radical may be a mono-, bi- or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; also, unless otherwise constrained by the definition the heterocyclic ring or heterocyclyl may optionally contain one or more olefinic bond(s). Examples of such heterocyclic ring radicals include, but are not limited to azepinyl, azetidinyl, benzodioxolyl, benzodioxanyl, chromanyl, dioxolanyl, dioxaphospholanyl, decahydroisoquinolyl, indanyl, indolinyl, isoindolinyl, isochromanyl, isothiazolidinyl, isoxazolidinyl, morpholinyl, oxazolinyl, oxazolidinyl, 2-oxopiperazinyl, 2-oxopiperidinyl, 2-oxopyrrolidinyl, 2-oxoazepinyl, octahydroindolyl, octahydroisoindolyl, perhydroazepinyl, piperazinyl, 4-piperidonyl, pyrrolidinyl, piperidinyl, phenothiazinyl, phenoxazinyl, quinuclidinyl, tetrahydroisquinolyl, tetrahydrofuryl or tetrahydrofuranyl, tetrahydropyranyl, thiazolinyl, thiazolidinyl, thiamorpholinyl, thiamorpholinyl sulfoxide and thiamorpholinyl sulfone. The heterocyclic ring radical may be attached to the main structure at any heteroatom or carbon atom that results in the creation of a stable structure.

The term "heterocyclylalkyl" refers to a heterocyclic ring radical directly bonded to an alkyl group (i.e. 3 to 15 membered heterocyclyl$C_{1-8}$alkyl). The 20 heterocyclylalkyl radical may be attached to the main structure at any carbon atom in the alkyl group that results in the creation of a stable structure.

The term "heteroaryl" unless otherwise specified refers to 5 to 14 membered aromatic heterocyclic ring radical with one or more heteroatom(s) independently selected from N, O or S (i.e. 5 to 14 membered heteroaryl). The heteroaryl may be a mono-, bi- or tricyclic ring system. The heteroaryl ring radical may be attached to the main structure at any heteroatom or carbon atom that results in the creation of a stable structure. Examples of such heteroaryl ring radicals include, but are not limited to oxazolyl, isoxazolyl, imidazolyl, furyl, indolyl, isoindolyl, pyrrolyl, triazolyl, triazinyl, tetrazoyl, thienyl, oxadiazolyl, thiazolyl, isothiazolyl, pyridyl, pyrimidinyl, pyrazinyl, pyridazinyl, pyrazolyl, benzofuranyl, benzothiazolyl, benzoxazolyl, benzimidazolyl, benzothienyl, benzopyranyl, carbazolyl, quinolinyl, isoquinolinyl, quinazolinyl, cinnolinyl, naphthyridinyl, pteridinyl, purinyl, quinoxalinyl, quinolyl, isoquinolyl, thiadiazolyl, indolizinyl, acridinyl, phenazinyl and phthalazinyl.

The term "pharmaceutically acceptable salt" includes salts prepared from pharmaceutically acceptable bases or acids including inorganic or organic bases and inorganic or organic acids. Examples of such salts include, but are not limited to, acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate, diphosphate, polygalacturonate, salicylate, stearate, sulfate, subacetate, succinate, tannate, tartrate, teoclate, tosylate, triethiodide and valerate. Examples of salts derived from inorganic bases include, but are not limited to, aluminum, ammonium, calcium, copper, ferric, ferrous, lithium, magnesium, manganic, mangamous, potassium, sodium, and zinc.

The term "treating" or "treatment" of a state, disorder or condition includes: (a) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition; (b) inhibiting the state, disorder or condition, i.e., arresting or reducing the development of the disease or at least one clinical or subclinical symptom thereof, or (c) relieving the disease, i.e., causing regression of the state, disorder or condition or at least one of its clinical or subclinical symptoms.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a state, disorder or condition, is sufficient to effect such treatment. The "therapeutically effective amount" will vary depending on the compound, the disease and its severity and the age, weight, physical condition and responsiveness of the subject to be treated.

The compounds of formula (I) may contain asymmetric or chiral centers, and, therefore, exist in different stereoisomeric forms. It is intended that all stereoisomeric forms of the compounds of formula (I) as well as mixtures thereof, including racemic mixtures, form part of the present invention. In addition, the present invention embraces all geometric and positional isomers. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolysing) the individual diastereomers to the corresponding pure enantiomers. Enantiomers can also be separated by use of chiral HPLC column. The chiral centres of the present invention can have the S or R configuration as defined by the IUPAC 1974.

The terms "salt" or "solvate", and the like, is intended to equally apply to the salt, solvate and prodrug of enantiomers, stereoisomers, rotamers, tautomers, positional isomers or racemates of the inventive compounds.

Pharmaceutical Compositions

The compounds of the invention are typically administered in the form of a pharmaceutical composition. Such compositions can be prepared using procedures well known in the pharmaceutical art and comprise at least one compound of the invention. The pharmaceutical compositions described herein comprise one or more compounds described herein and one or more pharmaceutically acceptable excipients.

Methods of Treatment

The compounds of Formula (I) as described herein are highly effective inhibitors of the MAP4K1 kinase, producing inhibition at nanomolar concentrations. MAP4K1 inhibitors according to the invention are therefore useful for treatment and prophylaxis of diseases associated with protein kinase signaling dysfunction. Accordingly, without being bound by any theory, it is believed that inhibition of MAP4K1 could, for example, reverse or prevent the cellular dysfunction associated with perturbations of the JNK signaling pathway, especially in T and B cells. Therefore, administration of a MAP4K1 inhibitor as described herein could provide a potential means to regulate MAPK signal transduction pathways, especially the JNK pathway, and by extension provide a treatment for a variety of diseases and disorders including autoimmune, neurodegenerative, neurological, inflammatory, hyperproliferative, and cardiovascular diseases and disorders.

In addition, without being bound by theory, selective MAP4K1 inhibition, as provided by the Compounds of the Invention, may provide a novel means of cancer treatment. Traditional signal transduction strategies relate to interference with the pathways that promote tumor cell proliferation or metastasis. The present invention provides instead a means of enhancing the activity and effectiveness of the body's T cells, for example, to overcome the immunosuppressive strategies used by many cancers. The U.S. Food and Drug Administration (FDA) has recently approved some monoclonal antibody-based treatments that achieve the same result by interfering with T-cell surface receptors which promote inhibition of TCR activity (e.g., anti-CTLA-4 and anti-PD-1 antibodies, marketed as Ipilimumab and Pembrolizumab, respectively). The success of the treatments demonstrates proof of the concept that cancer can be effectively treated by interfering with pathways which inhibit TCR signaling. Targeting these pathways using a small molecule inhibitor of MAP4K1 should produce improved results using more patient-friendly administration techniques.

Therefore, in the third aspect, the invention provides a method for the treatment or prophylaxis of a disease or disorder which may be ameliorated by modulating (e.g., inhibiting) MAP4K1-dependent signaling pathways, including the JNK pathway, e.g., autoimmune, neurodegenerative, neurological, inflammatory, hyperproliferative, and cardiovascular diseases and disorders, comprising administering to a patient in need thereof an effective amount of the compound of Formula (I) as described herein, in free or pharmaceutically acceptable salt form.

In particular embodiments, administration of the compounds of the present invention results in enhanced T cell receptor (TCR) signaling, such as resulting in an enhanced T cell-mediated immune response (e.g., increased T cell cytokine production).

In other particular embodiments, administration of the compounds of the present invention results in increased T cell resistance to PGE2-mediated T cell suppression.

In certain embodiments, the disease or disorder to be treated may also relate to impaired MAP4K1-dependent signaling. Impaired MAP4K1 signaling can lead to reduced immune cell, e.g. T and B cell, function which can permit or enhance the escape of nascent cancer cells from immune surveillance. Restoration of T and B cell function via treatment with a MAP4K1-inhibitor can therefore promote the clearance of carcinogenic and pre-carcinogenic cells from the body. Thus, in a particular embodiment, the invention provides a method for the treatment or prevention of hyperproliferative diseases, such as cancer.

General Methods of Preparation

The compounds, described herein, including those of general formula (I), intermediates and specific examples are prepared through the synthetic methods as depicted in synthetic schemes 1-15. Furthermore, in the following schemes, where specific acids, bases, reagents, coupling reagents, solvents, etc. are mentioned, it is understood that other suitable acids, bases, reagents, coupling reagents, solvents etc. may be used and are included within the scope of the present invention. The modifications to reaction conditions, for example, temperature, duration of the reaction or combinations thereof, are envisioned as part of the present invention. The compounds obtained using the general reaction sequences may be of insufficient purity. These compounds can be purified using any of the methods for purification of organic compounds known to persons skilled in the art, for example, crystallization or silica gel or alumina column chromatography using different solvents in suitable ratios. All possible geometrical isomers and stereoisomers are envisioned within the scope of this invention.

General Schemes

A general approach for the preparation of compounds of the formulae (I(a-c)) (wherein $X^1$, $X^2$, $X^3$ are CH or N; $X^5$ is CH or N; $R^3$ is hydrogen, $C_{1-8}$alkyl, deuterated $C_{1-8}$alkyl, halo$C_{1-8}$alkyl or 3-15 membered heterocyclyl; $R^6$ is $C_{1-8}$alkyl, deuterated $C_{1-8}$alkyl or halo$C_{1-8}$alkyl; $R^7$ is hydrogen, oxo, deuterium or $C_{1-8}$alkyl and $R^1$ is as defined in the general description) is depicted in synthetic scheme 1.

Synthetic Scheme 1

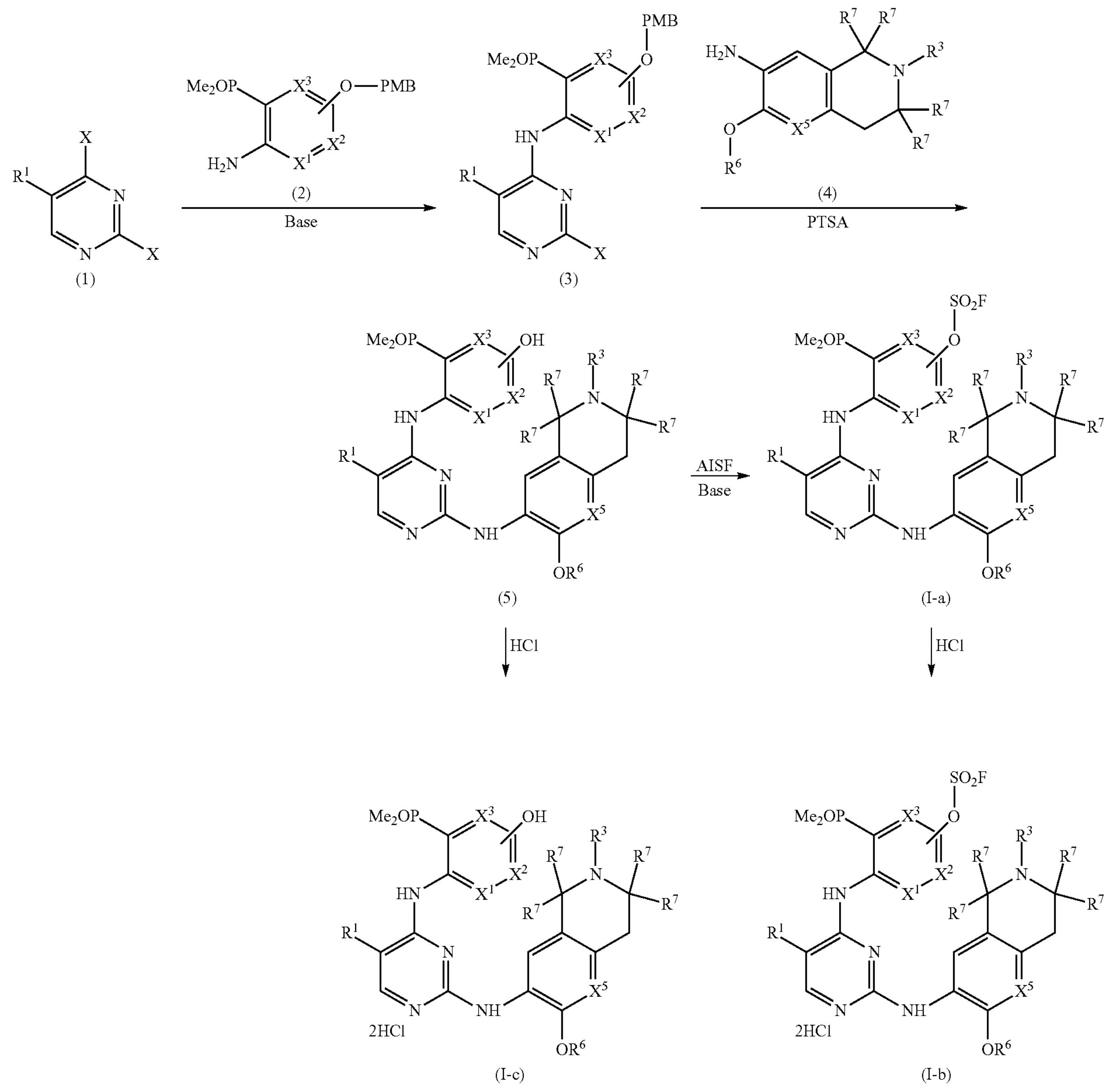

The substitution reaction of dihalo pyrimidine of formula (1) (wherein X is halogen) with amino phenyl phosphineoxide of formula (2) yields compound of formula (3) in presence of suitable base. The reaction may be carried out in the presence of suitable base such as diisopropyl ethyl amine and in presence of suitable solvent such as isopropyl alcohol. The compound of formula (3) is reacted with substituted isoquinoline of compound of formula (4) in presence of p-toluene sulphonic acid as catalyst and solvent such as isopropyl alcohol in sealed tube at high temperature to give the compound of formula (5). The compound of formula (5) reacted with AISF as fluorosulfating reagent in presence of base as DBU gives fluorosulphonated derivatives of formula (I-a). The compound of formula (I-a) is treated with inorganic acids such as hydrochloric acid to give the compound formula (I-b). Alternately, the compound of formula (5) is treated with inorganic acids such as hydrochloric acid to give compound formula (I-c).

A general approach for the preparation of compounds of the formulae (Id) (wherein $R^1$ is as defined in the general description) is depicted in synthetic scheme 2.

Synthetic Scheme 2

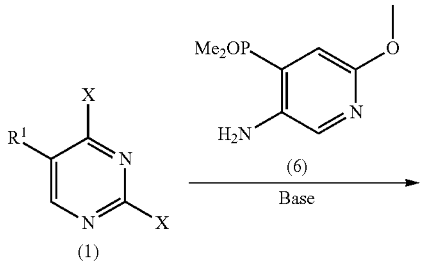

-continued

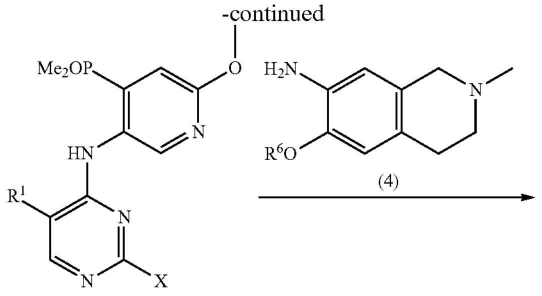

(7)

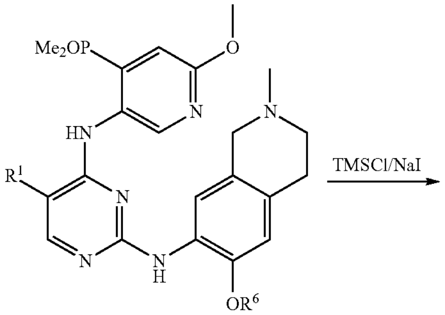

(8)

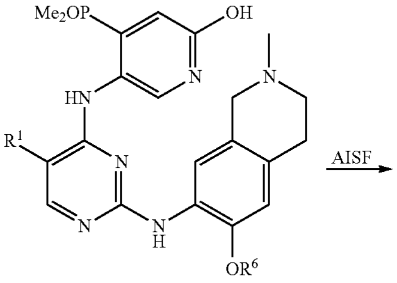

(9)

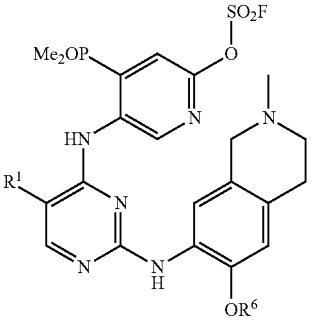

(I-d)

The substitution reaction of dihalo pyrimidine of formula (1) (wherein X is halogen) with amino phenyl phosphineoxide of formula (6) yields compound of formula (7) in the presence of suitable base. The reaction may be carried out in the presence of suitable base such as diisopropyl ethyl amine and in presence of suitable solvent such as isopropyl alcohol. The compound of formula (7) is reacted with substituted isoquinoline of compound of formula (4) (wherein $R^6$ is $C_{1-8}$alkyl, deuterated $C_{1-8}$alkyl or halo$C_{1-8}$alkyl) in presence of p-toluene sulphonic acid as catalyst and solvent such as isopropyl alcohol at high temperature to give compound of formula (8). Selective O-demethylation of compound of formula (8) in the presence of chlorotrimethylsilane and sodium iodide and suitable solvent such as acetonitrile yields the compound of formula (9). The compound of formula (9) is reacted with AISF as fluorosulfating reagent in presence of base as DBU yields the compound of formula (I-d).

A general approach for the preparation of compounds of the formulae (I-e) (wherein $R^6$ is $C_{1-8}$alkyl, deuterated $C_{1-8}$alkyl or halo$C_{1-8}$alkyl; $R^7$ is hydrogen, oxo, deuterium or $C_{1-8}$alkyl and $R^1$ is as defined in the general description) is depicted in synthetic scheme 3.

Synthetic Scheme 3

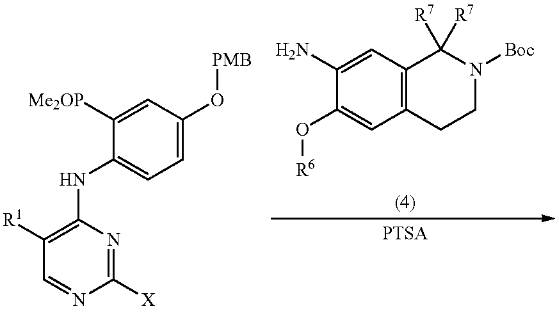

(3)

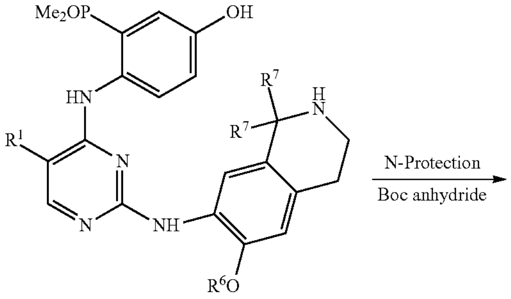

(10)

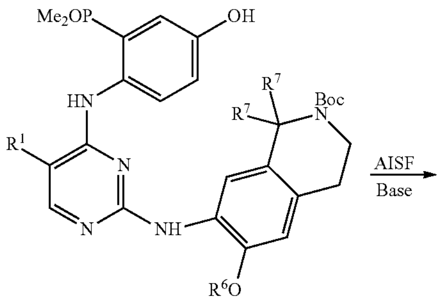

(11)

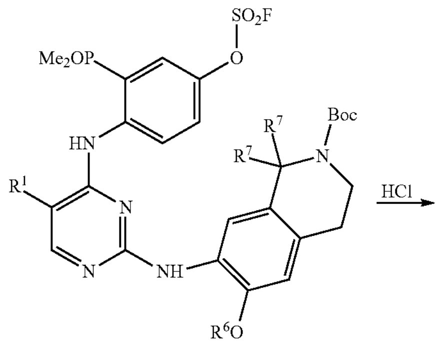

(12)

-continued

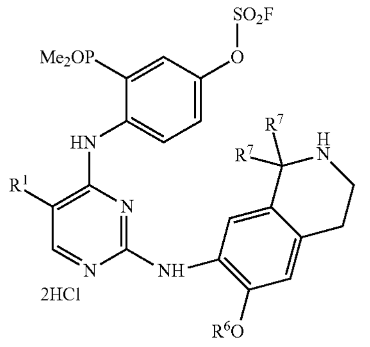

(I-e)

The substitution reaction of halo pyrimidine of formula (3) (wherein X is halogen) with substituted isoquinoline of compound of formula (4) in presence of p-toluene sulphonic acid as catalyst and suitable solvent such as isopropyl alcohol at high temperature gives compound of formula (11). The amine protection of compound of formula (10) is carried out by treating with Di-tert-butyl dicarbonate in presence of suitable base and solvent yields compound of formula (11). The reaction may be carried out in the presence of suitable base such as sodium hydroxide or potassium hydroxide and in the presence of suitable solvent such as methanol, ethanol, isopropyl alcohol. The compound of formula (12) is reacted with AISF as fluorosulfating reagent in presence of base as DBU to give fluorosulfated derivatives of formula (12). The compound of formula (12) is treated with inorganic acids such as hydrochloric acid to give the compound formula (I-e).

A general approach for the preparation of compounds of the formulae (I-f) (wherein $R^1$ is as defined in the general description) is depicted in synthetic scheme 4.

Synthetic Scheme 4

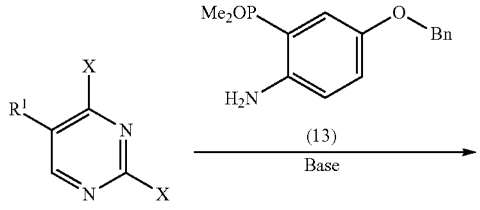

(1) (13)

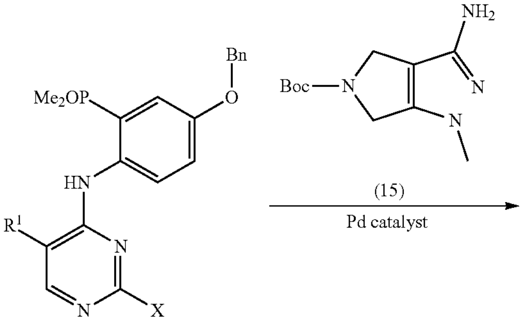

(14) (15)

-continued

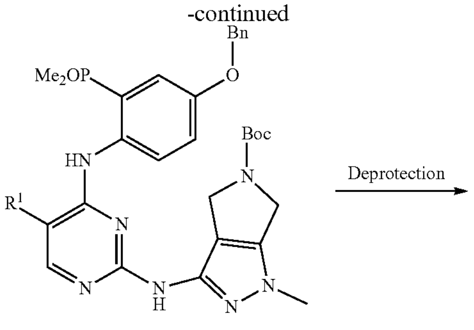

(16)

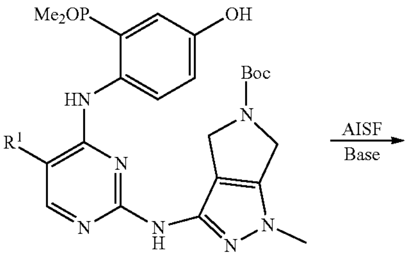

(17)

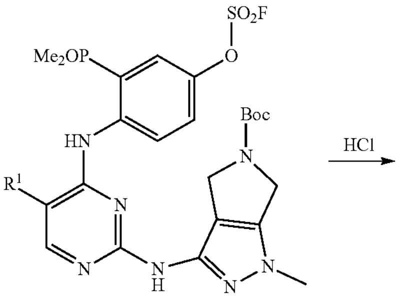

(18)

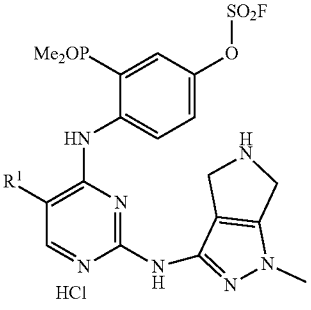

(I-f)

The substitution reaction of dihalo pyrimidine of formula (1) (wherein X is halogen) with amino phenyl phosphine oxide of formula (13) yields compound of formula (14) in presence of suitable base. The coupling reaction may be carried out in the presence of suitable base such as diisopropyl ethyl amine and in presence of suitable solvent such as isopropyl alcohol. The compound of formula (14) upon coupling with suitable substituted amino pyrrolo pyrazole boc protected compound of formula (15) in the presence of suitable diphosphine ligands, base, catalyst and solvent yields the compound of formula (16). The suitable base used in the reaction may be potassium acetate, sodium or potassium tert-butoxide, sodium carbonate, cesium carbonate, etc. and suitable diphosphine ligands such as Xantphos. The suitable palladium catalyst used in the reaction may be palladium acetate. The coupling reaction may be carried out in a suitable polar solvent or mixture thereof. The suitable solvent may be selected from 1,4-dioxane, DMSO, water or a combination thereof. Debenzylation of compound of formula (16) is carried out using 10% palladium on carbon to give compound of formula (17).

The compound of formula (17) is reacted with AISF as fluorosulfating reagent in presence of base as DBU to give boc protected fluorosulphonated derivatives of formula (18) which on deprotection with HCl dioxane gives compound of formula (I-f).

A general approach for the preparation of compounds of the formulae (Ig) (wherein $R^6$ is $C_{1-8}$alkyl, deuterated $C_{1-8}$alkyl or halo$C_{1-8}$alkyl; $R^7$ is hydrogen, oxo, deuterium or $C_{1-8}$alkyl and $R^1$ is as defined in the general description) is depicted in synthetic scheme 5.

Synthetic Scheme 5

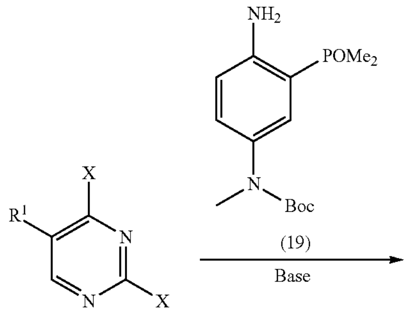

(1) (19)

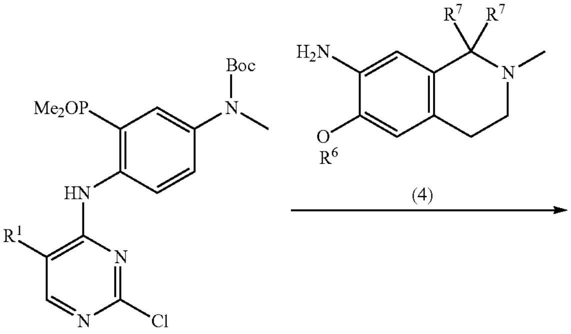

(4)

(20)

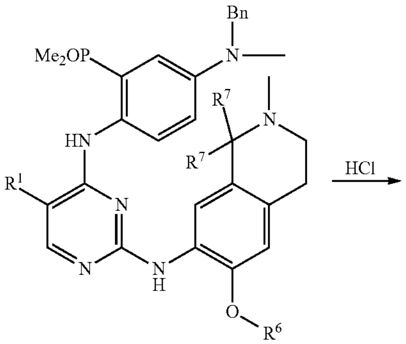

(21)

-continued

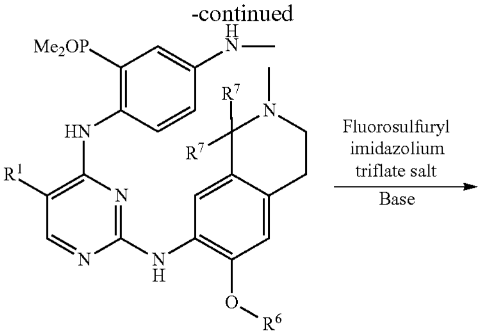

(22)

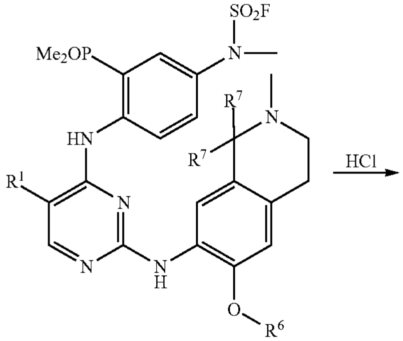

(23)

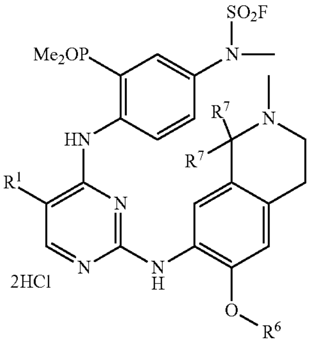

(I-g)

The substitution reaction of dihalo pyrimidine of formula (1) (wherein X is halogen) with amino phenyl phosphineoxide of formula (19) yields compound of formula (20) in presence of suitable base. The reaction may be carried out in the presence of suitable base such as diisopropyl ethyl amine and in presence of suitable solvent such as isopropyl alcohol. The compound of formula (20) upon coupling with suitable substituted isoquinoline protected compound of formula (4) in the presence of suitable diphosphine ligands, base, catalyst and solvent yields the compound of formula (21). The suitable base used in the reaction may be potassium acetate, sodium or potassium tert-butoxide, sodium carbonate, cesium carbonate, etc. and suitable diphosphine ligands such as Xantphos. The suitable palladium catalyst used in the reaction may be Tris(dibenzylideneacetone) dipalladium(0), Palladium acetate. The substitution reaction may be carried out in a suitable polar solvent or mixture thereof. The suitable solvent may be selected from 1,4-dioxane, DMSO, water or a combination thereof. The compound of formula (21) was treated with inorganic acids such as hydrochloric acid gives de-protected compound of formula (22). The compound of formula (22) is reacted with 1-(Fluorosulfonyl)-2,3-dimethyl-1H-imidazol-3-ium trifluoromethanesulfonate in presence of base as triethylamine and solvent such as dichloromethane to yield compound of formula (23). The compound of formula (23) is treated with inorganic acids such as hydrochloric acid gives compound formula (I-g).

A general approach for the preparation of compounds of the formulae (I-h) (wherein $R^4$ is hydrogen, halo$C_{1-8}$alkyl, $C_{1-8}$alkyl$C_{1-8}$alkoxy or 3-15 membered heterocyclyl; $R^6$ is $C_{1-8}$alkyl, deuterated $C_{1-8}$alkyl or halo$C_{1-8}$alkyl and $R^1$ is as defined in the general description) is depicted in synthetic scheme 6.

Synthetic Scheme 6

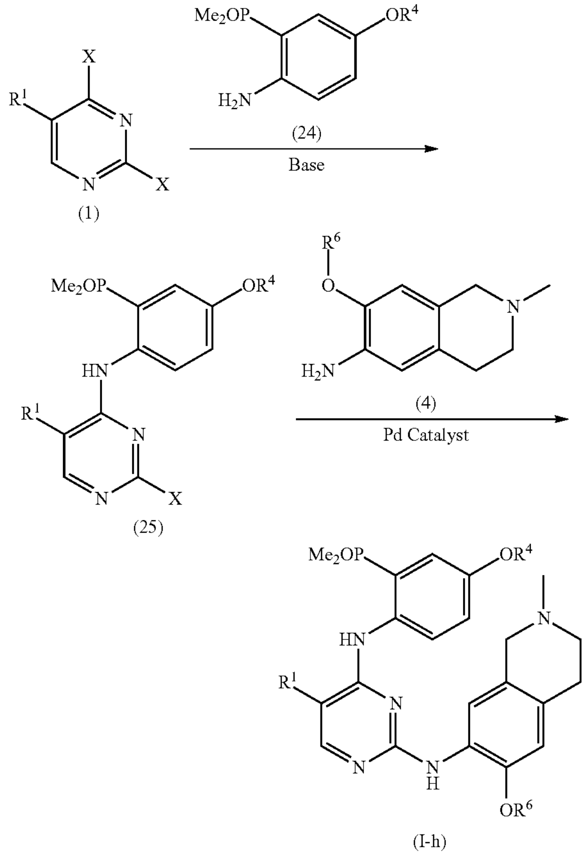

The substitution reaction of dihalo pyrimidine of formula (1) (wherein X is halogen) with amino phenyl phosphine oxide of formula (24) yields compound of formula (25) in presence of suitable base. The coupling may be carried out in the presence of suitable base such as diisopropyl ethyl amine and in presence of suitable solvent such as isopropyl alcohol thereof. The compound of formula (25) which on coupling with suitable substituted isoquinoline amine of compound of formula (4) in the presence of suitable diphosphine ligands, base, catalyst and solvent yields the compound of formula (I-h). The suitable base used in the reaction may be potassium acetate, sodium or potassium tert-butoxide, sodium carbonate, cesium carbonate, etc. and suitable diphosphine ligands such as Xantphos. The suitable palladium catalyst used in the reaction may be palladium triacetate. The coupling reaction may be carried out in a suitable polar solvent or mixture thereof. The suitable solvent may be selected from 1,4-dioxane, DMSO, water or a combination thereof.

A general approach for the preparation of compounds of the formulae (I-i) (wherein $R^4$ is hydrogen, halo$C_{1-8}$alkyl, $C_{1-8}$alkyl$C_{1-8}$alkoxy or 3-15 membered heterocyclyl; $R^6$ is $C_{1-8}$alkyl, deuterated $C_{1-8}$alkyl or halo$C_{1-8}$alkyl and $R^1$ is as defined in the general description) is depicted in synthetic scheme 7.

Synthetic Scheme 7

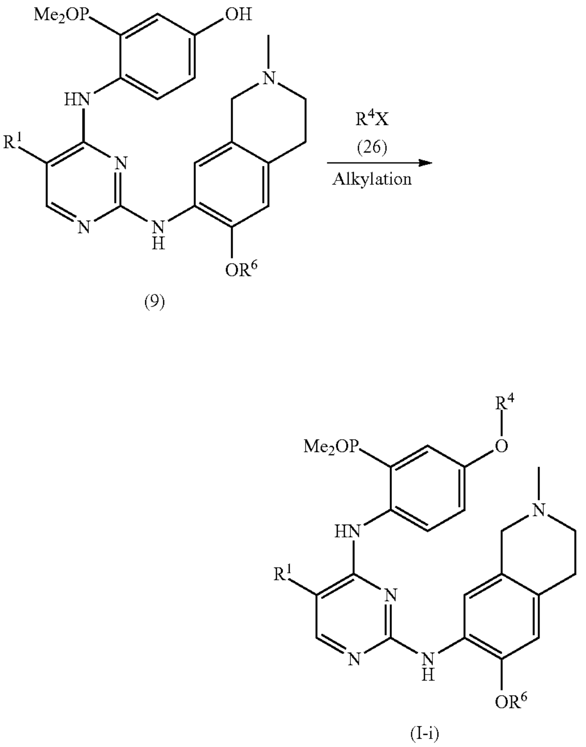

O-alkylation of compound of formula (9) with suitable alkylating reagent of compound of formula (26) in presence of base such as sodium or potassium tert-butoxide, sodium carbonate, potassium carbonate, sodium hydride, cesium carbonate in solvent such as DMF yields compound of formula (I-i).

A general approach for the preparation of compounds of the formulae (I-j) (wherein $R^6$ is $C_{1-8}$alkyl, deuterated $C_{1-8}$alkyl or halo$C_{1-8}$alkyl; $R^x$ is $C_{1-8}$alkyl; $R^y$ is halo$C_{1-8}$ alkyl and $R^1$ is as defined in the general description) is depicted in synthetic scheme 8.

Synthetic Scheme 8

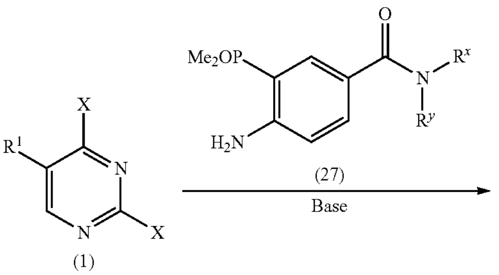

-continued

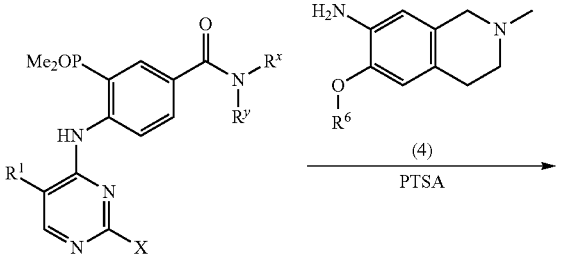

(28)

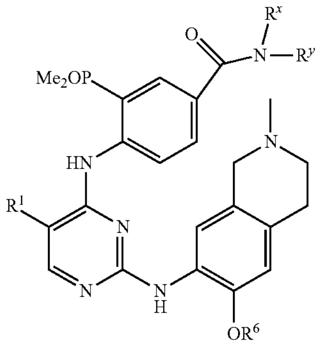

(I-j)

The substitution reaction of dihalo pyrimidine of formula (1) (wherein X is halogen) with amino phenyl phosphine oxide of formula (27) yields compound of formula (28) in presence of suitable base. The coupling reaction may be carried out in the presence of suitable base such as sodium hydride (60%), diisopropyl ethyl amine and in presence of suitable solvent such as dimethyl formamide, isopropyl alcohol. The compound of formula (28) coupled with substituted isoquinoline of compound of formula (4) (wherein $R^6$ is —$CH_3$, —$CD_3$ or —$CHF_2$) in presence of p-toluene sulphonic acid as catalyst and solvent such as isopropyl alcohol in sealed tube at high temperature gives compound of formula (I-j).

A general approach for the preparation of compounds of the formulae (I-k) (wherein $R^6$ is $C_{1-8}$alkyl, deuterated $C_{1-8}$alkyl or halo$C_{1-8}$alkyl; $R^x$ is $C_{1-8}$alkyl; $R^y$ is halo$C_{1-8}$ alkyl and $R^1$ is as defined in the general description) is depicted in synthetic scheme 9.

Synthetic Scheme 9

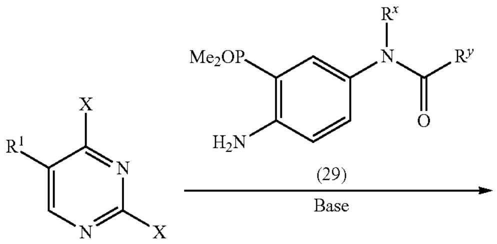

(1)

-continued

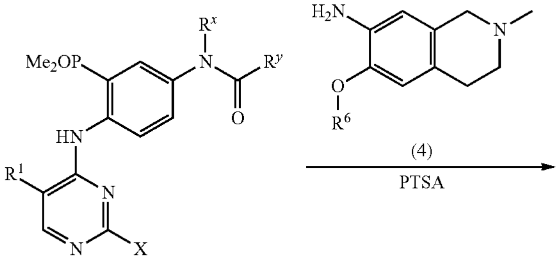

(30)

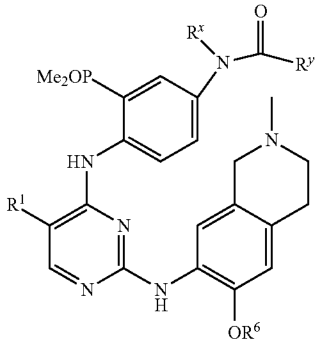

(I-k)

The substitution reaction of dihalo pyrimidine of formula (1) (wherein X is halogen) with amino phenyl phosphine oxide of formula (29) yields compound of formula (30) in presence of suitable base and catalyst. The coupling reaction may be carried out in the presence of suitable base such as diisopropylethylamine and in the presence of suitable solvent such as dimethyl formamide, isopropyl alcohol. The compound of formula (30) coupled with substituted isoquinoline of compound of formula (4) in presence of p-toluene sulphonic acid as catalyst and solvent such as isopropyl alcohol in sealed tube at high temperature to give the compound of formula (I-k).

A general approach for the preparation of compounds of the formulae (I-1) (wherein $R^6$ is $C_{1-8}$alkyl, deuterated $C_{1-8}$alkyl or halo$C_{1-8}$alkyl and R is as defined in the general description) is depicted in synthetic scheme 10.

Synthetic Scheme 10

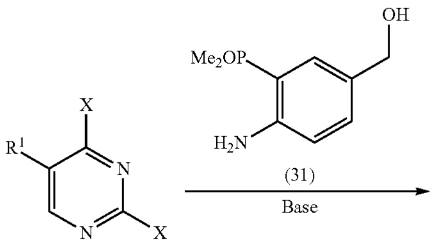

(1)

-continued

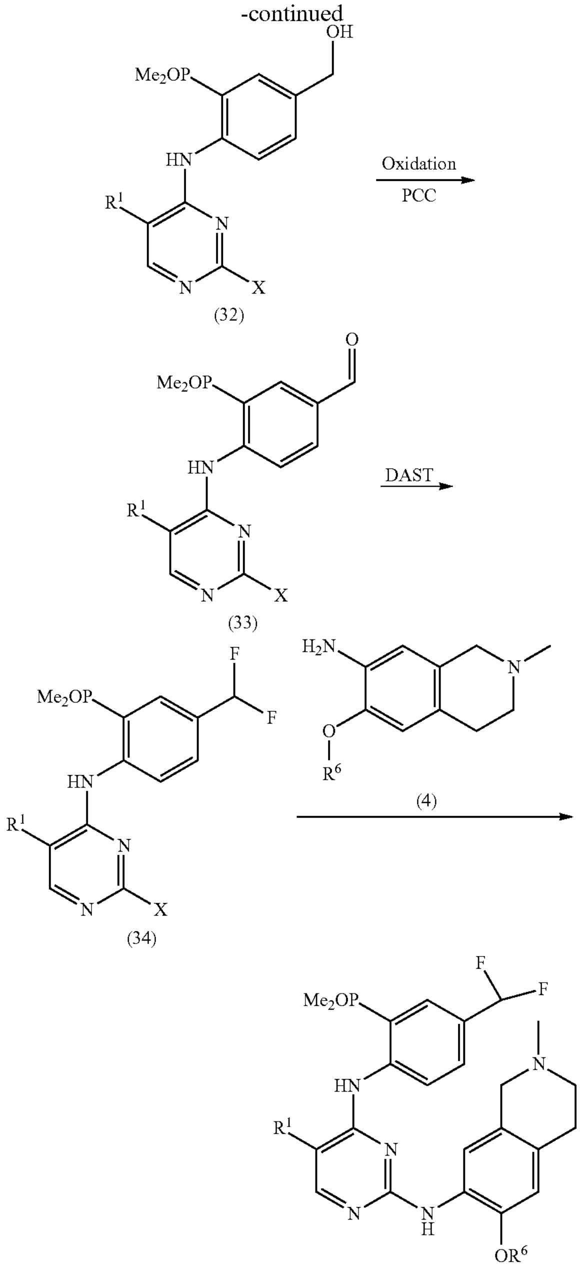

(32)
(33)
(34)
(4)
(I-l)

The substitution reaction of dihalo pyrimidine of formula (1) (wherein X is halogen) with amino phenyl phosphineoxide of formula (31) yields compound of formula (32) in presence of suitable base. The coupling reaction may be carried out in the presence of suitable base such as sodium hydride (60%), diisopropyl ethyl amine and in presence of suitable solvent such as dimethyl formamide, isopropyl alcohol. The oxidation of the compound of formula (32) using PCC as oxidizing agents and solvent such as dichloromethane, ethylene dichloride yields the aldehyde compound of formula (33). The fluorination of compound of formula (33) with DAST as a fluorinating agent in a suitable solvent such as dichloromethane yields the compound of formula (34). The compound of formula (34) upon coupling with suitable substituted isoquinoline protected compound of formula (4) in the presence of suitable diphosphine ligands, base, catalyst and solvent yields the compound of formula (I-1). The suitable base used in the reaction may be potassium acetate, sodium or potassium tert-butoxide, sodium carbonate, cesium carbonate, etc. and suitable diphosphine ligands such as Xantphos. The suitable palladium catalyst used in the reaction may be Tris(dibenzylideneacetone)dipalladium(0), Palladium acetate.

A general approach for the preparation of compounds of the formulae (I-m) (wherein $R^6$ is $C_{1-8}$alkyl, deuterated $C_{1-8}$alkyl or halo$C_{1-8}$alkyl and $R^1$ is as defined in the general description) is depicted in synthetic scheme 11.

Synthetic Scheme 11

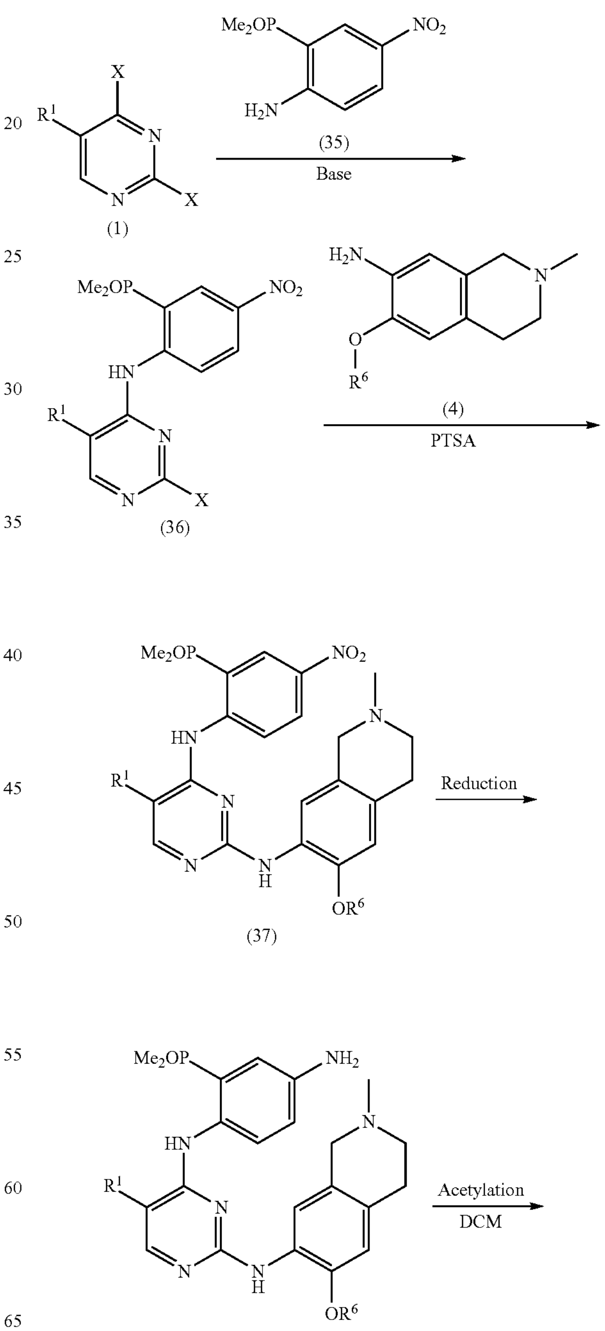

(1)
(35)
(36)
(4)
(37)
(38)

-continued

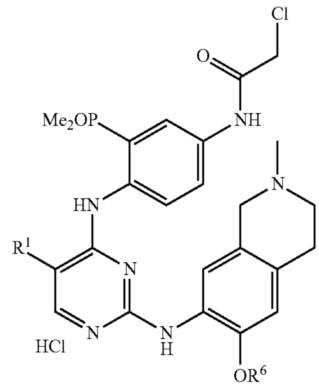

(I-m)

The substitution reaction of dihalo pyrimidine of formula (1) (wherein X is halogen) with amino phenyl phosphineoxide of formula (35) yields compound of formula (36) in presence of suitable base. The coupling reaction may be carried out in the presence of suitable base such as cesium carbonate, sodium carbonate, sodium hydride, diisopropyl ethyl amine and in presence of suitable solvent such as dimethyl formamide, isopropyl alcohol. The compound of formula (36) coupled with substituted isoquinoline of the compound of formula (4) in presence p-toluene sulphonic acid as catalyst and solvent such as isopropyl alcohol in sealed tube at high temperature gives compound of formula (37) which further on nitro reduction followed by N-acylation gives compound of formula (I-m).

A general approach for the preparation of compounds of the formulae (I-n) (wherein $R^6$ is $C_{1-8}$alkyl, deuterated $C_{1-8}$alkyl or halo$C_{1-8}$alkyl and $R^1$ is as defined in the general description) is depicted in synthetic scheme 12

Synthetic Scheme 12

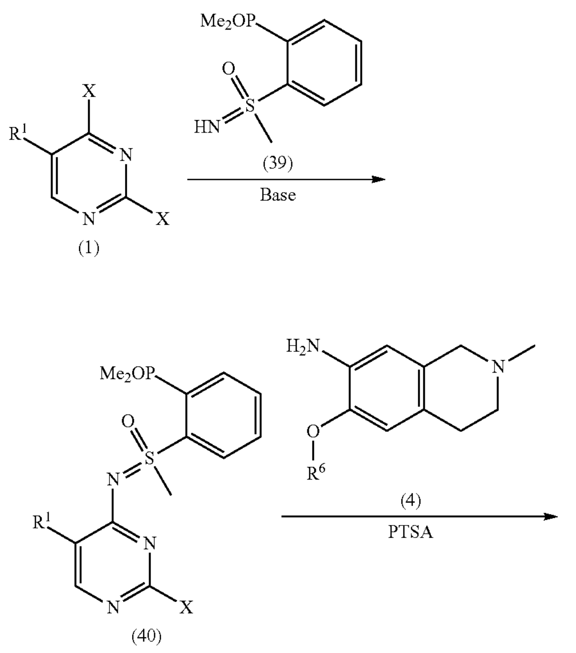

-continued

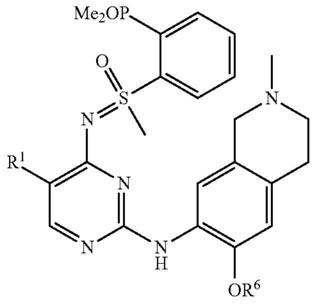

(I-n)

The substitution reaction of dihalo pyrimidine of formula (1) (wherein X is halogen) with sulfoximine compound of formula (39) yields compound of formula (40) in presence of suitable base. The coupling reaction may be carried out in the presence of suitable base such as sodium hydride (60%), cesium carbonate, sodium carbonate, using suitable solvent such as dimethyl formamide, THF. The compound of formula (40) coupled with substituted isoquinoline of compound of formula (4) in presence p-toluene sulphonic acid as catalyst and solvent such as isopropyl alcohol in sealed tube at high temperature gives compound of formula (I-n).

A general approach for the preparation of compounds of the formulae (I-o) (wherein $R^6$ is $C_{1-8}$alkyl, deuterated $C_{1-8}$alkyl or halo$C_{1-8}$alkyl and $R^1$ is as defined in the general description) is depicted in synthetic scheme 13.

Synthetic Scheme 13

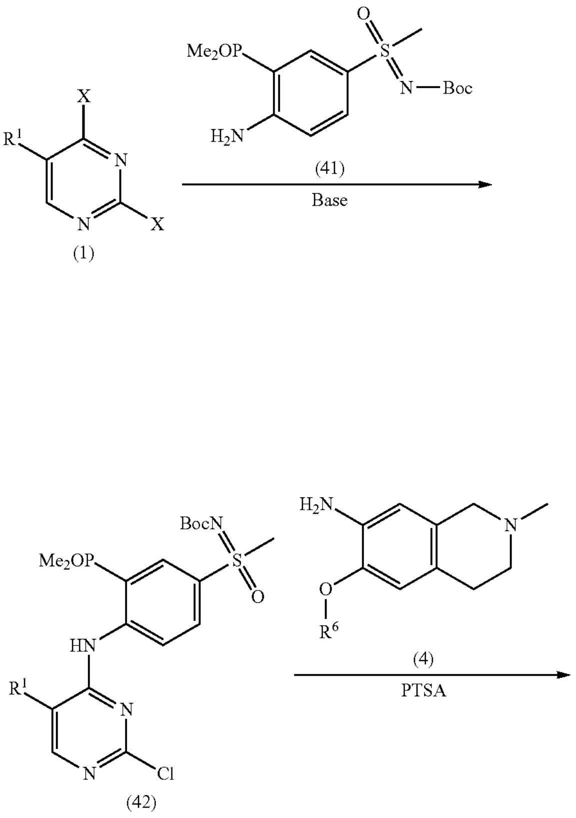

-continued

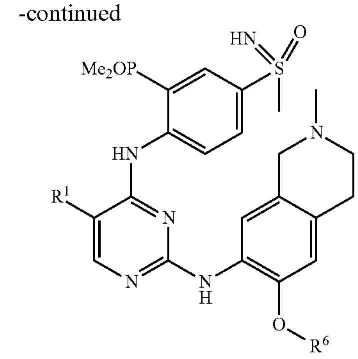

(I-o)

The substitution reaction of dihalo pyrimidine of formula (1) (wherein X is halogen) with compound of formula (41) yields compound of formula (42) in presence of suitable base. The coupling reaction may be carried out in the presence of suitable base such as sodium hydride (60%), cesium carbonate, sodium carbonate, diisopropyl ethyl amine and in presence of suitable solvent such as dimethyl formamide, tetrahydrofuran thereof. The compound of formula (42) coupled with substituted isoquinoline of compound of formula (4) in presence p-toluene sulphonic acid as catalyst and solvent such as isopropyl alcohol in sealed tube at high temperature to give compound of formula (I-o).

A general approach for the preparation of compounds of the formulae (I-p) (wherein $R^6$ is $C_{1-8}$alkyl, deuterated $C_{1-8}$alkyl or halo$C_{1-8}$alkyl and $R^1$ is as defined in the general description) is depicted in synthetic scheme 14.

Synthetic Scheme 14

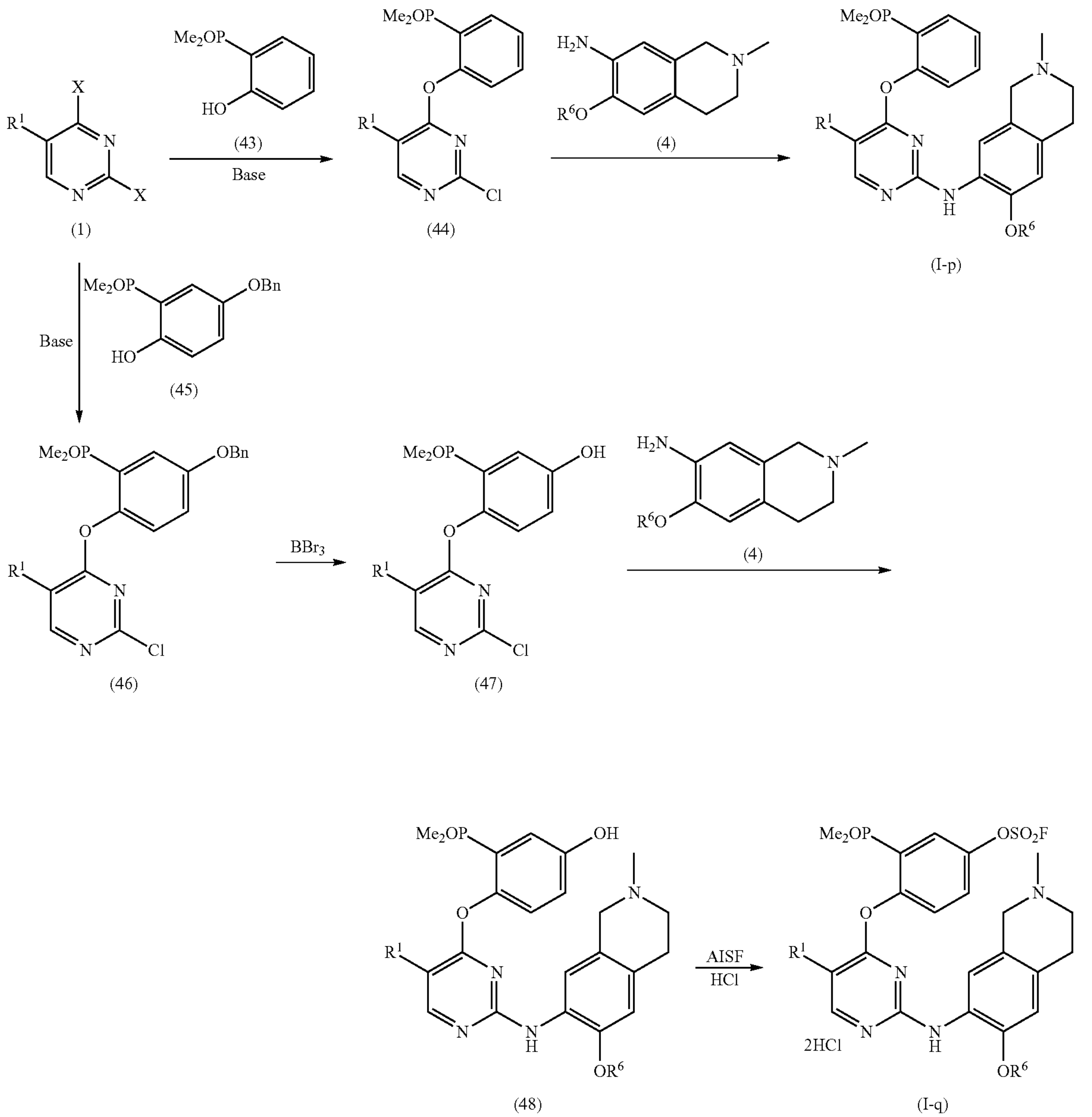

The substitution reaction of dihalo pyrimidine of formula (1) (wherein X is halogen) with compound of formula (43) yields compound of formula (44) in presence of suitable base. The coupling reaction may be carried out in the presence of suitable base such as sodium hydride (60%), cesium carbonate, sodium carbonate and using suitable solvent such as dimethyl formamide, tethydrofuran. The compound of formula (44) coupled with substituted isoquinoline of compound of formula (4) in presence p-toluene sulphonic acid as catalyst and solvent such as isopropyl alcohol at high temperature to give compound of formula (I-p).

The substitution reaction of dihalo pyrimidine of formula (1) with compound of formula (45) yields compound of formula (46) in presence of suitable base. The coupling reaction may be carried out in the presence of suitable base such as sodium hydride (60%), cesium carbonate, sodium carbonate and using suitable solvent such as dimethyl formamide, tethydrofuran. Debenzylation of the compound of formula (46) using $BBr_3$ yields the compound phenol compound of formula (47). The compound of formula (47) upon coupling with suitable substituted isoquinoline protected compound of formula (4) in the presence of suitable diphosphine ligands, base, catalyst and solvent yields the compound of formula (48). The suitable base used in the reaction may be potassium acetate, sodium or potassium tert-butoxide, sodium carbonate, cesium carbonate, etc. and suitable diphosphine ligands such as Xantphos.

The suitable palladium catalyst used in the reaction may be Tris(dibenzylideneacetone)dipalladium(0), Palladium acetate. Compound of formula (48) reacted with AISF as fluorosulfating reagent in presence of base as DBU gives fluorosulfate compound which upon treatment with inorganic acids such as hydrochloric acid to give the compound formula (I-q).

A general approach for the preparation of compounds of the formulae (I-r) (wherein $R^3$ is hydrogen, $C_{1-8}$alkyl, deuterated $C_{1-8}$alkyl, halo$C_{1-8}$alkyl or 3-15 membered heterocyclyl and $R^1$ is as defined in the general description) is depicted in synthetic scheme 15.

Synthetic Scheme 15

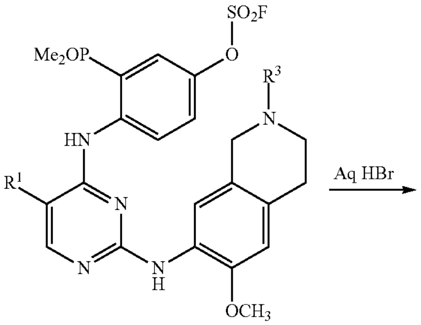

(49)

-continued

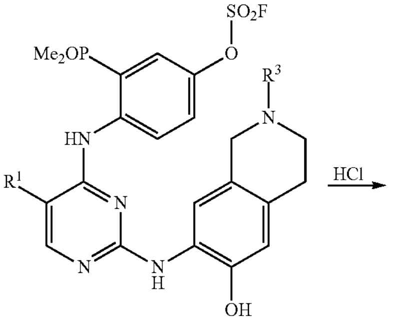

(50)

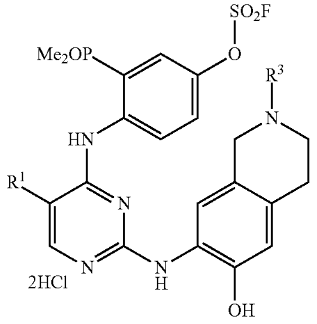

(I-r)

The demethylation reaction of compound of formula (49) in the presence of hydrobromic acid at high temperature yields compound of formula (50). The compound of formula (50) was treated with inorganic acids such as hydrochloric acid gives the compound of formula (I-r).

INTERMEDIATES

Intermediate A1

(2-Amino-5-((4-methoxybenzyl)oxy)phenyl)dimethylphosphine oxide

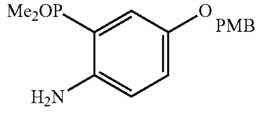

Step 1: 3-Iodo-4-nitro phenol

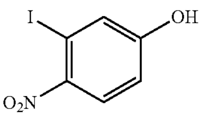

To a stirred solution of 3-iodophenol (40.0 g, 180 mmol) in glacial acetic acid (200 ml), a solution of fuming $HNO_3$ (8.4 ml, 100 mmol) in acetic acid (60 ml) was added at −10° C. in 30 min. The reaction mixture was stirred at RT for 30 min. The reaction mixture was quenched in ice cold water and extracted with ethyl acetate. The organic layers were separated, dried over anhydrous sodium sulfate and concentrated under vacuum. The crude material was purified on silica gel column and obtained solid was stirred in DCM for 1 h and filtered. The solid obtained was dried under vacuum to yield 14 g of the desired product. $^1$H NMR (400 MHz, DMSO-$d_6$) δ 6.94 (d, J=9.2 Hz 1H), 7.46 (s, 1H), 7.95 (d, J=8.8 Hz 1H), 11.07, (br s, 1H); ESI-MS (m/z)=265.2 $(M+H)^+$.

Step 2:
2-Iodo-4-((4-methoxybenzyl)oxy)-1-nitrobenzene

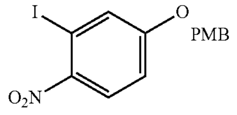

To a stirred suspension of 3-iodo-4-nitro phenol (step 1 Intermediate) (15 g, 56.60 mmol) and potassium carbonate (8.60 g, 62.26 mmol) in acetonitrile (500 ml), 4-methoxy benzyl chloride (9.75 g, 62.26 mmol) was added at RT. The reaction mixture was refluxed for overnight. The reaction mixture was diluted with water, extracted with ethyl acetate three times. The organic layers were separated, dried over anhydrous sodium sulphate and concentrated under reduced pressure. The residue thus obtained was purified by silica gel column chromatography to yield 12 g of the desired product. $^1$H NMR (400 MHz, DMSO-$d_6$) δ 3.76 (s, 3H), 5.15 (s, 2H), 6.95 (d, J=8.8 Hz, 2H), 7.20 (d, J=9.2 Hz, 1H), 7.38 (d, J=8.8 Hz, 2H), 7.70 (s, 1H), 8.01 (d, J=9.2 Hz, 1H); ESI-MS (m/z) 383 $(M-H)^+$.

Step 3: 2-Iodo-4-((4-methoxybenzyl)oxy)aniline

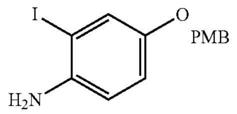

To a stirred suspension of 2-iodo-4-((4-methoxybenzyl)oxy)-1-nitrobenzene (12 g, 31.1 mmol) and iron powder (5.5 g, 95.5 mmol) in isopropyl alcohol (200 ml) were added ammonium chloride (16.7 g, 31.16 mmol) and water (20 ml) at RT. The reaction mixture was refluxed for 3 h. The reaction mixture was diluted with ethyl acetate, filtered through celite bed and the filtrate was extracted with ethyl acetate three times. The organic volume was dried over anhydrous sodium sulphate and concentrated under reduced pressure. The residue thus obtained was purified by silica gel column chromatography to yield 10 g of the desired product. $^1$H NMR (400 MHz, DMSO-$d_6$) δ 3.75 (s, 3H), 4.75 (s, 2H), 4.87 (s, 2H), 6.69 (d, J=8.8 Hz, 1H), 6.81 (d, J=8.8 Hz, 1H), 6.92 (d, J=6.8 Hz, 2H), 7.21 (s, 1H), 7.31 (d, J=8.4 Hz, 2H); ESI-MS (m/z) 355.9 $(M+H)^+$.

Step 4: (2-Amino-5-((4-methoxybenzyl)oxy)phenyl) dimethylphosphine oxide

To a degassed solution of 2-iodo-4-((4-methoxybenzyl)oxy)aniline (step 3 Intermediate) (10 g, 28.16 mmol) and dimethylphosphine oxide (3.3 g, 42.25 mmol) in DMF (60 ml) were added $K_3PO_4$ (9 g, 42.25 mmol), xantphos (0.814 g, 1.40 mmol) and $[Pd(OAc)_2]_3$ (1.9 g, 2.8 mmol) at RT. The reaction mixture was stirred at 115° C. for 3 h. The reaction mixture was diluted with ethyl acetate, filtered through celite bed and washed with ethyl acetate. The combined filtrate was washed with brine. The organic volume was dried over anhydrous sodium sulphate and concentrated under reduced pressure. The residue thus obtained was purified by silica gel column chromatography to yield 10 g of the desired product. $^1$H NMR (400 MHz, DMSO-$d_6$) δ 1.66 (d, J=13.2 Hz, 6H), 3.75 (s, 3H), 4.89 (s, 2H), 5.73 (s, 2H), 6.52-6.62 (m, 1H), 6.81-6.94 (m, 4H), 7.33 (d, J=8.4 Hz, 2H); ESI-MS (m/z) 306 $(M+H)^+$.

The analytical data of the intermediates prepared by following the procedure described above are given in below Table 1.

TABLE 1

Structure, chemical name and analytical data of Intermediates A2 to A6.

| Intermediate No. | Structure | Name and Analytical data |
|---|---|---|
| Intermediate A2 | 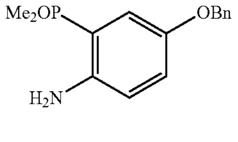 | (2-Amino-5-(benzyloxy)phenyl) dimethylphosphine oxide; $^1$H NMR (400 MHz, $CDCl_3$) δ (400 MHz, DMSO-$d_6$) δ 1.66 (d, J = 13.2 Hz, 6H), 4.98 (s, 2H), 5.77 (br s, 2H), 6.62 (d, J = 3.2 Hz, 1H), 6.84 (s, 1H), 6.94 (d, J = 2.8 Hz, 1H), 7.29-7.35 (m, 5H). |
| Intermediate A3 | 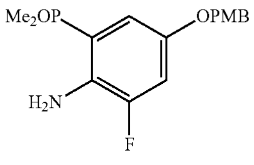 | (2-Amino-3-fluoro-5-((4-methoxybenzyl)oxy)phenyl)dimethyl phosphine oxide: $^1$H NMR (400 MHz, DMSO-$d_6$) δ1.70 (d, J = 13.6 Hz, 6H), 3.75 (s, 3H), 4.92 (s, 2H), 5.69 (brs, 2H), 6.73 (dd, J = 1.6 Hz, 14.4 Hz, 1H), 6.94 (d, J = 8.8 Hz, 2H), 7.00 (dd, J = 2.8 Hz, 12.8 Hz, 1H), 7.36 (d, J = 8.8 Hz, 2H); ESI-MS (m/z) 324.10 $[M + H]^+$ |

TABLE 1-continued

Structure, chemical name and analytical data of Intermediates A2 to A6.

| Intermediate No. | Structure | Name and Analytical data |
| --- | --- | --- |
| Intermediate A4 | 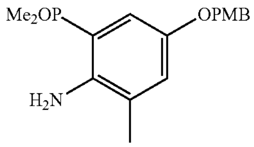 | (2-Amino-5-((4-methoxybenzyl)oxy)-3-methylphenyl)dimethyl phosphine oxide: $^{1}$H NMR (400 MHz, CDCl) δ 1.74 (d, J = 12.8 Hz, 6H), 2.16 (s, 3H), 3.83 (s, 3H), 4.90 (s, 2H), 5.15 (br s, 2H), 6.85-6.95 (m, 3H), 7.30-7.35 (m, 3H); ESI-MS (m/z) 320.10 [M + H]$^+$ |
| Intermediate A5 | 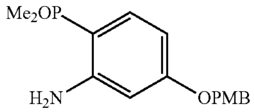 | (2-Amino-4-((4-methoxybenzyl) oxy)phenyl)dimethylphosphine oxide: $^{1}$H NMR (400 MHz, DMSO-d$_6$) δ 1.60 (d, J = Hz, 6H), 3.76 (s, 3H), 4.95 (s, 2H), 6.17 (br s, 2H), 6.20-6.30 (m, 2H), 6.94 (d, J = 8.8 Hz, 2H), 7.03-7.15 (m, 1H), 7.35 (d, J = 8.8 Hz, 2H); ESI-MS (m/z) 306.1 [M + H]$^+$ |
| Intermediate A6 | 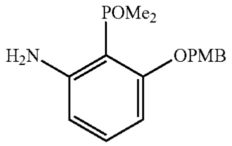 | (2-Amino-6-((4-methoxybenzyl) oxy)phenyl)dimethylphosphine oxide; $^{1}$H NMR (400 MHz, DMSO-d$_6$) δ 1.53 (d, J = 13.8 Hz, 6H), 3.72 (s, 3H), 4.92 (s, 2H), 5.77 (brs, 2H), 6.18-6.25 (m, 2H), 6.92 (d, J = 8.6 Hz, 2H), 7.06-7.10 (m, 1H), 7.35 (d, J = 8.6 Hz, 2H); ESI-MS (m/z) 306.21 [M + H]$^+$ |

Intermediate A7

(2-Amino-5-((4-methoxybenzyl)oxy)pyridine-3-yl) dimethylphosphineoxide

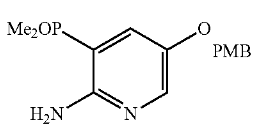

Step 1: 3,5-Dibromo-2-(2,5-dimethyl-1H-pyrrol-1-yl)pyridine

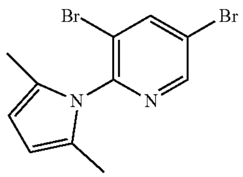

To a stirred solution of 2-amino-3,5-dibromo pyridine (3 g, 11.90 mmol) in toluene (50 mL) acetonyl acetone (1.62 g, 14.28 mmol), p-toluene sulphonic acid monohydrate (45 mg, 0.238 mg) were heated to reflux for 6 h in a dean stark apparatus. The reaction mixture was diluted with ethyl acetate and washed with aqueous sodium bicarbonate solution. The organic layer was separated and dried over anhydrous sodium sulphate. The solvent was removed under reduced pressure and the residue obtained was purified by silica gel column chromatography to yield 3.6 g of the desired product. $^{1}$H NMR (400 MHz, DMSO-d$_6$) δ 1.90 (s, 6H), 5.81 (s, 2H), 8.76 (d, J=2.4 Hz, 1H), 8.80 (d, J=2.0 Hz, 1H); ESI-MS (m/z) 328.9 (M+H)$^+$.

Step 2: 5-(Benzyloxy)-3-bromo-2-(2,5-dimethyl-1H-pyrrol-1-yl)pyridine

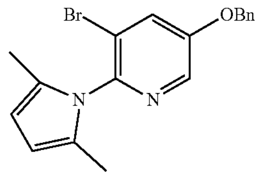 [SMILES: Cc1ccc(C)n1-c1ncc(OCc2ccccc2)cc1Br]

To a stirred solution of benzyl alcohol (1.87 g, 17.37 mmol) in DMF (25 mL) at 0° C. was added 60% sodium hydride (695 mg, 17.37 mmol) and stirred at RT for 1 h. The reaction mixture was cooled to 0° C. and added 3,5-dibromo-2-(2,5-dimethyl-1H-pyrrol-1-yl)pyridine (4.41 g, 13.36 mmol). The reaction mixture was stirred for 30 min and heated to 80-90° C. for 16 h. The reaction mixture was quenched with aqueous ammonium chloride, diluted with water and extracted thrice with DCM. The organic layers were separated, dried over anhydrous sodium sulphate and concentrated under reduced pressure. The residue thus obtained was purified by silica gel column chromatography to yield 2.6 g of the desired product. $^{1}$H NMR (400 MHz, DMSO-d$_6$) δ 1.88 (s, 6H), 5.28 (s, 2H), 5.78 (s, 2H), 7.37-7.52 (m, 5H), 8.08 (d, J=2.8 Hz, 1H), 8.41 (d, J=2.8 Hz, 1H); ESI-MS (m/z) 357.1 (M+H)$^+$

Step 3: 5-(Benzyloxy)-3-bromopyridine-2-amine

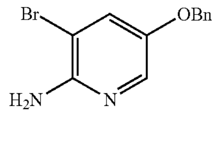

To a stirred suspension of 5-(benzyloxy)-3-bromo-2-(2,5-dimethyl-1H-pyrrol-1-yl)pyridine (2.6 g, 7.28 mmol) and hydroxylamine hydrochloride (10.12 g, 145 mmol) in isopropyl alcohol (50 mL) was added triethyl amine (1.83 g, 18.2 mmol) and water (25 mL). The reaction mixture was refluxed for 48 h. The reaction mixture was basified with aqueous sodium bicarbonate and extracted thrice with chloroform. The organic layer was dried over anhydrous sodium sulphate and concentrated under reduced pressure. The residue thus obtained was purified by silica gel column chromatography to yield 1.05 g of the desired product. $^1$H NMR (400 MHz, DMSO-$d_6$) δ 5.04 (s, 2H), 5.76 (brs, 2H), 7.31-7.43 (m, 5H), 7.60 (d, J=2.4 Hz, 1H), 7.80 (d, J=2.4 Hz, 1H); ESI-MS (m/z) 279.1 $(M+H)^+$ Step 4: (2-Amino-5-(benzyloxy)pyridine-3-yl) dimethyl phosphine oxide

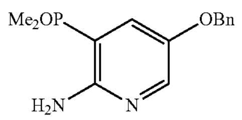

To a degassed solution of 5-(benzyloxy)-3-bromopyridine-2-amine (1.05 g, 3.76 mmol) and dimethylphosphine oxide (440 mg, 5.64 mmol) in DMF (10 mL) were added $K_3PO_4$ (2.4 g, 11.28 mmol), Xantphos (108 mg, 0.188 mmol) and $[Pd(OAc)_2]_3$ (126 mg, 0.188 mmol). The reaction mixture was stirred at 115° C. for 4 h. The reaction mixture was diluted with chloroform, filtered through celite bed and washed with chloroform. The combined filtrate was washed with brine solution. The organic layer was filtered, dried over anhydrous sodium sulphate and concentrated under reduced pressure. The residue thus obtained was purified by silica gel column chromatography to yield 580 mg of the desired product. $^1$H NMR (400 MHz, DMSO-$d_6$) δ 1.67 (d, J=13.2 Hz, 6H), 5.05 (s, 2H), 6.39 (s, 2H), 7.33-7.47 (m, 6H), 7.91 (s, 1H); ESI-MS (m/z) 277.1 $(M+H)^+$ Step 5: (2-Amino-5-hydroxypyridine-3-yl) dimethyl phosphine oxide

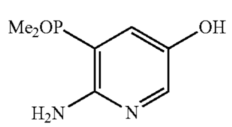

To a stirred suspension of (2-amino-5-(benzyloxy)pyridine-3-yl)dimethyl phosphineoxide (1.5 g, 8.06 mmol) in methanol (30 mL) was added 10% Pd/C (50% wet 1.5 g) and subjected to hydrogenation at 50 psi hydrogen pressure in a Parr Shaker for 6 h. The reaction mixture was filtered through celite bed and washed with methanol. The filtrate obtained was concentrated under reduced pressure. The residue thus obtained was purified by silica gel column chromatography to yield 760 mg of the desired product. $^1$H NMR (400 MHz, DMSO-$d_6$) δ 1.64 (d, J=13.6 Hz, 6H), 6.11 (s, 2H), 7.11 (s, J=14 Hz, 1H), 7.19 (s, 1H), 8.98 (s, 1H); ESI-MS (m/z) 187.2 $(M+H)^+$ Step 6: (2-Amino-5-((4-methoxybenzyl)oxy)pyridine-3-yl) methyl phosphine oxide

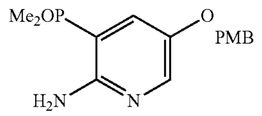

To a stirred solution of (2-amino-5-hydroxypyridine-3-yl) dimethylphosphine oxide (760 mg, 4.08 mmol) in DMF (15 mL) at 0° C. was added potassium-t-butoxide (571 mg, 5.1 mmol) and stirred at RT for 1 h. The reaction mixture was cooled to 0° C., added 4-methoxy benzyl chloride (735 mg, 4.69 mmol) and stirred at RT for 3 h. The reaction mixture was quenched with aqueous ammonium chloride, diluted with water and extracted thrice with DCM. The organic layers were separated, dried over anhydrous sodium sulphate and concentrated under reduced pressure. The residue thus obtained was purified by silica gel column chromatography to yield 800 mg of the desired product. $^1$H NMR (400 MHz, DMSO-$d_6$) δ 1.67 (d, J=13.6 Hz, 6H), 3.75 (s, 3H), 4.96 (s, 2H), 6.42 (brs, 2H), 6.93 (d, J=8.4 Hz, 2H), 7.33-7.42 (m, 3H), 7.88 (d, J=2.0 Hz, 1H); ESI-MS (m/z) 307.2 $(M+H)^+$ Intermediate A8

(3-Amino-6-((4-methoxybenzyl)oxy)pyridin-2-yl) dimethylphosphineoxide

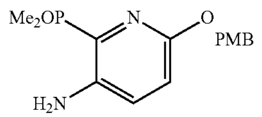

Step 1: 2-((4-Methoxybenzyl)oxy)-5-nitropyridine

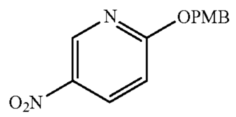

To a stirred suspension of 60% NaH (680 mg, 28.4 mmol) in THE was added 2-chloro-5-nitropyridine (3.0 g, 18.93 mmol) at 0° C. and stirred for 5 min. To this mixture was added 4-methoxy benzyl alcohol (3.29 g, 28.4 mmol) and stirred at RT for 16 h. The reaction mixture was quenched with water and extracted twice with ethyl acetate. The organic layer was separated, washed with brine, dried over anhydrous sodium sulphate and concentrated. The residue thus obtained was triturated with diethyl ether, filtered and dried under vacuum to yield 3.22 g of the desired product. $^1$H NMR (400 MHz, DMSO-$d_6$) δ 3.76 (s, 3H), 5.42 (s, 2H), 6.95 (d, J=8.8 Hz, 2H), 7.06 (d, J=9.2 Hz, 1H), 7.42 (d, J=8.8 Hz, 2H), 8.50 (dd, J=2.8 Hz, J=9.2 Hz, 1H), 9.12 (d, J=2.4 Hz, 1H)

Step 2: 6-((4-Methoxybenzyl)oxy)pyridin-3-amine

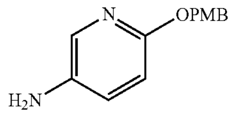

To a stirred suspension of 2-((4-methoxybenzyl)oxy)-5-nitropyridine (3.0 g, 11.53 mmol) and iron powder (3.22 g, 57.64 mmol) in isopropyl alcohol (120 mL) were added ammonium chloride (6.16 g, 115.3 mmol) and water (30 mL) and refluxed for 2 h. The reaction mixture was diluted with ethyl acetate and filtered through celite bed. The filtrate obtained was extracted with ethyl acetate, washed with brine, dried over anhydrous sodium sulphate and concentrated. The residue thus obtained was purified by silica gel column chromatography to yield 2.02 g of the desired product. $^1$H NMR (400 MHz, DMSO-$d_6$) δ 3.75 (s, 3H), 4.76 (s, 2H), 5.11 (s, 2H), 7.57 (d, J=8.4 Hz, 1H), 6.91 (d, J=8.8 Hz, 2H), 7.01 (dd, J=2.8 Hz, J=8.8 Hz 1H), 7.33 (d, J=8.4 Hz, 2H), 7.50 (d, J=2.8 Hz, 1H); ESI-MS (m/z) 231.1 $(M+H)^+$ Step 3: 2-Bromo-6-((4-methoxybenzyl)oxy)pyridin-3-amine

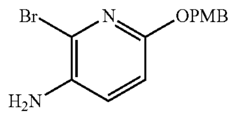

To a stirred solution of 6-((4-methoxybenzyl)oxy)pyridin-3-amine (1.5 g, 6.51 mmol) in acetonitrile (60 mL) was added NBS (1.16 g, 6.51 mmol) portion wise at 0° C. and stirred for 10 minutes. The reaction mixture was diluted with EtOAc and washed with water and brine solution. The organic layer was dried over anhydrous sodium sulphate and concentrated under reduced pressure. The residue obtained was purified by silica gel column chromatography to yield 1.4 g of the desired product. $^1$H NMR (400 MHz, DMSO-$d_6$) δ 3.75 (s, 3H), 4.96 (s, 2H), 5.09 (s, 2H), 6.67 (d, J=8.4 Hz, 1H), 6.92 (dd, J=2.0 Hz, J=6.8 Hz, 2H), 7.18 (d, J=8.4 Hz, 1H), 7.36 (d, J=8.8 Hz, 2H); ESI-MS (m/z) 310.9 $(M+2H)^+$.

Step 4: (3-Amino-6-((4-methoxybenzyl)oxy)pyridin-2-yl)dimethylphosphine oxide

The titled compound was prepared by the reaction of 2-bromo-6-((4-methoxybenzyl)oxy) pyridin-3-amine (100 mg, 0.323 mmol) with dimethylphosphine oxide (38 mg, 0.485 mmol), CuI (7 mg, 0.032 mmol), $K_3PO_4$ (206 mg, 0.97 mmol), xantphos (9.3 g, 0.016 mmol) and $[Pd(OAc)_2]_3$ (11 mg, 0.016 mmol) in DMF (5 ml) as per the procedure described in step 4 of Intermediate A1 to yield 44 mg of the desired product. $^1$H NMR (400 MHz, DMSO-$d_6$) δ 1.62 (d, J=13.2 Hz, 6H), 3.74 (s, 3H), 5.12 (s, 2H), 5.83 (s, 2H), 6.74 (d, J=8.8 Hz, 1H), 6.91 (d, J=8.4 Hz, 2H), 7.10 (d, J=8.8 Hz, 1H), 7.33 (d, J=8.4 Hz, 2H); ESI-MS (m/z) 307.10 $(M+H)^+$ Intermediate A9

(5-Amino-2-methoxypyridin-4-yl)dimethylphosphine oxide

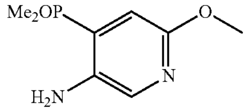

Step 1: tert-Butyl (6-methoxypyridin-3-yl) carbamate

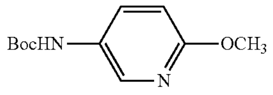 [SMILES: COc1ccc(NC(=O)OC(C)(C)C)cn1]

To a stirred solution of 6-methoxypyridin-3-amine (3 g, 24.17 mmol) in 1,4-dioxane (20 mL) was added Boc anhydride (7.37 g, 33.84 mmol) and heated to 70° C. for 18 h. The reaction mixture was diluted with water and extracted with ethyl acetate. The organic layer was separated, dried over anhydrous sodium sulfate and concentrated under vacuum. The residue obtained was purified by silica gel column chromatography to yield 4.5 g of the desired product. $^1$H NMR (400 MHz, $CDCl_3$) δ 1.53 (s, 9H), 3.91 (s, 3H), 6.38 (s, 1H), 6.73 (d, J=8.8 Hz, 1H), 7.83 (s, 1H), 8.01 (d, J=2.4 Hz, 1H); ESI-MS (m/z) 225.1 $(M+H)^+$.

Step 2: tert-Butyl (4-iodo-6-methoxypyridin-3-yl) carbamate

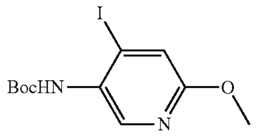 [SMILES: COc1cc(I)c(NC(=O)OC(C)(C)C)cn1]

To a stirred solution of tert-butyl (6-methoxypyridin-3-yl)carbamate (4.0 g, 17.85 mmol) in THE (110 mL) was added tetramethylethylenediamine (8.93 mL, 55.35 mmol) at RT. The reaction mixture was cooled to −78° C. and added dropwise n-BuLi (38 mL, 60.69 mmol) over a period of 15 min and stirred for 30 min. The mixture was slowly warmed to −20° C. and stirred for 20 min. The reaction mixture was again cooled to −78° C. and added solution of iodine (4.53 g, 17.85 mmol) in THE (40 mL). The reaction mixture was gradually warmed to RT and stirred at RT for 18 h. The reaction mixture was quenched with ammonium chloride solution and extracted with ethyl acetate. The organic layer was separated, dried over anhydrous sodium sulfate and concentrated under vacuum. The crude residue obtained was purified by silica gel column chromatography to yield 2 g of the desired product. $^1$H NMR (400 MHz, $CDCl_3$) δ 1.54 (s, 9H), 3.91 (s, 3H), 6.31 (s, 1H), 7.24 (s, 1H), 8.46 (s, 1H); ESI-MS (m/z) 351.2 $(M+H)^+$.

Step 3: 4-Iodo-6-methoxypyridin-3-amine

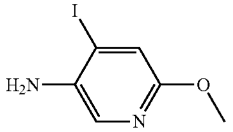

To a stirred solution of tert-butyl (4-iodo-6-methoxypyridin-3-yl) carbamate (2.0 g, 5.71 mmol) in DCM (10 mL) was added TFA (10 mL) and stirred at RT for 1 h. Then solvent was evaporated under vacuum, basified with $NaHCO_3$ solution and product was extracted with ethyl acetate. The organic layer was separated, dried over anhydrous sodium sulfate and concentrated under vacuum to yield 1.35 g of the desired product. $^1H$ NMR (400 MHz, DMSO-$d_6$) δ 3.71 (s, 3H), 4.84 (bs, 2H), 7.12 (s, 1H), 7.60 (s, 1H); ESI-MS (m/z) 250.1 $(M+H)^+$ Step 4: (5-Amino-2-methoxypyridin-4-yl)dimethylphosphine oxide The titled intermediate was prepared by the reaction of 4-Iodo-6-methoxypyridin-3-amine (1.3 g, 5.2 mmol) with dimethyl phosphine oxide (609 mg, 7.8 mmol), $K_3PO_4$ (1.6 g, 7.8 mmol) and Xantphos (150 mg, 0.26 mmol) in DMF (20 mL) as per the procedure described in Step 4 of intermediate A1 to yield 608 mg of the desired product. $^1H$ NMR (400 MHz, DMSO-$d_6$) δ 1.71 (d, J=14 Hz, 6H), 3.74 (s, 3H), 5.64 (bs, 2H), 6.73 (d, J=14 Hz, 1H), 7.67 (d, J=6 Hz, 1H); ESI-MS (m/z) 201.1 $(M+H)^+$ Intermediate A10

(5-(Benzyloxy)-2-hydroxyphenyl)dimethylphosphine oxide

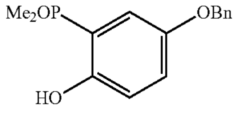

Step 1: 4-(Benzyloxy)phenol

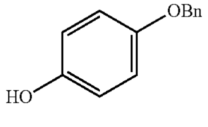 [SMILES: Oc1ccc(OCc2ccccc2)cc1]

To a stirred solution of hydroquinone (5 g, 45 mmol) in acetone (45 mL) was added $K_2CO_3$ (3.45 g, 25 mmol) followed by benzyl bromide (2.97 mL, 25 mmol) and the resulting reaction mixture was refluxed for 18 h. The reaction mixture was concentrated, diluted with ethyl acetate and washed with water. The organic layer was separated, dried over anhydrous sodium sulfate and concentrated. The residue obtained was purified by silica gel column chromatography to yield 2.6 g of the product. $^1H$ NMR (400 MHz, DMSO-$d_6$) δ 4.98 (s, 2H, 6.68-6.65 (m, 2H), 6.83-6.80 (m, 2H), 7.43-7.29 (m, 5H), 8.93 (s, 1H); ESI-MS (m/z) 201.2 $(M+H)^+$.

Step 2: 4-(Benzyloxy)-2-bromophenol

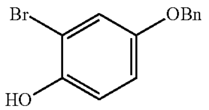 [SMILES: Oc1ccc(OCc2ccccc2)cc1Br]

To a stirred solution of 4-(benzyloxy)phenol (2.35 g, 11 mmol) in $CHCl_3$ (50 mL) was added at 0° C. bromine dropwise (947 mg, 11 mmol) and stirred at RT for 18 h. The reaction was quenched with sodium thiosulphate solution and extracted thrice with ethyl acetate. The organic layer was separated, dried over anhydrous sodium sulfate and concentrated under vacuum. The crude material was purified by silica gel column chromatography to yield 1.15 g of the desired product. $^1H$ NMR (400 MHz, DMSO-$d_6$) δ 4.98 (s, 2H); 6.86 (d, J=2.8 Hz, 1H), 6.92 (s, 1H), 7.09 (d, J=2.8 Hz, 1H); 7.41-7.32 (m, 5H); ESI-MS (m/z) 281 $(M+H)^+$.

Step 3: (5-(Benzyloxy)-2-hydroxyphenyl)dimethylphosphine oxide

To a degassed solution 4-(benzyloxy)-2-bromophenol (900 mg, 3.225 mmole) and dimethyl phosphine oxide was in DMF (14 mL) was added $K_3PO_4$ (1.02 g, 4.83 mmol) and Xantphos (186 mg, 0.322 mmole) in a sealed tube. The mixture was again degassed for 15 min and added [Pd $(OAc)_2]_3$ (49 mg, 0.322 mmole). The resulting mixture was stirred at 120° C. for 18 h. The reaction mixture was diluted with water and extracted thrice with ethyl acetate. The organic layer was separated, dried over anhydrous sodium sulfate and concentrated under vacuum. The residue obtained was purified by silica gel column chromatography to yield 201 mg of the product. $^1H$ NMR (400 MHz, DMSO-$d_6$) δ 1.68 (d, J=14 Hz, 6H); 5.03 (s, 2H), 6.78-6.82 (m, 1H), 7.04-7.07 (m, 1H), 7.20-7.24 (m, 1H), 7.32-75 (m, 5H), 10.30 (s, 1H); ESI-MS (m/z) 277 $(M+H)^+$.

Intermediate A11 t-Butyl[4-amino-3-(dimethylphosphoryl)phenyl](methyl)carbamate

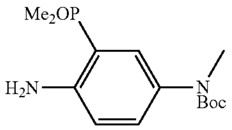

Step 1: 3-Iodo-N-methyl-4-nitroaniline

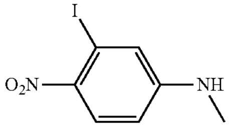

To a stirred solution of 4-fluoro-2-iodo-1-nitrobenzene (4.5 g, 10.86 mmol) in DMF (20 ml) at RT were added methylamine hydrochloride (1.5 g, 21.9 mmol) and potassium carbonate (3 g, 21.9 mmol) and heated to 80° C. for 4 h. The reaction mixture was quenched with ice cold water and extracted with chloroform. The organic layer was separated, dried over anhydrous sodium sulfate and concentrated under vacuum. The residue obtained was purified by silica gel column chromatography to yield 1.7 g of the desired product. $^{1}$H NMR (400 MHz, DMSO-$d_6$) 2.75 (d, J=4.8 Hz, 3H), 6.62 (d, J=9.2 Hz, 1H), 7.18 (d, J=2.0 Hz, 1H), 7.24 (brs, 1H), 7.96 (d, J=9.2 Hz, 1H); ESI-MS (m/z) 279.12 $(M+H)^+$ Step 2: t-Butyl(3-iodo-4-nitrophenyl) (methyl) carbamate

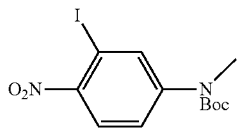 [SMILES: CN(C(=O)OC(C)(C)C)c1ccc([N+](=O)[O-])c(I)c1]

To a stirred solution of 3-iodo-N-methyl-4-nitroaniline (1.7 g, 6.115 mmol) in THF (30 mL) at 0° C. was added 60% sodium hydride (293 mg, 7.33 mmol) and stirred at same temperature for 20 min. Boc-anhydride was added dropsie and the reaction mixture was stirred at RT for 16 h.

The reaction mixture was quenched with aq. ammonium chloride, diluted with water and extracted thrice with DCM. The organic layers were separated, dried over anhydrous sodium sulphate and concentrated under reduced pressure. The residue thus obtained was purified by silica gel column chromatography to yield 1.4 g of the desired product. $^{1}$H NMR (400 MHz, DMSO-$d_6$) δ 1.44 (s, 9H), 3.24 (s, 3H), 7.54 (d, J=9.2 Hz, 1H), 7.95 (d, J=8.8 Hz, 1H), 8.06 (d, J=2.4 Hz, 1H).

Step 3: t-Butyl(4-amino-3-iodophenyl)(methyl)carbamate

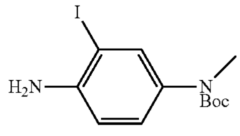

To a stirred suspension of t-Butyl(3-iodo-4-nitrophenyl)(methyl)carbamate (1.4 g, 5.64 mmol) and iron powder (1.9 g, 33.84 mmol) in isopropyl alcohol (25 mL) were added ammonium chloride (1.5 g, 28.2 mmol) and water (8 mL) and heated to reflux for 3 h. The reaction mixture was diluted with ethyl acetate, filtered through celite bed and the filtrate obtained was extracted thrice with ethyl acetate. The organic layer was separated, dried over anhydrous sodium sulphate and concentrated under reduced pressure. The residue thus obtained was purified by silica gel column chromatography to yield 950 mg of the desired product. ESI-MS (m/z) 348.9 $(M+H)^+$.

Step 4: t-Butyl[4-amino-3-(dimethylphosphoryl) phenyl](methyl)carbamate

To a degassed solution of t-Butyl(4-amino-3-iodophenyl) (methyl) carbamate (Intermediate-4) (950 mg, 2.73 mmol) and dimethylphosphine oxide (320 mg, 4.10 mmol) in DMF (10 mL) were added $K_3PO_4$ (870 mg, 4.10 mmol), Xantphos (0.78 g, 0.136 mmol) and $[Pd(OAc)_2]_3$ (180 mg, 0.273 mmol) and stirred at 115° C. for 16 h. The reaction mixture was diluted with ethyl acetate, filtered through celite bed and washed with ethyl acetate. The combined filtrate was washed with brine solution. The organic layer was separated, dried over anhydrous sodium sulphate and concentrated under reduced pressure. The residue thus obtained was purified by silica gel column chromatography to yield 690 mg of the desired product. $^{1}$H NMR (400 MHz, DMSO-$d_6$) δ 1.36 (s, 9H), 1.65 (d, J=13.2 Hz, 6H), 3.08 (s, 3H), 6.14 (brs, 2H), 6.59-6.62 (m, 1H), 7.03-7.07 (m, 2H); ESI-MS (m/z) 299.1 $(M+H)^+$.

Intermediate A12

(2-Amino-5-(difluoromethoxy) phenyl) dimethyl phosphine oxide

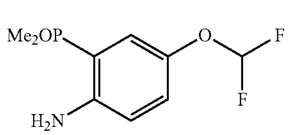

Step 1: 4-(Difluoromethoxy)-2-iodoaniline

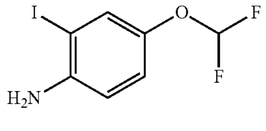 [SMILES: Nc1ccc(OC(F)F)cc1I]

To a stirred solution of 4-difluoro methoxy aniline (1.0 g, 6.28 mmol) in acetic acid (21 mL) was drop-wise added iodine monochloride (1.07 g, 6.65 mmol) at 65° C. The reaction mixture was stirred at 65° C. for 1.5 h. The reaction mixture was concentrated under reduced pressure, neutralized with aqueous $NaHCO_3$ solution and extract with ethyl acetate solution. The organic layer was separated and dried over anhydrous sodium sulphate. The solvent was removed under reduced pressure and collected crude products was purified by column chromatography (25-30% ethyl acetate in pet ether) to yield 800 mg of the desired product. $^{1}$H NMR (400 MHz, DMSO-$d_6$) δ 5.22 (brs, 2H), 6.76 (d, J=8.8 Hz, 1H), 6.97 (d, J=2.8 Hz, 8.8 Hz, 1H), 7.00 (t, J=74.8 Hz, 1H), 7.39 (d, J=2.0 Hz, 1H); ESI-MS (m/z) 286.1 $(M+H)^+$.

Step 2: (2-Amino-5-(difluoromethoxy) phenyl) dimethyl phosphine oxide

To a stirred solution of 4-difluoro methoxy-2-iodo aniline (200 mg, 0.70 mmol) in DMF (2 mL) were added dimethyl phosphine oxide (82 mg, 1.05 mmol) and potassium phosphate (223 mg, 1.05 mmol) followed by xantphos (4 mg, 0.0070 mmol) and palladium acetate trimer (47 mg, 0.070 mmol) under nitrogen atmosphere at RT. The reaction mixture was stirred at 120° C. for 12 h. The reaction mixture was cooled at RT, filtered through celite bed, washed with ethyl acetate, filtrate was concentrated under reduced pressure. The crude material was purified by flash column chromatography to yield 130 mg of the desired product. $^{1}$H NMR (400 MHz, DMSO-$d_6$) δ 1.67 (s, 3H), 1.70 (s, 3H), 6.16 (br s, 2H)), 6.68 (dd, J=4.4 & 8.8 Hz, 1H), 6.99 (t, J=74.8 Hz, 1H), 7.10-7.00 (m, 2H); ESI-MS (m/z) 236 $(M+H)^+$.

Intermediate A13

(2-Amino-5-(2,2-difluoroethoxy)phen 1 dimethylphosphine oxide

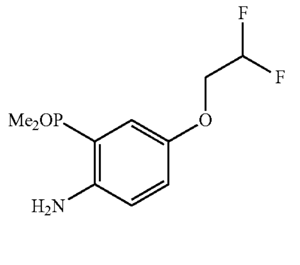

Step 1: 4-(2,2-Difluoroethoxy)-2-iodo-1-nitrobenzene

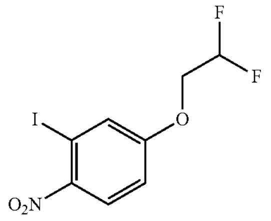 [SMILES: O=[N+]([O-])c1ccc(OCC(F)F)cc1I]

To a stirred solution of 3-iodo 4-nitrophenol (0.3 g, 1.13 mmol) in DMF (4 mL) were added potassium carbonate (0.470 g, 3.96 mmol) followed by 2-iodo-1, 1-difluoroethane (0.434 g, 2.26 mmol). The reaction mixture was stirred at 80° C. for overnight. The reaction mixture was diluted with water and extracted by ethyl acetate. The organic layer was separated and dried over anhydrous sodium sulphate. The solvent was removed under reduced pressure and collected crude products was purified by column chromatography to yield 300 mg of the desired product. $^1$H NMR (400 MHz, DMSO-$d_6$) δ 4.47-4.52 (m, 2H), 6.42 (tt, J=6.8 Hz, 54 Hz, 1H), 7.22 (d, J=8.8 Hz, 1H), 7.72 (s, 1H), 8.02 (d, J=9.2 Hz, 1H); ESI-MS (m/z) 328 $(M)^+$.

Step 2: 4-(2,2-Difluoroethoxy)-2-iodoaniline

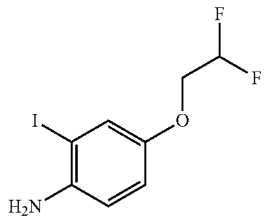

To stirred compound 4-(2,2-difluoroethoxy)-2-iodo-1-nitrobenzene (step 1 Intermediate) (0.3 g, 0.91 mmol) in IPA (5 mL) were added Iron (0.161 g, 2.74 mmol) and aqueous solution of ammonium chloride (0.492 g, 10 mmol) at RT. The reaction mixture was heated to reflux for 3 h. The mixture was filtered through celite, the filtrate was dried over sodium sulphate and concentrated under reduced pressure to yield 250 mg of the desired product. $^1$H NMR (400 MHz, DMSO-$d_6$) δ 3.30-3.41 (m, 2H), 5.38 (tt, J=3.6 Hz, 53.6 Hz, 1H), 6.00-6.15 (m, 2H), 6.52 (t, J=2.4 Hz, 1H); ESI-MS (m/z) 299 $(M)^+$.

Step 3: (2-Amino-5-(2,2-difluoroethoxy)phenyl) dimethylphosphine oxide

The titled compound was prepared by the reaction of 4-(2,2-difluoroethoxy)-2-iodoaniline (250 mg, 0.83 mmol) with dimethyl phosphine oxide (98 mg, 1.25 mmol), potassium triphosphate (266 mg, 1.25 mmol) and Xantphos (5 mg, 0.008 mmol), palladium acetate trimmer (56 mg, 0.083 mmol) in DMF (2 mL) as per the procedure described in step 4 of intermediate A1 to yield 250 mg of the desired product. $^1$H NMR (400 MHz, DMSO-$d_6$) δ 1.69 (d, J=13.2 Hz, 6H), 4.13-4.24 (m, 2H), 5.85 (br s, 2H), 6.32 (tt, J=3.6 Hz, 54.8 Hz, 1H), 6.60-6.67 (m, 1H), 6.83-6.95 (m, 2H); ESI-MS (m/z)=249.9 $(M+H)^+$.

Intermediate A14

(2-amino-4-fluoro-5-methoxyphenyl) dimethylphosphine oxide

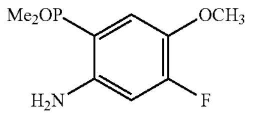

Step 1: 5-fluoro-2-iodo-4-methoxyaniline

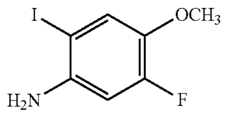 [SMILES: COc1cc(I)c(N)cc1F]

To a stirred solution of 3-fluoro-4-methoxyaniline (100 mg, 0.709 mmol) in methanol (5 mL) was added pyridinium iodochloride (241.46 mg, 0.709 mmol) and stirred at RT for 30 min. The reaction mixture was concentrated under reduced pressure and residue obtained was diluted with water and extracted with thrice with ethyl acetate. The organic layer was separated and further washed with water and brine solution. The organic layer was separated, dried over anhydrous sodium sulphate and concentrated under reduced pressure. The residue thus obtained was purified by column chromatography to yield 32 mg of the desired product. $^1$H NMR (400 MHz, DMSO-$d_6$) δ 3.71 (s, 3H), 5.0 (s, 2H), 6.65 (d, J=13.6 Hz, 1H), 7.29 (d, J=9.2 Hz, 1H); ESI-MS (m/z) 268 $(M+H)^+$.

Step 2: (2-amino-4-fluoro-5-methoxyphenyl) dimethylphosphine oxide

In a sealed tube, 5-fluoro-2-iodo-4-methoxyaniline (28 mg, 0.105 mmol) and dimethyl phosphine (12.3 mg, 0.157 mmol) were dissolved in DMF (2 mL) and the mixture was purged with nitrogen for 30 min. $K_3PO_4$ (44.5 mg, 0.209 mmol), Xantphos (3 mg, 0.0052 mmol) and $Pd(OAc)_2$ (2.35 mg, 0.0105 mmol) were added to the mixture. The reaction mixture was heated at 110° C. for 16 h. The reaction mixture was diluted with ethyl acetate and filtered. The filtrate obtained was concentrated under reduced pressure. The residue thus obtained was purified by column chromatography to get 11 mg of desired product. $^1H$ NMR (400 MHz, DMSO-$d_6$) δ 1.67 (d, J=13.2 Hz, 6H), 3.73 (s, 3H), 6.01 (s, 2H), 6.51 (dd, J=4.4 Hz, 14 Hz, 1H), 6.95 (dd, J=9.6 Hz, 14 Hz, 1H), ESI-MS (m/z) 218 $(M+H)^+$.

Intermediate A15

4-Amino-3-(dimethylphosphoryl)-N-(2-fluoroethyl)-N-methylbenzamide

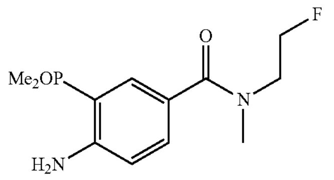

Step 1: Methyl 4-aminobenzoate

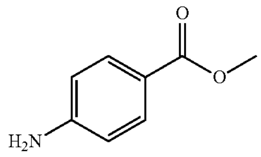

To a stirred solution of 4-amino benzoic acid (250 mg, 1.655 mmol) in methanol (4 ml) was added conc. sulfuric acid at RT. The reaction mixture was refluxed for 18 h. The solvent was removed under reduced pressure and the reaction mass was basified with aqueous sodium bicarbonate solution. The reaction mass was filtered and obtained residue was washed with water and dried under vacuum to yield 178 mg of the desired product. $^1H$ NMR (400 MHz, DMSO-$d_6$) δ 3.73 (s, 3H), 5.97 (bs, 2H), 7.56 (dd, J=1.6, 6.8 Hz 2H), 7.63 (d, J=8.8 Hz, 2H); ESI-MS (m/z) 152 $(M+H)^+$.

Step 2: Methyl 4-amino-3-iodobenzoate

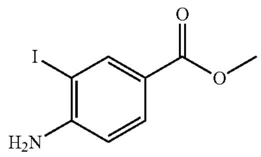

To a stirred solution of methyl 4-aminobenzoate (100 mg, 0.662 mmol) in DMF (1 ml) was added N-iodo succinamide (148 mg, 0.662 mmol) at 0° C. The reaction mixture was stirred at RT for 16 h. The reaction mixture was diluted with water and stirred for 5 min. The mixture was filtered and obtained solid was washed with water and dried to yield 150 mg as desired product. $^1H$ NMR (400 MHz, DMSO-$d_6$) δ 3.75 (s, 3H), 6.08 (bs, 2H), 6.77 (d, J=8.8 Hz, 1H), 7.67 (dd, J=2.08. 4 Hz, 1H), 8.11 (d, J=2 Hz, 1H); ESI-MS (m/z) 278.0 $(M+H)^+$.

Step 3: Methyl 4-amino-3-(dimethylphosphoryl)benzoate

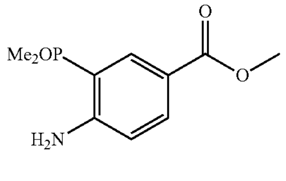

The titled compound was prepared by the reaction of methyl 4-amino-3-iodobenzoate (800 mg, 2.87 mmol) with dimethyl phosphine oxide (338 mg, 4.31 mmol), potassium phosphate (913 mg, 4.31 mmol), xanthpos (17 mg, 0.278 mmol) and palladium acetate trimer (194 mg, 0.287 mmol) in DMF (10 ml) as per the procedure described in step 4 of intermediate A1 to yield 605 mg desired product. $^1H$ NMR (400 MHz, DMSO-$d_6$) δ 1.72 (d, J=13.2 Hz, 6H), 3.76 (s, 3H), 6.67-6.71 (m, 1H), 6.98 (br s, 2H), 7.71-7.81 (m, 2H); ESI-MS (m/z) 228.1 $(M+H)^+$.

Step 4: 4-Amino-3-(dimethylphosphoryl)benzoic acid

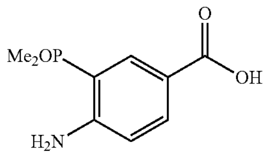

To a stirred solution of methyl 4-amino-3-(dimethylphosphoryl)benzoate (900 mg, 3.96 mmol) in methanol (10 ml) was added potassium hydroxide (333 mg, 5.94 mmol) and water (3 ml). The reaction was stirred at 70° C. for 16 h. The solvent was removed under reduced pressure. The reaction mass was acidified by 1N HCl. The aqueous mixture was extracted twice with ethyl acetate and the combined organic extracts were washed with water followed by brine. The organic layer was dried over anhydrous sodium sulfate, filtered and concentrated under reduced pressure. The residue obtained was purified by silica gel column chromatography to yield 450 mg desired product. $^1H$ NMR (400 MHz, DMSO-$d_6$) δ 1.71 (d, J=13.2 Hz, 6H), 6.66-6.69 (m, 2H), 6.90 (br s, 2H), 7.70-7.79 (m, 2H), 12.32 (br s, 1H), ESI-MS (m/z) 214.1 $(M+H)^+$.

Step 5: 4-Amino-3-(dimethylphosphoryl)-N-(2-fluoroethyl)-N-methylbenzamide

To a stirred solution of 4-amino-3-(dimethylphosphoryl) benzoic acid (350 mg, 1.64 mmol) and 2-fluoro-N-methylethanamine hydrochloride (186 mg, 1.64 mmol) in 1, 2-dichloroethane (10 mL) was added EDCI·HCl (470 mg, 2.46 mmol), HOBT (222 mg, 1.643 mmol) followed by N-methyl morpholine (0.548 ml, 4.929 mmol). The reaction mixture was stirred at RT for 16 h. The reaction mixture was diluted with water and extracted twice with ethyl acetate and the combined organic extracts were washed with water followed by brine. The organic layer was dried over anhydrous sodium sulfate, filtered and concentrated under reduced pressure. The residue obtained was purified by silica gel column chromatography to yield 415 mg as a desired product. $^1H$ NMR (400 MHz, DMSO-$d_6$) δ 1.69 (d, J=13.2 Hz, 6H), 2.99 (s, 3H), 3.55-3.68 (m, 2H), 4.55 (t, J=4.8 Hz, 1H), 4.67 (t, J=4.8 Hz, 1H), 6.56 (br s, 2H), 6.66-6.67 (m, 1H), 7.24-7.30 (m, 2H); ESI-MS (m/z) 273.1 $(M+H)^+$.

Intermediate A16

N-(4-Amino-3-(dimethylphosphoryl)phenyl)-2,2-difluoro-N-methylacetamide

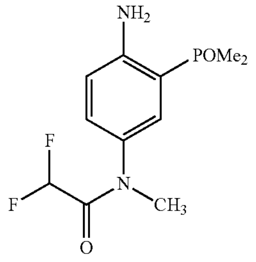

Step 1: 3-Iodo-N-methyl-4-nitroaniline

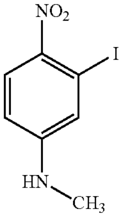

To a stirred solution of 4-fluoro-2-iodo-1-nitrobenzene (150 mg, 0.563 mmol) in DMF (1 mL) was added potassium carbonate (311 mg, 2.25 mmol) and methylamine hydrochloride (91 mg, 1.126 mmol). The reaction mixture was stirred at 80° C. for 4-5 h. The reaction mixture was cooled to RT and quenched with water. The aqueous mixture was extracted twice with ethyl acetate and the combined organic extracts were washed with water followed by brine. The organic layer was dried over anhydrous sodium sulfate, filtered and concentrated under reduced pressure. The residue obtained was purified by silica gel column chromatography to yield 85 mg of the desired product. $^1H$ NMR (400 MHz, $CDCl_3$) δ 2.97 (s, 3H), 6.55 (dd, J=2.4, 9.2 Hz, 1H), 7.18 (d, J=2.8 Hz, 1H), 8.03 (d, J=9.2 Hz, 1H).

Step 2: 2,2-Difluoro-N-(3-iodo-4-nitrophenyl)-N-methylacetamide

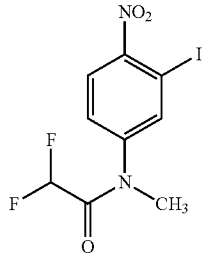 [SMILES: CN(C(=O)C(F)F)c1ccc([N+](=O)[O-])c(I)c1]

To a stirred solution of 3-iodo-N-methyl-4-nitroaniline (400 mg, 1.44 mmol) in THF (10 mL) at 0° C. was added TEA (436 mg, 4.32 mmol) and difluoroacetic anhydride (376 mg, 2.16 mmol). The reaction mixture was stirred at RT for 16 h and quenched with water. The aqueous mixture was extracted twice with ethyl acetate and the combined organic extracts were washed with water followed by brine. The organic layer was dried over anhydrous sodium sulfate, filtered and concentrated under reduced pressure. The residue obtained was purified by silica gel column chromatography to yield 300 mg of desired product. $^1H$ NMR (400 MHz, DMSO-$d_6$): δ 3.34 (s, 3H), 6.27-6.44 (m, 1H), 7.67 (d, J=7.2 Hz, 1H), 8.04 (d, J=8.8 Hz, 1H), 8.21 (br s, 1H).

Step 3: N-(4-Amino-3-iodophenyl)-2,2-difluoro-N-methylacetamide

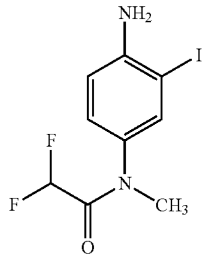

To a stirred solution of 2,2-difluoro-N-(3-iodo-4-nitrophenyl)-N-methylacetamide (300 mg, 0.845 mmol) in IPA/$H_2O$ mixture (6 mL/2 mL) were added iron powder (147 mg, 2.55 mmol) and ammonium chloride (447 mg, 8.45 mmol). The reaction mixture was stirred at 110° C. for 3 h. The reaction mixture was filtered through celite and washed with ethyl acetate. The filtrate obtained was concentrated and neutralized with saturated $NaHCO_3$. The aqueous mixture was extracted twice with ethyl acetate and the combined organic extracts were washed with water followed by brine. The organic layer was dried over anhydrous sodium sulfate, filtered and concentrated under reduced pressure. The residue obtained was purified by silica gel column chromatography to yield 255 mg of desired product. $^1H$ NMR (400 MHz, DMSO-$d_6$): δ 3.13 (s, 3H), 5.52 (br s, 2H), 6.09 (t, J=53.2 Hz, 1H), 6.76 (d, J=8.4 Hz, 1H), 7.08 (dd, J=2.4, 8.4 Hz, 1H), 7.59 (br s, 1H); ESI-MS (m/z) 326.9 $(M+H)^+$.

Step 4: N-(4-Amino-3-(dimethylphosphoryl)phenyl)-2,2-difluoro-N-methyl acetamide The titled compound was prepared by the reaction of N-(4-amino-3-iodophenyl)-2,2-difluoro-N-methylacetamide (250 mg, 0.769 mmol) with dimethylphosphine oxide (89 mg, 1.153 mmol), palladium diacetate trimer (51 mg, 0.0769 mmol), $K_3PO_4$ (244 mg, 1.153 mmol) and Xanphos (4.4 mg, 0.00769 mmol) in DMF (2 mL) as per the procedure described in step 4 of intermediate A1 to yield 200 mg of desired product. $^1$H NMR (400 MHz, DMSO-$d_6$): δ 1.67 (d, J=13.2 Hz, 6H), 3.15 (s, 3H), 6.08 (t, J=52.8 Hz, 1H), 6.45 (br s, 2H), 6.70-6.75 (m, 1H), 7.15 (dd, J=2.0, 8.4 Hz, 1H), 7.26 (dd, J=2.4, 14 Hz, 1H); ESI-MS (m/z) 277 $(M+H)^+$.

Intermediate A17

(2-Amino-5-(hydroxymethyl)phenyl)dimethylphosphine oxide

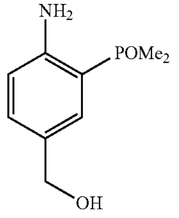

Step 1: (4-Amino-3-iodophenyl)methanol

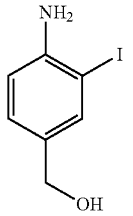

To a stirred solution of (4-aminophenyl)methanol (2.0 g, 16.26 mmol) in methanol (12 mL) was added aqueous solution of calcium carbonate (2.43 g, 24.39 mmol). The reaction mixture was stirred for 10-15 mins. ICl (0.8 mL, 16.26 mmol) was dropwise added to the reaction mixture. The reaction mixture was stirred at RT for 16 h. The reaction mixture was diluted with ether and quenched with water. The aqueous mixture was extracted twice with ethyl acetate and the combined organic extracts were washed with water followed by brine. The organic layer was dried over anhydrous sodium sulfate, filtered and concentrated under reduced pressure. The residue obtained was purified by silica gel column chromatography to yield 1.3 g of the desired product. $^1$H NMR (400 MHz, DMSO-$d_6$): δ 4.27 (d, J=5.6 Hz, 2H), 4.95 (t, J=6 Hz, 1H), 5.10 (br s, 2H), 6.70 (d, J=8 Hz, 1H), 7.00-7.05 (m, 1H), 7.49 (s, 1H).

Step 2: (2-Amino-5-(hydroxymethyl)phenyl)dimethylphosphine oxide

The titled compound was prepared by the reaction of (4-amino-3-iodophenyl)methanol (1.00 g, 4.016 mmol) with dimethylphosphine oxide (409 mg, 6.024 mmol), $K_3PO_4$ (1.28 g, 1.153 mmol4), Xanphos (116 mg, 0.200 mmol), palladium diacetate trimer (270 mg, 0.4016 mmol) in DMF (5 mL)) as per the procedure described in step 4 of intermediate A1 to yield 790 mg of product. $^1$H NMR (400 MHz, DMSO-$d_6$): δ 1.66 (d, J=13.6 Hz, 6H), 4.30 (d, J=5.6 Hz, 2H), 4.91 (t, J=5.6 Hz, 1H)), 6.06 (s, 2H), 6.60-6.63 (m, 1H), 7.10-7.12 (m, 1H), 7.14 (s, 1H).

Intermediate A18

(2-Amino-5-nitrophenyl)dimethylphosphine oxide

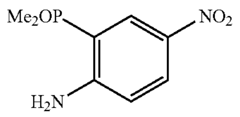

Step 1: 2-Iodo-4-nitroaniline

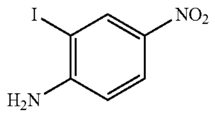 [SMILES: Nc1ccc([N+](=O)[O-])cc1I]

To a stirred solution of 4-Nitro aniline (5 gm, 36.23 mmol) in acetonitrile was added, N-Iodosuccinimide (9 gm, 39.85 mmol) followed by dropwise addition of TMS chloride (460 μl, 3.623 mmol). The reaction mixture was stirred at RT for 16 h. The reaction mixture was diluted with water. The aqueous mixture was extracted twice with ethyl acetate and the combined organic extracts were washed with water followed by brine. The organic layer was dried over anhydrous sodium sulfate, filtered and concentrated under reduced pressure. The residue obtained was purified by silica gel column chromatography to yield 9.1 g of desired product. $^1$H NMR (400 MHz, DMSO-$d_6$) δ 6.76 (d, J=8 Hz, 1H), 8.4 (d, J=2.4 Hz, 1H), 8.73 (brs, 2H), ESI-MS (m/z) 264 $(M+H)^+$.

Step 2: (2-Amino-5-nitrophenyl)dimethylphosphine oxide

The titled compound was prepared by the reaction 2-iodo-4-nitroaniline (2 g, 7.604 mmol) with dimethyl phosphine oxide (890 mg, 11.406 mmol), $K_3PO_4$ (2.4 gm, 11.406), Xantphos (219 mg, 0.380 mmol) and palladium acetate trimer (511 mg, 0.760 mmol) in DMF as per the procedure described in step 4 of intermediate A1 to yield 1.1 g of desired product. $^1$H NMR (400 MHz, DMSO-$d_6$) δ 1.77 (d, J=13.6 Hz, 6H); 6.73-6.77 (m, 1H), 7.59 (br s, 2H), 8.01-8.05 (m, 1H), δ 8.14-8.20 (m, 1H); ESI-MS (m/z) 215 $(M+H)^+$.

Intermediate A19

Dimethyl (2-(S-methylsulfonimidoyl)phenyl)phosphine oxide

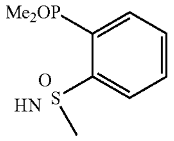

Step 1: (2-Iodophenyl)(methyl)sulfane

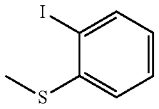

To a cooled solution of 2-(methylthio)aniline (1 g, 7.18 mmol) in 10% $H_2SO_4$ (10 ml) was dropwise added 3 ml aq. solution of $NaNO_2$ (545 mg, 7.9 mmol) at −10° C. The reaction mixture was stirred at 0-10° C. for 30 min and then 3 mL of aq. KI solution (2.1 g, 12.92 mmol) was added to reaction mixture. The reaction mixture was stirred at RT for 3 h. The reaction mixture was diluted with ethyl acetate and washed with 1N HCl, followed by water. The organic layer separated, concentrated and the residue thus obtained was purified by flash chromatography to yield 1 g of the desired product. $^1H$ NMR (400 MHz, DMSO-$d_6$) δ 2.46 (s, 3H), 6.89-6.94 (m, 1H), 7.19-7.22 (m, 1H), 7.40-7.45 (m, 1H), 7.79-7.82 (m, 1H).

Step 2: Dimethyl(2-(methylthio)phenyl)phosphine oxide

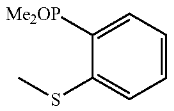

The titled compound was prepared by the reaction of (2-Iodophenyl)(methyl)sulfane (500 mg, 2 mmol) with dimethyl phosphine oxide (234 mg, 1.5 mmol), $K_3PO_4$ (636 mg, 1.5 mmol), Xanthphos (58 mg, 0.1 mmol), and Palladium acetate trimer (138 mg, 0.2 s mmol) in DMF (2 mL) as per the procedure described in step 4 of intermediate A1 to yield 325 mg of the desired product. $^1H$ NMR (400 MHz, DMSO-$d_6$) δ 1.77 d, J=13.6 Hz, 6H), 2.55 (s, 3H), 7.31-7.36 (m, 1H), 7.46-7.58 (m, 2H), 7.80-7.86 (m, 1H); ESI-MS (m/z) 201 $(M+H)^+$.

Step 3: Dimethyl (2-(S-methylsulfonimidoyl)phenyl)phosphine oxide

To a stirred solution of dimethyl(2-(methylthio)phenyl) phosphine oxide (300 mg, 1.5 mmol) in methanol (15 ml) was added ammonium carbonate (720 mg, 2.25 mmol) and Iodobenzene diacetate (1.1 g, 3.45 mmol). The reaction mixture was stirred at RT for 1 h. The reaction mixture was concentrated and the residue obtained was purified by flash chromatography to yield 245 mg of the desired product. $^1H$ NMR (400 MHz, DMSO-$d_6$) δ 1.84-1.92 (m, 6H), 3.36 (s, 3H), 4.50 (br s, 1H), 7.75-7.80 (m, 2H), 7.95-8.01 (m, 1H), 8.17-8.21 (m, 1H).

Intermediate A20 tert-Butyl ((4-amino-3-(dimethylphosphoryl)phenyl)(methyl)(oxo)-λ$^6$-sulfaneylidene)carbamate

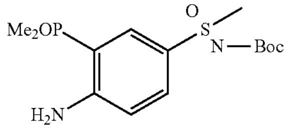

Step 1: 1-(S-Methylsulfonimidoyl)-4-nitrobenzene

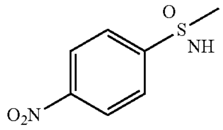

To a stirred solution of 4-nitro thioanisole (500 mg, 2.95 mmol) in MeOH (30 ml) was added ammonium carbonate (5.6 g, 4.43 mmol), iodo benzene diacetate (9.15 g, 6.79 mmoles). The reaction mixture was stirred at RT for 1 h. The reaction mixture was concentrated under reduced pressure and obtained residue was purified by column chromatography to yield 521 mg of desired product; $^1H$ NMR (400 MHz, DMSO-$d_6$) δ 3.17 (s, 3H), 4.61 (s, 1H), 8.19 (d, J=8.8 Hz, 2H), 8.42 (d, J=8.8 Hz, 2H); ESI-MS (m/z) 201 $(M+H)^+$.

Step 2: tert-Butyl (methyl(4-nitrophenyl)(oxo)-λ$^6$-sulfaneylidene)carbamate

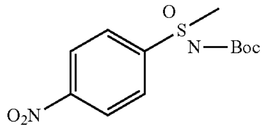

To a stirred solution of KOtBu (73 mg, 0.65 mmoles) in THE (8.0 ml) was added 1-(S-methylsulfonimidoyl)-4-nitrobenzene (100 mg, 0.5 mmol) at 0° C. The reaction mixture was stirred at RT for 15 min and then added boc anhydride (218 mg, 1.0 mmol) and stirred at RT for 16 h. The reaction mixture was quenched with water and extracted with ethyl acetate. The organic layer was separated, dried over anhydrous $Na_2SO_4$. The solvent was evaporated and residue obtained was purified by column chromatography to yield 122 mg of desired product. $^1H$ NMR (400 MHz, DMSO-$d_6$) δ 1.24 (s, 9H) 3.50 (s, 3H), 8.20-8.23 (m, 2H), 8.48-8.50 (m, 2H); ESI-MS (m/z) 301 $(M+H)^+$.

Step 3: tert-Butyl ((4-aminophenyl)(methyl)(oxo)-$\lambda^6$-sulfaneylidene)carbamate

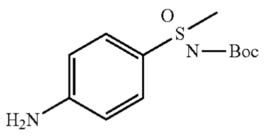

To a stirred solution of tert-Butyl (methyl(4-nitrophenyl)(oxo)-$\lambda^6$-sulfaneylidene)carbamate (650 mg) in MeOH (25 ml) was added 10% Pd/C (300 mg) at RT. The reaction mixture was stirred at RT for 2 h under hydrogen atmosphere (balloon pressure). The reaction mixture was filtered through celite and the filtrate obtained was concentrated to yield 563 mg of desired product. $^1$H NMR (400 MHz, DMSO-$d_6$) δ 1.29 (s, 9H) 3.25 (s, 3H), 6.16 (s, 2H), 6.67 (d, J=8.8, 2H), 7.51 (d, J=8.4 Hz, 2H); ESI-MS (m/z) 271 $(M+H)^+$.

Step 4: tert-Butyl ((4-amino-3-iodophenyl)(methyl)(oxo)-$\lambda^6$-sulfaneylidene) carbamate

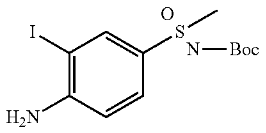

To a solution of tert-Butyl ((4-aminophenyl)(methyl)(oxo)-$\lambda^6$-sulfaneylidene) (100 mg, 0.369 mmol) in ethanol (4.0 mL) was added mixture of silver sulfate (115 mg, 0.369 mmol), iodine (94 mg, 0.369 mmol) The reaction mixture was stirred at RT for 16 h. The reaction mixture was diluted with MeOH, filtered, filtrate was concentrated. The obtained crude was purified by column chromatography to yield 67 mg of desired product. $^1$H NMR (400 MHz, DMSO-$d_6$) δ 1.28 (s, 9H), 3.34 (s, 3H), 6.252 (s, 2H), 6.83 (d, J=8.8 Hz, 1H), 7.56 (dd, J=2.0 Hz, 8.4 Hz, 1H), 7.96 (d, J=2 Hz, 1H); ESI-MS (m/z) 397 $(M+H)^+$.

Step 5: tert-Butyl ((4-amino-3-(dimethylphosphoryl)phenyl)(methyl)(oxo)-$\lambda^6$-sulfaneylidene)carbamate

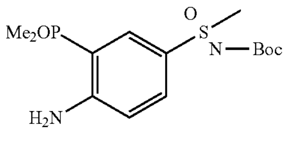

The titled compound was prepared by the reaction of dimethyl phosphine oxide (15 mg, 0.189 mmol), tert-Butyl ((4-amino-3-iodophenyl)(methyl)(oxo)-$\lambda^6$-sulfaneylidene) carbamate (50 mg, 0.126 mmol) in DMF (1 mL), Xantphos (7 mg, 0.012 mmol), potassium phosphate (40 mg, 0.189 mmol), palladium acetate trimer (9.0 mg, 0.012 mmole) in DMF) as per the procedure described in as per step 4 of Intermediate A1 to yield 27 mg as desired product. $^1$H NMR (400 MHz, DMSO-$d_6$) δ 1.27 (s, 9H), 1.70-1.74 (m, 6H), 3.30 (s, 3H), 6.80 (dd, J=4.0, 8.8 Hz, 1H), 7.61 (dd, J=2.0, 8.8 Hz, 1H), 7.68 (dd, J=2.40, 14.0 Hz, 1H); ESI-MS (m/z) 347 $(M+H)^+$.

Intermediate A21

(2-Hydroxyphenyl)dimethylphosphine oxide

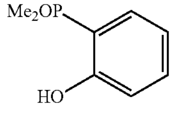

The titled compound was prepared by the reaction of dimethyl phosphine oxide (106 mg, 1.36 mmol), 2-iodo phenol (200 mg, 0.909 mmol), Xantphos (53 mg, 0.09 mmol), $K_3PO_4$ (289 mg, 1.36 mmol), palladium acetate trimer (61 mg, 0.09 mmol) in DMF (3 mL) as per step 4 of Intermediate A1 to yield 75 mg of the desired product. $^1$ NMR (400 MHz, DMSO-$d_6$) δ 1.68 (d, J=13.6 Hz, 6H), 6.85-6.95 (m, 2H), 7.36-7.41 (m, 1H), 7.56-7.61 (m, 1H), 10.73 (s, 1H); ESI-MS (m/z) 171 $(M+H)^+$.

Intermediate B1

6-Methoxy-2-methyl-1,2,3,4-tetrahydroisoquinolin-7-amine

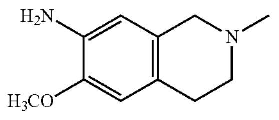

Step 1: Ethyl 3-methoxyphenethylcarbamate

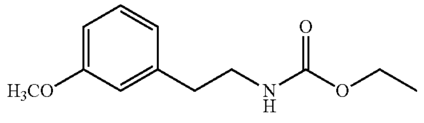 [SMILES: CCOC(=O)NCCc1cccc(OC)c1]

To a stirred solution of 2-(3-methoxyphenyl)ethylamine (50 g, 330.6 mmol) in dichloromethane (300 mL) at 0° C. was added ethyl chloroformate (34.8 mL, 363.7 mmol). The mixture was gradually warmed up to RT and stirred for 2 h. The mixture was basified with aq. $NaHCO_3$ and diluted with water. The aqueous layer was extracted thrice with DCM. The combined organic layers were dried over anhydrous sodium sulfate and concentrated under reduced pressure to yield 67.5 g of the desired product. $^1$H NMR (400 MHz, DMSO-$d_6$) δ 1.15 (t, J=6.8 Hz, 3H), 2.69 (t, J=7.6 Hz, 2H), 3.21-3.16 (m, 2H), 3.73 (s, 3H), 3.99 (q, J=7.2 Hz, 2H), 6.75-6.77 (m, 3H), 7.14-7.17 (m, 1H), 7.18-7.21 (m, 1H); ESI-MS (m/z) 224.1 $(M+H)^+$.

Step 2:
6-Methoxy-3,4-dihydroisoquinolin-1(2H)-one

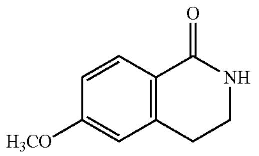

To a stirred solution of ethyl 3-methoxyphenethylcarbamate (67 g, 300 mmol) in polyphosphonic acid (80 g) was stirred at 120° C. for 2 h. The mixture was cooled to 0° C. and slowly basified with aqueous ammonia solution and stirred well. The solid obtained was filtered and washed with water and dried under vacuum to yield 26 g of the desired product. $^{1}$H NMR (400 MHz, DMSO-$d_6$) δ 2.88 (t, J=6.4 Hz, 2H), 3.34-3.36 (m, 2H), 3.80 (s, 3H), 6.85-6.89 (m, 2H), 7.78 (d, J=8.4 Hz, 1H), 7.73 (brs, 1H); ESI-MS (m/z) 177.08 $(M+H)^+$ Step 3: 6-Methoxy-2-methyl-3,4-dihydroisoquinolin-1(2H)-one

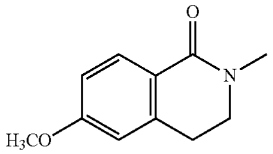

To a solution of 6-methoxy-3,4-dihydroisoquinolin-1(2H)-one (33 g, 186.4 mmol) in DMF (240 mL) was added sodium hydride (60% w/w, 11.18 g, 279.66 mmol). Methyl iodide (52.95 g, 372.89 mmol) was added to the mixture and stirred at RT for 2 h. The reaction mixture was quenched with water and extracted with ethyl acetate. The organic layer was separated and dried over anhydrous sodium sulphate. The solvent was filtered, concentrated and the residue thus obtained was purified by silica gel column chromatography to yield 35 g of the desired product. $^{1}$H NMR (400 MHz, DMSO-$d_6$) δ 2.99 (t, J=6.8 Hz, 2H), 3.56 (s, 3H), 3.56 (t, J=6.4 Hz, 2H), 3.85 (s, 3H), 6.67 (s, 1H), 6.35 (dd, J=2.4, 8.4 Hz, 1H), 8.04 (t, J=6.8 Hz, 1H).

Step 4: 6-Methoxy-2-methyl-7-nitro-3,4-dihydroisoquinolin-1(2H)-one

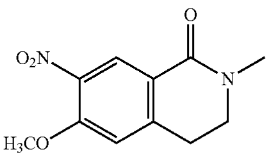

To a cooled sulfuric acid (100 mL) was slowly dropwise added fuming nitric acid (2.4 mL) at −20° C. and stirred for 20 min at same temperature. 6-methoxy-2-methyl-3,4-dihydroisoquinolin-1(2H)-one (10 g, 52.36 mmol) was added portion wise to the reaction mixture at −20° C. The mixture was stirred at −20° C. for 60 min. The mixture was quenched with ice-cooled water and extracted with ethyl acetate. The combined organic layers were dried over anhydrous sodium sulphate and the solvents were removed under reduced pressure. The crude was stirred in diethyl ether/ethyl acetate (1:1, 100 mL) for 16 h. The solid obtained was filtered to yield 9 g of the desired product. $^{1}$H NMR (400 MHz, DMSO-$d_6$) δ 3.02 (s, 3H), 3.06 (t, J=6.8 Hz, 2H), 3.58 (t, J=6.8 Hz, 2H), 3.98 (s, 3H), 7.33 (s, 1H), 8.26 (s, 1H); ESI-MS (m/z) 237 $(M+H)^+$.

Step 5: 7-Amino-6-methoxy-2-methyl-3,4-dihydroisoquinolin-1(2H)-one (Intermediate B1-a)

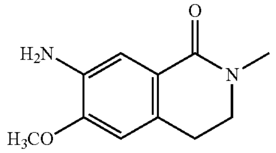

A solution of 6-methoxy-2-methyl-7-nitro-1,2,3,4-tetrahydroisoquinoline (9 g, 38.14 mmol) in methanol (200 mL) was subjected to hydrogenation in the presence of 10% palladium on carbon (3 g) under 50 psi of hydrogen pressure at RT for 3 h. The mixture was filtered and the filtrate was concentrated under reduced pressure. The solid obtained was triturated with n-pentane and dried under vacuum to yield 7 g of the desired product. $^{1}$H NMR (400 MHz, DMSO-$d_6$) δ 2.83 (t, J=6.8 Hz, 2H), 2.96 (s, 3H), 3.46 (d, J=6.40 Hz, 2H), 3.82 (s, 3H), 5.64 (br s, 2H), 6.73 (s, 1H), 7.27 (s, 1H); ESI-MS (m/z) 207 $(M+H)^+$.

Step 6: 6-Methoxy-2-methyl-1,2,3,4-tetrahydroisoquinolin-7-amine

To a stirred solution of 7-amino-6-methoxy-2-methyl-3,4-dihydroisoquinolin-1(2H)-one (7 g, 33.98 mmol) in THE (80 mL) at 0° C. was added lithium aluminum hydride (3.2 g, 84.95 mmol) portion wise and allowed to stirred at RT for 30 min. The reaction mixture was heated at 70° C. for 2 h. The mixture was cooled to 0° C. and quenched with ice-cooled water and 15% aq. sodium hydroxide solution. The mixture was diluted with ethyl acetate and filtered through celite bed. The filtrate was dried over anhydrous sodium sulphate and concentrated under reduced pressure to yield 3.5 g of the desired product. $^{1}$H NMR (400 MHz, DMSO-$d_6$) δ 2.28 (s, 3H), 2.48-2.51 (m, 2H), 2.65 (t, J=5.6 Hz, 2H), 3.27 (s, 2H), 3.70 (s, 3H), 4.45 (s, 2H), 6.27 (s, 1H), 6.49 (s, 1H); ESI-MS (m/z) 193 $(M+H)^+$.

The chemical structure, name and analytical data of the intermediates were prepared by the procedure described above are given in below Table 2.

TABLE 2

Structure, chemical name and analytical data of Intermediates B2 to B9.

| Intermediate No. | Structure | IUPAC Name and Analytical data |
| --- | --- | --- |
| Intermediate B2 | 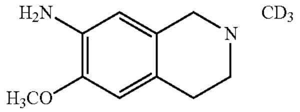 | 6-Methoxy-2-(methyl-$d_3$)-1,2,3,4-tetrahydroisoquinolin-7-amine; $^1$H NMR (400 MHz, DMSO-$d_6$) δ 2.45-2.50 (m, 2H), 2.65 (t, J = 5.6 Hz, 2H), 3.27 (s, 2H) 3.70 (s, 3H), 4.45 (brs, 2H), 6.27 (s, 1H), 6.49 (s, 1H); ESI-MS (m/z) 196 $(M + H)^+$ |
| Intermediate B3 | 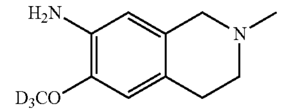 | 6-(Methoxy-$d_3$)-2-methyl-1,2,3,4-tetrahydroisoquinolin-7-amine; $^1$H NMR (400 MHz, DMSO-$d_6$) δ 2.29 (s, 3H), 2.45-2.52 (m, 2H), 2.65 (t, J = 5.6 Hz, 2H), 3.28 (s, 2H), 4.45 (brs, 2H), 6.28 (s, 1H), 6.49 (s, 1H); ESI-MS (m/z) 196.2 $(M + H)^+$ |
| Intermediate B4 | 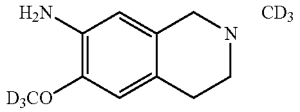 | 6-(Methoxy-$d_3$)-2-(methyl-$d_3$)-1,2,3,4-tetrahydroisoquinolin-7-amine: $^1$H NMR (400 MHz DMSO-$d_6$)) δ 2.48-2.50 (m, 2H), 2.63-2.66 (m, 2H), 3.25-3.26 (m, 2H), 4.45(brs, 2H), 6.48 (s, 1H), 6.27(s, 1H); ESI-MS (m/z) 199.3 $(M + H)^+$ |
| Intermediate B5 | 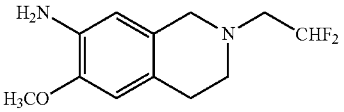 | 2-(2,2-Difluoroethyl)-6-methoxy-1,2,3,4-tetrahydroisoquinolin-7-amine: $^1$H NMR (400 MHz, DMSO-$d_6$) : 2.65 (t, J = 5.6 Hz, 2H), 2.74 (t, J = 5.2 Hz, 2H), 2.85 (td, J = 4.4 Hz, 15.6 Hz, 2H), 3.51 (s, 2H), 3.71 (s, 3H), 6.05-6.35 (m, 1H), 6.27 (s, 1H), 6.50 (s, 1H); ESI-MS (m/z) 243.1$(M + H)^+$ |
| Intermediate B6 | 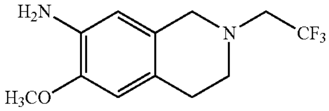 | 6-Methoxy-2-(2,2,2-trifluoroethyl)-1,2,3,4-tetrahydroisoquinolin-7-amine: $^1$H NMR (400 MHz, DMSO-$d_6$) : 2.64-2.68 (m, 2H), 2.82-2.85 (m, 2H), 3.24-3.40 (m, 2H), 3.61 (s, 2H), 3.71 (3, 3H), 4.49 (brs, 2H), 6.28 (s, 1H), 6.51 (s, 1H); ESI-MS (m/z) 261.1 $(M + H)^+$ |
| Intermediate B7 | 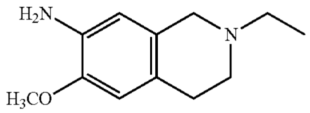 | 2-Ethyl-6-methoxy-1,2,3,4-tetrahydro isoquinolin-7-amine; $^1$H NMR (400 MHz, DMSO-$d_6$) δ 1.06 (t, J = 7.2 Hz, 3H), 2.40-2.42 (m, 2H), 2.44-2.51 (m, 2H), 2.56-2.65 (m, 2H), 3.32-3.35 (m, 2H), 3.70 (s, 3H), 4.45 (s, 2H), 6.28 (s, 1H), 6.48 (s, 1H); ESI-MS (m/z) 207.3 $(M + H)^+$ |
| Intermediate B8 | 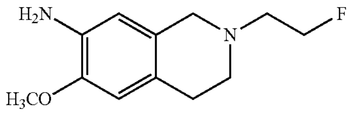 [SMILES: COc1cc2c(cc1N)CN(CCF)CC2] | 2-(2-Fluoroethyl)-6-methoxy-1,2,3,4-tetrahydroisoquinolin-7-amine; $^1$H NMR (400 MHz, DMSO-$d_6$) : δ 2.65-2.68 (m, 4H), 2.70-2.71(m, 1H), 2.76-2.78 (m, 1H), 3.43 (s, 2H), 3.71 (s, 3H), 4. 46 (bs, 2H), 4.52-4.54 (m, 1H), 4.64-4.66 (m, 1H), 6.28 (s, 1H), 6.49 (s, 1H); ESI-MS (m/z) 224.5 $(M)^+$ |
| Intermediate B9 | 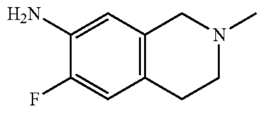 | 6-fluoro-2-methyl-1,2,3,4-tetrahydro isoquinolin-7-amine; $^1$H NMR (400 MHz, DMSO-$d_6$) δ 2.28 (s, 3H), 2.48-2.51 (m, 2H), 2.61-2.64 (m, 2H), 3.29 (s, 2H), 4.85 (bs, 2H), 6.72 (d, J = 12.4 Hz, 1H), 6.42 (d, J = 9.2 Hz, 1H); ESI-MS (m/z) 181 $(M + H)^+$ |

Intermediate B10 tert-Butyl 7-amino-6-methoxy-3,4-dihydroisoquinoline-2(1H)-carboxylate

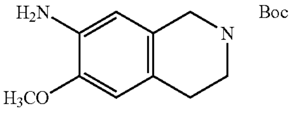

Step 1: 6-Methoxy-7-nitro-3,4-dihydroisoquinolin-1(2H)-one

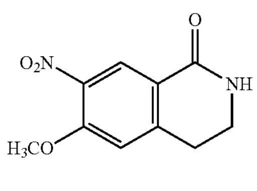

To a cooled sulfuric acid (256 mL) was slowly dropwise added fuming nitric acid (6.65 mL) at −20° C. and stirred for 20 min at same temperature. 6-methoxy-3,4-dihydroisoquinolin-1(2H)-one (25.6 g, 52.36 mmol) at −20° C. was added to the reaction mixture and stirred for 60 min. The reaction mixture was quenched with ice-cooled water. The solid obtained was filtered and washed with water and dried. The crude was purified by silica gel column chromatography to yield 18.05 g of the desired product. $^1$H NMR (400 MHz, DMSO-$d_6$) δ 3.02 (t, J=6.4 Hz, 2H), 3.39-3.43 (m, 2H), 3.98 (s, 3H), 7.35 (s, 1H), 8.09 (brs, 1H), 8.25 (s, 1H); ESI-MS (m/z) 222.0 $(M+H)^+$ Step 2: 6-Methoxy-7-nitro-1,2,3,4-tetrahydroisoquinoline

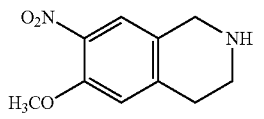 [SMILES: COc1cc2c(cc1[N+](=O)[O-])CNCC2]

To a solution of 6-methoxy-7-nitro-3,4-dihydroisoquinolin-1(2H)-one (18 g, 81.08 mmol) in THF (250 mL) at 0° C. was added Borane-THF (1M) (324 mL, 324 mmol) under nitrogen atmosphere. The reaction mixture was heated at 65° C. for 18 h. The reaction was treated with 6N HCl (120 mL) at 0° C. and heated at 80° C. for 60 min. The reaction mixture was basified with saturated aq. $K_2CO_3$ solution and extracted thrice with ethyl acetate. The combined organic layers were washed with water followed by brine. The solution was dried over anhydrous sodium sulphate, filtered and concentrated under reduced pressure. The residue thus obtained was purified by silica gel column chromatography to yield 9.65 g of the desired product. $^1$H NMR (400 MHz, DMSO-$d_6$) δ 2.91 (t, J=6.0 Hz, 2H), 3.13 (t, J=6.0 Hz, 2H), 3.89 (s, 3H), 3.99 (s, 2H), 7.15 (s, 1H), 7.71 (s, 1H); ESI-MS (m/z) 208.8 $(M+H)^+$ Step 3: tert-Butyl 6-methoxy-7-nitro-3,4-dihydroisoquinoline-2(1H)-carboxylate

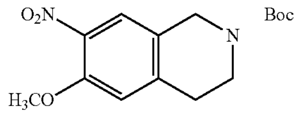 [SMILES: COc1cc2c(cc1[N+](=O)[O-])CNCC2 ; "Boc"]

To a stirred solution of 6-methoxy-7-nitro-1,2,3,4-tetrahydroisoquinoline (9.6 g, 46.15 mmol) in dichloromethane (100 mL) were added triethylamine (9.7 mL, 69.22 mmol) followed by di-tert-butyl bicarbonate (11.06 g, 50.76 mmol) and the mixture was stirred at RT for 16 h. The reaction mixture was diluted with water. The aqueous mixture was extracted twice with chloroform and the combined organic extracts were washed with brine solution. The organic layer was dried over anhydrous sodium sulphate, filtered and concentrated under reduced pressure. The residue thus obtained was purified by silica gel column chromatography to yield 8.61 g of the desired product. $^1$H NMR (400 MHz, DMSO-$d_6$) δ 1.43 (s, 9H), 2.85 (t, J=6.0 Hz, 2H), 3.57 (t, J=5.6 Hz, 2H), 3.89 (s, 3H), 4.48 (s, 2H), 7.18 (s, 1H), 7.79 (s, 1H); ESI-MS (m/z) 308.8 $(M+H)^+$.

Step 4: tert-Butyl 7-amino-6-methoxy-3,4-dihydroisoquinoline-2(1H)-carboxylate

To a stirred solution of tert-butyl-6-methoxy-7-nitro-3,4-dihydroisoquinoline-2(1H)-carboxylate (6.0 g, 19.45 mmol) in methanol (120 mL) was subjected to hydrogenation in the presence of 10% palladium on carbon (3 g) at 35 psi hydrogen pressure stirred at RT for 3 h. The mixture was filtered and the filtrate was concentrated under reduced pressure. The solid was triturated with n-pentane and dried under vacuum to yield 4.75 g of the desired product. $^1$H NMR (400 MHz, DMSO-$d_6$) δ 1.43 (s, 9H), 2.61 (t, J=6.0 Hz, 2H), 3.50 (t, J=5.6 Hz, 2H), 3.72 (s, 3H), 4.29 (brs, 2H), 4.55 (s, 2H), 6.36 (s, 1H), 6.55 (s, 1H); ESI-MS (m/z) 279.1 $(M+H)^+$.

Intermediate B11

6-(Methoxy-$d_3$)-3,4-dihydroisoquinolin-1(2H)-one

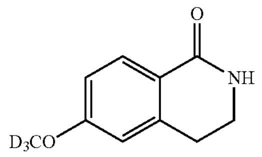

Step 1: 6-Hydroxy-3,4-dihydroisoquinolin-1(2H)-one

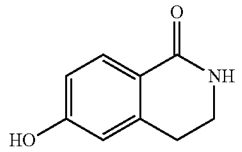 [SMILES: O=C1NCCc2cc(O)ccc21]

To a stirred solution of 6-Methoxy-3,4-dihydroisoquinolin-1(2H)-one (10 g, 56.49 mmol) in aqueous 47% HBr (150 mL) was heated to 100° C. for 18 h. The solvent was evaporated under vacuum and the residue obtained was basified with saturated sodium bicarbonate solution at 0° C. and stirred for 10 min. The solid obtained was filtered through sintered funnel, washed with water and dried under reduced pressure to yield 6.01 g of the desired product. $^1$H NMR (400 MHz, DMSO-$d_6$) δ 2.79-2.81 (m, 2H), 3.29-3.31 (m, 2H), 6.62 (s, 1H), 6.68-6.70 (m, 1H), 7.61 (bs, 1H), 7.67 (d, J=8.4 Hz, 1H), 9.99 (bs, 1H); ESI-MS (m/z) 163.2 $(M+H)^+$.

Step 2: 6-(Methoxy-$d_3$)-3,4-dihydroisoquinolin-1(2H)-one

To a stirred solution of 6-hydroxy-3, 4-dihydroisoquinolin-1(2H)-one (12.0 g, 73.61 mmol) in DMF (120 mL) was added $K_2CO_3$ (11.2 g, 80.97 mmol) and stirred at RT for 20 min. Methyl-d3 iodide (5.3 mL, 80.98 mmol) was added and stirred for overnight. The reaction mixture was diluted with water and extracted with ethyl acetate. The organic layer was dried over anhydrous sodium sulphate and concentrated. The residue obtained was stirred in diethyl ether, filtered and dried under vacuum to yield 11.56 g of the desired product. $^1$H NMR (400 MHz, DMSO-$d_6$) δ 2.86-2.89 (m, 2H), 3.34-3.65 (m, 2H), 6.84-6.89 (m, 2H), 7.76 (s, 1H), 7.83 (s, 1H); ESI+MS (m/z) 181.1 $(M+H)^+$.

The analytical data of the intermediate prepared by following the procedure described above are given in below Table 3.

TABLE 3

Structure, chemical name and analytical data of Intermediate B12.

| Intermediate No. | Structure | Chemical Name and Analytical data |
|---|---|---|
| Intermediate B12 | 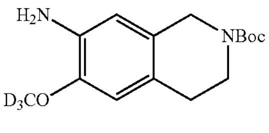 | tert-Butyl7-amino-6-(methoxy-$d_3$)-3,4-dihydroisoquinoline-2(1H)-carboxylate; $^1H$ NMR (400 MHz, DMSO-$d_6$) δ 1.42 (s, 9H), 2.60-2.63 (m, 2H), 3.47-3.50 (m, 2H), 4.29 (s, 2H), 5.00 (bs, 2H), 6.40 (s, 1H), 6.57 (s, 1H); ESI-MS (m/z) 282.1 $(M + H)^+$ |

Intermediate B13 tert-Butyl 7-amino-6-(methoxy-$d_3$)-3,4-dihydroisoquinoline-2(1H)-carboxylate-1,1-$d_2$

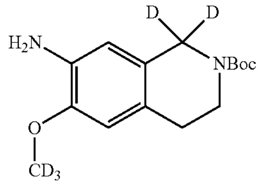 [SMILES: [2H]C([2H])([2H])Oc1cc2c(cc1N)C([2H])([2H])N(C(=O)OC(C)(C)C)CC2]

Step 1: 6-(Methoxy-$d_3$)-1,2,3,4-tetrahydroisoquinoline-1,1-$d_2$

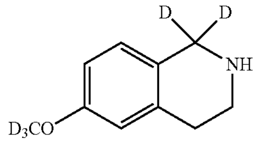

To a stirred suspension of Lithium aluminum deuteride (465 mg, 11.11 mmol) in THE (20 mL) was added 6-(Methoxy-$d_3$)-3,4-dihydroisoquinolin-1(2H)-one (500 mg, 2.77 mmol) at 0° C. and heated to 120° C. for 16 h in a sealed tube. The reaction mixture was quenched with slowly with 5 ml of water followed by 0.5 mL 15% NaOH solution and 1.5 mL of water and stirred for 30 min at RT. The reaction mixture was diluted with ethyl acetate and filtered through celite bed. The filtrate obtained was concentrated under vacuum to yield 476 mg of the desired product. $^1H$ NMR (400 MHz, DMSO-$d_6$) δ 2.64 (t, J=6 Hz, 2H), 2.89 (t, J=6 Hz, 2H), 6.62 (d, J=2.4 Hz, 1H), 6.70-6.80 (m, 1H), 6.9 (d, J=2.4 Hz, 1H); ESI-MS (m/z) 169 $(M+H)^+$.

Step 2: 2,2,2-Trifluoro-1-(6-(methoxy-$d_3$)-3,4-dihydroisoquinolin-2(1H)-yl-1,1-$d_2$)ethanone

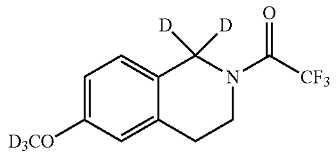

To a stirred solution of 6-(methoxy-$d_3$)-1,2,3,4-tetrahydroisoquinoline-1,1-$d_2$ (600 mg, 3.64 mmol) in DCM (20 mL) were added pyridine (875 μL, 10.843 mmol) followed by TFAA (1.5 mL, 10.84 mmol) at 0° C. The reaction mixture was stirred at RT for overnight. The reaction mixture was diluted with water and extracted with ethyl acetate. The organic layer was separated, dried over anhydrous sodium sulphate and concentrated. The residue obtained was purified by column chromatography to yield 435 mg of the desired product. $^1H$ NMR (400 MHz, DMSO-$d_6$) δ 2.80-2.95 (m, 2H), 3.70-3.85 (m, 2H), 6.70-6.85 (m, 2H), 7.15-7.25 (m, 1H); ESI-MS (m/z) 265.1 $(M+H)^+$.

Step 3: 2,2,2-Trifluoro-1-(6-(methoxy-$d_3$)-7-nitro-3,4-dihydroisoquinolin-2(1H)-yl-1,1-$d_2$) ethan-1-one

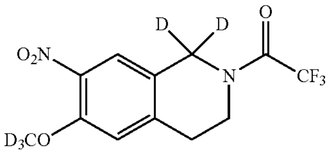

To a stirred solution of 2,2,2-trifluoro-1-(6-(methoxy-$d_3$)-3,4-dihydroisoquinolin-2(1H)-yl-1,1-$d_2$)ethanone (700 mg, 2.64 mmol) in TFA (12 mL) was added solution of 90% $HNO_3$ (203 mg, 2.905 mmol) in TFA (3 mL) dropwise at 0° C. and stirred for 1 h. The reaction mixture was basified with aqueous sodium bicarbonate and extracted with ethyl acetate. The organic layer was separated, dried over anhydrous sodium sulphate and concentrated. The residue obtained was purified by column chromatography to yield 372 mg of the desired product. $^1H$ NMR (400 MHz, DMSO-$d_6$) δ 2.95-3.10 (m, 2H), 3.80-3.95 (m, 2H), 7.24 (s, 1H), 7.90 (s, 1H).

Step 4: 6-(Methoxy-$d_3$)-7-nitro-1,2,3,4-tetrahydroisoquinoline-1,1-$d_2$

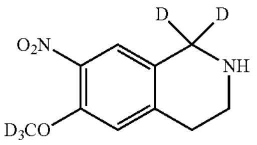

To a stirred solution of 2,2,2-trifluoro-1-(6-(methoxy-$d_3$)-7-nitro-3,4-dihydroisoquinolin-2(1H)-yl-1,1-$d_2$)ethan-1-one (360 mg, 1.165 mmol) in THE (7 mL) was added solution of NaOH (79 mg, 1.98 mmol) in water (2 mL) and stirred at RT for overnight. The reaction mixture was diluted with water and extracted with DCM. The organic layer was separated and dried over anhydrous sodium sulphate. The solvent was filtered and concentrated under reduced pressure to yield 257 mg of the desired product. $^1$H NMR (400 MHz, DMSO-$d_6$) δ 2.70-2.80 (m, 2H), 2.85 (brs, 1H), 2.90-3.00 (m, 2H), 7.05 (s, 1H), 7.59 (s, 1H)

Step 5: tert-Butyl 6-(methoxy-$d_3$)-7-nitro-3,4-dihydroisoquinoline-2(1H)-carboxylate-1,1-$d_2$

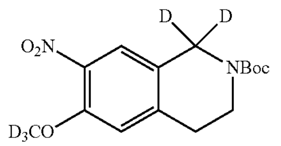

To a stirred solution of 6-(methoxy-$d_3$)-7-nitro-1,2,3,4-tetrahydroisoquinoline-1,1-$d_2$ (250 mg, 1.173 mmol) in DCM (5 mL) were added DIPEA (404 μl, 2.346 mmol) followed by Boc anhydride (383 mg, 1.76 mmol) and stirred at RT for overnight. The reaction mixture was diluted with water and extracted with ethyl acetate. The organic layer was dried over anhydrous sodium sulphate and concentrated. The residue obtained was purified by silica gel chromatography to yield 247 mg of the desired compound. $^1$H NMR (400 MHz, DMSO-$d_6$) δ 1.42 (s, 9H), 2.80-2.95 (m, 2H), 3.50-3.65 (m, 2H), 7.17 (s, 1H), 7.79 (s, 1H).

Step 6: tert-Butyl 7-amino-6-(methoxy-$d_3$)-3,4-dihydroisoquinoline-2(1H)-carboxylate-1,1-$d_2$ To a stirred solution of tert-butyl-6-(methoxy-$d_3$)-7-nitro-3,4-dihydroisoquinoline-2(1H)-carboxylate-1,1-$d_2$ (240 mg, 0.766 mmol) in MeOH (10 mL) was added Pd/C (10%, 100 mg) at RT. The reaction mixture was stirred at RT for 2 h under hydrogen atmosphere (balloon pressure). The reaction mixture was filtered through celite bed and the filtrate obtained was concentrated under reduced pressure to yield 195 mg of desired product. $^1$H NMR (400 MHz, DMSO-$d_6$) δ 1.41 (s, 9H), 2.6 (t, J=6 Hz, 2H), 3.40-3.55 (m, 2H), 4.62 (brs, 2H), 6.37 (s, 1H), 6.55 (s, 1H); ESI-MS (m/z) 228.1 $(M-55)^+$.

Intermediate B14

6-(Difluoromethoxy)-2-methyl-1,2,3,4-tetrahydroisoquinolin-7-amine

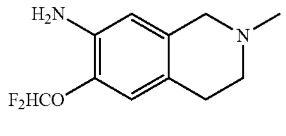

Step 1: tert-Butyl 6-hydroxy-7-nitro-3,4-dihydroisoquinoline-2(1H)-carboxylate

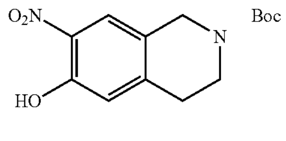 [SMILES: O=[N+]([O-])c1cc2c(cc1O)CCNC2 ; "Boc"]

To a stirred solution of tert-butyl 6-methoxy-7-nitro-3,4-dihydroisoquinoline-2(1H)-carboxylate (1.2 g) in 47% aq. HBr (20 mL) was heated to 120-130° C. for 18 h. The reaction mixture was concentrated under reduced pressure. The compound obtained 7-nitro-1, 2, 3, 4-tetrahydroisoquinolin-6-ol (1 g, 3.63 mmol) was dissolved in dichloromethane (20 mL) were added DIPEA (1.8 g, 14.52 mmol) followed by di-tert-butyl bicarbonate (801 mg, 4 mmol).

The reaction mixture was mixture was stirred at RT for 18 h. The reaction mixture was concentrated under reduced pressure. The residue thus obtained was purified by silica gel column chromatography to yield 700 mg of the desired product. $^1$H NMR (400 MHz, DMSO-$d_6$) δ 1.42 (s, 9H), 2.50-2.51 (m, 2H), 3.32-3.34 (m, 2H), 4.46 (brs, 2H), 6.92 (s, 1H), 7.80 (s, 1H), 10.73 (s, 1H); ESI-MS (m/z) 295.42 $(M+H)^+$.

Step 2: tert-Butyl 6-(difluoromethoxy-7-nitro-3,4-dihydroisoquinoline-2(1H)-carboxylate

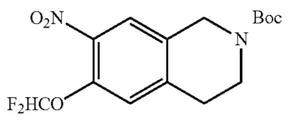

To a stirred solution of tert-butyl 6-hydroxy-7-nitro-3,4-dihydroisoquinoline-2(1H)-carboxylate (25 mg, 0.0085 mmol) in acetonitrile (2 mL) at 0° C. were added aqueous KOH (95 mg, 1.7 mmol) and followed by addition of Bromodifluoromethyl diethyl phosphate (45 mg, 0.170 mmol) at 0° C. and stirred at 0° C. for 30 min and at RT for 2 h. The mixture was quenched with water and extracted with ethyl acetate. The combined organic layers were dried over anhydrous sodium sulphate and the solvents were removed under reduced pressure. The residue thus obtained was purified by silica gel column chromatography to yield 19 mg of the desired product. $^1$H NMR (400 MHz, DMSO-$d_6$) δ (400 MHz, DMSO-$d_6$) δ 1.43 (s, 9H), 2.87-2.90 (m, 2H), 3.55-3.58 (m, 2H), 4.57 (bs, 2H), 7.29 (t, J=72.8 Hz, 1H), 7.35 (s, 1H), 8.00 (s, 1H).

Step 3: 6-(Difluoromethoxy)-2-methyl-7-nitro-1,2,3,4-tetrahydroisoquinoline

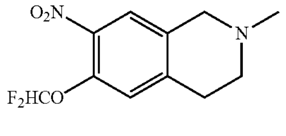 [SMILES: CN1CCc2cc(OC(F)F)c([N+](=O)[O-])cc2C1]

To a stirred solution of tert-butyl 6-(difluoromethoxy)-7-nitro-3,4-dihydroisoquinoline-2(1H)-carboxylate (300 mg) in DCM (10 mL) was added TFA (1 mL) and stirred at RT for 1 h. The reaction mixture was concentrated and neutralized with sat. $NaHCO_3$. The aqueous layer was extracted thrice with 10% DCM/MeOH. The organic layer was separated, dried over anhydrous sodium sulphate and concentrated. The residue thus obtained was taken for next step. To a stirred solution of 6-(difluoromethoxy)-7-nitro-1,2,3,4-tetrahydroisoquinoline (250 mg, 1.024 mmol) in DCM (5 mL) was added 37% formaldehyde solution (1 mL) and drop of acetic acid and stirred at RT for 30 min. Sodium cyanoborohydride (244 mg, 4.096) was added to this mixture at 0° C. and stirred at RT for 18 h. The mixture was quenched with sat. $NaHCO_3$ and extracted thrice with 10% DCM/MeOH. The combined organic layers were dried over anhydrous sodium sulphate and concentrated under reduced pressure. The residue obtained was purified by silica gel column chromatography to yield 130 mg of the desired product. $^1$H NMR (400 MHz, DMSO-$d_6$) δ 2.35 (s, 3H), 2.59-2.62 (m, 2H), 2.90-2.93 (m, 2H), 3.52 (brs, 2H), 7.28 (s, 1H), 7.28 (t, J=72 Hz, 1H), 7.85 (s, 1H); ESI-MS (m/z) 259.29 $(M+H)^+$.

Step 4: 6-(Difluoromethoxy)-2-methyl-1,2,3,4-tetrahydroisoquinolin-7-amine

To a stirred solution of 6-(difluoromethoxy)-2-methyl-7-nitro-1,2,3,4-tetrahydroisoquinoline (130 mg, 0.503 mmol) in Methanol/DCM (13 mL) was subjected to hydrogenation in the presence of palladium on carbon (75 mg) in a parr shaker at 50-60 psi hydrogen pressure for 2 h. The reaction mixture was filtered and the filtrate obtained was concentrated under reduced pressure. The solid obtained was triturated with n-pentane and dried under vacuum to yield 110 mg of the desired product. $^1$H NMR (400 MHz, DMSO-$d_6$) δ 2.68 (s, 3H), 2.79-2.83 (m, 2H), 3.11-3.16 (m, 2H), 3.92 (bs, 2H), 4.38 (bs, 2H), 6.48 (s, 1H), 6.82 (s, 1H) 7.00 (t, J=74.8 Hz, 1H); ESI-MS (m/z) 229.11 $(M+H)^+$.

Intermediate B15

6-Methoxy-1,2-dimethyl-1,2,3,4-tetrahydroisoquinolin-7-amine

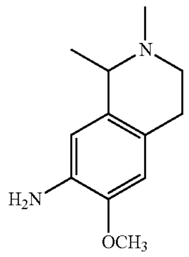

Step 1: N-(3-Methoxyphenethyl) acetamide

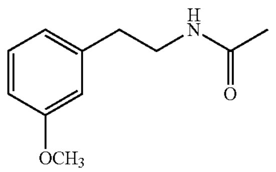

To a stirred solution of 2-(3-methoxyphenyl)ethanamine (5 g, 33 mmol) in dichloromethane (100 mL) at 0° C. was added triethylamine (14 mL, 99 mmol) followed by acetyl chloride (3.53 mL, 49.60 mmol). The mixture was stirred at RT for 2 h. The reaction mixture was acidified using 1N HCl and extracted with DCM. The organic layer was separated and dried over anhydrous sodium sulphate. The solvent was removed under reduced pressure to yield 6.7 g of the desired product. $^1$H NMR (400 MHz, DMSO-d6) δ 1.78 (s, 3H), 2.69 (t, J=7.6 Hz, 2H), 3.27-3.22 (m, 2H), 3.73 (s, 3H), 6.77-6.76 (m, 3H), 7.22-7.18 (m, 1H), 7.91 (bs, 1H); ESI-MS (m/z) 194.2 $(M+H)^+$ Step 2: 6-Methoxy-1-methyl-3,4-dihydroisoquinoline

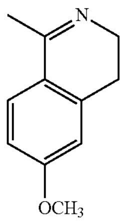

To a stirred solution of N-(3-methoxyphenethyl)acetamide (4.0 g, 20.72 mmol) in toluene (80 mL) at 40° C. was added $POCl_3$ (3.80 mL, 41.45 mmol) dropwise and heated to reflux for 2 h.

The reaction mixture was cooled to 0° C. and quenched with water and washed with DCM. The aqueous layer was basified with 50% NaOH solution and extracted with DCM. The organic layer was dried over anhydrous sodium sulphate and the solvent was removed under reduced pressure to yield 2.51 g of the desired product. $^1$H NMR (400 MHz, DMSO-d6) δ 2.24 (s, 3H), 2.62 (t, J=7.6 Hz, 2H), 3.49 (t, J=7.6 Hz, 2H), 3.79 (s, 3H), 6.86-6.82 (m, 2H), 7.48 (d, J=8.4 Hz, 1H); ESI-MS (m/z) 176.2 $(M+H)^+$ Step 3: 6-Methoxy-1,2-dimethyl-3,4-dihydroisoquinolin-2-ium iodide

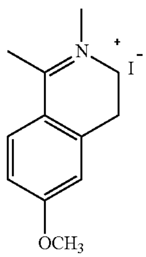

To a stirred solution of 6-methoxy-1-methyl-3,4-dihydroisoquinoline (1.5 g, 8.56 mmol) in acetone (30 mL) was added methyl iodide (0.590 mL, 9.41 mmol) and stirred at RT for 18 h. The solvent was removed under reduced pressure to yield 2.3 g of the desired product. $^1$H NMR (400 MHz, DMSO-d6) δ 2.75 (s, 3H), 3.13 (t, J=7.6 Hz, 2H), 3.65 (s, 3H), 3.91 (s, 3H), 3.99 (t, J=7.2 Hz, 2H), 7.07 (s, 1H), 7.06 (d, J=2.8 Hz, 1H), 8.07 (d, J=9.6 Hz, 1H), ESI-MS (m/z) 190.2 $(M+H)^+$.

Step 4: 6-Methoxy-1,2-dimethyl-1,2,3,4-tetrahydroisoquinoline

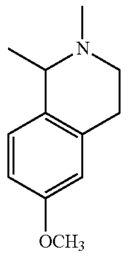

To a stirred solution of 6-Methoxy-1,2-dimethyl-3,4-dihydroisoquinolin-2-ium iodide (1.0 g, 3.154 mmol) in methanol (20 mL) at 0° C. was slowly added $NaBH_4$ (239 mg, 6.309 mmol) portion wise and stirred at RT for overnight. The reaction mixture was diluted with water and extracted with DCM. The organic layer was dried over anhydrous sodium sulphate and the solvent was removed under reduced pressure to yield 615 mg of the desired product. $^1H$ NMR (400 MHz, $CDCl_3$) δ 1.40 (d, J=6.4 Hz, 3H), 2.49 (s, 3H), 2.67-2.61 (m, 1H), 2.90-2.79 (m, 2H), 3.07-3.01 (m, 1H), 3.59-3.55 (m, 1H), 3.80 (s, 3H); ESI-MS (m/z) 192.2 $(M+H)^+$.

Step 5: 6-Methoxy-1,2-dimethyl-7-nitro-1,2,3,4-tetrahydroisoquinoline

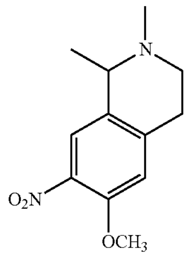

To a stirred solution of 6-methoxy-1,2-dimethyl-1,2,3,4-tetrahydroisoquinoline (600 mg, 3.14 mmol) in Conc. $H_2SO_4$ (9 mL) at 0° C. was added guanidine nitrate (326 mg, 2.67 mmol) and stirred for 1 h. The reaction mixture was basified with saturated $NaHCO_3$ solution and extracted with ethyl acetate. The organic layer was dried over anhydrous sodium sulphate and filtered. The solvent was removed under reduced pressure to yield 207 mg of the desired product. $^1H$ NMR (400 MHz, $CDCl_3$) δ 1.41 (d, J=6.8 Hz, 3H), 2.49 (s, 3H), 2.69-2.63 (m, 1H), 3.08-2.85 (m, 3H), 3.61 (m, 1H), 3.95 (s, 3H), 6.78 (s, 1H), 7.71 (s, 1H), ESI-MS (m/z) 237.2 $(M+H)^+$.

Step 6: 6-Methoxy-1,2-dimethyl-1,2,3,4-tetrahydroisoquinolin-7-amine

To a stirred solution of 6-methoxy-1,2-dimethyl-7-nitro-1,2,3,4-tetrahydroisoquinoline (220 mg, 0.932 mmol) in Methanol (5 mL) was subjected to hydrogenation in the presence of 10% Pd/C (100 mg) under hydrogen atmosphere for 1 h. The reaction mixture was diluted with methanol and filtered through celite bed. The filtrate obtained was concentrated under reduced pressure to yield 191 mg of the desired product. $^1H$ NMR (400 MHz, $CDCl_3$) δ 1.40 (d, J=6.8 Hz, 3H), 2.49 (s, 3H), 2.70-2.75 (m, 2H), 2.81-2.93 (m, 2H), 3.09-3.10 (m, 1H), 3.86 (s, 3H), 4.50 (brs, 2H), 6.48 (s, 1H), 6.50 (s, 1H); ESI-MS (m/z) 207.2 $(M+H)^+$ Intermediate B15 (a-b)

6-Methoxy-1,2-dimethyl-1,2,3,4-tetrahydroisoquinolin-7-amine (Isomer-1 & Isomer-2)

B15-a (Isomer-1)

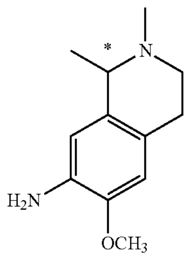 [SMILES: COc1cc2c(cc1[N+](=O)[O-])C(C)N(C)CC2]

B15-b (Isomer-2)

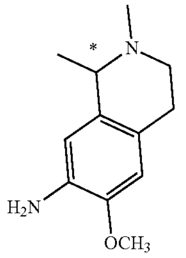

Racemic Methoxy-1,2-dimethyl-1,2,3,4-tetrahydroisoquinolin-7-amine (1.2 g) was purified by Supercritical Fluid Chromatography (SFC) using (S,S)-Whelk-O 1((4.6×150) mm, 5μ) column with 0.1% ammonia/methanol as mobile phase (wavelength 210-400 nm) to yield Isomer-1 (400 mg) and Isomer-2 (325 mg).

B15-a Isomer 1): $^1H$ NMR (400 MHz, DMSO-d6) δ 1.37 (d, J=6.4 Hz, 3H), 2.50 (s, 3H), 2.72-2.78 (m, 2H), 2.80-2.93 (m, 2H), 3.15-3.22 (m, 1H), 3.85 (s, 3H), 4.58 (brs, 2H), 6.42 (s, 1H), 6.52 (s, 1H); ESI-MS (m/z) 207.2 $(M+H)^+$ B15-b Isomer 2): $^1H$ NMR (400 MHz, DMSO-d6) δ 1.37 (d, J=6.4 Hz, 3H), 2.50 (s, 3H), 2.76-2.78 (m, 2H), 2.85-2.93 (m, 2H), 3.19-3.22 (m, 1H), 3.80 (s, 3H), 4.58 (brs, 2H), 6.40 (s, 1H), 6.52 (s, 1H); ESI-MS (m/z) 207.2 $(M+H)^+$.

Intermediate B16

6-Methoxy-1,1,2-trimethyl-1,2,3,4-tetrahydroisoquinolin-7-amine

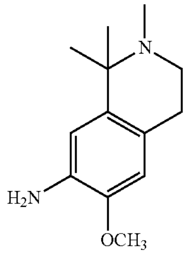 [SMILES: COc1cc2c(cc1N)C(C)(C)N(C)CC2]

Step 1: 6-Methoxy-1,1,2-trimethyl-1,2,3,4-tetrahydroisoquinoline

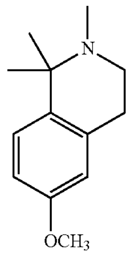

To a stirred solution of 6-methoxy-1,2-dimethyl-3,4-dihydroisoquinolin-2-ium iodide (800 mg, 2.52 mmol) in dry THF (8 mL) at −78° C. was slowly added methyl magnesium bromide (1.5 M solution in THF) (239 mg, 6.309 mmol) and stirred for 1 h. The reaction mixture was slowly warmed to RT and then stirred at RT for 2 days. The reaction mixture was diluted with water and extracted with ethyl acetate. The organic layer was dried over anhydrous sodium sulphate and filtered. The solvent was removed under reduced pressure to yield 697 mg of the desired product. $^1$H NMR (400 MHz, $CDCl_3$) δ 1.41 (s, 6H), 2.45 (s, 3H), 2.90-2.86 (m, 4H), 3.79 (s, 3H), 6.59 (d, J=2.4 Hz, 1H), 6.77 (dd, J=2.8 Hz, 8.8 Hz, 1H), 7.19 (d, J=8.8 Hz, 1H); ESI-MS (m/z) 206.2 $(M+H)^+$.

Step 2: 6-Methoxy-1,1,2-trimethyl-7-nitro-1,2,3,4-tetrahydroisoquinoline

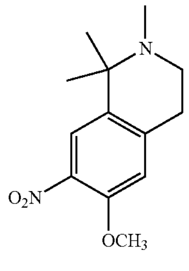 [SMILES: COc1cc2c(cc1[N+](=O)[O-])C(C)(C)N(C)CC2]

To a stirred solution of 6-methoxy-1,1,2-trimethyl-1,2,3,4-tetrahydroisoquinoline (550 mg, 2.68 mmol) in Conc $H_2SO_4$ (8 mL) at 0° C. was added guanidine nitrate (278 mg, 2.27 mmol) and stirred for 1 h. The reaction mixture was basified with saturated $NaHCO_3$ solution and extracted with ethyl acetate. The organic layer was dried over anhydrous sodium sulphate and filtered. The solvent was removed under reduced pressure to yield 117 mg of the desired product. $^1$H NMR (400 MHz, $CDCl_3$) δ1.42 (s, 3H), 2.46 (s, 2H), 2.91 (s, 2H), 3.94 (s, 3H), 6.74 (s, 1H), 7.84 (s, 1H), ESI-MS (m/z) 251.2 $(M+H)^+$.

Step 3: 6-Methoxy-1,1,2-trimethyl-1,2,3,4-tetrahydroisoquinolin-7-amine

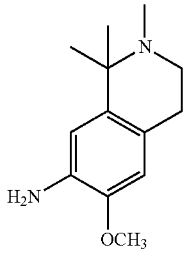 [SMILES: COc1cc2c(cc1N)C(C)(C)N(C)CC2]

To a stirred solution of 6-methoxy-1,1,2-trimethyl-7-nitro-1,2,3,4-tetrahydroisoquinoline (110 mg, 0.44 mmol) in methanol (5 mL) was subjected to hydrogenation in the presence of 10% Pd/C (20 mg) and stirred under hydrogen atmosphere for 1 h. The reaction mixture was diluted with methanol and filtered through celite bed. The filtrate obtained was concentrated under reduced pressure to yield 79 mg of the desired product. $^1$H NMR (400 MHz, $CDCl_3$) δ 1.42 (d, J=14.8 Hz, 6H), 2.45 (s, 3H), 2.80 (t, J=6.0 Hz, 2H), 2.91 (t, J=5.6 Hz, 2H), 3.83 (s, 3H), 3.86 (s, 2H), 6.46 (s, 1H), 6.62 (s, 1H), ESI-MS (m/z) 221.2 $(M+H)^+$.

Intermediate B17

6-Methoxy-2,3-dimethyl-1,2,3,4-tetrahydroisoquinolin-7-amine

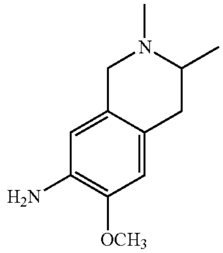

Step 1: (E)-N-(1-(3-Methoxyphenyl)propan-2-ylidene)-2-methylpropane-2-sulfinamide

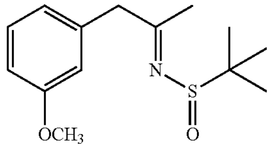 [SMILES: COc1cccc(C/C(C)=N/S(=O)C(C)(C)C)c1]

To a stirred solution of 1-(3-methoxyphenyl)propan-2-one (2.0 g, 12.18 mmol) and 2-methyl-2-propane sulphonamide (2.2 g, 18.27 mmol) in THE (50 mL) was added Titanium (IV) ethoxide (6.4 mL, 30.45 mmol) and heated to reflux for 18 h. The reaction mixture was diluted with ethyl acetate and quenched with water. The organic layer was separated and concentrated under reduced pressure to yield crude 3.26 g of the desired product. ESI-MS (m/z) 267.1 $(M)^+$.

Step 2: (E)-N-(1-(3-Methoxyphenyl)propan-2-ylidene)-2-methylpropane-2-sulfinamide

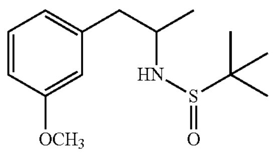 [SMILES: COc1cccc(CC(C)NS(=O)C(C)(C)C)c1]

To a stirred solution of (E)-N-(1-(3-methoxyphenyl)propan-2-ylidene)-2-methylpropane-2-sulfinamide (3.25 g, 12.17 mmol) in THE (60 mL) was sodium borohydride (920 mg, 24.34 mmol) and stirred at RT for overnight. The reaction mixture was quenched with methanol and concentrated. The residue obtained was diluted with ethyl acetate and washed with water. The organic layer was separated, dried over anhydrous sodium sulphate and concentrated. The residue obtained was purified by silica gel chromatography to yield 3.27 g of the desired compound. $^1$H NMR (400 MHz DMSO-$d_6$) δ 1.03 (d, J=6.4 Hz, 3H), 1.09 (s, 9H), 2.61-2.67 (m, 1H), 2.92-2.96 (m, 1H), 2.30-2.34 (m, 1H), 3.79 (s, 3H), 4.97 (d, J=6.4 Hz, 1H), 6.76-6.79 (m, 1H), 7.18-7.22 (m, 3H); ESI-MS (m/z) 270.1 $(M+H)^+$.

Step 3: 1-(3-Methoxyphenyl)propan-2-amine

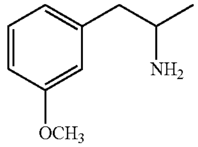

To a stirred solution of N-(1-(3-methoxyphenyl)propan-2-yl)-2-methylpropane-2-sulfinamide (3.26 g) in 1-4-dioxane (20 mL) was added 4 M HCl in dioxane (10 mL) and stirred at RT for overnight. The reaction mixture was basified with saturated sodium bicarbonate solution and extracted with ethyl acetate. The organic layer was dried over anhydrous sodium sulphate and concentrated under reduced pressure to yield 1.97 g of the desired product. ESI-MS (m/z) 166.2 $(M+H)^+$ Step 4: 6-Methoxy-3-methyl-1,2,3,4-tetrahydroisoquinoline formate

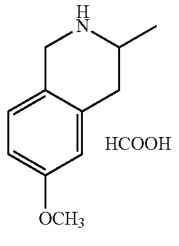

To a stirred solution of 1-(3-methoxyphenyl)propan-2-amine (1.96 g, 11.87 mmol) in formic acid (20 mL) was added formaldehyde (4.8 mL, 59.39 mmol) and stirred at RT for overnight. The solvent was evaporated under vacuum and the residue obtained was diluted with methanol (30 mL) added acetyl chloride dropwise (2 mL) and stirred at RT for 30 min. The solvent was evaporated under reduced pressure and the obtained residue was washed with ethyl acetate and diethyl ether. The solid obtained was filtered and dried to obtain yield 1.64 g of the desired product as formate salt. ESI-MS (m/z) 178.2 $(M+H)^+$ Step 5: 6-Methoxy-2,3-dimethyl-1,2,3,4-tetrahydroisoquinoline

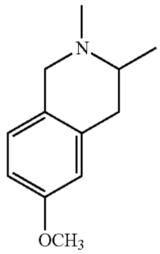

To a stirred solution of 6-methoxy-3-methyl-1,2,3,4-tetrahydroisoquinoline formate (1.6 g, 8.37 mmol) in methanol (20 mL) at 0° C. were added formaldehyde (4.8 mL), $NaBH_4$ (1.1 g, 29.3 mmol) portionwise and stirred at RT for 3 h. The reaction mixture was concentrated under reduced pressure and the residue obtained was basified using $NaHCO_3$ solution and extracted with ethyl acetate. The organic layer was dried over anhydrous sodium sulphate. The solvent was removed under reduced pressure to yield 1.2 g of the desired compound. $^1$H NMR (400 MHz $CDCl_3$) δ 1.18 (d, J=6 Hz, 3H), 2.42 (s, 3H), 2.61-2.70 (m, 2H), 2.81-2.83 (m, 1H), 3.49-3.53 (m, 1H), 3.80 (s, 3H), 6.62 (s, 1H), 6.69-6.72 (m, 1H), 6.95 (d, J=8.4 Hz, 1H); ESI-MS (m/z) 192.1 $(M+H)^+$ Step 6: 6-Methoxy-2,3-dimethyl-7-nitro-1,2,3,4-tetrahydroisoquinoline

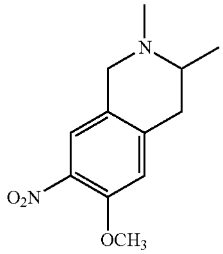 [SMILES: COc1cc2c(cc1[N+](=O)[O-])CN(C)C(C)C2]

To a stirred solution of 6-methoxy-2,3-dimethyl-1,2,3,4-tetrahydroisoquinoline (1 g, 5.23 mmol) in TFA (10 mL) at −10° C. was added Conc $HNO_3$ (0.218 mL) and stirred for 30 min and warmed to RT for 1 h. The reaction mixture was slowly quenched at 0° C. with 1 N NaOH solution and stirred for 5 min. The solid obtained was filtered and washed with water. The solid obtained was purified by silica gel column chromatography to yield 405 mg of the desired compound. $^1$H NMR (400 MHz DMSO-$d_6$)) δ 1.06 (d, J=6

Hz, 3H), 2.28 (s, 3H), 2.56-2.61 (m, 2H), 2.88-2.94 (m, 1H), 3.38-3.42 (m, 1H), 3.69-3.72 (m, 1H), 3.87 (s, 3H), 7.07 (s, 1H), 7.63 (s, 1H); ESI-MS (m/z) 237.1 $(M+H)^+$

Step 7: 6-Methoxy-2,3-dimethyl-1,2,3,4-tetrahydroisoquinolin-7-amine

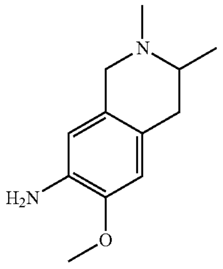

To a stirred solution of 6-methoxy-2,3-dimethyl-7-nitro-1,2,3,4-tetrahydroisoquinoline (390 mg, 164 mmol) in methanol (10 mL) was subjected to hydrogenation in the presence of 10% Pd/C (180 mg) and stirred under hydrogen atmosphere for 1 h. The reaction mixture was diluted with methanol, filtered through celite bed and washed with methanol. The filtrate obtained was concentrated under reduced pressure to yield 305 mg of the desired compound. $^1$H NMR (400 MHz DMSO-$d_6$)) δ 1.02 (d, J=6 Hz, 3H), 2.24 (s, 3H), 2.44-2.47 (m, 2H), 2.60-2.65 (m, 1H), 3.22-3.26 (m, 1H), 3.48-3.52 (m, 1H), 3.72 (s, 3H), 4.44 (brs, 2H), 6.27 (s, 1H), 6.46 (s, 1H); ESI-MS (m/z) 207.1 $(M+H)^+$ Intermediate B18

6-Methoxy-2,3,3-trimethyl-1,2,3,4-tetrahydroisoquinolin-7-amine

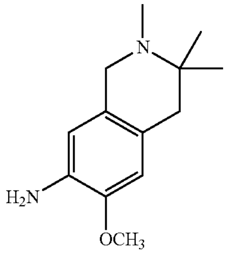 [SMILES: COc1cc2c(cc1N)CN(C)C(C)(C)C2]

Step 1: 1-(3-Methoxyphenyl)-2-methylpropan-2-ol

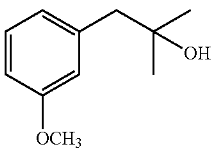

To a stirred suspension of 1-(3-methoxyphenyl)propan-2-one (9 g, 49 mmol in dry THF (100 mL) was added 1.5 M methyl magnesium bromide (100 mL, 143 mmol) at 0° C. and stirred for 3 h at same temperature and room temperature for overnight. The reaction mixture was diluted with saturated ammonium chloride solution, extracted thrice with ethyl acetate. The organic layer was dried over anhydrous sodium sulphate, filtered and concentrated under vacuum. The residue thus obtained was purified by column chromatography to yield 5.10 g of the desired product. $^1$H NMR (400 MHz, DMSO-$d_6$) δ 1.26 (s, 6H), 2.77 (s, 2H), 3.82 (s, 3H), 6.79-6.84 (m, 3H), 7.23-7.28 (m, 1H); ESI-MS (m/z) 181.26 $(M+H)^+$.

Step-2: 1-(2-Azido-2-methylpropyl)-3-methoxybenzene

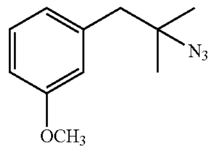

To a stirred suspension of 1-(3-methoxyphenyl)-2-methylpropan-2-ol (5.0 g, 27.0 mmol in dry DCM (100 mL) were added sodium azide (3.97 g, 61.11 mmol) and TFA (11 mL, 135 mmol) at 0° C. The reaction mixture was stirred at RT for overnight. The reaction mixture was basified with sodium bicarbonate solution, extracted thrice with DCM. The organic layers were separated, dried over anhydrous sodium sulphate and concentrated under reduced pressure. The residue thus obtained was purified by silica gel column chromatography to yield 5 g of the desired product. $^1$H NMR (400 MHz, DMSO-$d_6$) δ 1.24 (s, 6H), 2.61 (s, 2H), 3.72 (s, 3H), 6.75-6.77 (m, 3H), 7.14-7.18 (m, 1H); ESI-MS (m/z) 206.38 $(M+H)^+$.

Step 3: 1-(3-Methoxyphenyl)-2-methylpropan-2-amine

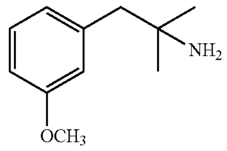

To a stirred suspension of 1-(2-azido-2-methylpropyl)-3-methoxybenzene (5.0 g, 24.3 mmol) in dry EtOAc (100 mL) was subjected to hydrogenation (balloon) in the presence of 10% Pd/C (1 g). The reaction mixture was stirred at RT for overnight. The reaction mixture was filtered through celite bed and washed with ethyl acetate. The filtrate obtained was concentrated under reduced pressure. The residue thus obtained was purified by silica gel column chromatography to yield 2.50 g of the desired product. $^1$H NMR (400 MHz, DMSO-$d_6$) δ 1.12 (s, 6H), 1.87 (brs, 2H), 2.71 (s, 2H), 3.74 (s, 3H), 6.79-6.84 (m, 3H), 7.21-7.25 (m, 1H); ESI-MS (m/z) 180.13 $(M+H)^+$.

Step 4: 6-Methoxy-3,3-dimethyl-1,2,3,4-tetrahydroisoquinoline

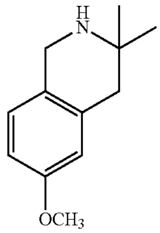

To a stirred suspension of 1-(3-methoxyphenyl)-2-methylpropan-2-amine (2.5 g, 13.80 mmol) in formic acid (25 mL) was added 37% formaldehyde solution (6 mL, 69.40 mmol) at 0° C. The reaction mixture was stirred at RT for overnight. The reaction mixture was basified with sodium bicarbonate solution, extracted thrice with DCM. The organic layers were separated, dried over anhydrous sodium sulphate and concentrated under reduced pressure. The residue thus obtained was purified by silica gel column chromatography to yield 1.5 g of the desired product. $^1$H NMR (400 MHz, DMSO-$d_6$) δ 1.34 (s, 6H), 2.72 (s, 2H), 2.88 (s, 2H), 3.74 (s, 3H), 6.75 (s, 1H), 6.84 (d, J=8.4 Hz, 1H), 7.16 (d, J=8.4 Hz, 1H); ESI-MS (m/z) 192.56 $(M+H)^+$ Step 5: 6-Methoxy-2,3,3-trimethyl-1,2,3,4-tetrahydroisoquinoline

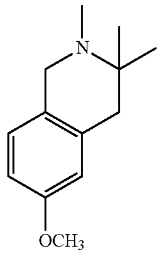

To a stirred suspension of 6-methoxy-3,3-dimethyl-1,2,3,4-tetrahydroisoquinoline (1.5 g, 7.80 mmol) in methanol (10 mL) was added 37% formaldehyde solution (3 mL, 23.4 mmol) and acetic acid (0.2 ml) at 0° C. The reaction mixture was stirred at RT for 5 h and then added sodium borohydride (0.59 g, 15.7 mmol) and stirred at RT for overnight. The reaction mixture was basified with aqueous sodium bicarbonate solution and extracted thrice with DCM. The organic layers were separated, dried over anhydrous sodium sulphate and concentrated under reduced pressure. The residue thus obtained was purified by silica gel column chromatography to yield 1.2 g of the desired product. $^1$H NMR (400 MHz, DMSO-$d_6$) δ 0.98 (s, 6H), 2.22 (s, 2H), 2.57 (s, 2H), 3.52 (s, 3H), 3.74 (s, 3H), 6.60 (s, 1H), 6.67 (d, J=8.4 Hz, 1H), 6.96 (d, J=8.4 Hz, 1H); (m/z) 206.97 $(M+H)^+$.

Step 6: 6-Methoxy-2,3,3-trimethyl-7-nitro-1,2,3,4-tetrahydroisoquinoline

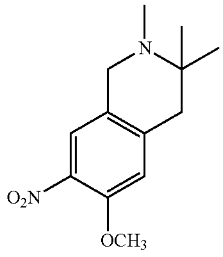 [SMILES: COc1cc2c(cc1[N+](=O)[O-])CN(C)C(C)(C)C2]

To a stirred suspension of 6-methoxy-2,3,3-trimethyl-1,2,3,4-tetrahydroisoquinoline (1.0 g, 48.0 mmol) in TFA (10 mL) was added portion wise potassium nitrate (0.44 g, 44.30 mmol) at −10° C. The reaction mixture was stirred at −10° C. for 3 h. The reaction mixture was basified with sodium bicarbonate solution and extracted thrice with DCM. The organic layers were separated, dried over anhydrous sodium sulphate and concentrated under reduced pressure. The residue thus obtained was purified by silica gel column chromatography to yield 0.60 g of the desired product. $^1$H NMR (400 MHz, DMSO-$d_6$) δ 1.00 (s, 6H), 2.24 (s, 2H), 2.51 (s, 2H), 3.59 (s, 3H), 3.87 (s, 3H), 7.70 (s, 1H), 7.64 (s, 1H); (m/z) 251.45 $(M+H)^+$. Step 7: 6-Methoxy-2,3,3-trimethyl-1,2,3,4-tetrahydroisoquinolin-7-amine

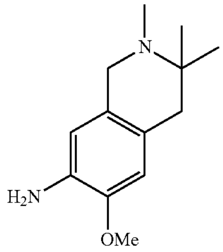 [SMILES: COc1cc2c(cc1N)CN(C)C(C)(C)C2]

To a stirred suspension of 6-methoxy-2,3,3-trimethyl-7-nitro-1,2,3,4-tetrahydro isoquinoline (0.5 g, 20 mmol) in dry MeOH (100 mL) was subjected to hydrogenation (balloon) in the presence of 10% Pd/C (0.1 g). The reaction mixture was stirred at RT for overnight. The reaction mixture was filtered through celite bed and washed with methanol. The filtrate obtained was concentrated under reduced pressure. The residue thus obtained was purified by silica gel column chromatography to yield 0.25 g of the desired product. $^1$H NMR (400 MHz, DMSO) δ 0.96 (s, 6H|), 2.19 (s, 3H|), 2.45 (s, 2H), 3.40 (s, 2H), 3.70 (s, 3H), 4.42 (brs, 2H), 6.28 (s, 1H), 6.44 (s, 1H); ESI-MS (m/z) 221.32 $(M+H)^+$ Intermediate B19

2-Methoxy-6-methyl-5,6,7,8-tetrahydro-1,6-naphthyridin-3-amine

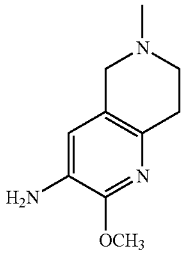

Step 1: 6-Methyl-3-nitro-5,6,7,8-tetrahydro-1,6-naphthyridine

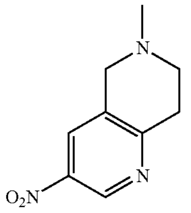

To a stirred suspension of 1-methyl-3,5-dinitro-1H-pyridine-2-one (200 mg, 1.00 mmol) and 1-methyl-4-piperidone (125 mg, 1.11 mmol) in 7M $NH_3$ in Dioxane (3 mL) was heated at 60° C. in sealed tube for 16 h. The reaction mixture was concentrated and diluted with DCM. The organic layer was washed with aqueous sodium bicarbonate solution followed by brine solution.

The organic layer was separated, dried over anhydrous sodium sulfate and concentrated under reduced pressure. The residue obtained was purified by silica gel column chromatography to yield 110 mg of desired product. $^1H$ NMR (400 MHz, $CDCl_3$) δ 2.54 (s, 3H), 2.87 (t, J=6 Hz, 2H), 3.19 (t, J=5.6 Hz, 2H), 3.71 (s, 2H), 8.15 (d, J=2.4 Hz, 1H), 8.24 (d, J=2.4 Hz, 1H), ESI-MS (m/z) 194.2 $(M+H)^+$.

Step 2: 6-Methyl-5,6,7,8-tetrahydro-1,6-naphthyridin-3-amine

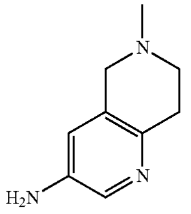

To a stirred suspension of 6-methyl-3-nitro-5,6,7,8-tetrahydro-1,6-naphthyridine (105 mg, 0.54 mmol) in MeOH (10 mL) was subjected to hydrogenation in the presence of 10% Pd/C (40 mg) and stirred for 2 h. The reaction mixture was diluted with MeOH and filtered through celite bed. The filtrate obtained was concentrated under vacuum to yield 76 mg of the desired product. $^1H$ NMR (400 MHz, DMSO-$d_6$)) δ 2.31 (s, 3H), 2.61 (t, J=5.6 Hz, 2H), 2.69 (t, J=6 Hz, 2H), 3.36 (s, 2H), 5.02 (brs, 2H), 6.57 (d, J=2.4 Hz, 1H), 7.73 (d, J=2.4 Hz, 1H); ESI-MS (m/z) 164.3 $(M+H)^+$.

Step 3: 2-Bromo-6-methyl-5,6,7,8-tetrahydro-1,6-naphthyridin-3-amine

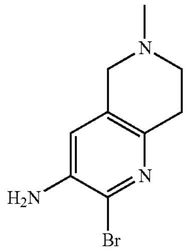

To a stirred suspension of 6-methyl-5,6,7,8-tetrahydro-1,6-naphthyridin-3-amine (700 mg, 4.29 mmol) in AcOH (13.5 mL) was added sodium acetate (704 mg, 8.58 mmol) followed by drop wise addition of bromine (682 mg, 4.29 mmol). The resultant mixture was stirred at RT for 2 h. The reaction mixture was diluted with DCM and washed with aqueous $NaHCO_3$ solution. The organic layer was separated and washed with brine solution. The organic layer was separated, dried over anhydrous sodium sulfate and concentrated under reduced pressure. The residue obtained was triturated with diethyl ether, filtered under vacuum to yield 691 mg of the desired product. $^1H$ NMR (400 MHz, DMSO-$d_6$)) δ 2.32 (s, 3H), 2.61 (t, J=5.6 Hz, 2H), 2.70 (t, J=5.6 Hz, 2H), 3.37 (s, 2H), 5.23 (s, 2H), 6.78 (s, 1H), ESI-MS (m/z) 243.12 $(M+2H)^+$.

Step 4: 2-Methoxy-6-methyl-5,6,7,8-tetrahydro-1,6-naphthyridin-3-amine

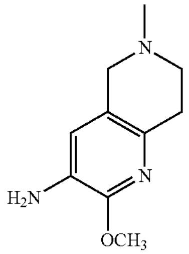

In a microwave vial, to a stirred suspension of 2-bromo-6-methyl-5,6,7,8-tetrahydro-1,6-naphthyridin-3-amine (500 mg, 2.06 mmol) and 1,10-phenanthroline (74.4 mg, 0.413 mmol) in a degassed MeOH (12 mL) were added cesium carbonate (1.35 g, 4.13 mmol) followed by CuI (39 mg, 0.206 mmol). The reaction mixture was subjected to microwave irradiation heated at 100° C. for 2 h. The reaction mixture was concentrated and the residue obtained was dissolved in ethyl acetate (100 mL) and washed with brine solution. The organic layer was dried over anhydrous sodium sulfate and concentrated under reduced pressure. The residue thus obtained was purified by silica gel column chromatography using to yield 146 mg of desired product. $^1$H NMR (400 MHz, DMSO-$d_6$)) δ 2.32 (s, 3H), 2.61-2.65 (m, 4H), 3.34 (s, 2H), 3.80 (s, 3H), 4.69 (brs, 2H), 6.55 (s, 1H); ESI-MS (m/z) 194.2 $(M+H)^+$.

Intermediate B20

6-Methoxyisochroman-7-amine

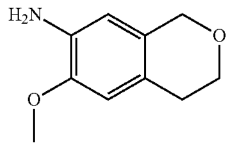

Step 1: Diethyl 2-(3-methoxy-4-nitrophenyl)malonate

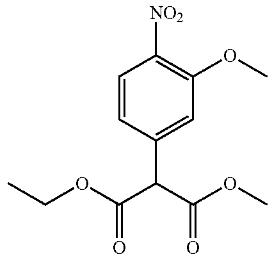 [SMILES: CCOC(=O)C(C(=O)OC)c1ccc([N+](=O)[O-])c(OC)c1]

To a stirred suspension of diethyl malonate (7.0 gm, 43.8 mmol) in DMF (50 mL) was added NaH (3.5 gm, 73.0 mmol) portion wise and stirred for 30 min at 0° C. To this reaction mixture was added 4-fluoro-2-methoxy-1-nitrobenzene (5.0 g, 29.2 mmol) and stirred at 100° C. for 2 h. The reaction mixture was quenched with ice cold water and extracted with ethyl acetate. The organic layer was separated, dried over anhydrous sodium sulphate and concentrated. The residue obtained was purified by column chromatography to yield 4.1 g of the desired product. $^1$H NMR (400 MHz, $CDCl_3$) δ 1.29 (t, J=7.2 Hz, 6H), 3.90 (s, 3H), 4.20-4.29 (m, 4H), 7.05 (d, J=8.4 Hz, 1H), 7.23 (s, 1H), 7.84 (d, J=8.4 Hz, 1H); ESI-MS (m/z) 312.1 $(M+H)^+$.

Step 2: 2-(3-Methoxy-4-nitrophenyl)acetic acid

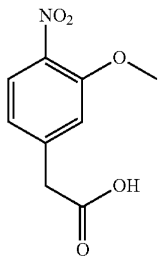

To a stirred solution of diethyl 2-(3-methoxy-4-nitrophenyl)malonate (4.0 g, 12.8 mmol) in AcOH (20 mL) and Conc. HCl (20 mL) was stirred at 100° C. for 16 h. The reaction mixture was concentrated and diluted with water. The aqueous layer was extracted twice with EtOAC. The organic layer was separated out and dried over anhydrous sodium sulphate. The organic layer was concentrated under vacuum to yield 2.2 g of the desired compound. $^1$H NMR (400 MHz, DMSO-$d_6$) δ 3.71 (s, 2H), 3.90 (s, 3H), 7.00-7.02 (m, 1H), 7.29 (d, J=1.2 Hz, 1H). 7.83 (d, J=8.4 Hz, 1H), 12.57 (s, 1H).

Step 3: 2-(3-Methoxy-4-nitrophenyl)ethanol

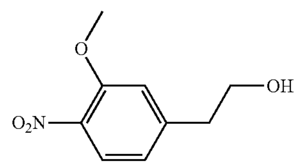

To a stirred solution of 2-(3-methoxy-4-nitrophenyl)acetic acid (2.2 g, 10.4 mmol) in THE (20 mL) was added LAH (0.79 g, 20.8 mmol) at 0° C. The reaction mixture was stirred for 30 min at RT. The reaction mixture was quenched with water and extracted twice with ethyl acetate. The organic layer was separated out and dried over anhydrous sodium sulphate. The organic layer was concentrated under vacuum and the residue obtained was purified by column chromatography to yield 700 mg of the desired compound. $^1$H NMR (400 MHz, $CDCl_3$) δ 2.94 (t, J=6.4 Hz, 2H), 3.86-3.98 (m, 6H), 6.92 (d, J=8.4 Hz, 1H), 6.98 (s, 1H), 7.85, (d, J=8.4 Hz, 1H), ESI-MS (m/z) 198.2 $(M+H)^+$.

Step 4: 2-Methoxy-4-(2-(methoxymethoxy)ethyl)-1-nitrobenzene

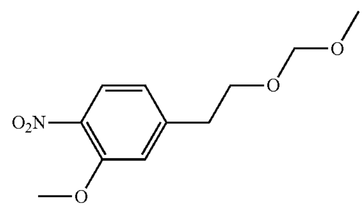

To a stirred solution 2-(3-methoxy-4-nitrophenyl)ethanol (700 mg, 3.04 mmol) in DCM (6 mL) were added DIPEA (1.5 mL, 9.13 mmol) and MOM-$C_1$ (1.15 mL, 15.2 mmol) at 0° C. The reaction mixture was stirred for 3 h at RT. The reaction mixture was diluted with water, extracted twice with ethyl acetate. The organic layer was dried over anhydrous sodium sulphate, filtered and concentrated under vacuum to yield 705 mg of the desired compound. $^1$H NMR (400 MHz, $CDCl_3$) δ δ 2.97 (t, J=6.8 Hz, 2H), 3.31 (s, 3H), 3.81 (t, J=6.4 Hz, 2H), 3.98 (s, 3H), 4.63 (s, 2H), 6.93, (d, J=8.0 Hz, 1H), 6.98 (s, 1H), 7.84, (d, J=8.4 Hz, 1H), ESI-MS (m/z) 242.2 $(M+H)^+$.

Step 5: 6-Methoxy-7-nitroisochroman

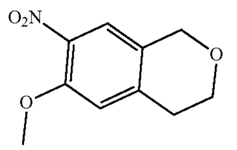

To a stirred mixture of 2-methoxy-4-(2-(methoxymethoxy)ethyl)-1-nitrobenzene (700 mg, 2.90 mmol) in DCE (10 mL) was added PTSA (275 mg, 1.45 mmol) and stirred at 90° C. for 16 h. The reaction mixture was diluted with water and extracted with DCM. The organic layer was dried over anhydrous sodium sulphate, filtered and concentrated under vacuum. The residue obtained was purified by column chromatography to yield 350 mg of the desired compound. $^{1}H$ NMR (400 MHz, $CDCl_3$) δ 2.92 (t, J=5.6 Hz, 2H), 3.96-4.01 (m, 5H), 4.75 (s, 2H), 6.84 (s, 1H), 7.58 (s, 1H).

Step 6: 6-Methoxyisochroman-7-amine

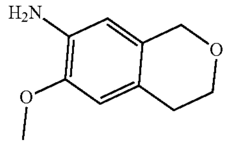

To a stirred solution of 6-methoxy-7-nitroisochroman (step 5 Intermediate) (360 mg, 1.72 mmol) in IPA (7 mL) and $H_2O$ (3 mL) was added $NH_4Cl$ (460 mg, 8.6 mmol) and iron powder (506 mg, 8.6 mmol) and stirred at 100° C. for 2 h. The reaction mixture was filtered through celite bed and filtrate obtained was diluted with water and extracted twice with ethyl acetate.

The organic layer was dried over anhydrous sodium sulphate, filtered and concentrated under vacuum. The residue obtained was purified by column chromatography to yield 192 mg of the desired compound. $^{1}H$ NMR (400 MHz, $CDCl_3$) δ 2.76 (t, J=5.6 Hz, 2H), 3.72 (s, 2H), 3.85 (s, 3H), 3.95 (t, J=5.6 Hz, 2H), 4.66 (s, 2H), 6.35 (s, 1H), 6.54 (s, 1H). ESI-MS (m/z) 180.2 $(M+H)^+$ Intermediate B21 tert-butyl 3-amino-1-methyl-4,6-dihydropyrrolo[3,4-c]pyrazole-5(1H)-carboxylate

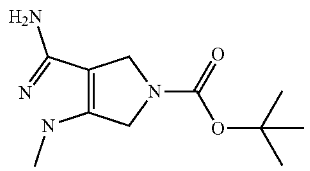 [SMILES: CNC1=C(C(=N)N)CN(C(=O)OC(C)(C)C)C1]

To a stirred solution of tert-butyl 3-cyano-4-oxopyrrolidine-1-carboxylate (5 g, 23 mmol) in IPA (60 mL) were added methylhydrazine sulphate (6.85 g, 47 mmol), triethylamine (8.3 mL, 59 mmol) and heated to reflux for 18 h. The reaction mixture was concentrated under vacuum. The residue obtained was basified with aqueous potassium carbonate and extracted thrice with ethyl acetate. The organic layer was separated, dried over sodium sulphate and concentrated under reduced pressure to yield 2.6 g of the desired product. $^{1}H$ NMR (400 MHz, DMSO-$d_6$) δ 1.43 (s, 9H), 3.47 (s, 3H), 4.10-4.14 (m, 4H), 5.31 (brs, 2H).

EXAMPLES

Method A (2-((5-Chloro-2-((6-methoxy-2-methyl-1,2,3,4-tetrahydroisoquinolin-7-yl)amino)pyrimidin-4-yl)amino)-5-hydroxyphenyl)dimethylphosphineoxide dihydrochloride (Example 1)

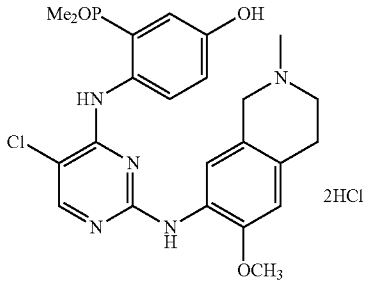

Step 1: (2-((2,5-Dichloropyrimidin-4-yl)amino)-5-((4-methoxybenzyl)oxy)phenyl) dimethylphosphine oxide

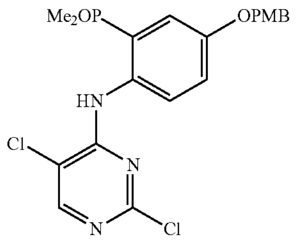

To a stirred solution of 2,4,5-trichloro pyrimidine (7 g, 38.3 mmol) in isopropyl alcohol (50 mL) were added (2-amino-5-((4-methoxybenzyl)oxy)phenyl)dimethylphosphine oxide (Intermediate A1) (5.84 g, 19.14 mmol), DIPEA (5 g, 38.3 mmol) at RT. The reaction mixture was heated at 100° C. for overnight in a sealed tube. The reaction mixture was concentrated under reduced pressure. The residue thus obtained was purified by silica gel column chromatography to yield 5.83 g of the desired product. $^{1}H$ NMR (400 MHz, DMSO-$d_6$) δ 1.79 (d, J=13.6 Hz, 6H), 3.76 (s, 3H), 5.07 (s, 2H) 6.97 (d, J=8.8 Hz, 2H), 7.27-7.30 (m, 2H), 7.42 (d, J=8.8 Hz, 2H), 8.26-8.29 (m, 1H), 8.39 (s, 1H), 11.50 (s, 1H); ESI-MS (m/z) 452.1 $(M+H)^+$.

Step 2: (2-((5-Chloro-2-((6-methoxy-2-methyl-1,2,3,4-tetrahydroisoquinolin-7-yl) amino) pyramidin-4-yl)amino)-5-hydroxyphenyl)dimethylphosphine oxide

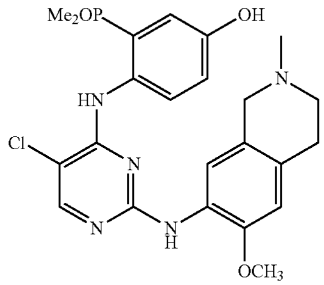

To a stirred suspension of (2-((2,5-dichloropyrimidin-4-yl)amino)-5-((4-methoxybenzyl)oxy) phenyl) dimethylphosphine oxide (step 1 Intermediate) (5.2 g, 11.44 mmol) in IPA (40 mL) were added 6-methoxy-2-methyl-1,2,3,4-tetrahydroisoquinolin-7-amine (Intermediate B1) (2 g, 10.4 mmol) and p-toluene sulfonic acid monohydrate (2 g, 10.4 mmol). The mixture was heated at 120° C. in a sealed tube for overnight. The reaction mixture was diluted with water, basified with aqueous ammonia and extracted thrice with 10% methanol in chloroform. The combined organic layer was dried over anhydrous sodium sulfate and concentrated under reduced pressure. The solid thus obtained was purified by stirring in IPA (30 mL) at reflux temperature for 2 h and then cooled to RT and filtered to yield 2.2 g of the desired product. $^1$H NMR (400 MHz, DMSO-$d_6$) δ 1.68 (d, J=13.6 Hz, 6H), 2.33 (s, 3H), 2.50-2.54 (m, 2H), 2.74-2.77 (m, 2H), 3.19 (s, 2H), 3.77 (s, 3H), 6.72 (s, 1H), 6.92 (d, J=8.8 Hz, 1H), 7.03-7.07 (m, 1H), 7.45 (s, 1H), 7.77 (s, 1H), 7.86-7.88 (m, 1H), 8.08 (s, 1H), 9.72 (s, 1H), 10.10 (s, 1H); ESI-MS (m/z) 488.2 $(M+H)^+$.

Step 3: (2-((5-Chloro-2-((6-methoxy-2-methyl-1,2,3,4-tetrahydroisoquinolin-7-yl) amino) pyrimidin-4-yl)amino)-5-hydroxyphenyl)dimethylphosphineoxide dihydrochloride To a stirred suspension of (2-((5-chloro-2-((6-methoxy-2-methyl-1,2,3,4-tetrahydroisoquinolin-7-yl)amino)pyrimidin-4-yl)amino)-5-hydroxyphenyl)dimethyl phosphine oxide (200 mg, 0.409 mmol) in diethyl ether (2 mL) was added 4M HCl in Dioxane (0.5 mL) and stirred at RT for 1 h. The reaction mixture was triturated with pentane, decanted and dried under vacuum to yield 175 mg of desired product. $^1$H NMR (400 MHz, DMSO-d6) δ 1.69 (d, J=13.6 Hz, 6H), 2.93 (s, 3H), 3.15-3.40 (m, 2H), 3.60-3.70 (m, 2H), 3.83 (s, 3H), 3.90-4.05 (m, 2H), 4.05 (brs, 1H), 6.96 (s, 1H), 7.10-7.15 (m, 2H), 7.46 (s, 1H), 7.83 (brs, 1H), 8.29 (s, 1H), 8.85 (brs, 1H), 10.06 (brs, 1H), 10.69 (brs, 1H), 10.86 (brs, 1H); ESI-MS (m/z) 488.2 $(M+H)^+$.

4-((5-Chloro-2-((6-methoxy-2-methyl-1,2,3,4-tetrahydroisoquinolin-7-yl)amino)pyrimidin-4-yl)amino)-3-(dimethylphosphoryl)phenylsulfurofluoridate dihydrochloride (Example 2)

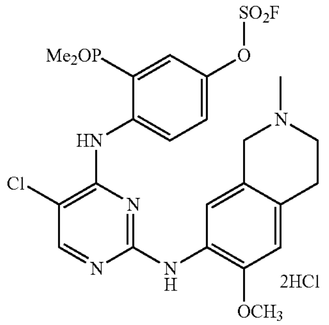

Step 1: 4-((5-Chloro-2-((6-methoxy-2-methyl-1,2,3,4-tetrahydroisoquinolin-7-yl)amino) pyrimidin-4-yl) amino)-3-(dimethylphosphoryl)phenyl sulfofluoridate

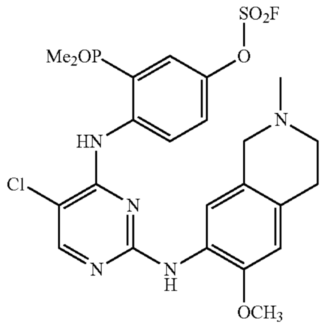

To a stirred suspension of (2-((5-chloro-2-((6-methoxy-2-methyl-1,2,3,4-tetrahydroisoquinolin-7-yl)amino)pyrimidin-4-yl)amino)-5-hydroxyphenyl) dimethylphosphine oxide (Step 2 Intermediate of Example 1) (2 g, 4.09 mmol) and [4-(acetylamino)phenyl] imidosulfuryl difluoride (1.54 g, 4.91 mmol) in THF (25 mL) at 0° C. was added DBU (1.24 g, 8.18 mmol). The reaction mixture was stirred at RT for 1 h. The reaction mixture was diluted with water and extracted with chloroform. The combined organic layers were dried over anhydrous sodium sulfate and concentrated under reduced pressure. The residue obtained was purified by silica gel column chromatography to yield 1.40 g of desired product. $^1$H NMR (400 MHz, DMSO-$d_6$)) δ 1.83 (d, J=13.6 Hz, 6H), 2.34 (s, 3H), 2.62 (t, J 5.2 Hz, 2H), 2.82 (t, J=5.2 Hz, 2H), 3.38 (s, 2H), 3.77 (s, 3H), 6.81 (s, 1H), 7.34 (s, 1H), 7.54 (dd, J=2.4, 9.2 Hz, 1H), 7.90 (dd, J=2.8 Hz, 13.6 Hz, 1H), 8.18 (s, 1H), 8.27 (s, 1H), 8.64 (brs, 1H), 11.39 (brs, 1H); ESI-MS (m/z) 570.1 $(M+H)^+$.

Step 2: 4-((5-Chloro-2-((6-methoxy-2-methyl-1,2,3,4-tetrahydroisoquinolin-7-yl)amino) pyrimidin-4-yl) amino)-3-(dimethylphosphoryl)phenylsulfofluoridate dihydrochloride To a stirred suspension of 4-((5-chloro-2-((6-methoxy-2-methyl-1,2,3,4-tetrahydroisoquinolin-7-yl)amino)pyrimidin-4-yl)amino)-3-(dimethylphosphoryl) phenyl sulfofluoridate (1.4 g, 0.409 mmol) in diethyl ether (15 mL) was added 4M HCl in Dioxane (5 mL) and stirred at RT for 1 h. The solvent was decanted and dried under vacuum to yield 1.37 g dihydrochloride salt of desired product. $^1$H NMR (400 MHz, DMSO-$d_6$)) δ 1.88 (d, J=14.0 Hz, 6H), 2.87 (s, 3H), 2.99-3.04 (m, 1H), 3.27-3.35 (m, 2H), 3.55-3.65 (m, 1H), 3.81 (s, 3H), 4.09-4.15 (m, 1H), 4.24-4.27 (m, 1H), 4.79 (brs, 1H), 7.02 (s, 1H), 7.43 (s, 1H), 7.84 (dd, J=2.4 Hz, 9.2 Hz, 1H), 7.99 (dd, J=2.8 Hz, 13.6 Hz, 1H), 8.36 (s, 1H), 8.60 (brs, 1H), 9.32 (brs, 1H), 11.30 (brs, 1H), 11.95 (brs, 1H); ESI-MS (m/z) 570.2 $(M+H)^+$.

The details of synthesis and analytical data of the examples prepared from the above mentioned methods are given below in Table 4.

TABLE 4

Structure, chemical name, method, intermediate used and analytical data of Examples (3-28)

| Example No. | Structure | Method and Intermediate | Chemical Name and Analytical data |
|---|---|---|---|
| Example 3 | 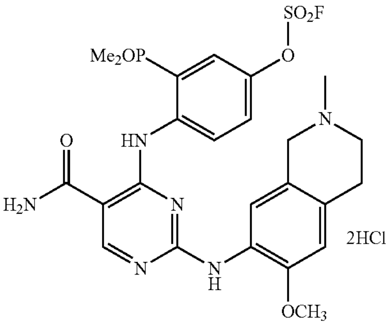 | Method A A1/B1 | 4-((5-Carbamoyl-2-((6-methoxy-2-methyl-1,2,3,4-tetrahydroisoquinolin-7-yl)amino)pyrimidin-4-yl)amino)-3-(dimethylphosphoryl)phenyl sulfurofluoridate dihydrochloride; $^1$H NMR (400 MHz, DMSO-$d_6$) δ 1.75 (d, J = 13.6 Hz, 6H), 2.88 (s, 3H), 2.90 3.00 (m, 1H), 3.10-3.31 (m, 2H), 3.57-3.71 (m, 1H), 3.79 (s, 3H), 3.90-4.20 (m, 2H), 6.95 (s, 1H), 7.33 (s, 1H), 7.73 (s, 1H), 8.15-7.85 (m, 3H), 8.30 (s, 1H), 8.78 (s, 1H), 9.10 (brs, 1H), 10.88 (brs, 1H)[, 11.64, (brs, 1H); ESI-MS (m/z) 578.9 $(M)^+$ |
| Example 4 | 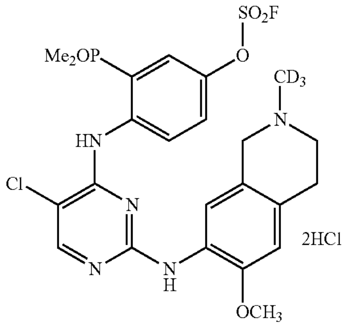 | Method A A1/B2 | 4-((5-Chloro-2-((6-methoxy-2-(methyl-$d_3$)-1,2,3,4-tetrahydroisoquinolin-7-yl) amino)pyramidin-4-yl)amino)-3-(dimethylphosphoryl) phenylsulfurofluoridate dihydrochloride; $^1$H NMR (400 MHz, DMSO-$d_6$) δ 1.88 (d, J = 14 Hz, 6H), 2.97-3.05 (m, 1H), 3.10-3.40 (m, 2H) 3.60-3.70 (m, 1H), 3.81 (s, 3H), 4.10-4.20 (m, 1H), 4.20-4.32 (m, 1H), 7.01 (s, 1H), 7.48 (s, 1H), 7.79 (d, J = 4.4 Hz, 1H), 7.94 (d, J = 13.6 Hz, 1H), 8.29 (d, J = 6 Hz, 1H), 8,66 (brs, 1H), 8.93 (brs, 1H), 10.92 (brs, 1H), 11.75 (brs, 1H); ESI-MS (m/z) 573.1 $(M + H)^+$ |
| Example 5 | 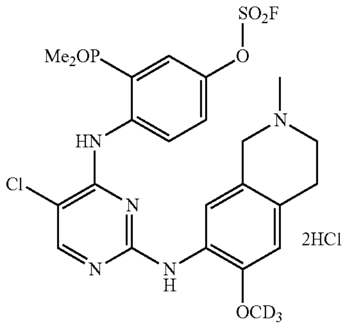 | Method A A1/B3 | 4-((5-Chloro-2-((6-(methoxy-$d_3$)-2-methyl-1,2,3,4-tetrahydroisoquinolin-7-yl)amino)pyrimidin-4-yl)amino)-3-(dimethylphosphoryl)phenyl sulfurofluoridate dihydrochloride; $^1$H NMR (400 MHz, DMSO-$d_6$) δ 1.86 (d, J = 13.6 Hz, 6H), 2.88 (s, 3H), 3.00-3.20 (m, 1H), 3.20-3.40 (m, 2H), 3.60-3.80 (m, 1H), 4.05-4.21 (m, 1H), 4.21-4.31 (m, 1H), 6.99 (s, 1H), 7.49 (s, 1H), 7 (dd, J = 2.8 Hz, 12.0 Hz, 1H), 7.93 (dd, J = 2.8 Hz, 12 Hz, 1H), 8.28 (s, 1H), 8.68 (brs, 1H), 8.83 (brs, 1H), 10.98 (brs, 1H), 11.71 (brs, 1H); ESI-MS (m/z) 573.2 $(M + H)^+$ |

TABLE 4-continued

Structure, chemical name, method, intermediate used and analytical data of Examples (3-28)

| Example No. | Structure | Method and Intermediate | Chemical Name and Analytical data |
|---|---|---|---|
| Example 6 | 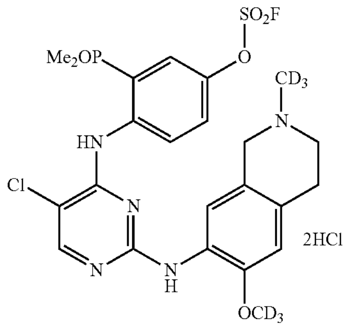 | Method A A1/B4 | 4-((5-Chloro-2-((6-methoxy-$d_3$)-2-(methyl-$d_3$)-1,2,3,4-tetrahydro isoquinolin-7-yl)amino) pyrimidin-4-yl)amino)-3-(dimethylphosphoryl)phenyl sulfurofluoridate dihydrochloride; $^1H$ NMR (400 MHz DMSO-$d_6$)) δ 1.86 (d, J = 14 Hz, 6H), 3.00-3.10 (m, 1H), 3.23-3.30 (m, 2H), 3.60-3.62 (m, 1H), 4.10-4.30 (m, 2H), 6.99 (s, 1H), 7.49 (s, 1H), 7.78 (d, J = 9.2 Hz, 1H), 7.93 (d, J = 14 Hz, 1H), 8.28 (s, 1H), 8.66 (s, 1H), 8.86 (s, 1H), 10.98 (brs, 2H), 11.73 (brs, 1H); ESI-MS (m/z) 576.3 $(M + H)^+$ |
| Example 7 | 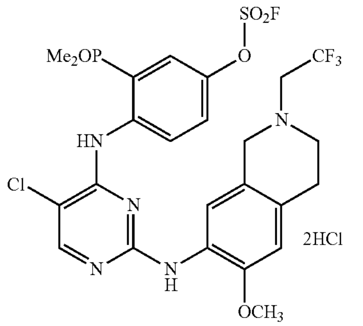 | Method A A1/B6 | 4-((5-Chloro-2-((6-methoxy-2-(2,2,2-trifluoroethyl)-1,2,3,4-tetrahydroisoquinolin-7-yl) amino)pyrimidin-4-yl)amino)-3-(dimethyllphosphoryl)phenyl sulfurofluoridate dihydrochloride; $^1H$ NMR (400 MHz, DMSO-$d_6$) δ 1.86 (d, J = 14 Hz, 6H), 2.90-3.20 (m, 4H), 3.60-3.70 (m, 2H), 3.78 (s, 3H), 3.80-3.90 (m, 2H), 6.92 (s, 1H), 7.34 (s, 1H), 7.63 (d, J = 9.6 Hz, 1H), 7.96 (dd, J1 = 2.8 Hz, J2 = 13.6 Hz, 1H), 8.33 (s, 1H), 8.55 (brs, 1H), 9.25 (brs, 1H), 11.92 (brs, 1H); ESI-MS (m/z): 638.1 $(M + H)^+$ |
| Example 8 | 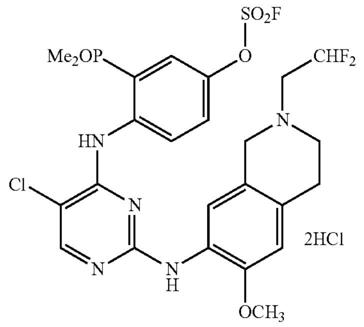 | Method A A1/B5 | 4-((5-Chloro-2-((2-(2,2-difluoroethyl)-6-methoxy-1,2,3,4-tetrahydroisoquinolin-7-yl)amino)pyrimidin-4-yl)amino)-3-(dimethylphosphoryl)phenyl sulfurofluoridate dihydrochloride; $^1H$ NMR (400 MHz, DMSO-$d_6$) δ 1.86 (d, J = 14 Hz, 6H), 3.00-3.45 (m, 4H), 3.82-3.85 (m, 2H), 3.85 (s, 3H), 4.25-4. 35 (m, 2H), 6.50-6.90 (m, 1H), 6.99 (s, 1H), 7.55 (s, 1H), 7.75 (d, J = 9.2 Hz, 1H), 7.94 (d, J = 14.4 Hz, 1H), 8.25 (d, J = 2.8 Hz, 1H), 8.70 (brs, 2H), 11.64 (brs, 1H); ESI-MS (m/z): 620.3 $(M + H)^+$ |
| Example 9 | 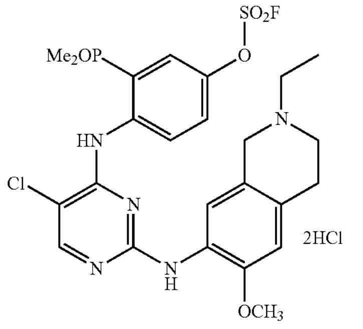 | Method A A1/B7 | 4-((5-Chloro-2-((2-ethyl-6-methoxy-1,2,3,4-tetrahydroisoquinolin-7-yl) amino)pyrimidin-4-yl) amino)-3-(dimethylphosphoryl) phenyl sulfofluoridate dihydrochloride; $^1H$ NMR (400 MHz, DMSO-$d_6$) δ 1.34 (t, J = 6.8 Hz, 3H), 1.86 (d, J = 13.6 Hz, 6H), 2.99-3.02 (m, 1H), 3.21-3.26 (m, 4H), 3.69-3.70 (m, 1H), 3.81 (s, 3H), 4.10-4.35 (m, 2H), 7.00 (s, IH), 7.51 (s, 1H), 7.78 (d, J = 9.6 Hz, 1H), 7.93 (d, J = 11.2 Hz, 1H), 8.27 (s, 1H), 8.67 (brs, 1H), 8.86 (brs, 1H), 10.84 (s, 1H), 11.73 (s, 1H); ESI-MS (m/z) 584.4 $(M + H)^+$ |

TABLE 4-continued

| Structure, chemical name, method, intermediate used and analytical data of Examples (3-28) | | | |
|---|---|---|---|
| Example No. | Structure | Method and Intermediate | Chemical Name and Analytical data |
| Example 10 | 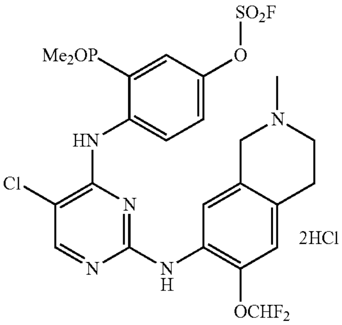 2HCl | Method A A1/B14 | 4-((5-Chloro-2-((6-(difluoromethoxy)-2-methyl-1,2,3,4-tetrahydroqisoquinolin-7-yl)amino)pyrimidin-4-yl)amino)-3-(dimethylphosphoryl)phenyl sulfurofluoridate dihydrochloride; $^1$H NMR (400 MHz, DMSO-$d_6$) δ 1.87 (d, J = 13.6 Hz, 6H), 2.90 (s, 3H), 3.02-3.06 (m, 1H), 3.21-3.30 (m, 2H), 3.46-3.49 (m, 1H), 3.67-3.70 (m, 2H), 7.06 (t, J = 74 Hz, 1H), 7.19 (s, 1H), 7.49 (s, 1H), 7.70 (d, J = 9.2 Hz, 1H), 7.91 (d, J = 13.6 Hz, 1H), 8.22 (s, 1H), 8.67 (s, 1H), 8.98 (brs, 1H), 10.85 (brs, 1H), 11.57 (brs, 1H) ; ESI-MS (m/z): 606.1 (M + H)$^+$ |
| Example 11 | 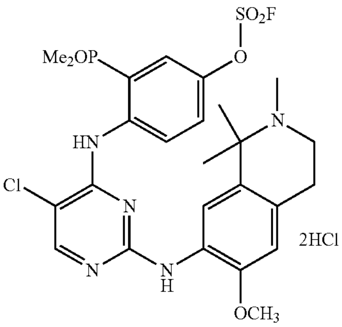 2HCl | Method A A1/B16 | 4-((5-Chloro-2-((6-methoxy-1,1,2-trimethyl-1,2,3,4-tetrahydroiso quinolin-7-yl)amino)pyrimidin-4-yl)amino)-3-(dimethylphosphoryl)phenyl sulfurofluoridate dihydrochloride; $^1$H NMR (400 MHz, DMSO-$d_6$) δ 1.48 (s, 3H), 1.68 (s, 3H), 1.89 (d, J = 13.6 Hz, 6H), 2.77 (s, 3H), 2.96-3.00 (m, 1H), 3.39-3.60 (m, 3H), 3.78 (s, 3H), 6.95 (s, 1H), 7.57 (s, 1H), 7.66 (d, J = 8.4 Hz, 1H), 7.95 (d, J = 13.6 Hz, 1H), 8.30 (s, 1H), 8.58 (brs, 1H), 9.37 (brs, 1H), 11.48 (brs, 1H), 11.90 (brs, 1H); ESI-MS (m/z): 598.03 (M + H)$^+$ |
| Example 12 | 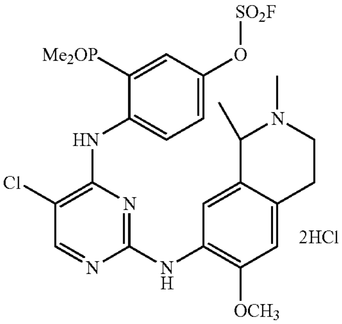 2HCl | Method A A1/B15 | ±4-((5-chloro-2-((6-methoxy-1,2-dimethyl-1,2,3,4-tetrahydro isoquinolin-7-yl)amino)pyrimidin-4-yl)amino)-3-(dimethylphos-phoryl)phenylsulfurofluoridate dihydrochloride; $^1$H NMR (400 MHz, DMSO-$d_6$) δ 1.55 (d, J = 6.8 Hz, 3H), 1.80-1.95 (m, 6H), 2.85 (s, 3H), 2.95-3.35 (m, 2H), 3.35-3.50 (m, 2H), 3.81 (s, 3H), 4.30-4.40 (m, 1H), 6.99 (s, 1H), 7.53 (s, 1H), 7.60-7.70 (m, 1H), 7.93 (d, J = 13.6 Hz, 1H), 8.26 (s, 1H), 8.63 (s, 1H), 8.85 (br s, 1H), 10.87 (br s, 1H), 11.68 (br s, 1H); ESI-MS (m/z) 584 (M + H)$^+$ |
| Example 13 | 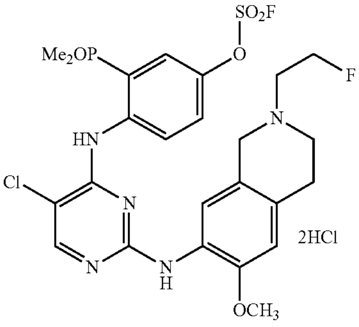 2HCl | Method A A1/B8 | 4-((5-Chloro-2-((2-(2-fluoroethyl)-6-methoxy-1,2,3,4-tetrahydro isoquinolin-7-yl)amino)pyrimidin-4-yl)amino)-3-(dimethylphos-phoryl)phenylsulfofluoridate dihydrochloride; $^1$H NMR (400 MHz, DMSO-$d_6$) δ1.85 (d, J = 14 Hz, 6H), 3.00-3.04 (m, 1H), 3.29-3.39 (m, 2H), 3.57-3.81 (m, 3H), 3.81 (s, 3H), 4.23-4.29 (m, 1H), 4.37-4.40 (m, 1H), 4.92-4.94 (m, 1H), 5.04-5.06 (m, 1H), 7.01 (s, 1H), 7.51 (s, 1H), 7.78 (d, J = 9.2 Hz, 1H), 7.94 (d, J = 13.6 Hz, 1H), 8.30 (s, 1H), 8.67 (brs, 2H), 8.99 (brs, 1H), 11.40 (brs, 1H), 11.80 (brs, 1H); ESI-MS (m/z) 602.2 (M + H)$^+$ |

TABLE 4-continued

Structure, chemical name, method, intermediate used and analytical data of Examples (3-28)

| Example No. | Structure | Method and Intermediate | Chemical Name and Analytical data |
| --- | --- | --- | --- |
| Example 14 | 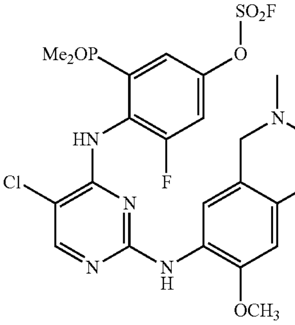 2HCl | Method A A3/B1 | 4-((5-Chloro-2-((6-methoxy-2-methyl-1,2,3,4-tetrahydroisoquinolin-7-yl)amino)pyrimidin-4-yl)amino)-3-(dimethylphosphoryl)-5-fluorophenylsulfurofluoridate dihydrochloride; $^1$H NMR (400 MHz, DMSO-$d_6$) δ 1.73 (d, J = 13.6 Hz, 6H), 2.91 (s, 3H), 3.00-3.20 (m, 2H), 3.30-3.40 (m, 1H), 3.60-3.70 (m, 1H), 3.76 (s, 3H), 3.86 (s, 2H), 6.85 (s, 1H), 7.25 (s, 1H), 7.98 (d, J = 12 Hz, 1H), 8.23-8.29 ( m, 2H), 8.29 (s, 1H), 9.71 (brs, 1H), 10.79 (brs, 1H); ESI-MS (m/z): 588.2 (M + H)$^+$ |
| Example 15 | 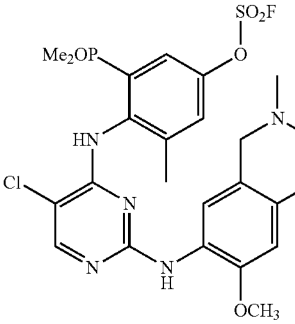 2HCl | Method A A4/B1 | 4-((5-Chloro-2-((6-methoxy-2-methyl-1,2,3,4-tetrahydroisoquinolin-7-yl)amino)pyrimidin-4-yl)amino)-3-(dimethylphosphoryl)-5-methylphenyl sulfurofluoridate dihydrochloride; $^1$H NMR (400 MHz, DMSO-$d_6$) δ 1.50-1.82 (m, 6H), 2.20 (s, 3H), 2.90 (s, 3H), 3.10-3.30 (m, 2H), 3.30-3.40 (m, 2H), 3.75 (s, 3H), 3.85 (s, 2H), 6.85 (s, 1H), 7.08 (s, 1H), 7.90-8.10 (m, 2H), 8.38 (s, 1H), 8.72 (br s, 1H), 9.81 (br s, 1H), 10.83 (br s, 1H); ESI-MS (m/z): 584.1 (M + H)$^+$ |
| Example 16 | 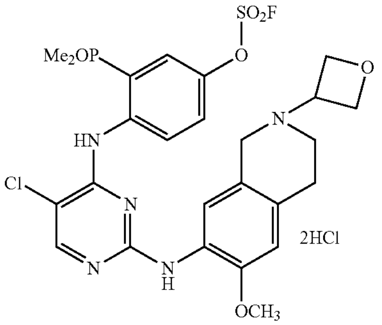 2HCl | Method A A1/B10 | 4-((5-Chloro-2-((6-methoxy-2-(oxetan-3-yl)-1,2,3,4-tetrahydro isoquinolin-7-yl)amino)pyrimidin-4-yl)amino)-3-(dimethylphosphoryl)phenyl sulfurofluoridate dihydrochloride; $^1$H NMR (400 MHz, DMSO-$d_6$) δ 1.87 (d, J = 13.6 Hz, 6H,) 3.00-3.10 (m, 1H), 3.15-3.50 (m, 3H), 3.50-3.75 (m, 2H), 3.81 (s, 3H), 3.90-4.20 (m, 2H), 4.50-4.55 (m, 1H), 4.60-4.80 (m, 2H), 4.80-4.95 (m, 1H), 7.01 (s, 1H), 7.52 (s, 1H), 7.76 (d, J = 8.4 Hz, 1H), 7.94 (d, J = 8.4 Hz, 1H), 8.26 (s, 1H), 8.60-8.90 (m, 2H), 11.66 (s, 1H), 12.05 (brs, 1H); ESI-MS (m/z): 612.2 (M + H)$^+$ |
| Example 17 | 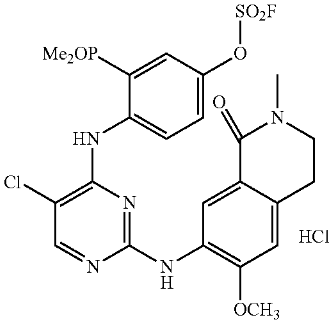 HCl | Method A A1/B1a | 4-((5-Chloro-2-((6-methoxy-2-methyl-1-oxo-1,2,3,4-tetrahydroisoquinolin-7-yl)amino)pyrimidin-4-yl)amino)-3-(dimethylphosphoryl)phenyl sulfurofluoridatehydrochloride; $^1$HNMR (400 MHz, DMSO-$d_6$) δ 1.85 (d, J = 13.6 Hz, 6H), 2.98-3.02 (m, 2H), 3.03 (s, 3H), 3.54-3.57 (m, 2H), 3.86 (s, 3H), 7.08 (s, 1H), 7.50 (d, J = 8.0 Hz, 1H), 7.93-7.97 (m, 1H), 8.01 (s, 1H), 8.43 (bs, 2H), 9.79 (s, 1H), 12.12 (s, 1H); ESI-MS (m/z) 584.1 (M + H)$^+$ |

TABLE 4-continued

Structure, chemical name, method, intermediate used and analytical data of Examples (3-28)

| Example No. | Structure | Method and Intermediate | Chemical Name and Analytical data |
|---|---|---|---|
| Example 18 | 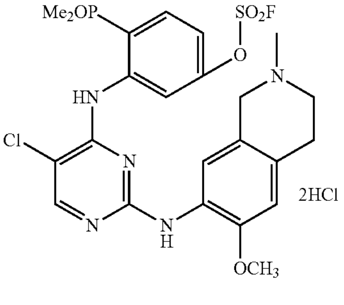 | Method A A5/B1 | 3-((5-Chloro-2-((6-methoxy-2-methyl-1,2,3,4-tetrahydroisoquinolin-7-yl)amino)pyrimidin-4-yl)amino)-4-(dimethylphosphoryl)phenyl sulfurofluoridate dihydrochloride; $^1$H NMR (400 MHz, DMSO-$d_6$) δ1.86 (d, J = 13.6 Hz, 6H), 2.87 (s, 3H), 2.95-3.05 (m, 1H), 3.20-3.30 (m, 2H), 3.60-3.70 (m 1H), 3.81 (s, 3H), 4.15 (br s, 2H), 6.98 (s, 1H), 7.40-7.60 (m, 2H), 7.80-7.90 (m, 1H), 8.31 (s, 1H), 8.78 (s, 1H), 9.10 (br s, 1H), 11.20 (br s, 1H), 12.06 (br s, 1H); ESI-MS (m/z) 570.4 $(M + H)^+$ |
| Example 19 | 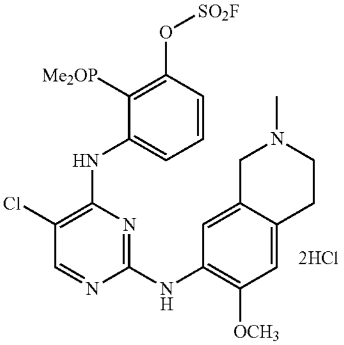 | Method A A6/B1 | 3-((5-Chloro-2-((6-methoxy-2-methyl-1,2,3,4-tetrahydroisoquinolin-7-yl)amino)pyrimidin-4-yl) amino)-2-(dimethylphosphoryl) phenylsulfofluoridate dihydrochloride; $^1$H NMR (400 MHz, DMSO-$d_6$) δ 1.91 (d, J = 14 Hz, 6H), 2.98 (s, 3H), 3.11-3.19 (m, 1H), 3.21-3.35 (m, 2H), 3.61-3.65 (m, 1H), 3.76 (s, 3H), 4.12-4.32 (m, 2H), 6.55 (s, 1H), 7.35-7.37 (m, 1H), 7.47 (s, 1H), 7.74-7.78 (m, 1H), 8.29 (s, 1H), 8.56 (brs, 1H), 8.85 (brs, 1H), 11.09 (brs, 1H), 12.26 (brs, 1H); |
| Example 20 | 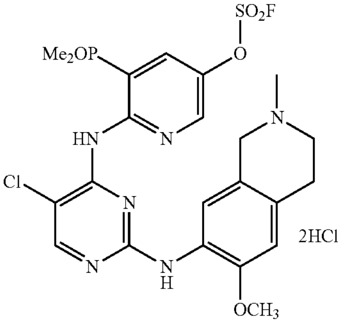 | Method A A7/B1 | 6-((5-Chloro-2-((6-methoxy-2-methyl-1,2,3,4-tetrahydroisoquinolin-7-yl)amino)pyrimidin-4-yl)amino)-5-(dimethylphosphoryl)pyridin-3-yl sulfofluoridate dihydrochloride; $^1$H NMR (400 MHz, DMSO-$d_6$) δ 1.88 (d, J = 14 Hz, 6H), 2.88-2.98 (m, 4H), 3.17-3.61 (m, 3H), 3.85 (s, 3H), 4.16-4.33 (m, 2H), 6.92 (s, 1H), 8.01 (s, 1H), 8.12 (brs, 1H), 8.37 (s, 1H), 8.47 (d, J = 92 Hz, 1H), 8.94 (s, 1H), 10.49 (brs, 2H), 11.47 (brs, 1H); ESI-MS (m/z) 571.1 $(M + H)^+$ |
| Example 21 | 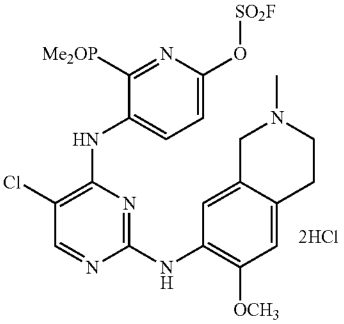 | Method A A8/B1 | 5-((5-Chloro-2-((6-methoxy-2-methyl-1,2,3,4-tetrahydroisoquinolin-7-yl)amino)pyrimidin-4-yl)amino)-6-(dimethylphosphoryl)pyridin-2-yl sulfofluoridate dihydrochloride: $^1$H NMR (400 MHz, DMSO-$d_6$) ) δ 1.82 (d, J = 14 Hz, 6H), 2.88 (s, 3H), 3.04-3.15 (m, 1H), 3.26-3.33 (m, 3H), 3.64 (s, 2H), 3.81 (s, 3H), 7.01 (s, 1H), 7.47(s, 1H), 7.76 (d, J = 9.2 Hz, 1H), 8.30 (s, 1H), 8.93 (brs, 1H), 9.26 (brs, 1H), 11.07 (brs, 1H), 11.57 (brs, 1H),; ESI-MS (m/z) 571.2 $(M + H)^+$ |

TABLE 4-continued

| Structure, chemical name, method, intermediate used and analytical data of Examples (3-28) | | | |
|---|---|---|---|
| Example No. | Structure | Method and Intermediate | Chemical Name and Analytical data |
| Example 22 | 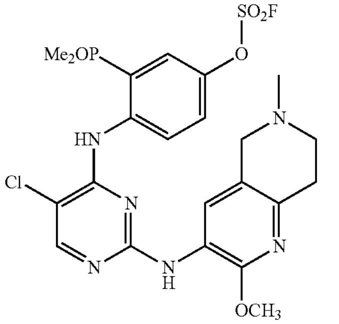 | Method A A1/B19 | 4-((5-Chloro-2-((2-methoxy-6-methyl-5,6,7,8-tetrahydro-1,6-naphthyridin-3-yl)amino)pyrimidin-4-yl)amino)-3-(dimethylphosphoryl)phenyl sulfofluoridate; $^{1}$H NMR (400 MHz, DMSO-$d_6$) δ 1.85 (d, J = 13.6 Hz, 6H), 2.36 (s, 3H), 2.67 (t, J = 5.6 Hz, 2H), 2.79 (t, J = 5.6 Hz, 2H), 3.37 (s, 2H), 3.86 (s, 3H), 7.57(d, J = 6.8 Hz, 1H), 7.74(s, 1H), 7.88-7.92(m, 1H), 8.22(s, 1H), 8.41 (s, 1H), 8.63(brs, 1H), 11.43 (s, 1H); ESI-MS (m/z) 571.1 $(M + H)^+$ |
| Example 23 | 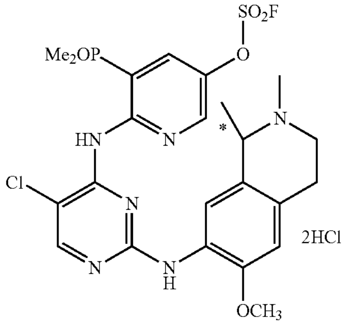 Isomer 1 | Method A A7/B15-a | 6-((5-Chloro-2-((6-m ethoxy-1,2-dimethyl-1,2,3,4-tetrahydroisoquinolin-7-yl)amino) pyrimidin-4-yl)amino)-5-(dimethylphosphory)pyridin-3-yl sulfofluoridate dihyrochloride (Isomer 1); $^{1}$H NMR (400 MHz, DMSO-$d_6$) δ 1.33-1.44 (m, 3H), 1.86-1.92 (m, 6H), 2.73-2.85 (m, 3H), 2.95-3.00 (m, 1H), 3.14-3.21 (m, 1H), 3.27-3.32 (m, 2H), 3.84 (s, 3H), 4.34-4.45 (m, 1H), 6.91 (d, J = 6.8 Hz, 1H), 7.85-7.93 (m, 1H), 8.33 (brs, 2H), 8.47 (d, J = 13.2 Hz, 1H), 8.86 (brs, 1H), 10.78 (brs, 1H), 10.99 (brs, 1H), 11.40 (brs, 1H); ESI-MS (m/z) 585.1 $(M + H)^+$ |
| Example 24 | 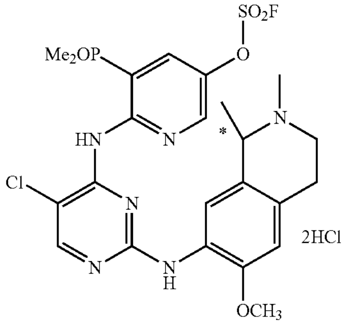 Isomer 2 | Method A A7/B15-b | 6-((5-Chloro-2-((6-methoxy-1,2-dimethyl-1,2,3,4-tetrahydroisoquinolin-7-yl)amino) pyrimidin-4-yl)amino)-5-(dimethylphosphoryl)pyridin-3-yl sulfofluoridate dihydrochloride (Isomer 2); $^{1}$H NMR (400 MHz, DMSO-$d_6$) δ 1.33-1.44 (m, 2H), 1.86-1.92 (m, 6H), 2.74-2.85 (m, 3H), 2.95-3.00 (m, 1H), 3.09-3.14 (m, 1H), 3.19-3.41 (m, 2H), 3.83 (s, 3H), 4.36-4.46 (m, 1H), 6.90 (d, J = 6.4 Hz, 1H), 7.85-7.94 (m, 1H), 8.38 (brs, 2H), 8.47 (d, J = 12.8 Hz, 1H), 8.86 (brs, 1H), 10.81 (brs, 1H), 11.03 (brs, 1H), 11.39 (brs, 1H). ESI-MS (m/z) 585.1 $(M + H)^+$ |
| Example 25 | 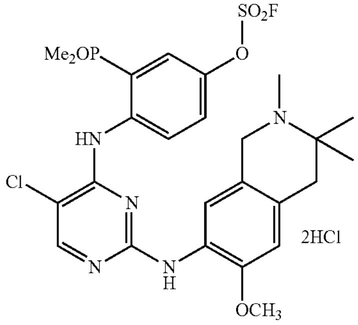 | Method A A1/B18 | 4-((5-Chloro-2-((6-methoxy-2,3,3-trimethyl-1,2,3,4-tetrahydroisoquinolin-7-yl)amino) pyrimidin-4-yl)amino)-3-(dimethylphosphoryl)phenyl sulfofluoridate dihydrochloride; $^{1}$H NMR (400 MHz, DMSO-$d_6$) δ 1.23 (s, 3H), 1.48 (s, 3H), 1.86 (d, J = 13.7 Hz, 6H), 2.98 (s, 3H), 2.91-3.00 (m, 1H), 3.22-3.31 (m, 1H), 3.78 (s, 3H), 4.10-4.35 (m, 2H), 6.94 (s, 1H), 7.50 (s, 1H), 7.75-7.78 (m, 1H), 7.92-7.96 (m, 1H), 8.28 (s, 1H), 8.67 (brs, 1H), 8.93 (brs, 1H), 11.36 (brs, 1H), 11.78 (brs, 1H); |

TABLE 4-continued

Structure, chemical name, method, intermediate used and analytical data of Examples (3-28)

| Example No. | Structure | Method and Intermediate | Chemical Name and Analytical data |
|---|---|---|---|
| Example 26 | 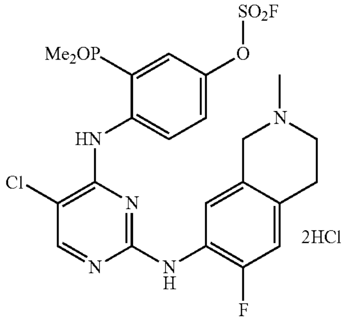 | Method A A1/B9 | 4-((5-Chloro-2-((6-fluoro-2-methyl-1,2,3,4-tetrahydroisoquinolin-7-yl) amino)pyrimidin-4-yl)amino)-3-(dimethylphosphoryl)phenyl sulfofluoridate dihydrochloride; $^1H$ NMR (400 MHz, DMSO-$d_6$) δ 1.86(d, J = 13.6 Hz, 6H), 2.90 (s, 3H), 3.01-3.12 (m, 1H), 3.11-3.40 (m, 2H), 3.52-3.65 (m, 1H), 4.15-4.42 (m, 2H), 7.28 (d, J = 11.2 Hz, 1H), 7.42 (d, J = 7.6 Hz, 1H), 7.65-7.68 (m, 1H), 7.87-7.91 (m, 1H), 8.21 (s, 1H), 8.70 (s, 1H), 9.26 (brs, 1H), 10.55 (s, 1H), 11.55 (brs, 1H) ESI-MS (m/z) = 558 $(M + H)^+$ |
| Example 27 | 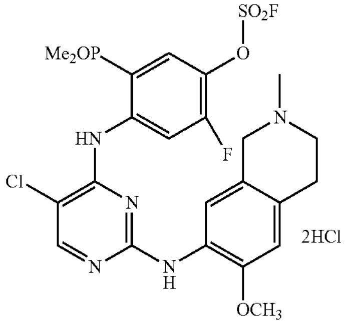 | Method A A14/B1 | 4-((5-Chloro-2-((6-methoxy-2-methyl-1,2,3,4-tetrahydroisoquinolin-7-yl)amino)pyrimidin-4-yl)amino)-5-(dimethylphosphoryl)-2-fluorophenyl sulfofluoridate dihydrochloride; $^1H$ NMR (400 MHz, DMSO-$d_6$) δ 1.88 (d, J = 14 Hz, 6H), 2.89 (s, 3H), 2.98-2.99 (m, 1H), 3.17-3.35 ( m, 3H), 3.79 (s, 3H), 4.11-4.17 (m, 1H), 4.34-4.38 (m, 1H), 7.01 (s, 1H), 7.40 (s, 1H), 8.10-8.16 (m, 1H), 8.22 (s, 1H), 8.82-8.85 (m, 2H), 10.49 (brs, 1H), 11.89 (brs, 1H); ESI-MS (m/z) 588 $(M + H)^+$ |
| Example 28 | 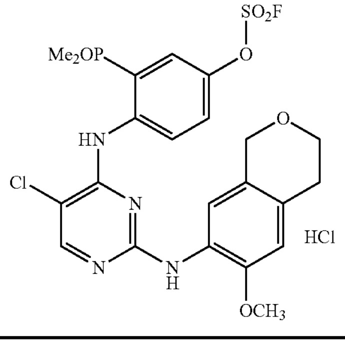 | Method A A1/B20 | 4-((5-Chloro-2-((6-methoxyisochroman-7-yl)amino) pyrimidin-4-yl)amino)-3-(dimethylphosphoryl)phenyl sulfofluoridate hydrochloride; $^1H$ NMR (400 MHz, DMSO-$d_6$) δ 1.85 (d, J = 13.6 Hz, 6H), 2.78 (t, J = 5.6 Hz, 2H), 3.79 (s, 3H), 3.87 (t, J = 5.6 Hz, 2H), 4.52-4.61 (m, 3H), 6.90 (s, 1H), 7.29 (s, 1H), 7.61 (d, J = 8.4 Hz, 1H), 7.93-7.97 (m, 1H), 8.28 (s, 1H), 8.56 (s, 1H), 8.98 (brs, 1H), 11.77 (brs , 1H); ESI-MS (m/z) 557.2 $(M + H)^+$ |

Method A1:

Examples mentioned below are prepared from corresponding racemic compounds by SFC purification using Chiralpak IH (4.6×150) mm, 5μ column (detection wavelength 210-400 nm) with 0.100 $NH_3$ in methanol as mobile phase to yield Isomer 1 & Isomer 2 respectively. The details of synthesis and analytical data of the examples prepared from the above mentioned methods are given below in Table 5.

TABLE 5

Structure, chemical name, method, intermediate used and analytical data of Examples (29-36)

| Example No. | Structure | Method and Intermediate | Chemical Name and Analytical data |
|---|---|---|---|
| Example 29 | 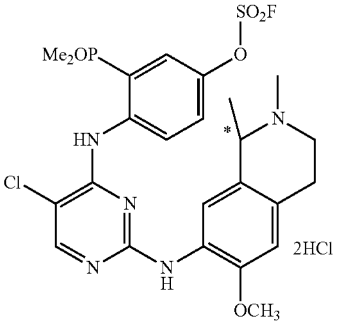 Isomer 1 | Method A/A1 A1/B15 | 4-((5-Chloro-2-((6-methoxy-1,2-dimethyl-1,2,3,4-tetrahydroisoquinolin-7-yl)amino)pyrimidin-4-yl)amino)-3-(dimethylphosphoryl)phenyl sulfofluoridate dihydrochloride (Isomer 1); $^1$H NMR (DMSO-$d_6$)) δ 1.39-1.55 (m, 3H), 1.85 (d, J = 14 Hz, 6H), 2.73-2.86 (m, 3H), 2.90-2.99 (m, 1H), 2.99-3.033 (m, 1H), 3.17-3.20 (m, 1H), 3.29-3.59 (m, 2H), 3.80 (s, 3H), 4.35-4.46 (m, 1H), 6.98 (m, 1H), 7.49 ( d, J = 6 Hz, 1H), 7.64 ( d, J = 9.6 Hz, 1H), 7.91-7.95 (m, 1H), 8.27 (s, 1H), 8.62 (brs, 1H), 8.93 (brs, 1H), 10.99 (brs, 1H), 11.71 (brs, 1H); ESI-MS (m/z) 584.1 $(M + H)^+$ |
| Example 30 | 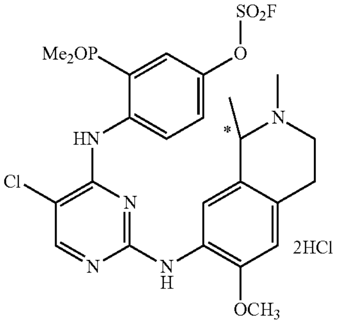 Isomer 2 | Method A/A1 A1/B15 | 4-((5-Chloro-2-((6-methoxy-1,2-dimethyl-1,2,3,4-tetrahydroisoquinolin-7-yl) amino)pyrimidin-4-yl)amino)-3-(dimethylphosphoryl)phenyl sulfofluoridate dihydrochloride (Isomer 2); $^1$H NMR (DMSO-$d_6$)) δ 1.39-1.55 (m, 3H), 1.85 (d, J = 14 Hz, 6H), 2.73-2.86 (m, 3H), 2.90-2.99 (m, 1H), 2.99-3.033 (m, 1H), 3.17-3.20 (m, 1H), 3.29-3.59 (m, 2H), 3.80 (s, 3H), 4.35-4.46 (m, 1H), 6.98 (m, 1H), 7.49 ( d, J = 6 Hz, 1H), 7.64 (d, J = 9.6 Hz, 1H), 7.91-7.95 (m, 1H), 8.27 (s, 1H), 8.62 (brs, 1H), 8.93 (brs, 1H), 10.99 (brs, 1H), 11.71 (brs, 1H); ESI-MS (m/z) 584.1 $(M + H)^+$ |
| Example 31 | 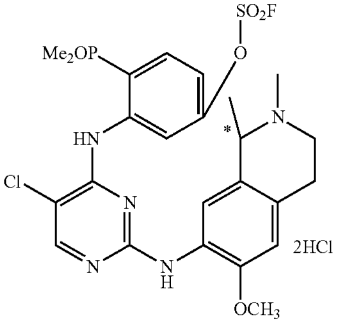 Isomer 1 | Method A/A1 A5/B15 | 3-((5-Chloro-2-((6-methoxy-1,2-dimethyl-1,2,3,4-tetrahydroisoquinolin-7-yl) amino)pyrimidin-4-yl)amino)-4-(dimethylphosphoryl)phenyl sulfofluoridate dihydrochloride (Isomer 1); $^1$H NMR (400 MHz, DMSO-$d_6$) δ 1.41-1.57 (m, 3H), 1.85 (d, J = 13.6 Hz, 6H), 2.76-2.87 (m, 3H), 3.03-3.10 (m, 1H), 3.13-3.17 (m, 1H), 3.31-3.57 (m, 2H), 3.79 (s, 3H), 4.39-4.55 (m, 1H), 6.94 (d, J = 4.8 Hz, 1H), 7.37 (d, J = 7.2 Hz, 1H), 7.58 (s, 1H), 7.81-7.86 (m, 1H), 8.24 (s, 1H), 8.64 (brs, 1H), 8.82 (brs, 1H), 11.84 (brs , 1H); ESI-MS (m/z) 584.2 $(M + H)^+$. |
| Example 32 | 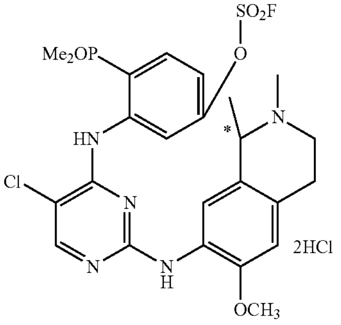 Isomer 2 | Method A/A1 A5/B15 | 3-((5-Chloro-2-((6-methoxy-1,2-dimethyl-1,2,3,4-tetrahydroisoquinolin-7-yl) amino)pyrimidin-4-yl)amino)-4-(dimethylphosphoryl)phenyl sulfofluoridate dihydrochloride (Isomer 2); $^1$H NMR (400 MHz, DMSO-$d_6$) δ 1.41-1.57 (m, 3H), 1.85 (d, J = 13.6 Hz, 6H), 2.76-2.87 (m, 3H), 3.03-3.10 (m, 1H), 3.13-3.17 (m, 1H), 3.31-3.57 (m, 2H), 3.79 (s, 3H), 4.39-4.55 (m, 1H), 6.94 (d, J = 4.8 Hz, 1H), 7.37 (d, J = 7.2 Hz, 1H), 7.58 (s, 1H), 7.81-7.86 (m, 1H), 8.24 (s, 1H), 8.64 (brs, 1H), 8.82 (brs, 1H), 11.84 (brs , 1H); ESI-MS (m/z) 584.2 $(M + H)^+$. |

TABLE 5-continued

Structure, chemical name, method, intermediate used and analytical data of Examples (29-36)

| Example No. | Structure | Method and Intermediate | Chemical Name and Analytical data |
|---|---|---|---|
| Example 33 | 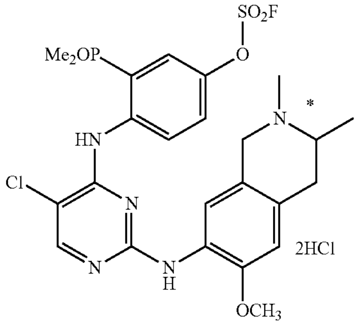 Isomer 1 | Method A/A1 A1/B17 | 4-((5-Chloro-2-((6-methoxy-2,3-dimethyl-1,2,3,4-tetrahydroisoquinolin-7-yl) amino)pyrimidin-4-yl)amino)-3-(dimethylphosphoryl)phenyl sulfofluoridate dihydrochloride (Isomer 1); $^1$H NMR (400 MHz DMSO-$d_6$) δ 1.27-1.43 (m, 3H), 1.85 (d, J = 14 Hz, 6H), 2.71-2.85 (m, 3H), 3.03-3.33 (m, 2H), 3.56-3.59 (m, 1H), 3.84 (s, 3H), 4.09-4.21 (m, 1H), 4.30-4.34 (m, 1H), 6.98 (d, J = 8.8 Hz, 1H), 7.49 (s, 1H), 7.71-7.81 (m, 1H), 7.93-7.96 (m, 1H), 8.29 (s, 1H), 8.66 (brs, 1H), 8.93 (s, 1H), 11.17 (brs, 1H), 11.76 (brs, 1H); ESI-MS (m/z) 584.2 $(M + H)^+$ |
| Example 34 | 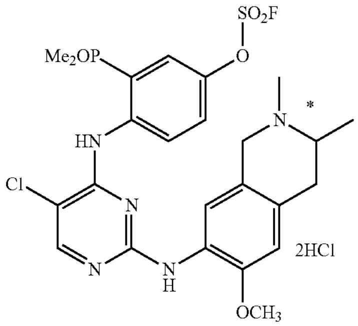 Isomer 2 | Method A/A1 A1/B17 | 4-((5-Chloro-2-((6-methoxy-2,3-dimethyl-1,2,3,4-tetrahydroisoquinolin-7-yl) amino)pyrimidin-4-yl)amino)-3-(dimethylphosphoryl)phenyl sulfofluoridate dihydrochloride (Isomer 2); $^1$H NMR (400 MHz DMSO-$d_6$) δ 1.27-1.43 (m, 3H), 1.85 (d, J = 14 Hz, 6H), 2.71-2.85 (m, 3H), 3.03-3.33 (m, 2H), 3.56-3.59 (m, 1H), 3.84 (s, 3H), 4.09-4.21 (m, 1H), 4.30-4.34 (m, 1H), 6.98 (d, J = 8.8 Hz, 1H), 7.49 (s, 1H), 7.71-7.81 (m, 1H), 7.93-7.96 (m, 1H), 8.29 (s, 1H), 8.66 (brs, 1H), 8.93 (s, 1H), 11.17 (brs, 1H), 11.76 (brs, 1H); ESI-MS (m/z) 584.2 $(M + H)^+$ |
| Example 35 | 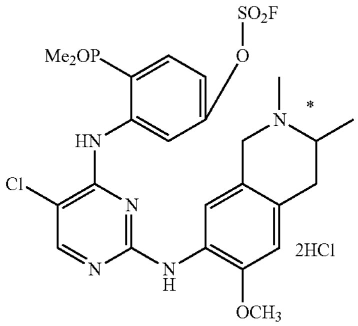 Isomer 1 | Method A/A1 A5/B17 | 3-((5-Chloro-2-((6-methoxy-2,3-dimethyl-1,2,3,4-tetrahydroisoquinolin-7-yl) amino)pyrimidin-4-yl)amino)-4-(dimethylphosphoryl)phenyl sulfofluoridate dihydrochloride (Isomer 1); $^1$H NMR (400 MHz, DMSO-$d_6$) δ 1.31-1.42 (m, 3H), 1.85 (d, J = 13.6 Hz, 6H), 2.67-2.85 (m, 3H), 2.99-3.25 (m, 2H), 3.56-3.59 (m, 1H), 3.81 (s, 3H), 4.07-4.19 (m, 1H), 4.37-4.40 (m, 1H), 6.94 (d, J = 5.2 Hz, 1H), 7.40 (d, J = 8.4 Hz, 1H), 7.58 (s, 1H), 7.83-7.88 (m, 1H), 8.27 (s, 1H), 8.73 (brs, 1H), 8.83 (d, J = 9.2 Hz, 1H), 10.92 (brs, 1H), 11.18 (brs, 1H), 11.90 (s , 1H); ESI-MS (m/z) 584.1 $(M + H)^+$ |
| Example 36 | 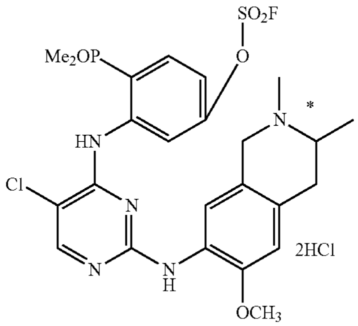 Isomer 2 | Method A/A1 A5/B17 | 3-((5-Chloro-2-((6-methoxy-2,3-dimethyl-1,2,3,4-tetrahydroisoquinolin-7-yl) amino)pyrimidin-4-yl)amino)-4-(dimethylphosphoryl)phenyl sulfofluoridate dihydrochloride (Isomer 2); $^1$H NMR (400 MHz, DMSO-$d_6$) δ 1.31-1.42 (m, 3H), 1.85 (d, J = 13.6 Hz, 6H), 2.67-2.85 (m, 3H), 2.99-3.25 (m, 2H), 3.56-3.59 (m, 1H), 3.81 (s, 3H), 4.07-4.19 (m, 1H), 4.37-4.40 (m, 1H), 6.94 (d, J = 5.2 Hz, 1H), 7.40 (d, J = 8.4 Hz, 1H), 7.58 (s, 1H), 7.83-7.88 (m, 1H), 8.27 (s, 1H), 8.73 (brs, 1H), 8.83 (d, J = 9.2 Hz, 1H), 10.92 (brs, 1H), 11.18 (brs, 1H), 11.90 (s, 1H); ESI-MS (m/z) 584.1 $(M + H)^+$ |

Method B:

5-((5-Chloro-2-((6-methoxy-2-methyl-1,2,3,4-tetrahydroisoquinolin-7-yl)amino)pyrimidin-4-yl)amino)-4-(dimethylphosphoryl)pyridin-2-ylsulfofluoridate (Example 37)

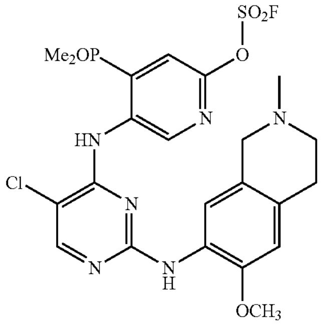

Step 1: (5-((2,5-Dichloropyrimidin-4-yl)amino)-2-methoxypyridin-4-yl) dimethyl phosphine oxide

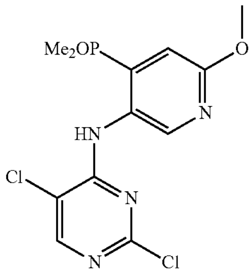

The titled intermediate was prepared by the reaction of (5-Amino-2-methoxypyridin-4-yl) dimethyl phosphine oxide (290 mg, 1.45 mmol) with DIPEA (0.5 mL, 2.9 mmol), 2,4,5-trichloropyrimidine (531 mg, 2.9 mmol) in IPA (5 mL) as per the procedure described in Step 1 of Example 1 to yield 268 mg of the desired product. $^1$H NMR (400 MHz, DMSO-$d_6$) δ 1.82 (d, J 14 Hz, 6H), 3.91 (s, 3H), 7.19 (d, J=14 Hz, 1H), 8.43 (s, 1H), 9.03 (d, J=5.2 Hz, 1H), 10.97 (s, 1H); ESI-MS (m/z) 347.2 $(M+H)^+$ Step 2: (5-((5-Chloro-2-((6-methoxy-2-methyl-1,2,3,4-tetrahydroisoquinolin-7-yl)amino) pyrimidin-4-yl)amino)-2-methoxypyridin-4-yl)dimethylphosphine oxide

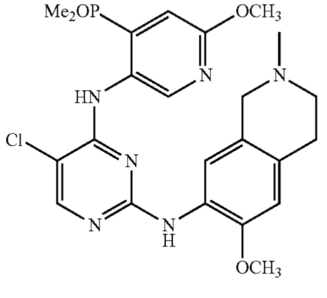

The titled intermediate was prepared by the reaction of 5-((2,5-Dichloropyrimidin-4-yl) amino)-2-methoxypyridin-4-yl) dimethyl phosphine oxide (260 mg, 0.749 mmol) with PTSA (171 mg, 0.898 mmol), 6-methoxy-2-methyl-1,2,3,4-tetrahydroisoquinolin-7-amine (Intermediate B1) (143 mg, 0.749 mmol) in IPA (10 mL) as per the procedure described in Step 2 of Example 1 to yield 171 mg of the desired product. $^1$H NMR (400 MHz, DMSO-$d_6$) δ 1.75 (d, J=14, Hz 6H), 2.33 (s, 3H), 2.50-2.56 (m, 2H), 2.75-2.77 (m, 2H), 3.30-3.34 (m, 2H), 3.80 (s, 3H), 3.93 (s, 3H), 6.73 (s, 1H), 7.14 (s, 1H), 7.25 (d, J=6.8 Hz, 1H), 7.45 (s, 1H), 7.90 (s, 1H), 8.13 (s, 1H), 9.01 (d, J=4.4 Hz, 1H), 10.21 (s, 1H); ESI+MS (m/z) 503.2 $(M+H)^+$.

Step 3: (5-((5-Chloro-2-((6-methoxy-2-methyl-1,2,3,4-tetrahydroisoquinolin-7-yl)amino) pyrimidin-4-yl)amino)-2-hydroxypyridin-4-yl)dimethylphosphine oxide

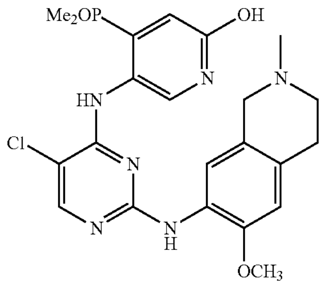

To a stirred solution of (5-((5-Chloro-2-((6-methoxy-2-methyl-1,2,3,4-tetrahydroisoquinolin-7-yl)amino)pyrimidin-4-yl)amino)-2-methoxypyridin-4-yl)dimethylphosphine oxide (160 mg, 0.318 mmol) in $CH_3CN$ (12 mL) were added NaI (239 mg, 1.593 mmol), chlorotrimethyl silane (0.241 mL, 1.593 mmol) followed by water (0.060 mL) and heated to 80° C. for 3 h. The reaction mixture was cooled to RT, basified with $NaHCO_3$ solution and extracted with ethyl acetate. The organic layer was separated, dried over anhydrous sodium sulfate and concentrated under vacuum. The crude residue obtained was purified by silica gel column chromatography to yield 91 mg of the desired product. $^1$H NMR (400 MHz, DMSO-$d_6$) δ 1.63 (d, J=14 Hz, 6H), 2.38 (s, 3H), 2.51-2.62 (m, 2H), 2.75-2.76 (m, 2H), 2.40-2.47 (m, 2H), 3.80 (s, 3H), 6.73 (s, 1H), 6.85 (d, J=15.2 Hz, 1H), 7.59 (s, 1H), 7.72 (s, 1H), 7.93 (s, 1H), 8.10 (s, 1H), 9.21 (s, 1H); ESI-MS (m/z) 488.6 $(M)^+$ Step 4: 5-((5-Chloro-2-((6-methoxy-2-methyl-1,2,3,4-tetrahydroisoquinolin-7-yl) amino) pyrimidin-4-yl)amino)-4-(dimethylphosphoryl)pyridin-2-ylsulfofluoridate The titled intermediate was prepared by the reaction of (5-((5-chloro-2-((6-methoxy-2-methyl-1,2,3,4-tetrahydroisoquinolin-7-yl)amino)pyrimidin-4-yl)amino)-2-hydroxypyridin-4-yl) dimethylphosphine oxide (85 mg, 0.174 mmol) with AISF (60 mg, 0.191 mmol), DBU (0.058 mL, 0.382 mmol) in THF (8 mL) as per the procedure described in Step 1 of Example 2 to yield 34 mg of the desired product. $^1$H NMR (400 MHz, DMSO-$d_6$) δ 1.91 (d, J=14 Hz, 6H), 2.33 (s, 3H), 2.57-2.59 (m, 2H), 2.77-2.79 (m, 2H), 3.40-3.42 (m, 2H), 3.78 (s, 3H), 6.77 (s, 1H), 7.31 (s, 1H), 7.89

(d, J=12.8 Hz, 1H), 8.21 (s, 1H), 8.42 (s, 1H), 9.65 (s, 1H), 11.28 (s, 1H); ESI-MS (m/z) 571.1 $(M+H)^+$

Method C:

4-((5-Chloro-2-((6-methoxy-1,2,3,4-tetrahydroisoquinolin-7-yl)amino)pyrimidin-4-yl) amino)-3-(dimethylphosphoryl)phenylsulfofluoridate dihydrochloride (Example 38)

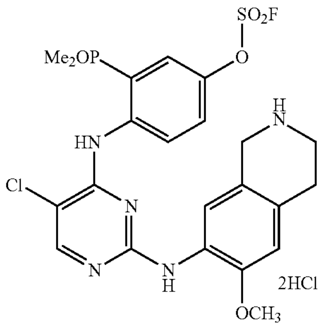

Step 1: (2-((5-Chloro-2-((6-methoxy-1,2,3,4-tetrahydroisoquinolin-7-yl)amino)pyrimidin-4-yl) amino)-5-hydroxyphenyl)dimethylphosphine oxide

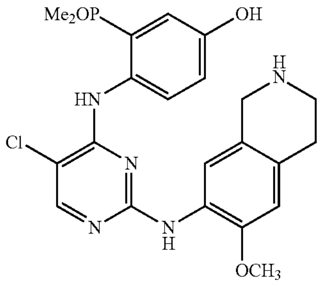

To a stirred solution of (2-((2,5-dichloropyrimidin-4-yl) amino)-5-((4-methoxybenzyl)oxy)phenyl)dimethylphosphine oxide (4.0 g, 8.83 mmol) in IPA (50 mL) were added tert-butyl 7-amino-6-methoxy-3,4-dihydroisoquinoline-2(1H)-carboxylate (Intermediate B10) (2.46 g, 8.83 mmol) and PTSA (1.7 g, 8.83 mmol) heated to 120° C. for overnight in a sealed tube. The solvent was evaporated under reduced pressure, basified with aqueous ammonia solution and stirred for 10 min. The solid obtained was filtered, washed with water and dried under vacuum. The solid thus obtained was stirred in diethyl ether and filtered to yield 3.23 g of the desired product. $^1H$ NMR (400 MHz DMSO-$d_6$)) δ 1.69 (d, J=13.2 Hz, 6H), 2.64-2.70 (m, 2H), 2.91-2.94 (m, 2H), 3.65 (s, 2H), 3.77 (s, 3H), 6.69 (s, 1H), 6.90 (d, J=8.8 Hz, 1H), 6.97-7.01 (m, 1H), 7.43 (s, 1H), 7.81 (s, 1H), 7.99-8.02 (m, 1H), 8.08 (s, 1H), 10.32 (s, 1H; ESI-MS (m/z) 474.2 $(M+H)^+$.

Step 2: tert-Butyl 7-((5-chloro-4-((2-(dimethylphosphoryl)-4-hydroxyphenyl) amino) pyrimidin-2-yl) amino)-6-methoxy-3,4-dihydroisoquinoline-2(1H)-carboxylate

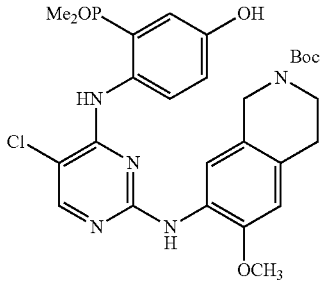

To a stirred solution of (2-((5-chloro-2-((6-methoxy-1,2,3,4-tetrahydro isoquinolin-7-yl)amino)pyrimidin-4-yl) amino)-5-hydroxyphenyl)dimethyl phosphine oxide (3.2 g, 6.75 mmol) in MeOH (60 mL) was added solution of NaOH (540 mg, 13.5 mmol) in water (12 mL) followed by Boc-anhydride (2.2 g, 10.12 mmol) and stirred at RT for overnight. The reaction mixture was diluted with water and extracted with ethyl acetate. The organic layer was dried over anhydrous sodium sulphate and concentrated. The residue obtained was purified by silica gel chromatography to yield 2.58 g of the desired product. $^1H$ NMR (400 MHz DMSO-$d_6$)) δ 1.43 (s, 9H), 1.70 (d, J=13 Hz, 6H), 2.70-2.80 (m, 2H), 3.53-3.56 (m, 2H), 3.78 (s, 3H), 4.33 (s, 2H), 6.81 (s, 1H), 6.87-6.90 (m, 1H), 6.94-6.98 (m, 1H), 7.58 (s, 1H), 7.91 (s, 1H), 8.04 (s, 1H), 8.09 (s, 1H), 9.60 (s, 1H), 10.46 (s, 1H); ESI-MS (m/z) 574.1 $(M+H)^+$.

Step 3: tert-Butyl 7-((5-chloro-4-((2-(dimethylphosphoryl)-4-((fluorosulfonyl)oxy)phenyl) amino)pyrimidin-2-yl)amino)-6-methoxy-3,4-dihydroisoquinoline-2(1H)-carboxylate

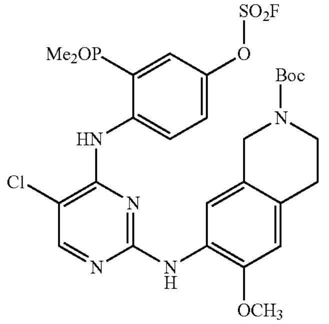

To a stirred solution of tert-butyl 7-((5-chloro-4-((2-(dimethylphosphoryl)-4-hydroxy phenyl) amino)pyrimidin-2-yl)amino)-6-methoxy-3,4-dihydroisoquinoline-2(1H)-carboxylate (2.5 g, 4.35 mmol) in THE (60 mL) at 0° C. was added AISF (1.36 g, 4.35 mmol) followed by DBU (1.42 ml, 9.57 mmol) and stirred for 30 min. The reaction mixture was diluted with water and extracted thrice with ethyl acetate. The organic layers were separated, dried over anhydrous sodium sulphate and concentrated. The residue thus obtained was purified by silica gel chromatography to yield 1.59 g of the desired product. $^1H$ NMR (400 MHz DMSO-$d_6$)) δ 1.43 (s, 9H), 1.85 (d, J=13.6 Hz, 6H), 2.75-2.78 (m, 2H), 3.50-3.56 (m, 2H), 3.78 (s, 3H), 4.37 (s, 2H), 6.88 (s, 1H), 7.48 (s, 1H), 7.56 (s, 1H), 7.87-7.91 (m, 1H), 8.20 (s, 1H), 8.31-8.33 (m, 1H), 8.65 (s, 1H), 11.42 (s, 1H); ESI-MS (m/z) 656.3 $(M+H)^+$.

Step 4: 4-((5-Chloro-2-((6-methoxy-1,2,3,4-tetrahydroisoquinolin-7-yl)amino)pyrimidin-4-yl)amino)-3-(dimethylphosphoryl)phenylsulfofluoridate dihydrochloride To a stirred solution of tert-butyl 7-((5-chloro-4-((2-(dimethylphosphoryl)-4-((fluorosulfonyl)oxy)phenyl)amino) pyrimidin-2-yl)amino)-6-methoxy-3,4-dihydroisoquinoline-2(1H)-carboxylate (1.5 g, 3.03 mmol) in diethyl ether (10 mL) was added 4 M HCl in dioxane (20 mL) and stirred at RT for 3 h. The solvent was evaporated under vacuum and stirred with diethyl ether:acetonitrile (1:1, 50 mL) and filtered. The solid thus obtained was dried under vacuum to yield 1.95 g of the desired product. $^1H$ NMR (400 MHz DMSO-$d_6$)) δ 1.86 (d, J=13.6 Hz, 6H), 3.00-3.03 (m, 2H), 3.34-3.70 (m, 2H), 3.80 (s, 3H), 4.10 (s, 2H), 6.99 (s, 1H), 7.49 (s, 1H), 7.74 (dd, J=2.8 Hz, 13.6 Hz, 1H), 7.96 (dd, J=2.8 Hz, 9.6 Hz, 1H), 8.29 (s, 1H), 8.65 (s, 1H), 8.99 (s, 1H), 9.49 (brs, 2H), 11.78 (s, 1H); ESI-MS (m/z) 556.0 $(M+H)^+$.

The details of synthesis and analytical data of the examples prepared from the above mentioned methods are given below in Table 6.

TABLE 6

Structure, chemical name, method, intermediate used and analytical data of Examples 39-40.

| Example No. | Structure | Method and Intermediate | Chemical Name and Analytical data |
| --- | --- | --- | --- |
| Example 39 | 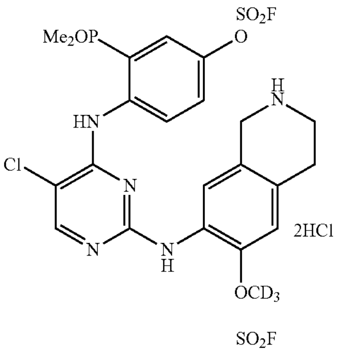 | Method C A1/B12 | 4-((5-Chloro-2-((6-methoxy-$d_3$-1,2,3,4-tetrahydroisoquinolin-7-yl) amino)pyrimidin-4-yl)amino)-3-(dimethylphosphoryl)phenyl sulfofluoridate dihydrochloride; 1H NMR (400 MHz, DMSO-$d_6$) δ 1.86 (d, J = 14 Hz, 6H), 3.00-3.43 (m, 2H), 3.34-3.60 (m, 2H), 4.05-4.15 (m, 2H), 6.99 (s, 1H), 7.45 (s, 1H), 7.71-7.74 (m, 1H), 7.92-7.97 (m, 1H), 8.29 (s, 1H), 8.64 (brs, 1H), 9.01 (brs, 1H), 9.49 (brs, 2H), 11.80 (brs, 1H); ESI-MS (m/z) 559.1 $(M + H)^+$ |
| Example 40 | 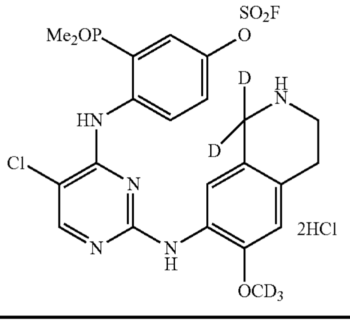 | Method C A1/B13 | 4-((5-Chloro-2-((6-methoxy-$d_3$-1,2,3,4-tetrahydroisoquinolin-7-yl-1,1-$d_2$)amino)pyrimidin-4-yl)amino)-3-(dimethylphosphoryl)phenyl sulfofluoridate dihydrochloride; $^1H$ NMR (400 MHz, DMSO-$d_6$) δ 1.86 (d, J = 13.6 Hz, 6H), 3.02 (t, J = 6 Hz, 2H), 3.30-3.45 (m, 2H), 6.98 (s, 1H), 7.49 (s, 1H), 7.73 (dd, J = 2.8 Hz, 9.2 Hz, 1H), 7.80-7.95 (m, 1H), 8.29 (brs, 1H), 8.64 (brs, 1H), 8.99 (brs, 1H), 9.46 (brs, 2H), 11.78 (s, 1H); ESI-MS (m/z) 561.2 $(M + H)^+$ |

Method D:

4-((5-Chloro-2-((1-methyl-1,4,5,6-tetrahydropyrrolo[3,4-c]pyrazol-3-yl)amino) pyrimidin-4-yl) amino)-3-(dimethylphosphoryl)phenyl sulfurofluoridate dihydrochloride (Example 41)

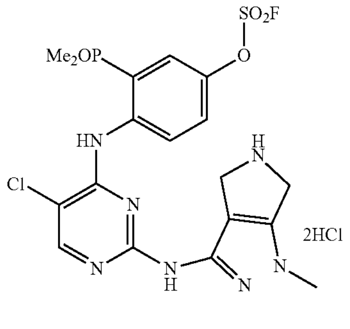

Step 1: (5-(Benzyloxy)-2-((2,5-dichloropyrimidin-4-yl)amino)phenyl)dimethyl phosphine oxide

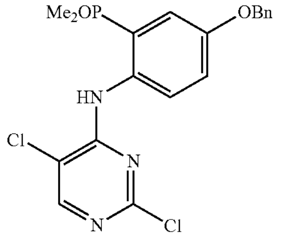

The titled compound was prepared by the reaction (2-amino-5-(benzyloxy) phenyl) dimethylphosphine oxide (400 mg, 0.36 mmol) with 2, 4, 5-trichloro pyrimidine (0.72 mmol), DIPEA (0.72 mmol) in IPA (4 mL) as per the procedure described in step 1 of Example 1 to yield 360 mg of the desired compound. $^1$H NMR (400 MHz, DMSO-$d_6$) δ 1.78 (d, J=13 Hz, 6H), 5.16 (s, 2H), 7.30-7.42 (m, 5H) 7.42-7.45 (m, 2H), 8.25-8.30 (m, 1H), 8.40 (s, 1H), 11.49 (s, 1H); ESI-MS (m/z) 424.2 $(M+2H)^+$.

Step 2: tert-Butyl 3-((4-((4-(benzyloxy)-2-(dimethylphosphoryl)phenyl)amino)-5-chloro pyrimidin-2-yl)amino)-1-methyl-4,6-dihydropyrrolo[3,4-c]pyrazole-5(1H)-carboxylate

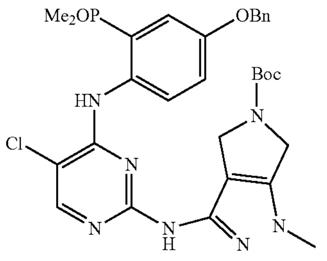

To a stirred solution of tert-butyl 3-amino-1-methyl-4,6-dihydropyrrolo[3,4-c]pyrazole-5-carboxylate (202 mg, 0.84 mmol) in 1,4-dioxane (6 mL) were added (5-(benzyloxy-2-((2,5 dichloropyrimidine-4-yl)amino)phenyl)dimethyl phosphine oxide (360 mg, 0.84 mmol), cesium carbonate (828 mg, 2.54 mmol), palladium acetate (77.7 mg, 0.084 mmol) and Xantphos (98 mg, 0.16 mmol). The reaction was heated in a microwave for 1 h at 140° C. The reaction mixture was concentrated under vacuum and purified by silica gel column chromatography to yield 300 mg of the desired product. $^1$H NMR (400 MHz, DMSO-$d_6$) δ 1.32 (s, 9H), 1.80 (d, J=13.6 Hz, 6H), 3.69 (s, 3H), 4.03 (s, 2H), 4.33 (s, 2H), 5.06 (s, 2H), 6.94-7.05 (m, 1H), 7.10-7.23 (m, 1H), 7.42-7.48 (m, 5H), 8.14 (s, 1H), 8.32 (s, 1H), 9.39 (s, 1H), 11.15 (s, 1H); ESI-MS (m/z) 626.7 $(M+2H)^+$ Step 3: tert-Butyl 3-((5-chloro-4-((2-(dimethylphosphoryl)-4-hydroxyphenyl)amino) pyrimidin-2-yl) amino)-1-methyl-4,6-dihydropyrrolo[3,4-c]pyrazole-5(1H)-carboxylate

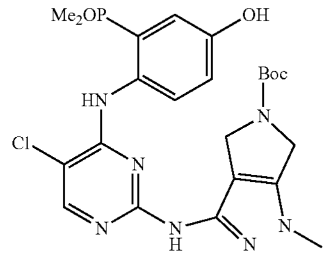

To a stirred solution of tert-butyl 3-((4-((4-(benzyloxy)-2-(dimethylphosphoryl) phenyl)amino)-5-chloropyrimidin-2-yl)amino)-1-methyl-4,6-dihydropyrrolo[3,4-c]pyrazole-5(1H)-carboxylate (270 mg, 0.43 mmol) in methanol (10 mL) was subjected to hydrogenation in the presence of 20% palladium on carbon (50 mg) and stirred at RT for 16 h. The mixture was filtered and the filtrate was concentrated under reduced pressure to yield 90 mg of the desired product. $^1$H NMR (400 MHz, DMSO-$d_6$) δ 1.41 (s, 9H), 1.75 (d, J=13.6 Hz, 6H), 3.41 (s, 3H), 3.66 (s, 2H), 4.01 (s, 2H), 6.69 (d, J=8 Hz, 1H), 6.91 (d, J=8 Hz, 1H), 7.46 (s, 1H), 8.10 (s, 1H), 9.26 (s, 1H), 9.59 (br s, 1H), 10.58 (s, 1H); ESI-MS (m/z) 533.2 $(M)^+$ Step 4: 4-((5-Chloro-2-((1-methyl-1,4,5,6-tetrahydropyrrolo[3,4-c]pyrazol-3-yl) amino) pyrimidin-4-yl)amino)-3-(dimethylphosphoryl)phenyl sulfofluoridate hydrochloride To a stirred suspension of tert-butyl 3-((5-chloro-4-((2-(dimethylphosphoryl)-4-hydroxyphenyl)amino)pyrimidin-2-yl)amino)-1-methyl-4,6-dihydropyrrolo[3,4-c]pyrazole-5(1H)-carboxylate (70 mg, 0.13 mmol) and [4-(acetyl amino) phenyl] imidosulfuryl difluoride (50 mg, 0.15 mmol) in THE (5 mL) DBU was added (43.7 mg, 0.28 mmol) at 0° C. The mixture was stirred at RT for 1 h. The reaction mixture was diluted with water and extracted with chloroform three times. The combined organic layers were dried over anhydrous sodium sulfate and concentrated under reduced pressure. The solid thus obtained was stirred in 4M HCl in dioxane (1 mL) for 30 min and triturated with ethyl acetate. The solid obtained was filtered and dried under vacuum to yield 25 mg of the desired product. $^1$H NMR (400 MHz, DMSO-$d_6$) δ 1.50 (d, J=13.6 Hz, 6H), 3.81 (s, 3H), 4.20-4.30 (m, 4H), 7.71 (d, J=9.2 Hz, 1H), 7.91-7.95 (m, 1H), 8.26 (s, 1H), 8.85 (s, 1H), 9.65 (s, 1H), 9.97 (br s, 2H), 11.60 (br s, 1H); ESI-MS (m/z) 516.3 $(M+H)^+$ The details of synthesis and analytical data of the example prepared from the above-mentioned methods are given below in Table 7.

TABLE 7

| Structure, chemical name, intermediate used, method of preparation and analytical data of the Example 42. | | | |
|---|---|---|---|
| Example No. | Structure | Method and Intermediate | Chemical Name and Analytical data |
| Example 42 | 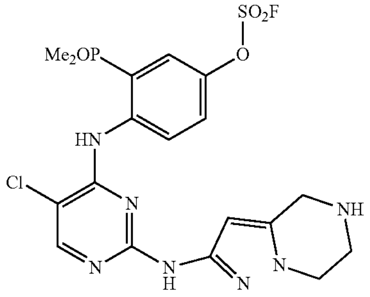 2HCl | Method D Intermediate A1/tert-Butyl 2-amino-6,7-dihydropyrazolo [1,5-a]pyrazine-5(4H)-carboxylate | 4-((5-Chloro-2-((4,5,6,7-tetrahydropyrazolo[1,5-a]pyrazin-2-yl)amino)pyrimidin-4-yl)amino)-3-(dimethylphosphoryl)phenyl sulfofluoridate dihydrochloride; $^1$H NMR (400 MHz, DMSO-$d_6$) δ 1.88 (d, J = 14 Hz, 6H), 3.66 (t, J = 4.0 Hz, 2H), 4.24 (t, J = 5.6 Hz, 2H), 4.35-4.40 (m, 2H), 7.73 (s, 1H), 7.93 (t, J = 5.2 Hz, 1H), 7.85-8.00 (m, 1H), 8.43 (s, 1H), 9.10 (br s, 1H) 9.71 (br s, 2H), 9.96 (s, 1H), 11.53 (br s, 1H); ESI-MS (m/z) 516.3 (M + H)$^+$. |

Method E:

4-((5-Chloro-2-((6-methoxy-2-methyl-1,2,3,4-tetrahydroisoquinolin-7-yl)amino)pyrimidin-4-yl)amino)-3-(dimethylphosphoryl)phenyl)(methyl)sulfamoylfluoride dihydrochloride (Example 43)

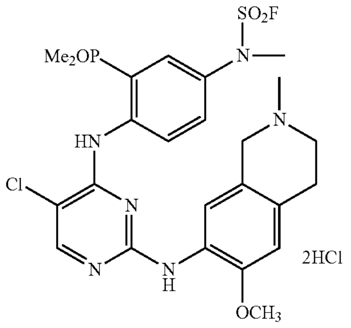

2HCl

Step 1: t-Butyl[4-((2,5-dichloropyrimidin-4-yl) amino)-3-(dimethylphosphoryl) phenyl](methyl) carbamate

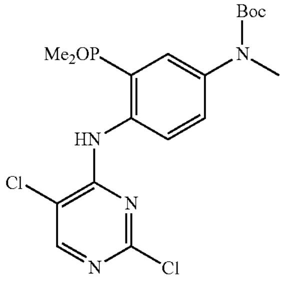

To a stirred solution of 2,4,5-trichloropyrimidine (510 mg, 2.32 mmol) in isopropyl alcohol (12 mL) t-Butyl[4-amino-3-(dimethyl phosphoryl) phenyl] (methyl) carbamate (690 mg, 2.32 mmol), DIPEA (598 mg, 4.64 mmol) were added in a sealed tube and heated at 120° C. for overnight. The reaction mixture was concentrated under reduced pressure. The residue thus obtained was purified by silica gel column chromatography to yield 690 mg of the desired product. $^1$H NMR (400 MHz, DMSO-$d_6$) δ 1.40 (s, 9H), 1.82 (d, J=13.2 Hz, 6H), 3.21 (s, 3H), 7.51-7.55 (m, 2H), 8.32-8.39 (m, 1H), 8.45 (s, 1H), 11.77 (s, 1H); ESI-MS (m/z) 445.1 (M+H)$^+$.

Step 2: t-Butyl[4-((5-chloro-2-((6-methoxy-2-methyl-1,2,3,4-tetrahydroisoquinolin-7-yl) amino) pyrimidin-4-yl)amino)-3-(dimethylphosphoryl)phenyl](methyl) carbamate

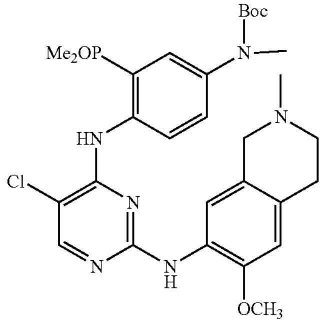

To a degassed solution of t-Butyl[4-((2,5-dichloropyrimidin-4-yl)amino)-3-(dimethylphosphoryl)phenyl](methyl) carbamate (690 mg, 1.55 mmol) and 6-methoxy-2-methyl-1,2,3,4-tetrahydroisoquinolin-7-amine (Intermediate B1) (268 mg, 1.39 mmol) in dioxane (10 mL) were added $Cs_2CO_3$ (1 g, 3.1 mmol), Xantphos (179 mg, 0.31 mmol) $Pd_2(dba)_3$ (141 mg, 0.155 mmol) in a microwave vial and stirred under microwaves at 140° C. for 1 h. The reaction mixture was diluted with chloroform, filtered through celite bed and washed with chloroform. The combined filtrate was washed with brine solution. The organic layer was dried over anhydrous sodium sulphate and concentrated under reduced pressure. The residue thus obtained was purified by silica gel column chromatography to yield 390 mg of the desired product. $^1$H NMR (400 MHz, DMSO-$d_6$) δ 1.40 (s, 9H), 1.78 (d, J=13.6 Hz, 6H), 2.34-2.36 (m, 5H), 2.66-2.68 (m, 2H), 2.81-2.83 (m, 2H), 3.21 (s, 3H), 3.77 (s, 3H), 6.80 (s, 1H), 7.32-7.47 (m, 3H), 8.07 (s, 1H), 8.14 (s, 1H), 11.16 (s, 1H), 11.57 (s, 1H); ESI-MS (m/z) 601.6 $(M+H)^+$ Step 3: (2-((5-Chloro-2-((6-methoxy-2-methyl-1,2,3,4-tetrahydroisoquinolin-7-yl)amino) pyrimidin-4-yl)amino)-5-(methylamino)phenyl)dimethylphosphine oxide

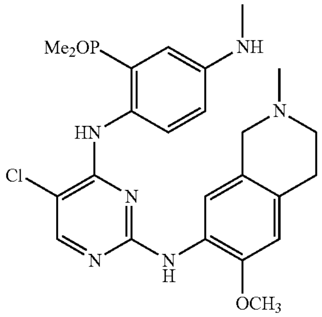

To a stirred solution of t-Butyl[4-((5-chloro-2-((6-methoxy-2-methyl-1,2,3,4-tetrahydroisoquinolin-7-yl) amino)pyrimidin-4-yl)amino)-3-(dimethylphosphoryl)phenyl](methyl) carbamate (390 mg) in DCM (4 mL) 4M HCl in Dioxane (5 mL) was added and stirred at RT for 3 h. The reaction mixture was concentrated under reduced pressure, basified with aqueous sodium bicarbonate solution and extracted with DCM. The organic layer was separated, dried over anhydrous sodium sulphate and concentrated under reduced pressure. The residue thus obtained was purified by silica gel column chromatography to yield 390 mg of the desired product. $^1$H NMR (400 MHz, DMSO-d6) δ 1.63 (d, J=13.6 Hz, 6H), 2.36 (s, 3H), 2.58-2.60 (brs, 2H), 2.67-2.76 (m, 5H), 3.20-3.21 (brs, 2H), 3.78 (s, 3H), 5.88 (q, J=5.2 Hz, 1H), 6.69-6-71 (m, 2H), 6.82 (d, J=14.4 Hz, 1H), 7.51 (s, 1H), 7.68-7.72 (m, 2H), 8.06 (s, 1H), 9.84 (s, 1H); ESI-MS (m/z) 501.3 $(M+H)^+$.

Step 4: (4-((5-Chloro-2-((6-methoxy-2-methyl-1,2,3,4-tetrahydroisoquinolin-7-yl) amino) pyrimidin-4-yl)amino)-3-(dimethylphosphoryl)phenyl)(methyl) sulfamoylfluoride

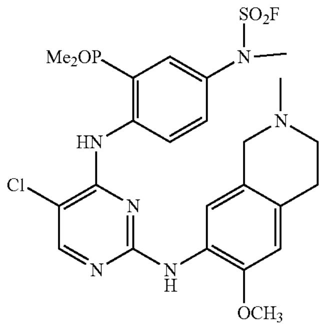

To a stirred solution of (2-((5-chloro-2-((6-methoxy-2-methyl-1,2,3,4-tetrahydroisoquinolin-7-yl)amino)pyrimidin-4-yl)amino)-5-(methylamino)phenyl)dimethyl phosphine oxide (150 mg, 0.3 mmol) and triethylamine (303 mg, 3 mmol) in DCM (3 mL) at 0° C. 1-(fluorosulfonyl)-23-dimethyl-1h-imidazol-3-ium trifluoromethanesulfonate (984 mg, 3 mmol) was added. The reaction mixture was stirred at RT for 16 h. The reaction mixture was diluted with water and extracted thrice with chloroform. The combined organic layers were dried over anhydrous sodium sulfate and concentrated under reduced pressure. The residue obtained was purified by silica gel column chromatography to yield 20 mg of desired product. $^1$H NMR (400 MHz, DMSO-$d_6$)) δ 1.82 (d, J=13.6 Hz, 6H), 2.35-2.36 (m, 3H), 2.49-2.50 (m, 2H), 2.63-2.65 (m, 2H), 2.82-2.83 (m, 2H), 3.45 (s, 3H), 3.77 (s, 3H), 6.81 (s, 1H), 7.38 (s, 1H), 7.47 (d, J=8.4 Hz, 1H), 7.72 (d, J=14.0 Hz, 1H), 8.17 (s, 1H), 8.24 (s, 1H), 8.59 (brs, 1H), 11.45 (s, 1H); ESI-MS (m/z) 583.1 $(M+H)^+$.

Step 5: [4-((5-Chloro-2-((6-methoxy-2-methyl-1,2,3,4-tetrahydroisoquinolin-7-yl)amino) pyrimidin-4-yl)amino)-3-(dimethylphosphoryl)phenyl](methyl) sulfamoylfluoride dihydrochloride To a stirred suspension [4-((5-chloro-2-((6-methoxy-2-methyl-1,2,3,4-tetrahydroisoquinolin-7-yl)amino)pyrimidin-4-yl)amino)-3-(dimethylphosphoryl) phenyl](methyl) sulfamoylfluoride (11 mg) in DCM (0.5 mL) 4M HCl in Dioxane (0.1 mL) was added and stirred at RT for 1 h. The solvent was evaporated under reduced pressure and the solid obtained was triturated with diethyl ether, filtered and dried under vacuum to yield 14 mg dihydrochloride salt of desired product. $^1$H NMR (400 MHz, DMSO-$d_6$) δ 1.85 (d, J=13.6 Hz, 6H), 2.87 (d, J=4.8 Hz, 3H), 2.98-3.03 (m, 1H), 3.12-3.50 (m, 3H), 3.62 (s, 3H), 3.82 (s, 3H), 4.16-4.18 (m, 1H), 4.30-4.33 (m, 1H), 7.00 (s, 1H), 7.55 (s, 1H), 7.66 (d, J=9.2 Hz, 1H), 7.77-7.80 (m, 1H), 8.25 (s, 1H), 8.61-8.69 (m, 2H), 10.75 (brs, 1H), 11.70 (s, 1H); ESI-MS (m/z) 583.2 $(M+H)^+$ The details of synthesis and analytical data of the example 44 prepared from the above-mentioned methods are given below in Table 8.

TABLE 8

Structure, chemical name, intermediate used, method of preparation and analytical data of the Example 44.

| Example No. | Structure | Method and Intermediate | Chemical Name and Analytical data |
|---|---|---|---|
| Example 44 | 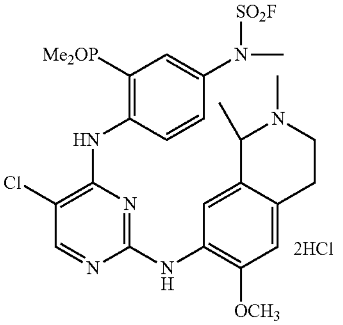 | Method E All/B15 | ±(4-((5-Chloro-2-((6-methoxy-1,2-dimethyl-1,2,3,4-tetrahydroisoquinolin-7-yl)amino)pyrimidin-4-yl)amino)-3-dimethylphosphoryl)phenyl) (methyl)sulfamoylfluoride dihydrochloride; $^1$H NMR (400 MHz, DMSO-$d_6$) δ 1.39-1.55 (m, 3H), 1.82-1.87 (m, 6H), 2.73-2.85 (m, 3H), 3.00-3.04 (m, 1H), 3.16-3.20 (m, 1H), 3.48-3.59 (m, 2H), 3.59 (s, 3H), 3.80 (s, 3H), 4.32-4.47 (m, 1H), 6.99 (d, J = 10.8 Hz, 1H), 7.51-7.54 (m, 2H), 7.76 (d, J = 14 Hz, 1H), 8.26 (s, 1H), 8.56 (brs, 1H), 8.89 (brs, 1H), 11.00 (brs, 1H), 11.75 (brs, 1H); ESI-MS (m/z) 597.2 (M + H)$^+$ |

Method F (2-((5-Chloro-2-((6-methoxy-2-methyl-1,2,3,4-tetrahydroisoquinolin-7-yl)amino)pyrimidin-4-yl)amino)-5-(difluoromethoxy)phenyl)dimethylphosphineoxide (Example 45)

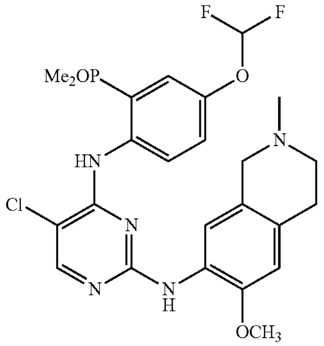

Step 1: (2-((2, 5-Dichloropyrimidin-4-yl) amino)-5-(difluoromethoxy) phenyl) dimethyl

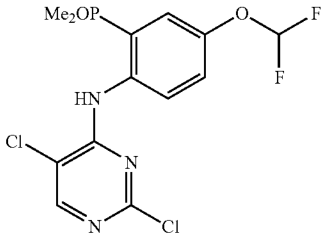

The titled compound was prepared by the reaction (2-amino-5-(difluoromethoxy) phenyl) dimethyl phosphine oxide (130 mg, 0.55 mmol) with 2,4,5-trichloropyrimidine (203 mg, 1.106 mmol), DIPEA (2 mL) in IPA (2 mL) as per the procedure described in Step 1 of example 1 to yield 100 mg of the desired compound. $^1$H NMR (400 MHz, DMSO-$d_6$) δ. $^1$H NMR (400 MHz, DMSO-$d_6$) δ 1.82 (s, 3H), 1.86 (s, 3H), 7.11 (t, J=74 Hz, 1H), 7.50-7.46 (m, 2H), 8.43 (dd, J=4.4 & 9.2 Hz, 1H), 8.46 (s, 1H), 11.68 (brs, 1H); ESI-MS (m/z) 382 (M+H)$^+$ Step 2: (2-((5-Chloro-2-((7-methoxy-2-methyl-1, 2, 3, 4-tetrahydroisoquinolin-6-yl) amino) pyrimidin-4-yl) amino)-5-(difluoromethoxy) phenyl) dimethyl phosphine oxide To a stirred solution of (2-((2,5-dichloropyrimidin-4-yl) amino)-5-(difluoromethoxy)phenyl) dimethyl phosphine oxide (60 mg, 0.31 mmol), 6-methoxy-2-methyl-1,2,3,4-tetrahydroisoquinolin-7-amine (Intermediate B1) (155 mg, 0.041 mmol) and cesium carbonate (304 mg, 0.94 mmol) in 1,4 dioxane (3 mL) were added, the reaction mixture was degassed under nitrogen for 5 min and added Xantphos (36 mg, 0.06 mmol) and Palladium acetate trimer (42 mg, 0.062 mmol). The mixture was stirred at 90° C. for 16 h. The reaction mixture was cooled at RT, filtered through celite bed and concentrated under reduced pressure. The crude material was purified by flash column chromatography (5% chloroform in methanol) to yield 9 mg of the desired product. $^1$H NMR (400 MHz, DMSO-$d_6$) δ 1.78 (s, 3H), 1.81 (s, 3H), 2.34 (s, 3H), 2.59-2.48 (m, 4H), 2.81 (s, 2H), 3.78 (s, 3H), 6.55 (s, 1H), 7.11 (t, J=74.0, 1H), 7.22 (s, 1H), 7.49-7.38 (m, 2H), 8.19-8.00 (m, 2H), 8.40 (s, 1H), 11.01 (br s, 1H); ESI-MS (m/z) 538 (M+H)$^+$ The analytical data of the examples prepared by following the procedure described above are given in below Table 9.

TABLE 9

Structure, chemical name, intermediate used, method of preparation and analytical data of the Example 46-47.

| Example No. | Structure | Method and Intermediate | Chemical Name and Analytical data |
|---|---|---|---|
| Example 46 | 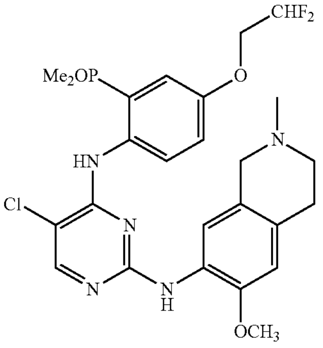 | Method F A13/B1 | (2-((5-Chloro-2-((6-methoxy-2-methyl-1,2,3,4-tetrahydroisoquinolin-7-yl)amino)pyrimidin-4-yl)amino)-5-(2,2-difluoroethoxy)phenyl) dimethylphosphine oxide; $^1$H NMR (400 MHz, DMSO-$d_6$) δ 1.77 (d, J = 13.6 Hz, 6H), 2.32 (s, 3H), 2.55 (t, J = 5.6 Hz, 2H), 2.79 (t, J = 5.2 Hz, 2H), 3.28 (s, 2H), 3.77 (s, 3H), 4.30-4.45 (m, 2H), 6.43 (tt, J = 3.6 Hz, 52.4 Hz, 1H), 6.77 (s, 1H), 7.05-7.25 (m, 2H), 7.44 (s, 1H), 7.95 (s, 1H), 8.11 (s, 1H), 8.24 (bs, 1H), 10.78 (s, 1H); ESI-MS (m/z) 552 $(M + H)^+$ |
| Example 47 | 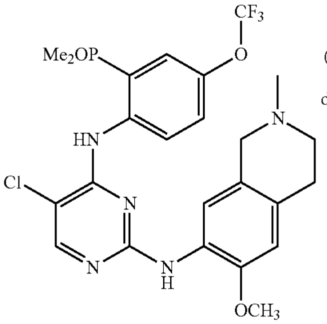 | Method F (2-Amino-5-(trifluoromethoxy) phenyl) dimethylphosphine oxide/B1 | 2-((5-Chloro-2-((6-methoxy-2-methyl-1,2,3,4-tetrahydroisoquinolin-7-yl) amino)pyrimidin-4-yl)amino)-5-(trifluoromethoxy)phenyl) dimethylphosphineoxide; $^1$H NMR (400 MHz, DMSO-$d_6$) δ 1.82 (d, J = 13.6 Hz, 6H), 2.31 (s, 3H), 2.59 (t, J = 5.6 Hz, 2H), 2.80 (d, J = 5.2 Hz, 2H), 3.23 (s, 2H), 3.76 (s, 3H), 6.79 (s, IH), 7.32-7.37 (m, 2H), 7.63 (dd, J = 2.0, 13.6 Hz, 1H), 8.17 (d, J = 6 Hz, 2H), 8.52 ( br s, 1H), 11.25 (br s, 1H) ; ESI-MS (m/z) 556.2 $(M + H)^+$ |

Method G (S)-(2-((5-Chloro-2-((6-methoxy-2-methyl-1,2,3,4-tetrahydroisoquinolin-7-yl)amino) pyrimidin-4-yl) amino)-5-((tetrahydrofuran-3-yl)oxy)phenyl)dimethylphosphineoxide (Example 48)

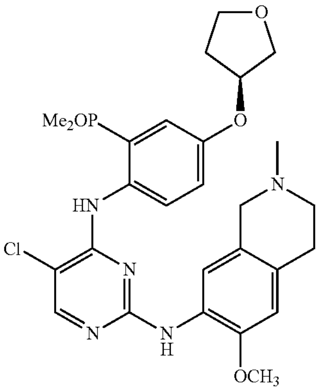

To a stirred solution of (2-((5-chloro-2-((6-methoxy-2-methyl-1,2,3,4-tetrahydroisoquinolin-7-yl)amino)pyrimidin-4-yl)amino)-5-hydroxyphenyl)dimethylphosphineoxide (Step 2 intermediate of Example 1) (150 mg, 0.30 mmol) in DMF (5 mL) cesium carbonate (293 mg, 0.90 mmol), (R)-tetrahydrofuran-3-yl4-methylbenzenesulfonate (79.92 mg, 0.33 mmol) were added and stirred at 80° C. for 2 h. The reaction mixture was cooled to RT, diluted with water and extracted with ethyl acetate. The combined organic layers were separated, dried over sodium sulphate and filtered and concentrated under reduced pressure. The obtained crude was purified by silica gel chromatography to yield 21.7 mg of the desired product. $^1$H NMR (400 MHz, DMSO-$d_6$) 1.75 (d, J=14.4 Hz, 6H), 1.95-2.01 (m, 1H), 2.24-2.26 (m, 1H), 2.34 (s, 3H), 2.50-2.65 (m, 2H), 2.78-2.85 (m, 2H), 3.30-3.35 (m, 2H), 3.80 (s, 3H), 3.80-3.95 (m, 4H), 5.05-5.10 (m, 1H), 6.77 (s, 1H), 7.01 (dd, J=2.8, 9.2 Hz, 1H), 7.10-7.15 (m, 1H), 7.44 (s, 1H), 7.93 (s, 1H), 8.10 (s, 1H), 8.20 (br s, 1H), 10.70 (s, 1H); ESI-MS (m/z) 558.4 $(M+H)^+$.

The analytical data of the examples prepared by following the procedure described above are given in below Table 10.

TABLE 10

Structure, chemical name, intermediate used, method of preparation and analytical data of the Example 49-51

| Example No. | Structure | Method and Intermediate | Chemical Name and Analytical data |
|---|---|---|---|
| Example 49 | 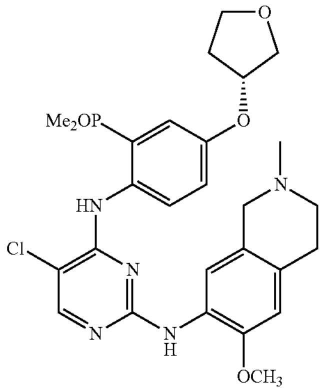 | Method G Step 2 intermediate of Example 1/ (S)-tetrahydrofuran-3-yl4-methyl-benzene-sulfonate | (R)-(2-((5-Chloro-2-((6-methoxy-2-methyl-1,2,3,4-tetrahydroisoquinolin-7-yl)amino)pyrimidin-4-yl) amino)-5-((tetrahydrofuran-3-yl)oxy)phenyl)dimethyl phosphine oxide; $^1$H NMR (400 MHz, DMSO-$d_6$) δ 1.75 (d, J = 13.6 Hz, 6H), 1.97-1.99 (m, 1H), 2.22-2.24 (m, 1H), 2.32 (s, 3H), 2.55-2.67 (m, 2H), 2.77-2.80 (m, 2H), 3.33-3.39 (m, 2H), 3.80 (s, 3H), 3.80-3.94 (m, 4H), 5.05-5.10 (m, 1H), 6.76 (s, 1H), 7.01 (dd, J = 2.8 Hz, 9.2 Hz, 1H), 7.12 (dd, J = 2.8 Hz, 14.4 Hz, 1H), 7.43 (s, 1H), 7.93 (s, 1H), 8.09 (s, 1H), 8.21 (s, 1H), 10.69 (s, 1H); ESI-MS (m/z) 558.14 $(M + H)^+$. |
| Example 50 | 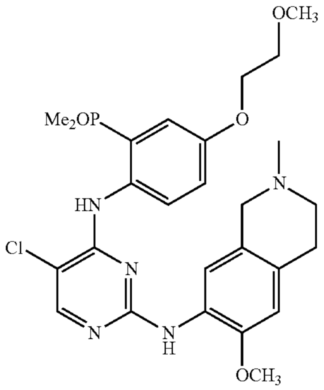 | Step 2 intermediate of Example 1/ 2-methoxy ethyl-4-methyl-benzene-sulfonate | (2-((5-Chloro-2-((6-methoxy-2-methyl-1,2,3,4-tetrahydroisoquinolin-7-yl)amino)pyrimidin-4-yl)amino)-5-(2-methoxyethoxy)phenyl)dimethyl phosphine oxide; $^1$H NMR (400 MHz, DMSO-$d_6$) δ 1.77 (d, J = 13.6 Hz, 6H), 2.99 ( s, 3H), 2.50-2.62 (m, 2H), 3.14-3.28 (m, 2H), 3.40-3.61 (m, 2H), 3.68 (s, 3H), 3.83 (s, 3H), 4.05-4.15 (m, 2H), 4.20 (t, J = 8 Hz, 2H), 6.93 (s, 1H), 7.15-7.18 (m, 1H), 7.65 (s, 1H), 7.99 (s, 1H), 8.13 (s, 1H), 8.20 (s, 1H), 10.45 (s, 1H) 10.70 (s, 1H); ESI-MS (m/z) 546.7 $(M + H)^+$. |
| Example 51 | 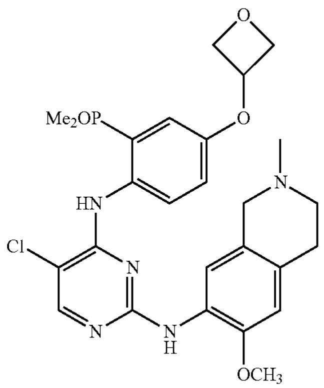 | Step 2 intermediate of Example 1/ Oxetan-3yl 4-methyl-benzene-sulfonate | (2-((5-Chloro-2-((6-methoxy-2-methyl-1,2,3,4-tetrahydroisoquinolin-7-yl)amino)pyrimidin-4-yl)amino)-5-(oxetan-3-yloxy)phenyl)dimethyl phosphine oxide; $^1$H NMR (400 MHz, DMSO-$d_6$) δ 1.76 (d, J = 13.6 Hz, 6H), 2.31 (s, 3H), 2.30-2.35 (m, 2H), 2.59 (t, J = 6 Hz, 2H), 2.79 (t, J = 6 Hz, 2H), 3.77 (s, 3H), 4.56 (d, J = 7 Hz, 2H), 4.97 (d, J = 7 Hz, 2H), 5.34 (m, 1H), 6.77 (s, 1H), 6.87 (d, J = 9 Hz, 1H), 7.02 (d, J = 9 Hz, 1H), 7.39 (s, 1H), 7.94 (s, 1H), 8.10 (s, 1H), 8.19 (bs, 1H), 10.66 (s, 1H); ESI-MS (m/z) 543.18 $(M)^+$. |

Method H 4-((5-Chloro-2-((6-methoxy-2-methyl-1,2,3,4-tetrahydroisoquinolin-7-yl)amino)pyrimidin-4-yl)amino)-3-(dimethylphosphoryl)-N-(2-fluoroethyl)-N-methyl benzamide (Example 52)

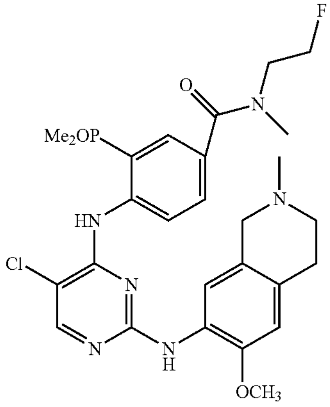

Step 1: 4-((2,5-Dichloropyrimidin-4-yl)amino)-3-(dimethylphosphoryl)-N-(2-fluoro ethyl)-N-methylbenzamide

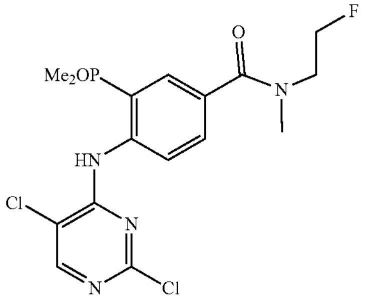

To a cooled solution of 4-amino-3-(dimethylphosphoryl)-N-(2-fluoroethyl)-N-methyl benzamide (215 mg, 0.790 mmol) in DMF (5 mL) at 0° C. was added NaH (63 mg, 1.58 mmol) and stirred for 5 min and then added 2,4,5-trichloro pyrimidine (0.180 mL, 1.58 mmol). The reaction mixture was stirred at RT for 16 h. The reaction mixture was diluted with water. The aqueous mixture was extracted twice with ethyl acetate and the combined organic layer was washed with water followed by brine solution. The organic layer was dried over anhydrous sodium sulfate, filtered and concentrated under reduced pressure. The residue obtained was purified by silica gel column chromatography to yield 151 mg of the desired product. $^1$H NMR (400 MHz, DMSO-$d_6$) δ 1.86 (d, J=13.6, 6H), 3.03 (s, 3H), 3.54-3.60 (m, 1H), 3.75-3.81 (m, 1H), 4.52-4.74 (m, 2H), 7.62-7.67 (m, 2H), 8.50 (s, 1H), 8.53 (t, J=3.6 Hz, 1H), 12.03 (s, 1H); ESI-MS (m/z) 419.2 $(M+H)^+$.

Step 2: 4-((5-Chloro-2-((6-methoxy-2-methyl-1,2,3,4-tetrahydroisoquinolin-7-yl) amino) pyrimidin-4-yl)amino)-3-(dimethylphosphoryl)-N-(2-fluoroethyl)-N-methyl benzamide To a stirred solution of 4-((2,5-dichloropyrimidin-4-yl) amino)-3-(dimethyl phosphoryl)-N-(2-fluoroethyl)-N-methylbenzamide (70 mg, 0.167 mmol) in IPA (2 mL) were added 6-methoxy-2-methyl-1,2,3,4-tetrahydro isoquinolin-7-amine (Intermediate B1) (31 mg, 0.167 mmol) and PTSA (32 mg, 0.167 mmol). The reaction mixture was heated at 120° C. for 18 h. The reaction mixture was cooled to RT. The reaction mixture was basified with saturated $NaHCO_3$ solution. The aqueous solution was extracted twice with ethyl acetate. The combined organic layers were dried over anhydrous sodium sulfate and the solvents were removed under reduced pressure. The crude was purified by SFC to yield 10 mg of the desired product. $^1$H NMR (400 MHz, DMSO-$d_6$) δ 1.82 (d, J=13.2 Hz, 6H), 2.37 (s, 3H), 2.60-2.67 (m, 2H), 2.80-2.85 (m, 2H), 2.99 (s, 3H), 3.33-3.36 (m, 2H), 3.35-3.38 (m, 2H), 3.62-3.54 (m, 2H), 3.77 (s, 3H), 6.81 (s, 1H), 7.39-7.45 (m, 2H), 7.67-7.70 (m, 1H), 8.17 (s, 1H), 8.19 (s, 1H), 8.51 (d, J=4.4 Hz, 1H), 11.40 (br s, 1H); ESI-MS (m/z) 573.1 $(M+H)^+$.

Method I

N-(4-((5-Chloro-2-((6-methoxy-2-methyl-1,2,3,4-tetrahydroisoquinolin-7-yl)amino) pyrimidin-4-yl) amino)-3-(dimethylphosphoryl)phenyl)-2,2-difluoro-N-methylacetamide (Example 53)

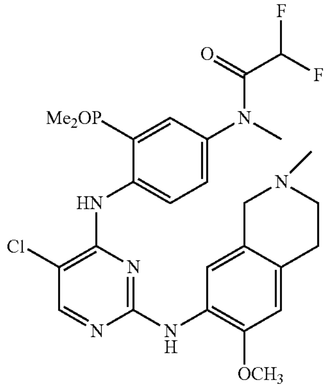

Step 1: N-(4-((2,5-Dichloropyrimidin-4-yl)amino)-3-(dimethylphosphoryl)phenyl)-2,2-difluoro-N-methylacetamide

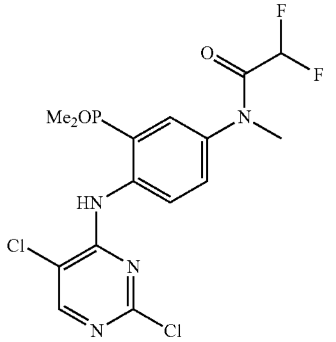

The titled compound was prepared by the reaction N-(4-amino-3-(dimethyl phosphoryl)phenyl)-2,2-difluoro-N-methylacetamide (75 mg, 0.271 mmol), DIPEA (70 mg, 0.543 mmol), 2,4,5-trichloropyrimidine (99 mg, 0.543 mmol) in IPA (3 mL) as per the procedure described in step 1 of Example 1 to yield 50 mg of the desired product. $^{1}H$ NMR (400 MHz, DMSO-$d_6$): δ 1.84 (d, J=13.6 Hz, 6H), 3.26 (s, 3H), 6.20 (t, J=52.8 Hz, 1H), 6.66-7.76 (m, 2H), 8.50 (s, 1H), 8.53-8.56 (m, 1H), 11.97 (s, 1H); ESI-MS (m/z) 423.1 $(M+H)^+$.

Step 2: N-(4-((5-Chloro-2-((6-methoxy-2-methyl-1,2,3,4-tetrahydroisoquinolin-7-yl)amino) pyrimidin-4-yl)amino)-3-(dimethylphosphoryl)phenyl)-2,2-difluoro-N-methylacetamide The titled compound was prepared by the reaction of N-(4-((2,5-dichloropyrimidin-4-yl)amino)-3-(dimethylphosphoryl)phenyl)-2,2-difluoro-N-methylacetamide (40 mg, 0.094 mmol) with 6-methoxy-2-methyl-1,2,3,4-tetrahydroisoquinolin-7-amine (Intermediate B1) (16.3 mg, 0.085 mmol), cesium carbonate, (92 mg, 0.28 mmol), $Pd_2(dba)_3$ (8.6 mg, 0.009 mmol) and Xantphos (11 mg, 0.018 mmol) in 1,4 Dioxane (2 mL) as per the procedure described in step 2 of example 43 to yield 15 mg of the desired product. $^{1}H$ NMR (400 MHz, DMSO-$d_6$): δ 1.81 (d, J=13.2 Hz, 6H), 2.37 (s, 3H), 2.67-2.68 (m, 2H), 2.68-2.82 (m, 2H), 3.24 (s, 3H), 3.68-3.72 (m, 2H), 3.77 (s, 3H), 6.29 (t, J=56 Hz, 1H)), 6.81 (s, 1H), 7.39-7.40 (m, 2H), 7.60-7.65 (m, 1H), 8.16 (s, 1H), 8.23 (s, 1H), 8.63 (br s, 1H), 11.42 (s, 1H); ESI-MS (m/z) 579.2 $(M+H)^+$.

Method J (2-((5-Chloro-2-((6-methoxy-2-methyl-1,2,3,4-tetrahydroisoquinolin-7-yl)amino)pyrimidin-4-yl)amino)-5-(difluoromethyl)phenyl)dimethylphosphine oxide (Example 54)

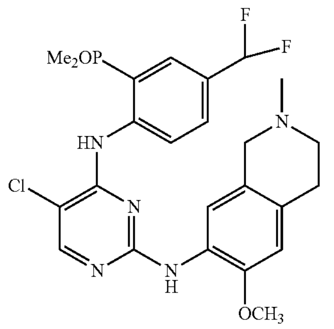

Step 1: (2-((2,5-Dichloropyrimidin-4-yl)amino)-5-(hydroxymethyl)phenyl) dimethylphosphine oxide

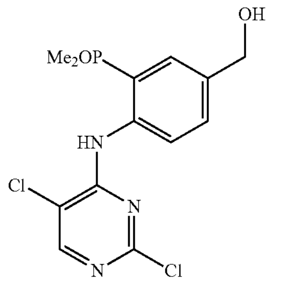

The titled compound was prepared by the reaction of (2-amino-5-(hydroxymethyl)phenyl)dimethylphosphine oxide (50 mg, 0.253 mmol), DIPEA (65 mg, 0.507 mmol) and 2,4,5-trichloropyrimidine (94 mg, 0.507 mmol) in IPA (2-3 mL) as per the procedure described in step 1 of example 1 to yield 40 mg of desired product. $^{1}H$ NMR (400 MHz, DMSO-$d_6$): δ 1.80 (d, J=13.6 Hz, 6H), 4.51 (d, J=5.6 Hz, 2H), 5.30 (t, J=5.6 Hz, 1H), 7.55-7.58 (m, 2H), 8.32-8.36 (m, 1H), 8.44 (s, 1H), 11.71 (s, 1H); ESI-MS (m/z) 346 $(M+H)^+$.

Step 2: 4-((2,5-Dichloropyrimidin-4-yl)amino)-3-(dimethylphosphoryl)benzaldehyde

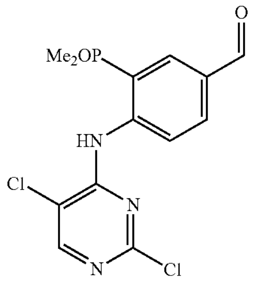

To a stirred solution of (2-((2,5-dichloropyrimidin-4-yl) amino)-5(hydroxymethyl) phenyl)dimethylphosphine oxide (50 mg, 0.251 mmol) in DCM/EDC (8 mL) was added pyridinium chlorochromate (PCC) (81 mg, 0.376 mmol) and stirred at RT for 1 h. The reaction mixture was filtered through celite bed and washed with ethyl acetate. The filterate was concentrated under reduced pressure and the residue obtained was purified by silica gel column chromatography to yield 30 mg of the desired product. $^{1}H$ NMR (400 MHz, DMSO-$d_6$): δ 1.90 (d, J=13.6 Hz, 6H), 8.12 (d, J=8.8 Hz, 1H), 8.10-8.21 (m, 1H), 8.57 (s, 1H), 8.70 (dd, J=3.6, 8.4 Hz, 1H), 9.95 (s, 1H), 12.31 (s, 1H); ESI-MS (m/z) 343.7 $(M)^+$ Step 3: (2-((2,5-Dichloropyrimidin-4-yl)amino)-5-(difluoromethyl)phenyl) dimethyl phosphine oxide

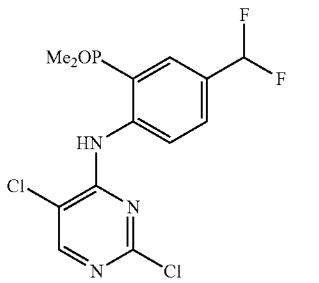

To a stirred solution of 4-((2,5-dichloropyrimidin-4-yl) amino)-3-(dimethyl phosphoryl) benzaldehyde (50 mg, 0.145 mmol) in dry DCM (5 mL) at −78° C. was added drop wise Diethylaminosulfur trifluoride (DAST) (56 mg, 0.34 mmol). And stirred at RT for 16 h. The reaction mixture was quenched with sat. ammonium chloride solution. The aqueous mixture was extracted twice with ethyl acetate. The combined organic layer was washed with water followed by brine solution. The organic layer was dried over anhydrous sodium sulfate, filtered and concentrated under reduced pressure. The residue obtained was purified by silica gel column chromatography to yield 41 mg of the desired product. $^1$H NMR (400 MHz, DMSO-$d_6$): δ 1.86 (d, J=13.6 Hz, 6H), 7.02 (t, J=56 Hz, 1H), 7.82-7.88 (m, 2H), 7.51 (s, 1H), 8.55-8.58 (m, 1H), 12.01 (s, 1H); ESI-MS (m/z) 365.9 (M+H).

Step 4: (2-((5-Chloro-2-((6-methoxy-2-methyl-1,2,3,4-tetrahydroisoquinolin-7-yl)amino) pyrimidin-4-yl)amino)-5-(difluoromethyl)phenyl) dimethylphosphine oxide The titled compound was prepared by the reaction of (2-((2,5-dichloropyrimidin-4-yl)amino)-5-(difluoromethyl) phenyl)dimethyl phosphine oxide (65 mg, 0.178 mmol) with 6-methoxy-2-methyl-1,2,3,4-tetrahydroisoquinolin-7-amine (Intermediate B1) (30 mg, 0.16 mmol), cesium carbonate (173 mg, 0.534 mmol), $Pd_2(dba)_3$ (16 mg, 0.0178 mmol) and Xantphos (20 mg, 0.035 mmol) in 1,4 Dioxane (2 mL) as per the procedure described in step 2 of example 43 to yield 35 mg of the desired product. $^1$H NMR (400 MHz, DMSO-$d_6$): δ 1.85 (d, J=13.6 Hz, 6H), 2.70 (s, 3H), 2.95-3.00 (m, 2H), 3.10-3.20 (m, 2H), 3.80 (s, 3H), 3.85-3.92 (i, 2H), 6.91 (s, 1H), 7.01 (t, J=56 Hz, 1H), 7.55 (s, 1H), 7.67 (d, J=8.8 Hz, 1H), 7.80 (d, J=14.4 Hz, 1H), 8.20 (s, 1H), 8.26 (s, 1H), 8.60 (br s, 1H), 11.43 (br s, 1H); ESI-MS (m/z) 522.2 $(M+H)^+$.

The analytical data of the examples prepared by following the procedure described above are given in below Table 11.

Method K

2-Chloro-N-(4-((5-chloro-2-((6-methoxy-2-methyl-1,2,3,4-tetrahydroisoquinolin-7-yl)amino) pyrimidin-4-yl)amino)-3-(dimethylphosphoryl)phenyl)acetamide hydrochloride (Example 56)

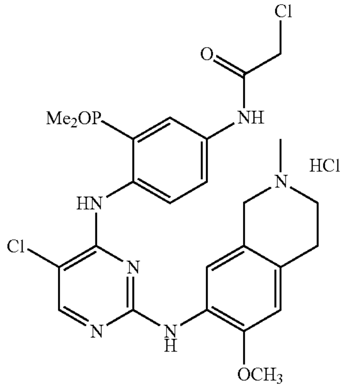

Step 1: (2-((2,5-Dichloropyrimidin-4-yl)amino)-5-nitrophenyl)dimethylphosphine oxide

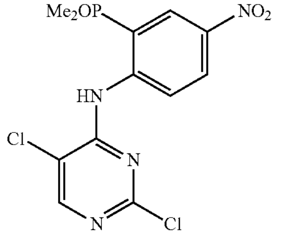

To a stirred solution of (2-amino-5-nitrophenyl)dimethylphosphine oxide (1 g, 4.67 mmol) and 2, 4, 5-trichloropyrimidine (1.7 gm, 9.345 mmol) in DMF (10 ml) was added $Cs_2CO_3$ (3 gm, 9.345 mmol) at RT. The reaction mixture was heated to 110° C. for 14 h in a sealed tube. The

TABLE 11

Structure, chemical name, intermediate used, method of preparation and analytical data of the Example 55.

| Example No. | Structure | Method and Intermediate | Chemical Name and Analytical data |
|---|---|---|---|
| Example 55 | 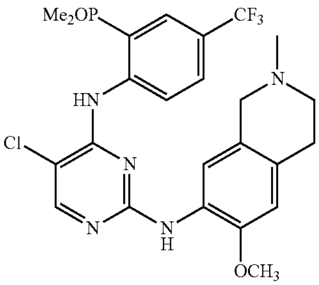 | Method J (2-amino-5-(trifluoromethyl) phenyl) dimethylphosphine-oxide/ Intermediate B1 | (2-((5-Chloro-2-((6-methoxy-2-methyl-1,2,3,4-tetrahydroisoquinolin-7-yl)amino)pyrimidin-4-yl)amino)-5-(trifluoromethyl)phenyl) dimethylphosphine oxide; $^1$H NMR (400 MHz, DMSO-$d_6$) δ 1.86 (d, J = 13 Hz, 6H), 2.40 (s, 3H), 2.70-2.75 (m, 2H), 2.80-2.90 (m, 2H), 3.47 (s, 2H), 3.78 (s, 3H), 6.74 (s, 1H), 7.45 (br s, 1H), 7.71 (d, J = 4 Hz, 1H), 7.93 (d, J = 4 Hz, 1H), 8.22 (s, 1H), 8.26 (s, 1H), 8.65 (br s, 1H), 11.63 (s, 1H); ESI-MS (m/z) 540 $(M + H)^+$ |

reaction mixture was quenched with water and extracted with ethyl acetate. The organic layer was concentrated and the residue obtained was purified by silica gel column chromatography to yield 610 mg of the desired product. $^1$H NMR (400 MHz, DMSO-$d_6$) δ 1.94 (d, J=14 Hz, 6H), 8.46-8.50 (m, 2H), 8.60 (s, 1H), 8.71-8.76 (m, 1H), 12.44 (s, 1H); ESI-MS (m/z) 361 $(M+H)^+$.

Step-2: (2-((5-Chloro-2-((6-methoxy-2-methyl-1,2,3,4-tetrahydroisoquinolin-7-yl)amino) pyrimidin-4-yl)amino)-5-nitrophenyl)dimethylphosphine oxide

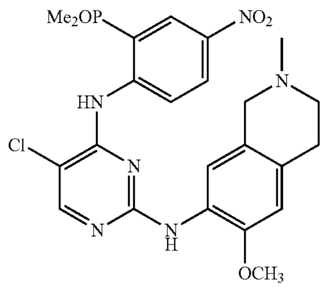

The titled compound was prepared by the reaction (2-((2,5-dichloropyrimidin-4-yl)amino)-5-nitrophenyl)dimethylphosphine oxide (230 mg, 0.637 mmol) with 6-methoxy-2-methyl-1,2,3,4-tetrahydroisoquinolin-7-amine (Intermediate B1) (123 mg, 0.637 mmol) and PTSA (121 mg, 0.637 mmol) in IPA as per the procedure described in step 2 of example 1 to yield 210 mg of the desired product. $^1$H NMR (400 MHz, DMSO-$d_6$) 1.9 (d, J=14 Hz, 6H), δ 2.35 (s, 3H), 2.66-2.64 (m, 2H), 2.87-2.83 (m, 2H), 3.40 (s, 2H), 3.77 (s, 3H), 6.84 (s, 1H), 7.38 (s, 1H), 8.15 (s, 1H), 8.32 (s, 1H), 8.39-8.44 (m, 2H), 8.72 (brs, 1H), 11.90 (s, 1H); ESI-MS (m/z) 517 $(M+H)^+$.

Step 3: (5-Amino-2-((5-chloro-2-((6-methoxy-2-methyl-1,2,3,4-tetrahydroisoquinolin-7-yl)amino) pyrimidin-4-yl)amino)phenyl)dimethylphosphine oxide

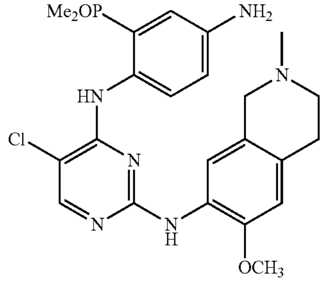

To a stirred mixture of (2-((5-chloro-2-((6-methoxy-2-methyl-1,2,3,4-tetrahydroisoquinolin-7-yl)amino)pyrimidin-4-yl)amino)-5-nitrophenyl) dimethyl phosphine oxide (205 mg, 0.397 mmol) in ethanol/water was added iron powder (107 mg, 1.98 mmol) and $NH_4Cl$ (107 mg, 1.986 mmol) at RT. The reaction mixture was refluxed for 3 h. The reaction mixture was filtered through celite and the filtrate obtained was concentrated. The residue obtained was basified with saturated sodium bicarbonate and extracted with ethyl acetate. The organic layer was separated, filtered and concentrated to yield 165 mg of the desired product. $^1$H NMR (400 MHz, DMSO-$d_6$) δ 1.61 (d, J=13.6 Hz, 6H), 2.35 (s, 3H), 2.49-2.55 (m, 2H), 2.53-2.75 (m, 2H), 3.18 (s, 2H), 3.78 (s, 3H), 5.3 (s, 2H), 7.53 (s, 1H), 6.70-6.76 (m, 2H), 6.88-6.93 (m, 1H), 7.61 (br s, 1H), 7.66 (s, 1H), 8.05 (s, 1H), 9.74 (s, 1H), ESI-MS (m/z) 487 $(M+H)^+$.

Step 4: 2-Chloro-N-(4-((5-chloro-2-((6-methoxy-2-methyl-1,2,3,4-tetrahydroisoquinolin-7-yl)amino) pyrimidin-4-yl)amino)-3-(dimethylphosphoryl)phenyl)acetamide hydrochloride To a stirred solution of (5-amino-2-((5-chloro-2-((6-methoxy-2-methyl-1,2,3,4-tetrahydroisoquinolin-7-yl) amino)pyrimidin-4-yl)amino)phenyl)dimethyl phosphine oxide (73 mg, 0.150 mmol) in DCM (2 mL) at 0° C. was added chloroacetyl chloride (13 μL, 0.165 mmol).

The reaction mixture was stirred at RT for 30 min. The solvent was removed under reduced pressure. The obtained residue was stirred in ethyl acetate, filtered and dried under vacuum to yield 84 mg of the desired product. $^1$H NMR (400 MHz, DMSO-$d_6$), δ 1.76 (d, J=13.6 Hz, 6H), 2.93 (d, J=4 Hz, 3H), 3.05-3 (m, 1H), 3.22-3.26 (m, 1H), 3.39-3.40 (m, 1H), 3.60-3.65 (m, 1H), 3.82 (s, 3H), 3.90-4.04 (m, 2H), 4.36 (s, 2H), 6.98 (s, 1H), 7.49 (s, 1H), 7.84-7.94 (m, 2H), 8.19 (br s, 1H), 8.33 (s, 1H), 9.09 (br s, 1H), 10.81 (br s, 1H), 11.05 (br s, 1H), 11.37 (br s, 1H); ESI-MS (m/z) 564 $(M+H)^+$.

Method L (2-(N-(5-Chloro-2-((6-methoxy-2-methyl-1,2,3,4-tetrahydroisoquinolin-7-yl)amino) pyrimidin-4-yl)-S-methylsulfonimidoyl)phenyl)dimethylphosphine oxide (Example 57)

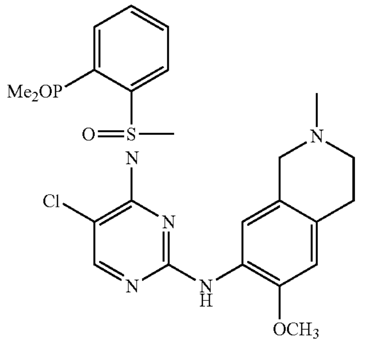

Step 1: (2-(N-(2,5-dichloropyrimidin-4-yl)-S-methylsulfonimidoyl)phenyl)dimethyl phosphine oxide

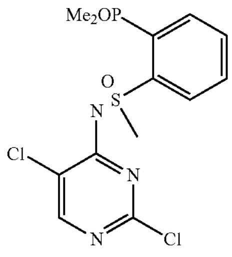

To a stirred solution of Dimethyl (2-(S-methylsulfonimidoyl)phenyl)phosphine oxide (240 mg, 1.038 mmol) in DMF (5 mL) was added sodium hydride (83 mg, 2.077 mmol) at −10° C. The reaction mixture was stirred for 10 min and then 2,4,5-trichloropyrimidine (381 mg, 2.077 mmol) was added and stirred at 100° C. for 16 h. The reaction was acidified with 1N HCl and extracted with ethyl acetate. The organic layer was concentrated and the residue obtained was purified by column chromatography to yield 114 mg of the desired product. $^1$H NMR (400 MHz, DMSO-$d_6$) δ 1.92 (d, J=14 Hz, 6H), 4.01 (s, 3H), 7.83-7.92 (m, 2H), 8.12-8.19 (m, 2H), 8.47 (s, 1H).

Step 2: 2-(N-(5-chloro-2-((6-methoxy-2-methyl-1,2,3,4-tetrahydroisoquinolin-7-yl)amino) pyrimidin-4-yl)-S-methylsulfonimidoyl) phenyl) dimethylphosphine oxide The titled compound was prepared by the reaction of (2-(N-(2,5-dichloro pyrimidin-4-yl)-S-methylsulfonimidoyl)phenyl)dimethylphosphine oxide (100 mg, 0.264 mmol) with 6-methoxy-2-methyl-1,2,3,4-tetrahydroisoquinolin-7-amine (Intermediate B1) (51 mg, 0.264 mmol) and PTSA (50 mg, 0.264 mmol) in IPA (2 mL) as per the procedure described in step 2 of example 1 to yield 11 mg of the desired product. $^1$H NMR (400 MHz, DMSO-$d_6$) δ 1.93 (d, J=13.6 Hz, 6H), 2.50 (s, 3H), 2.67-2.73 (m, 3H), 2.80-2.94 (m, 3H), 3.81 (s, 3H), 4.03 (s, 3H), 6.81 (s, 1H), 7.80-7.93 (m, 4H), 8.07-8.20 (m, 1H), 8.33 (s, 1H), 8.35 (brs, 1H); ESI-MS (m/z) 534.2 (M+H)$^+$ Method M

(2-((5-Chloro-2-((6-methoxy-2-methyl-1,2,3,4-tetrahydroisoquinolin-7-yl) amino) pyrimidin-4-yl) amino)-5-(S-methylsulfonimidoyl)phenyl)dimethylphosphine oxide (Example 58)

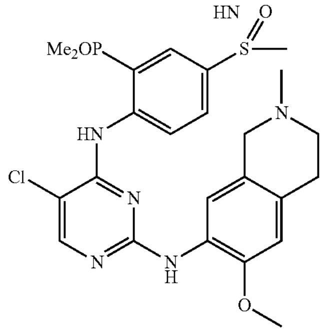

Step 1: tert-butyl ((4-((2,5-dichloropyrimidin-4-yl) amino)-3-(dimethyl phosphoryl) phenyl) (methyl) (oxo)-λ$^6$-sulfaneylidene)carbamate

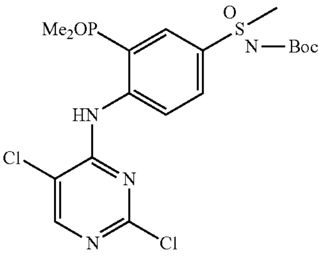

The titled compound was prepared by the reaction of aniline 67 mg (0.193 mmol) with 2,4,5-trichloropyrimidine (71 mg, 0.386 mmol), sodium hydride (60%, 15 mg (0.386 mmol) in DMF (1 mL) as per the procedure described in step 1 of example 57 to yield 19 mg of the desired product. $^1$H NMR (400 MHz, DMSO-$d_6$) δ 1.26 (s, 9H), 1.87-1.93 (m, 6H), 3.44 (s, 3H), 8.06 8.12 (m, 2H), 8.68 (dd, J=4.0, 9.6 Hz, 1H), 12.19 (s, 1H); ESI-MS (m/z) 491 (M+H)$^+$.

Step 2: (2-((5-chloro-2-((6-methoxy-2-methyl-1,2,3,4-tetrahydroisoquinolin-7-yl)amino) pyrimidin-4-yl) amino)-5-(S-methylsulfonimidoyl)phenyl)dimethyl phosphine oxide The titled compound was prepared by the reaction of tert-butyl ((4-((2,5-dichloropyrimidin-4-yl)amino)-3-(dimethyl phosphoryl)phenyl)(methyl)(oxo)-λ$^6$-sulfaneylidene) carbamate (50 mg, 0.101 mmol), 6-methoxy-2-methyl-1,2,3,4-tetrahydroisoquinolin-7-amine (Intermediate B1) (9.7 mg (0.05 mmol), PTSA (9.66 mg, 0.101 mmol) in IPA (2 mL) as per the procedure described in step 2 of Example 1 to yield 9 mg of the desired product. $^1$H NMR (400 MHz, DMSO-$d_6$) δ 1.73 (d, J=13.6 Hz, 6H), 2.38 (s, 3H), 2.62-2.65 (m, 2H), 2.82-2.85 (m, 2H), 3.33 (s, 3H), 3.45 (brs, 2H), 3.77 (s, 3H), 4.30 (brs, 1H), 6.83 (s, 1H), 7.40 (s, 1H), 7.88 (d, J 9.6 Hz, 1H), 7.98 (d, J=13.2 Hz, 1H), 8.21 (s, 1H), 8.29 (s, 1H), 8.66 (s, 1H), 11.58 (s, 1H); ESI-MS (m/z) 549.1 (M+H)$^+$.

Method N

(2-((5-Chloro-2-((6-methoxy-2-methyl-1,2,3,4-tetrahydroisoquinolin-7-yl)amino)pyrimidin-4-yl)oxy) phenyl)dimethylphosphine oxide (Example 59)

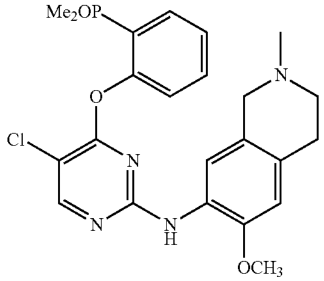

Step 1: (2-((2,5-Dichloropyrimidin-4-yl)oxy)phenyl) dimethylphosphine oxide

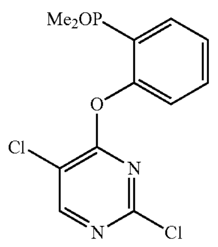

The titled compound was prepared by the reaction of (2-hydroxyphenyl)dimethylphosphine oxide (50 mg, 0.294 mmol) with 2,4,5 trichloropyrimidine (300 mg, 0.588 mmol), sodium hydride (141 mg, 0.588 mmol) in DMF (1 mL) as per the procedure described in step 1 of example 57 to yield 361 mg of the desired product. $^1$H NMR (400 MHz, DMSO-$d_6$) δ=1.78 (d, J=13.6 Hz, 6H), 7.29-7.32 (m, 1H), 7.47-7.52 (m, 1H), 7.64-7.69 (m, 1H), 8.06-8.12 (m, 1H), 8.57 (s, 1H); ESI-MS (m/z) 317 $(M+H)^+$ Step 2: (2-((5-Chloro-2-((6-methoxy-2-methyl-1,2,3,4-tetrahydroisoquinolin-7-yl)amino) pyrimidin-4-yl)oxy)phenyl)dimethylphosphine oxide To a degassed solution of (2-((2,5-dichloropyrimidin-4-yl)oxy)phenyl) dimethyl phosphine oxide (75 mg, 0.237 mmol) and 6-methoxy-2-methyl-1,2,3,4-tetra hydroisoquinolin-7-amine (Intermediate B1) (45 mg, 0.237 mmol) in dry 1,4-dioxane (2 mL) were added Xantphos (28 mg, 0.04 mmol), $Cs_2CO_3$ (154 mg, 0.47 mmol), $Pd_2(dba)_3$ (22 mg, 0.023 mmol) and heated to 120° C. for 18 h. The reaction mixture was quenched with water and extracted with ethyl acetate. The organic layer was separated, dried over anhydrous sodium sulphate and concentrated. The residue obtained was purified by SFC to yield 10 mg of the desired product. $^1$H NMR (400 MHz, DMSO-$d_6$) δ 1.63 (d, J=13.6 Hz, 6H), 2.34 (s, 3H), 2.50-2.53 (m, 2H), 2.70-2.75 (m, 2H), 3.00-3.05 (m, 2H), 3.75 (s, 3H), 6.69 (s, 1H), 7.14 (s, 1H), 7.46-7.52 (m, 2H), 7.70-7.72 (m, 1H), 7.89-7.94 (m, 1H), 8.18 (s, 1H), 8.50 (s, 1H); ESI-MS (m/z) 473 $(M+H)^+$ 4-((5-Chloro-2-((6-methoxy-2-methyl-1,2,3,4-tetrahydroisoquinolin-7-yl)amino)pyrimidin-4-yl)oxy)-3-(dimethylphosphoryl)phenylsulfofluoridate dihydrochloride (Example 60)

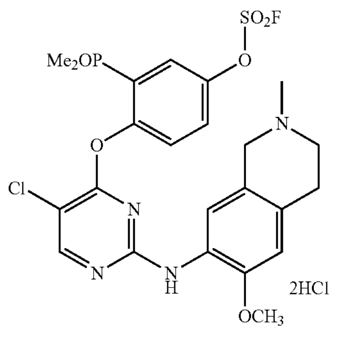

Step 1: (5-(Benzyloxy)-2-((2,5-dichloropyrimidin-4-yl)oxy)phenyl) dimethyl phosphine oxide

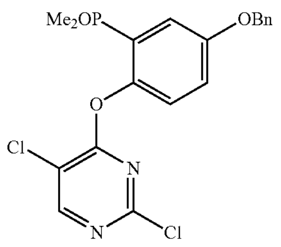

The titled compound was prepared by the reaction of (5-(benzyloxy)-2-hydroxyphenyl)dimethylphosphine oxide (800 mg, 2.89 mmol) with 2,4,5 trichloropyrimidine (1 g, 5.79 mmol), sodium hydride (231 mg, 5.79 mmol) in DMF (10 mL) as per the procedure described in Step 1 of example 57 to yield 402 mg of the desired product. ESI-MS (m/z) 423 $(M+H)^+$.

Step 2: (2-((2,5-Dichloropyrimidin-4-yl)oxy)-5-hydroxyphenyl)dimethyl phosphine oxide

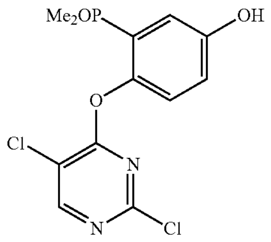

To a stirred solution of 5-(benzyloxy)-2-((2,5-dichloropyrimidin-4-yl)oxy)phenyl) dimethyl phosphine oxide (110 mg, 0.26 mmol) in DCM (4 mL) at 0° C. was added bromine dropwise and stirred at RT for 2 h. The reaction mixture was concentrated, basified with saturated sodium bicarbonate solution and extracted with DCM. The organic layer was separated, dried over sodium sulphate and concentrated. The residue thus obtained was purified by silica gel chromatography to yield 35 mg of the desired product. $^1$H NMR (400 MHz, DMSO-$d_6$) δ 1.62 (d, J=13.2 Hz, 6H), 7.01-7.04 (m, 1H), 7.18-7.22 (m, 1H), 7.26-7.29 (m, 1H), 8.84 (s, 1H), 9.98 (s, 1H); ESI-MS (m/z) 334 $(M+H)^+$ Step 3: (2-((5-Chloro-2-((6-methoxy-2-methyl-1,2,3,4-tetrahydroisoquinolin-7-yl)amino) pyrimidin-4-yl)oxy)-5-hydroxyphenyl)dimethylphosphineoxide

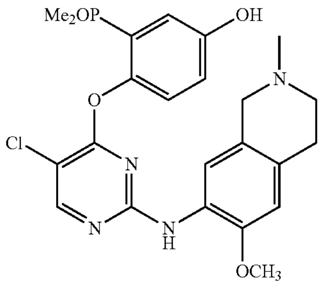

The titled compound was prepared by the reaction of (2-((2,5-dichloropyrimidin-4-yl)oxy)-5-hydroxyphenyl)dimethyl phosphine oxide (47 mg, 0.14 mmol) with 6-methoxy-2-methyl-1,2,3,4-tetrahydroisoquinolin-7-amine (Intermediate B1) (27 mg, 0.14 mmol) in Xantphos (16 mg, 0.028 mmol), $Cs_2CO_3$ (93 mg, 0.28 mmol), $Pd_2(dba)_3$ (12.9 mg, 0.014 mmol) in dry 1,4-dioxane (2 mL) in Dioxane (10 mL) as per the procedure described in step 2 of Example 59 to yield 37 mg of the desired product. ESI-MS (m/z) 489 $(M+H)^+$.

Step 4: 4-((5-Chloro-2-((6-methoxy-2-methyl-1,2,3,4-tetrahydroisoquinolin-7-yl)amino) pyrimidin-4-yl)oxy)-3-(dimethylphosphoryl)phenylsulfofluoridate dihydrochloride The titled compound was prepared by the reaction of (2-((5-chloro-2-((6-methoxy-2-methyl-1,2,3,4-tetrahydroisoquinolin-7-yl)amino)pyrimidin-4-yl)oxy)-5-hydroxyphenyl) dimethylphosphine oxide (35 mg, 0.071 mmol) with AISF (27 mg, 0.086 mmol) as per the procedure described in Step 1 & 2 of Example 2 to yield 7 mg of the desired product. $^1H$ NMR (400 MHz, DMSO-$d_6$) δ 1.70-1.80 (m, 6H), 2.91 (s, 3H), 3.10-3.20 (m, 1H), 3.20-3.40 (m, 2H), 3.60-3.72 (m, 1H), 3.73 (s, 3H), 4.05-4.12 (m, 2H), 6.86 (s, 1H), 7.14 (s, 1H), 7.70-7.90 (m, 3H), 8.49 (s, 1H), 8.52 (s, 1H), 10.42 (brs, 1H); ESI-MS (m/z) 571.1 $(M+H)^+$.

Method O 4-((5-Chloro-2-((6-hydroxy-2-methyl-1,2,3,4-tetrahydroisoquinolin-7-yl)amino)pyrimidin-4-yl)amino)-3-(dimethylphosphoryl)phenylsulfofluoridate dihydrochloride (Example 61)

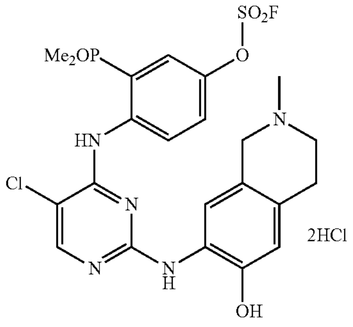

Step 1: 4-((5-chloro-2-((6-hydroxy-2-methyl-1,2,3,4-tetrahydroisoquinolin-7-yl)amino) pyrimidin-4-yl)amino)-3-(dimethylphosphoryl)phenyl sulfofluoridate

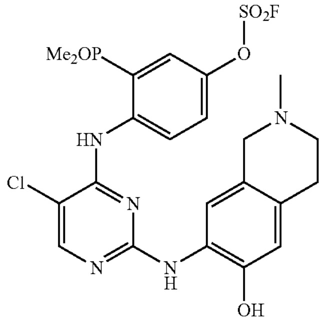

To a stirred solution of 4-((5-chloro-2-((6-methoxy-2-methyl-1,2,3,4-tetrahydroisoquinolin-7-yl)amino)pyrimidin-4-yl)amino)-3-(dimethylphosphoryl)phenyl sulfofluoridate dihydrochloride (Example 2) (200 mg, 0.311 mmol) in aqueous 47% HBr (5 mL) and heated to 110° C. for overnight. The reaction mixture was concentrated and the residue obtained was basified with saturated $NaHCO_3$ solution. The precipitated solid was filtered and dried under vacuum. The crude obtained was purified by column chromatography to yield 53 mg of the desired product. $^1H$ NMR (400 MHz, DMSO-$d_6$) δ 1.84 (d, J=13.6 Hz, 6H), 2.33 (s, 3H), 2.50-2.70 (m, 4H), 2.70-2.80 (m, 2H), 6.63 (s, 1H), 7.25 (s, 1H), 7.57 (d, J=8 Hz, 1H), 7.85-7.95 (m, 1H), 8.18 (s, 1H), 8.24 (s, 1H), 8.7 (brs, 1H), 9.51 (s, 1H), 11.39 (s, 1H); ESI-MS (m/z) 556 $(M+H)^+$.

Step 2: 4-((5-Chloro-2-((6-hydroxy-2-methyl-1,2,3,4-tetrahydroisoquinolin-7-yl) amino)pyrimidin-4-yl)amino)-3-(dimethylphosphoryl)phenylsulfofluoridate dihydrochloride To a stirred solution of 4-((5-chloro-2-((6-hydroxy-2-methyl-1,2,3,4-tetrahydroisoquinolin-7-yl)amino)pyrimidin-4-yl)amino)-3-(dimethylphosphoryl)phenyl sulfofluoridate (30 mg, 0.054 mmol) in DCM (2 mL) at 0° C. was added 4M HCl in Dioxane (0.1 mL) and stirred at RT for 1 h. The reaction mixture was concentrated and triturated with diethyl ether. The solid obtained was filtered and dried under vacuum to yield 19 mg of the desired product. $^1H$ NMR (400 MHz, DMSO-$d_6$) δ 1.86 (d, J=14 Hz, 6H), 2.86 (s, 3H), 2.85-3.00 (m, 1H), 3.05-3.20 (m, 1H), 3.20-3.35 (m, 1H), 3.50-3.65 (m, 1H), 4.00-4.15 (m, 1H), 4.20-4.35 (m, 1H), 6.82 (s, 1H), 7.39 (s, 1H), 7.77 (d, J=8.4 Hz, 1H), 7.90-8.00 (m, 1H), 8.31 (s, 1H), 8.71 (brs, 1H), 8.96 (brs, 1H), 10.87 (brs, 1H), 11.79 (brs, 1H); ESI-MS (m/z) 554 $(M-H)^+$.

Pharmacological Activity

FRET Assay:

This is a one step binding assay based on the binding and displacement of the labeled tracer, where compound addition is followed by addition of the anti-GST tagged europium (Eu) as the donor and Alexa Fluor-labeled tracer as the acceptor. Simultaneous binding of both the tracer and GST-antibody to the kinase domain of HPK1 results in a high degree of FRET (fluorescence resonance energy transfer)

from the anti-GST tagged europium (Eu) fluorophore to the Alexa Fluor® 647 fluorophore on the kinase tracer and this signal is reduced in presence of the inhibitor that can be measured.

Test compounds were dissolved in dimethylsulfoxide (DMSO) to prepare 10.0 mM stock solutions and diluted to the desired concentration. The final concentration of DMSO in the reaction was 3% (v/v). The assay mixture was prepared by mixing 2 nM of the Eu-Anti-GST Antibody and 5 nM MAP4K-1 enzyme in the Kinase buffer containing 50 mM HEPES (pH 7.5), 10 mM $MgCl_2$, 1 mM EGTA, 0.01% Brij-35 with or without the desired concentration of the compound. The reaction was incubated on ice for 15 min. The pre-incubation step was followed by addition of the 10 nM Kinase Tracer 222 into the reaction mixture. After shaking for 5 min the reaction was further incubated for 1 hour at room temperature and this was kept at 4° C. and read on ARTEMIS reader as per the kit instructions (Thermo). The inhibition of test compound was calculated based on the FRET ratio of 665 nm/620 nm. The activity was calculated as percent of control reaction. IC50 values were calculated from dose response curve by nonlinear regression analysis using GraphPad Prism software.

The compounds prepared were tested using the above assay procedure and the results obtained are given in Table 12. Percentage inhibition at concentrations of 1.0 μM and 10.0 μM are given in the table along with $IC_{50}$ (nM) details for selected examples.

The $IC_{50}$ (nM) values are set forth in Table 12 wherein "A" refers to an $IC_{50}$ value of less than 50 nM, "B" refers to $IC_{50}$ value in range of 50.01 to 100.0 nM, "C" refers to $IC_{50}$ values more than 100.01 to 500 nM and "D" refers to $IC_{50}$ values more than 500 nM.

TABLE 12

| | | % Inhibition at | | $IC_{50}$ |
|---|---|---|---|---|
| Sr. No. | Compound No. | 1 μM | 10 μM | (nM) |
| 1. | Example 1 | 87.21 | 86.53 | A |
| 2. | Example 2 | 85.96 | 82.12 | A |
| 3. | Example 3 | 85.57 | 91.21 | A |
| 4. | Example 4 | 72.86 | 78.37 | A |
| 5. | Example 5 | 78.13 | 82.54 | A |
| 6. | Example 6 | 79.99 | 81.96 | A |
| 7. | Example 7 | 37.71 | 69.74 | — |
| 8. | Example 8 | 63.72 | 80.01 | A |
| 9. | Example 9 | 78.49 | 78.80 | A |
| 10. | Example 10 | 92.33 | 89 | A |
| 11. | Example 11 | 75.10 | 87.16 | A |
| 12. | Example 12 | 87.51 | 85.91 | A |
| 13. | Example 13 | 79.71 | 81.04 | A |
| 14. | Example 14 | 89.73 | 93.26 | A |
| 15. | Example 15 | 78.6 | 91.79 | D |
| 16. | Example 16 | 87.26 | 86 | A |
| 17. | Example 17 | 86.6 | 90.25 | A |
| 18. | Example 18 | 87.27 | 83.15 | A |
| 19. | Example 19 | 76.59 | 78.23 | A |
| 20. | Example 20 | 80.14 | 75.52 | A |
| 21. | Example 21 | 79.17 | 81.60 | A |
| 22. | Example 22 | 75.12 | 82.60 | A |
| 23. | Example 23 | 86.13 | 89.64 | B |
| 24. | Example 24 | 86.68 | 85.52 | A |
| 25. | Example 25 | 85.87 | 90.67 | A |
| 26. | Example 26 | 75.83 | 76.45 | A |
| 27. | Example 27 | 81.09 | 82.6 | A |
| 28. | Example 28 | 69.72 | 75.94 | A |
| 29. | Example 29 | 76.50 | 76.92 | A |
| 30. | Example 30 | 79.12 | 82.70 | A |
| 31. | Example 31 | 84.44 | 89.03 | A |
| 32. | Example 32 | 84.51 | 89.25 | A |
| 33. | Example 33 | 92.79 | 87.80 | A |
| 34. | Example 34 | 84.26 | 86.64 | A |
| 35. | Example 35 | 83.03 | 79.06 | A |
| 36. | Example 36 | 85.29 | 83.76 | A |
| 37. | Example 37 | 84.45 | 84.73 | A |
| 38. | Example 38 | 84.53 | 85.68 | A |
| 39. | Example 39 | 75.13 | 86.96 | A |
| 40. | Example 40 | 83.27 | 83.95 | A |
| 41. | Example 41 | 90.41 | 84.95 | A |
| 42. | Example 42 | 84.04 | 83.05 | A |
| 43. | Example 43 | 79.99 | 80.53 | A |
| 44. | Example 44 | 81.58 | 79.59 | A |
| 45. | Example 45 | 74.8 | 79.0 | A |
| 46. | Example 46 | 73.59 | 73.91 | A |
| 47. | Example 47 | 91.4 | 88.04 | A |
| 48. | Example 48 | 84.18 | 81.44 | A |
| 49. | Example 49 | 94.31 | 91.66 | A |
| 50. | Example 50 | 92.74 | 94.84 | A |
| 51. | Example 51 | 93.09 | 94.31 | A |
| 52. | Example 52 | 88.2 | 85.51 | A |
| 53. | Example 53 | 82.44 | 90.05 | B |
| 54. | Example 54 | 93.44 | 93.68 | A |
| 55. | Example 55 | 94.61 | 95.34 | A |
| 56. | Example 56 | 88.68 | 88.24 | A |
| 57. | Example 57 | 83.01 | 79.33 | B |
| 58. | Example 58 | 96.6 | 96.4 | A |
| 59. | Example 59 | 83.08 | 87.35 | A |
| 60. | Example 60 | 70.54 | 83.37 | C |
| 61. | Example 61 | 89.61 | 89.66 | A |

(—): Not determined

Evaluation of Anti-Tumor Efficacy of Example 2 and Example 30 on a Syngeneic Mouse Colon Tumor Model of CT26.

Animals

Healthy female BALB/c mice (7 to 9 weeks old and 15 to 2a1 g) were obtained from Glenmark animal facility. Animals were group housed in polypropylene cages at a controlled temperature of 20-22° C. with a light/dark cycle of 12/12 hours. They were maintained on an ad lib standard mouse pellet diet and water and all animal experiments were performed as per protocols approved by the Institutional Animal Ethics Committee (IAEC).

CT26 Cell Culture

CT-26 cell line was obtained from American type culture (ATCC® CRL-2638™). Cells were revived in T-flask (passage 5) with complete RPMI-1640 media and incubated at 37° C. in 5% $CO_2$, 80% relative humidity. Cells were re-suspended, pooled and split into 1:10 ratio per flask, maintained for 3 passages and passage 8 was used for cell inoculation into animals.

CT26 Cell Implantation

The right flank region of mice was shaved by electronic shaver. Required number of CT26 cells (10 million per mL of serum free media) received on ice from cell culture lab. The mice were anesthetized by isoflurane with $O_2$ (oxygen flow meter to 1-2 liter/min and turn isoflurane vaporizer dial to 2-3%). The cells were inoculated into the right flank region of mice at cell concentration of 1 million cells/100 μL/mouse. The inoculated mice were housed in the animal room with daily observation for any undue clinical signs.

Animal Grouping

On day 10 after cell inoculation, mice were randomized based on tumor volume and grouped into different treatment groups. The mice with tumor volume range of 57 $mm^3$ to 119 $mm^3$ were included in efficacy study. Tumor volume was measured using digital vernier caliper.

The volume calculations were obtained using the formula $$V(\text{mm}^3)=[L\times(W\times W)]\times 0.52$$

V is tumor volume, L is tumor length and W is tumor width

TABLE 13

| Treatment groups | | | |
|---|---|---|---|
| Groups | Group Code | Dose | Number of animals/group |
| A | Vehicle | 10 mL/kg | 12 |
| B | Example 2 | 10 mg/kg/10 mL p.o. QD | 13 |
| C | Example 2 | 50 mg/kg/10 mL p.o. QD | 13 |
| D | Example 30 | 10 mg/kg/10 mL p.o. QD | 13 |
| E | Example 30 | 50 mg/kg/10 mL p.o. QD | 13 |

p.o.—per oral;
QD—Once Daily;
Q4 D—once every four days;
µg—Microgram

Compound Preparation and Administration 0.5% v/v Tween 80 and 0.5% w/v Methyl Cellulose in distilled water was used as vehicle for oral formulation. Example 2 and Example 30 were weighed and a stock suspension of 50 mg/kg/10 mL was prepared in a mortar and pestle by adding Tween 80 (0.5% v/v), Methyl cellulose (MC, 0.5% w/v). Using serial dilution method, 10 mg/kg/10 mL was prepared by diluting the stock with 0.5% MC. The body weights were recorded on daily basis and the dosing time was maintained throughout the study.

Assessment of Treatments Effect by Tumor Volume Measurement

Tumor volume was measured in a blinded manner throughout the study. Tumor volume measurement time was maintained during the course of study. Animals with necrotic tumors were removed from the study and data analysis. The % TGI was calculated by following the formula:

$$[1-\{(Tt-T0)/(Ct-C0)\}]\times 100.$$

Tt=Tumor volume of treatment group on day of tumor volume

T0=Tumor volume of treatment group on day of randomization

Ct=Tumor volume of vehicle control group on day of tumor volume

C0=Tumor volume of control group on day of randomization

Sacrifice Plan

On termination day, the mice were segregated for pharmacodynamics (PD) and pharmacokinetic (PK) time points for blood and tumor sampling.

Data Analysis

Tumor volume data was statistically analyzed using Two-way ANOVA followed by Bonferroni's Multiple Comparison Test. Statistical analysis and graphs were derived using Graph Pad Prism version 7. The Grubbs' outlier test was performed to remove outlier data sets as applicable.

Results:

Tumor growth inhibition (TGI) at day 24, is shown in FIG. 1 for Example 2. Tumor growth inhibition was observed in response to treatment with Example 2 with 10 mg/kg and 50 mg/kg QD by 40% and 61% respectively when compared with vehicle group.

Figure 2:
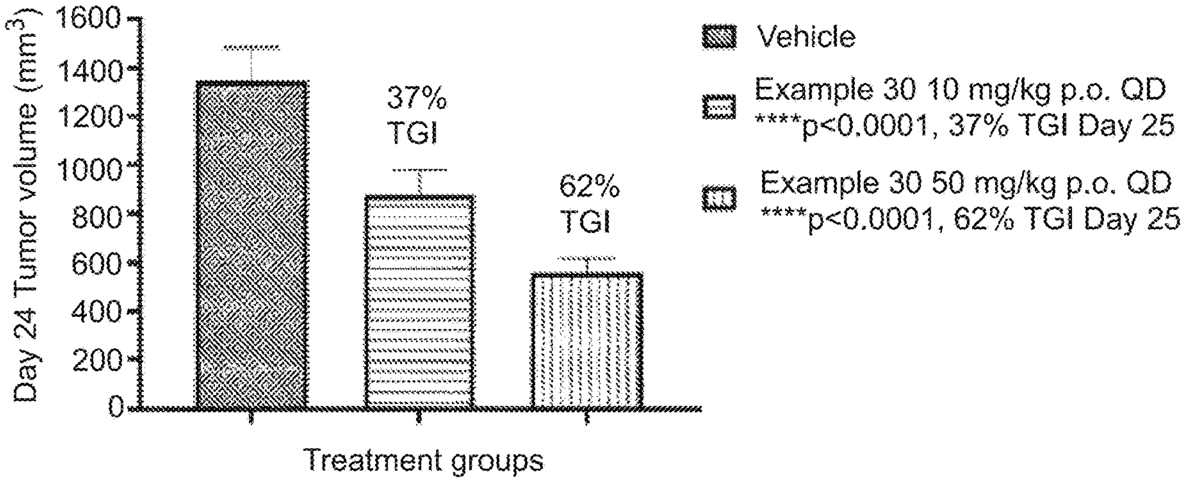
FIG. 2 shows Tumor Growth Inhibition by Example 30 in a CT26 tumor model.

Tumor growth inhibition (TGI) at day 25, is shown in FIG. 2 for Example 30. Tumor growth inhibition was observed in response to treatment with Example 30 with 10 mg/kg and 50 mg/kg QD by 37% and 62% respectively when compared with vehicle group.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described above.

All publications and patent applications cited in this application are herein incorporated by reference to the same extent as if each individual publication or patent application was specifically and individually indicated to be incorporated herein by reference.

What is claimed is:

1. A compound of formula (I)

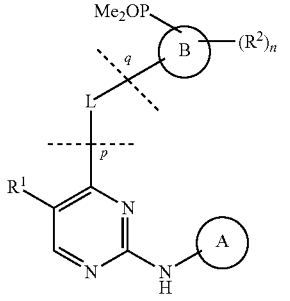

(I)

or a tautomer thereof, stereoisomer thereof, or a pharmaceutically acceptable salt thereof, wherein $R^1$ is selected from chloro and —$CONH_2$;

L is selected from

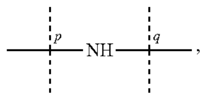

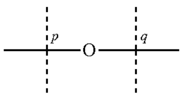

and

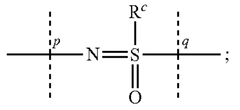

p and q are the point of attachments;

$R^c$ is selected from $C_{1-8}$alkyl;

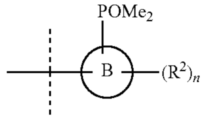

is selected from

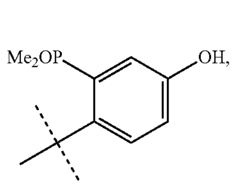

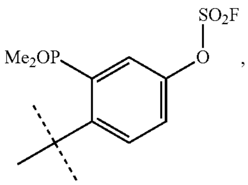

,

-continued
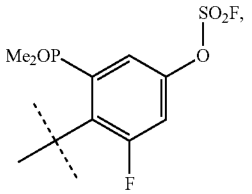
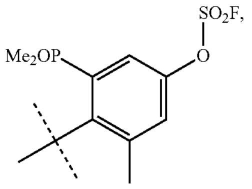
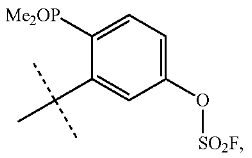
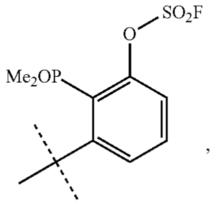
,
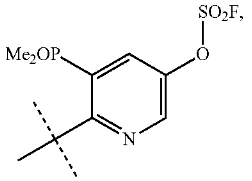
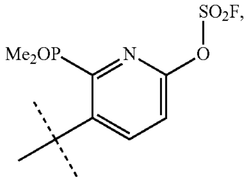
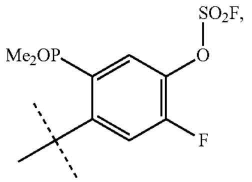
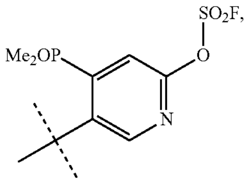
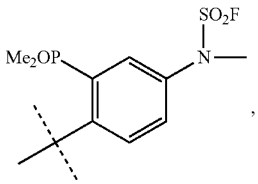
,
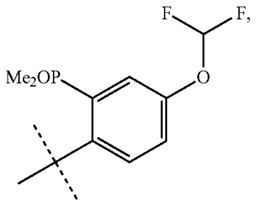
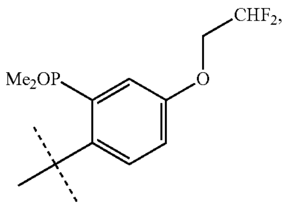
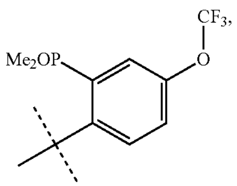
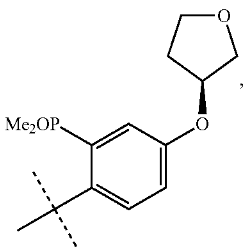
,
-continued
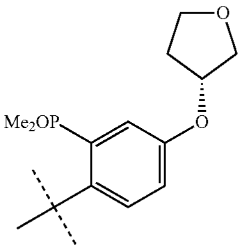
,
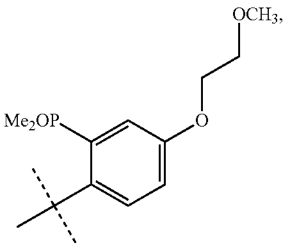
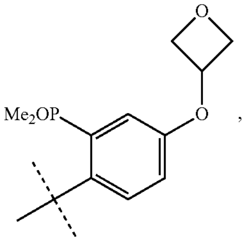
,
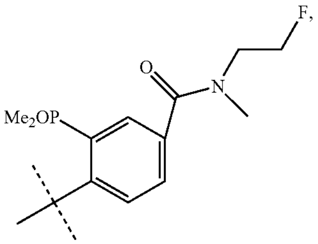
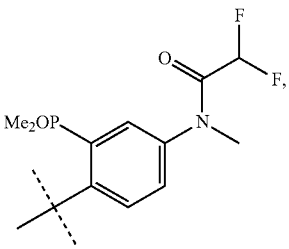
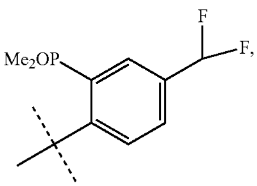
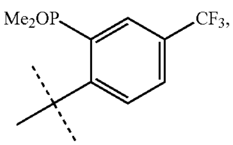
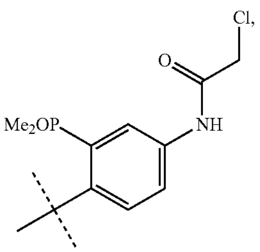
and -continued
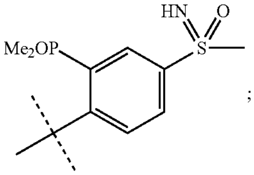
;
Ring A is selected from
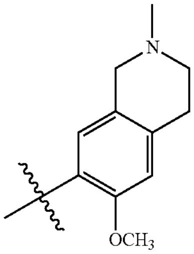
,
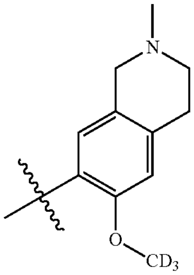
,
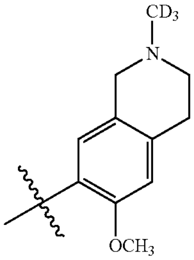
,
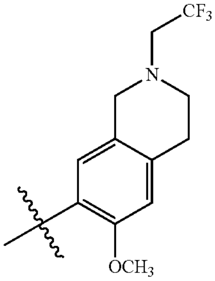
,
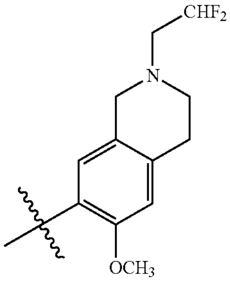
,
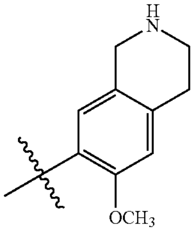
,
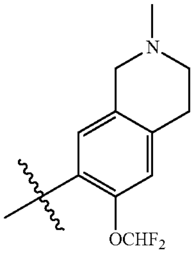
,
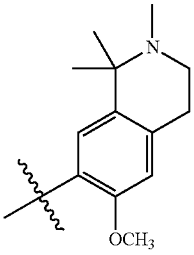
,
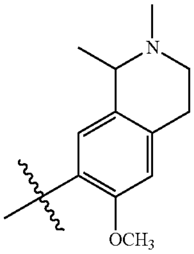
,
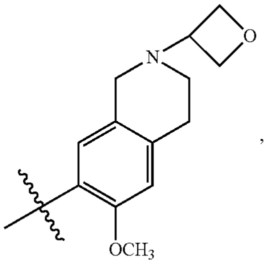
,
-continued
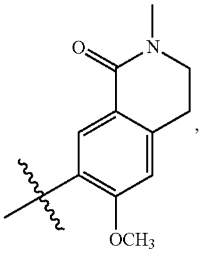
,
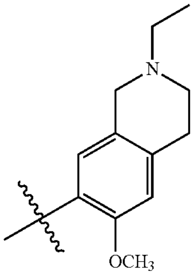
,
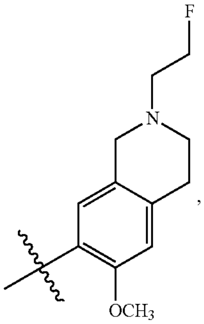
,
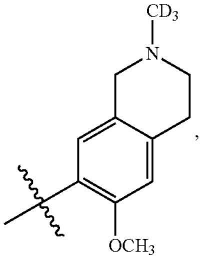
,
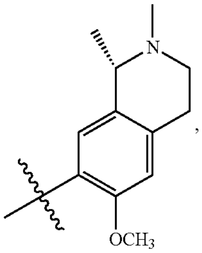
,
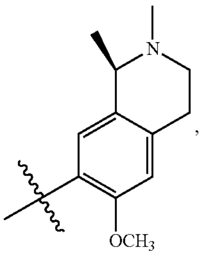
,
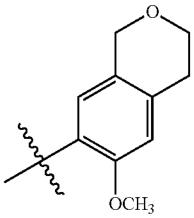
,
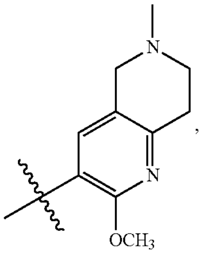
,
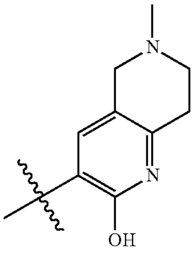
,
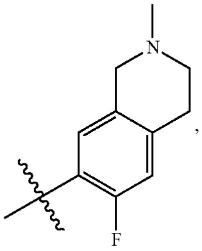
,
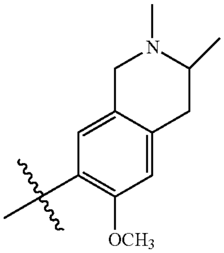
, -continued

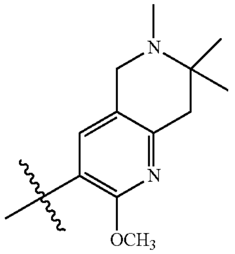,
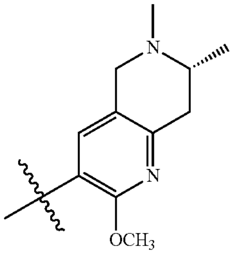,
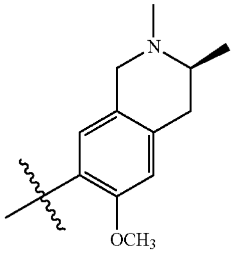,
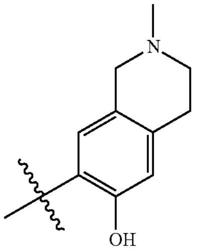,
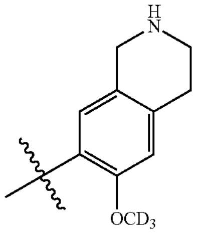,
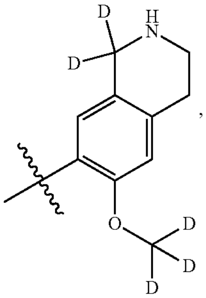,
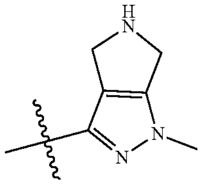,
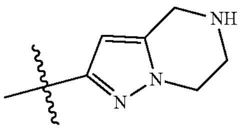 and
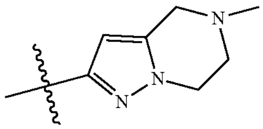.

2. The compound according to claim 1, wherein $R^1$ is chloro.

3. The compound according to claim 1, wherein $R^1$ is $—CONH_2$.

4. The compound according to claim 1, wherein L is

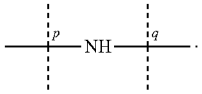.

5. The compound according to claim 1, wherein L is

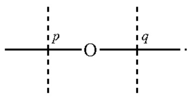.

6. The compound according to claim 1, wherein L is

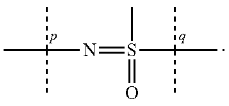.

7. The compound according to claim 1, wherein

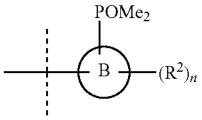
is
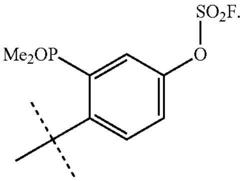

8. The compound according to claim 1, wherein

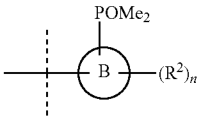
is
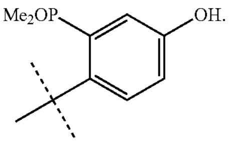

9. The compound according to claim 1, wherein ring A is

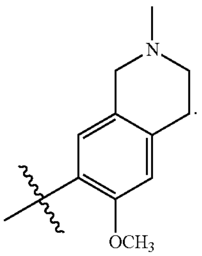 [SMILES: *c1cc2c(cc1OC)CCN(C)C2].

10. The compound according to claim 1, wherein ring A is

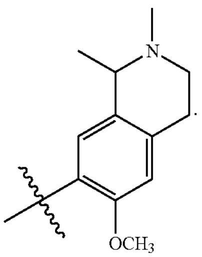 [SMILES: *c1cc2c(cc1OC)CCN(C)C2C].

11. The compound according to claim 1, wherein
$R^1$ is chloro,
L is

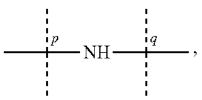,

-continued
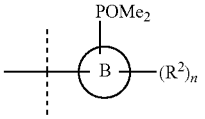
is
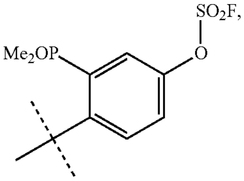
and
ring A is
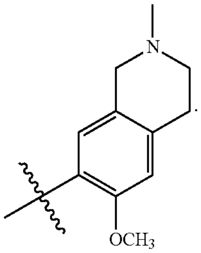 [SMILES: *c1cc2c(cc1OC)CCN(C)C2]
12. The compound according to claim 1, wherein
$R^1$ is chloro,
L is
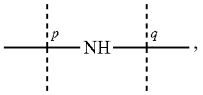
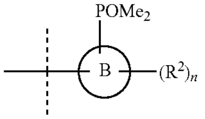
is
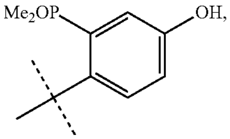
and
ring A is
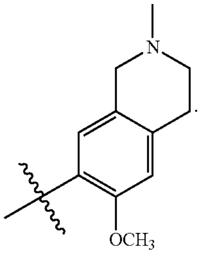 [SMILES: *c1cc2c(cc1OC)CCN(C)C2]
13. The compound according to claim 1, wherein
$R^1$ is chloro,
L is
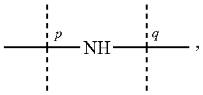
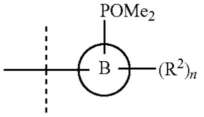
is
-continued
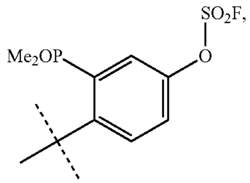
and
ring A is
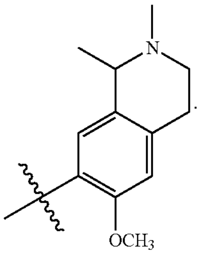 [SMILES: *c1cc2c(cc1OC)CCN(C)C2C]
14. The compound according to claim 1, wherein
$R^1$ is chloro;
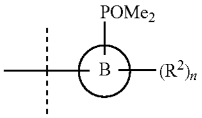
is
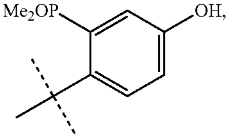
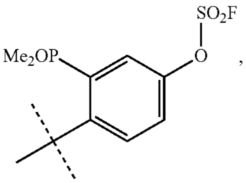
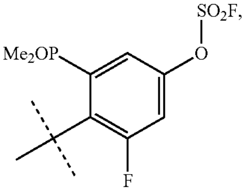
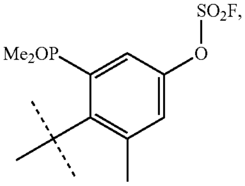
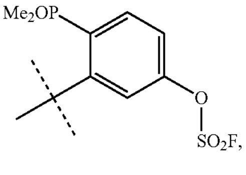
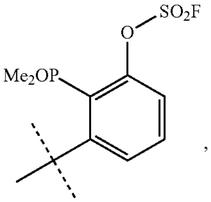
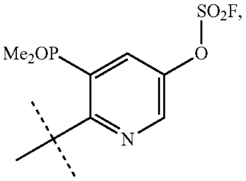
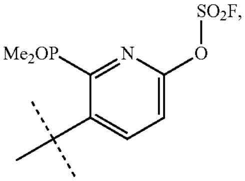

-continued
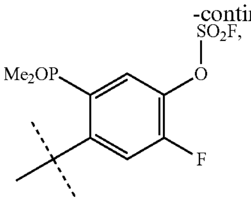
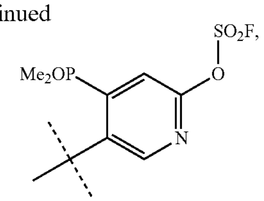
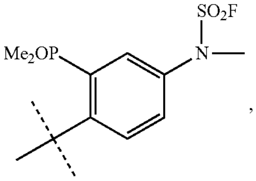
,
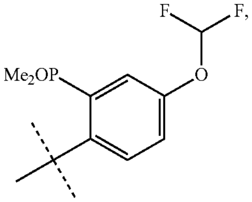
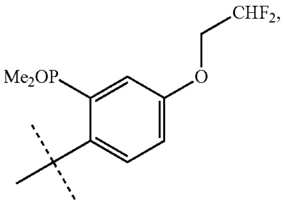
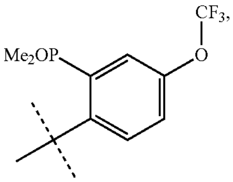
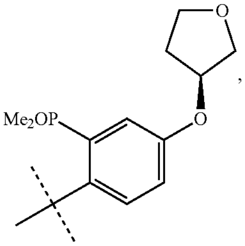
,
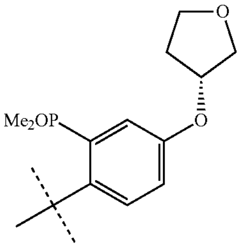
,
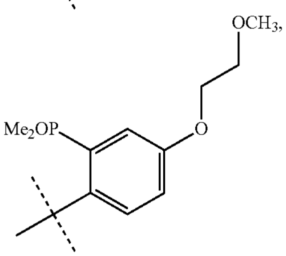
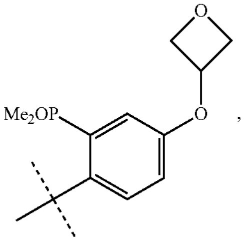
,
-continued
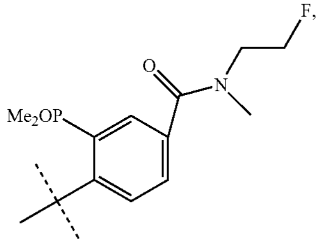
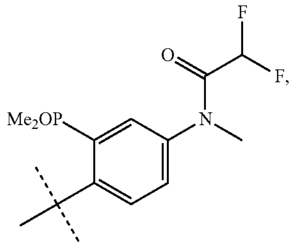
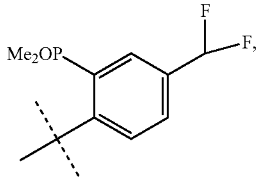
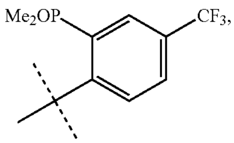
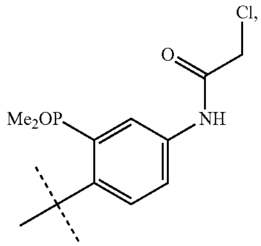
or
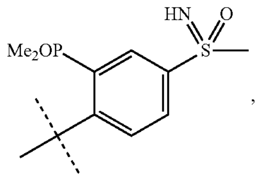
,
L is
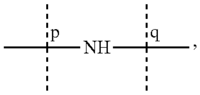
,
and
ring A is
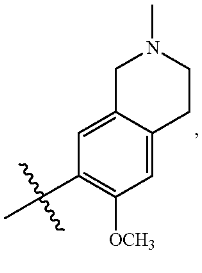
,
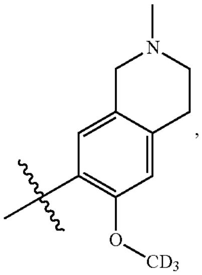
, -continued
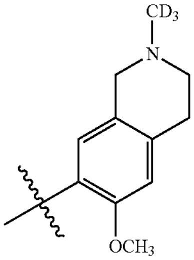,
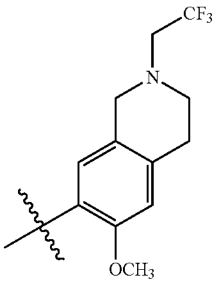,
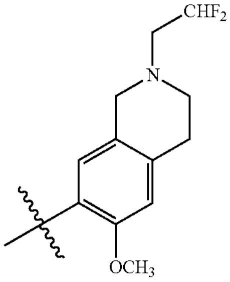,
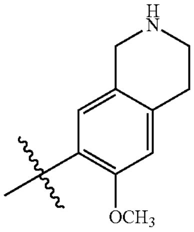,
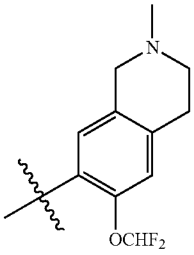,
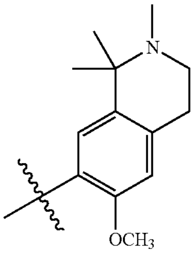,
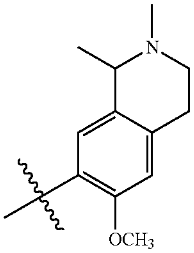,
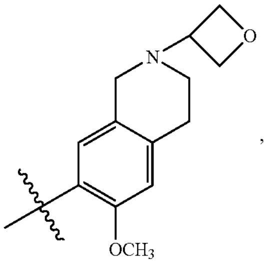,
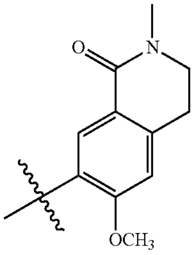,
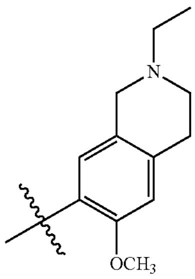,
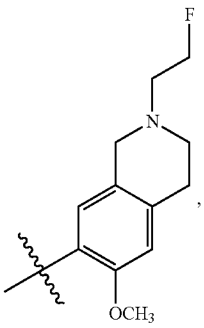,
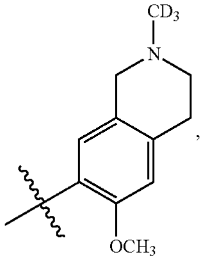,
-continued
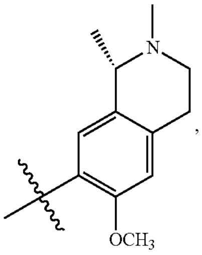,
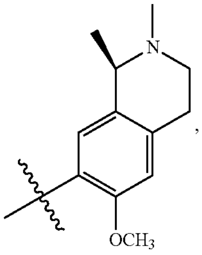,
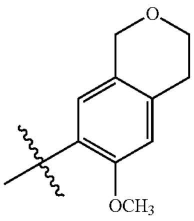,
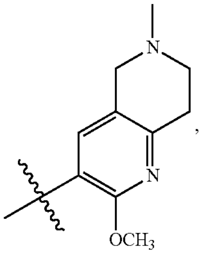,
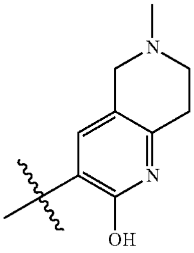,
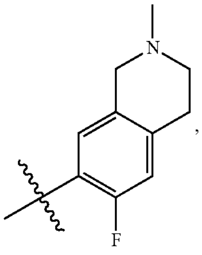,
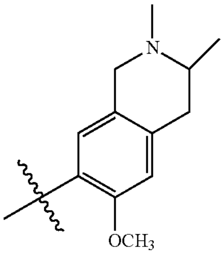,
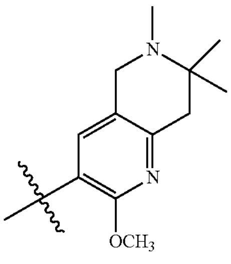,
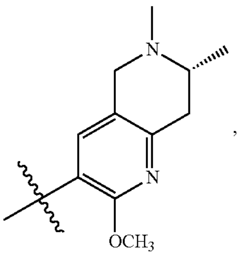,
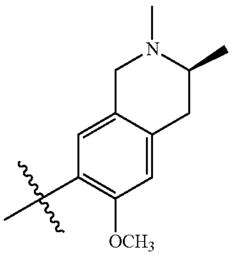,
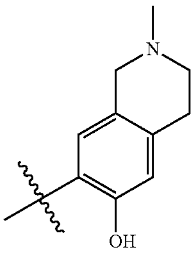, -continued

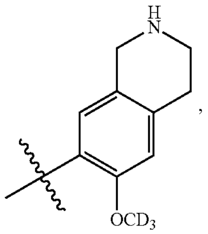
,
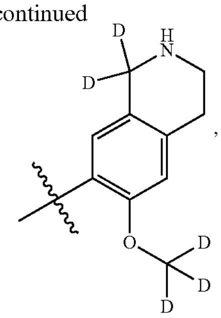
,
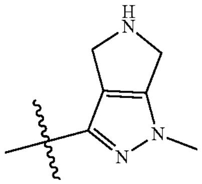
,
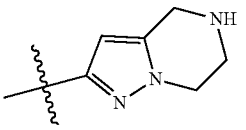
or
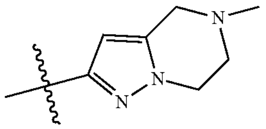
.

15. The compound according to claim 1 selected from (2-((5-Chloro-2-((6-methoxy-2-methyl-1,2,3,4-tetrahydroisoquinolin-7-yl)amino) pyrimidin-4-yl)amino)-5-hydroxyphenyl)dimethylphosphineoxide;

4-((5-Chloro-2-((6-methoxy-2-methyl-1,2,3,4-tetrahydroisoquinolin-7-yl)amino) pyrimidin-4-yl)amino)-3-(dimethylphosphoryl)phenylsulfurofluoridate;

4-((5-Carbamoyl-2-((6-methoxy-2-methyl-1,2,3,4-tetrahydroisoquinolin-7-yl) amino)pyrimidin-4-yl)amino)-3-(dimethylphosphoryl)phenylsulfurofluoridate;

4-((5-Chloro-2-((6-methoxy-2-(methyl-d3)-1,2,3,4-tetrahydroisoquinolin-7-yl) amino)pyramidin-4-yl)amino)-3-(dimethylphosphoryl)phenylsulfurofluoridate;

4-((5-Chloro-2-((6-(methoxy-d3)-2-methyl-1,2,3,4-tetrahydroisoquinolin-7-yl) amino)pyrimidin-4-yl)amino)-3-(dimethylphosphoryl)phenylsulfurofluoridate;

4-((5-Chloro-2-((6-methoxy-d3)-2-(methyl-d3)-1,2,3,4-tetrahydroisoquinolin-7-yl)amino)pyrimidin-4-yl) amino)-3-(dimethylphosphoryl)phenylsulfurofluoridate;

4-((5-Chloro-2-((6-methoxy-2-(2,2,2-trifluoroethyl)-1,2,3,4-tetrahydroisoquinolin-7-yl)amino)pyrimidin-4-yl) amino)-3-(dimethyllphosphoryl)phenylsulfuro fluoridate;

4-((5-Chloro-2-((2-(2,2-difluoroethyl)-6-methoxy-1,2,3,4-tetrahydroisoquinolin-7-yl)amino)pyrimidin-4-yl) amino)-3-(dimethylphosphoryl)phenylsulfurofluoridate;

4-((5-Chloro-2-((2-ethyl-6-methoxy-1,2,3,4-tetrahydroisoquinolin-7-yl)amino) pyrimidin-4-yl)amino)-3-(dimethylphosphoryl)phenylsulfofluoridate;

4-((5-Chloro-2-((6-(difluoromethoxy)-2-methyl-1,2,3,4-tetrahydroisoquinolin-7-yl)amino)pyrimidin-4-yl) amino)-3-(dimethylphosphoryl)phenylsulfurofluoridate;

4-((5-Chloro-2-((6-methoxy-1,1,2-trimethyl-1,2,3,4-tetrahydroisoquinolin-7-yl) amino pyrimidin-4-yl) amino)-3-(dimethylphosphoryl)phenylsulfurofluoridate;

4-((5-chloro-2-((6-methoxy-1,2-dimethyl-1,2,3,4-tetrahydroisoquinolin-7-yl)amino)pyrimidin-4-yl)amino)-3-(dimethylphosphoryl)phenylsulfurofluoridate;

4-((5-Chloro-2-((2-(2-fluoroethyl)-6-methoxy-1,2,3,4-tetrahydroisoquinolin-7-yl) amino)pyrimidin-4-yl) amino)-3-(dimethylphosphoryl)phenylsulfofluoridate;

4-((5-Chloro-2-((6-methoxy-2-methyl-1,2,3,4-tetrahydroisoquinolin-7-yl)amino) pyrimidin-4-yl)amino)-3-(dimethylphosphoryl)-5-fluorophenylsulfurofluoridate;

4-((5-Chloro-2-((6-methoxy-2-methyl-1,2,3,4-tetrahydroisoquinolin-7-yl)amino) pyrimidin-4-yl)amino)-3-(dimethylphosphoryl)-5-methylphenylsulfurofluoridate;

4-((5-Chloro-2-((6-methoxy-2-(oxetan-3-yl)-1,2,3,4-tetrahydroisoquinolin-7-yl) amino)pyrimidin-4-yl) amino)-3-(dimethylphosphoryl)phenylsulfurofluoridate;

4-((5-Chloro-2-((6-methoxy-2-methyl-1-oxo-1,2,3,4-tetrahydroisoquinolin-7-yl) amino)pyrimidin-4-yl) amino)-3-(dimethylphosphoryl)phenylsulfurofluoridate;

3-((5-Chloro-2-((6-methoxy-2-methyl-1,2,3,4-tetrahydroisoquinolin-7-yl)amino) pyrimidin-4-yl)amino)-4-(dimethylphosphoryl)phenylsulfurofluoridate;

3-((5-Chloro-2-((6-methoxy-2-methyl-1,2,3,4-tetrahydroisoquinolin-7-yl)amino) pyrimidin-4-yl)amino)-2-(dimethylphosphoryl)phenylsulfofluoridate;

6-((5-Chloro-2-((6-methoxy-2-methyl-1,2,3,4-tetrahydroisoquinolin-7-yl)amino) pyrimidin-4-yl)amino)-5-(dimethylphosphoryl) pyridin-3-ylsulfofluoridate;

5-((5-Chloro-2-((6-methoxy-2-methyl-1,2,3,4-tetrahydroisoquinolin-7-yl)amino) pyrimidin-4-yl)amino)-6-(dimethylphosphoryl) pyridin-2-yl sulfofluoridate;

4-((5-Chloro-2-((2-methoxy-6-methyl-5,6,7,8-tetrahydro-1,6-naphthyridin-3-yl) amino)pyrimidin-4-yl) amino)-3-(dimethylphosphorryl)phenylsulfofluoridate;

6-((5-Chloro-2-((6-methoxy-1,2-dimethyl-1,2,3,4-tetrahydroisoquinolin-7-yl) amino)pyrimidin-4-yl)amino)-5-(dimethylphosphoryl) pyridin-3-yl sulfofluoridate;

4-((5-Chloro-2-((6-methoxy-2,3,3-trimethyl-1,2,3,4-tetrahydroisoquinolin-7-yl) amino)pyrimidin-4-yl) amino)-3-(dimethylphosphoryl)phenylsulfofluoridate;

4-((5-Chloro-2-((6-fluoro-2-methyl-1,2,3,4-tetrahydroisoquinolin-7-yl)amino) pyrimidin-4-yl)amino)-3-(dimethylphosphoryl)phenylsulfofluoridate;

4-((5-Chloro-2-((6-methoxy-2-methyl-1,2,3,4-tetrahydroisoquinolin-7-yl)amino) pyrimidin-4-yl)amino)-5-(dimethylphosphoryl)-2-fluorophenyl sulfofluoridate;

4-((5-Chloro-2-((6-methoxyisochroman-7-yl)amino)pyrimidin-4-yl)amino)-3-(dimethylphosphoryl)phenylsulfofluoridate;

4-((5-Chloro-2-((6-methoxy-1,2-dimethyl-1,2,3,4-tetrahydroisoquinolin-7-yl) amino)pyrimidin-4-yl)amino)-3-(dimethylphosphoryl)phenylsulfofluoridate;

3-((5-Chloro-2-((6-methoxy-1,2-dimethyl-1,2,3,4-tetrahydroisoquinolin-7-yl) amino)pyrimidin-4-yl)amino)-4-(dimethylphosphoryl)phenylsulfofluoridate;

4-((5-Chloro-2-((6-methoxy-2,3-dimethyl-1,2,3,4-tetrahydroisoquinolin-7-yl amino)pyrimidin-4-yl)amino)-3-(dimethylphosphoryl)phenylsulfofluoridate;

3-((5-Chloro-2-((6-methoxy-2,3-dimethyl-1,2,3,4-tetrahydroisoquinolin-7-yl) amino)pyrimidin-4-yl)amino)-4-(dimethyl phosphoryl)phenylsulfofluoridate;

5-((5-Chloro-2-((6-methoxy-2-methyl-1,2,3,4-tetrahydroisoquinolin-7-yl)amino) pyrimidin-4-yl)amino)-4-(dimethylphosphoryl) pyridin-2-ylsulfofluoridate;

4-((5-Chloro-2-((6-methoxy-1,2,3,4-tetrahydroisoquinolin-7-yl)amino)pyrimidin-4-yl)amino)-3-(dimethylphosphoryl)phenylsulfofluoridate;

4-((5-Chloro-2-((6-methoxy-d3-1,2,3,4-tetrahydroisoquinolin-7-yl)amino) pyrimidin-4-yl)amino)-3-(dimethylphosphoryl)phenylsulfofluoridate;

4-((5-Chloro-2-((6-methoxy-d3-1,2,3,4-tetrahydroisoquinolin-7-yl-1,1-d2)amino) pyrimidin-4-yl)amino)-3-(dimethylphosphoryl)phenylsulfofluoridate;

4-((5-Chloro-2-((1-methyl-1,4,5,6-tetrahydropyrrolo[3,4-c]pyrazol-3-yl)amino) pyrimidin-4-yl)amino)-3-(dimethylphosphoryl)phenylsulfurofluoridate;

4-((5-Chloro-2-((4,5,6,7-tetrahydropyrazolo[1,5-a] pyrazin-2-yl)amino)pyrimidin-4-yl)amino)-3-(dimethylphosphoryl)phenylsulfofluoridate;

4-((5-Chloro-2-((6-methoxy-2-methyl-1,2,3,4-tetrahydroisoquinolin-7-yl)amino) pyrimidin-4-yl)amino)-3-(dimethylphosphoryl)phenyl)(methyl)sulfamoylfluoride;

(4-((5-Chloro-2-((6-methoxy-1,2-dimethyl-1,2,3,4-tetrahydroisoquinolin-7-yl) amino)pyrimidin-4-yl)amino)-3-dimethylphosphoryl)phenyl)(methyl)sulfamoyl fluoride;

(2-((5-Chloro-2-((6-methoxy-2-methyl-1,2,3,4-tetrahydroisoquinolin-7-yl)amino) pyrimidin-4-yl)amino)-5-(difluoromethoxy)phenyl)dimethylphosphineoxide;

(2-((5-Chloro-2-((6-methoxy-2-methyl-1,2,3,4-tetrahydroisoquinolin-7-yl)amino) pyrimidin-4-yl)amino)-5-(2,2-difluoroethoxy)phenyl)dimethylphosphine oxide;

2-((5-Chloro-2-((6-methoxy-2-methyl-1,2,3,4-tetrahydroisoquinolin-7-yl)amino) pyrimidin-4-yl)amino)-5-(trifluoromethoxy)phenyl)dimethylphosphineoxide;

(S)-(2-((5-Chloro-2-((6-methoxy-2-methyl-1,2,3,4-tetrahydroisoquinolin-7-yl) amino)pyrimidin-4-yl)amino)-5-((tetrahydrofuran-3-yl)oxy)phenyl)dimethylphosphine oxide;

(R)-(2-((5-Chloro-2-((6-methoxy-2-methyl-1,2,3,4-tetrahydroisoquinolin-7-yl) amino)pyrimidin-4-yl)amino)-5-((tetrahydrofuran-3-yl)oxy)phenyl)dimethyl phosphine oxide;

(2-((5-Chloro-2-((6-methoxy-2-methyl-1,2,3,4-tetrahydroisoquinolin-7-yl)amino) pyrimidin-4-yl)amino)-5-(2-methoxyethoxy)phenyl)dimethyl phosphine oxide;

(2-((5-Chloro-2-((6-methoxy-2-methyl-1,2,3,4-tetrahydroisoquinolin-7-yl)amino) pyrimidin-4-yl)amino)-5-(oxetan-3-yloxy)phenyl)dimethyl phosphine oxide;

4-((5-Chloro-2-((6-methoxy-2-methyl-1,2,3,4-tetrahydroisoquinolin-7-yl)amino) pyrimidin-4-yl)amino)-3-(dimethylphosphoryl)-N-(2-fluoroethyl)-N-methylbenzamide;

N-(4-((5-Chloro-2-((6-methoxy-2-methyl-1,2,3,4-tetrahydroisoquinolin-7-yl)amino)pyrimidin-4-yl)amino)-3-(dimethylphosphoryl)phenyl)-2,2-difluoro-N-methylacetamide;

(2-((5-Chloro-2-((6-methoxy-2-methyl-1,2,3,4-tetrahydroisoquinolin-7-yl)amino) pyrimidin-4-yl)amino)-5-(difluoromethyl)phenyl)dimethyl phosphine oxide;

(2-((5-Chloro-2-((6-methoxy-2-methyl-1,2,3,4-tetrahydroisoquinolin-7-yl)amino) pyrimidin-4-yl)amino)-5-(trifluoromethyl)phenyl)dimethylphosphine oxide;

2-Chloro-N-(4-((5-chloro-2-((6-methoxy-2-methyl-1,2,3,4-tetrahydro isoquinolin-7-yl)amino)pyrimidin-4-yl) amino)-3-(dimethylphosphoryl)phenyl) acetamide;

(2-((5-Chloro-2-((6-methoxy-2-methyl-1,2,3,4-tetrahydroisoquinolin-7-yl)amino) pyrimidin-4yl)amino)-5-(S-methylsulfonimidoyl)phenyl)dimethyl phosphineoxide;

4-((5-Chloro-2-((6-methoxy-2-methyl-1,2,3,4-tetrahydroisoquinolin-7-yl)amino) pyrimidin-4-yl)oxy)-3-(dimethylphosphoryl)phenylsulfofluoridate; and 4-((5-Chloro-2-((6-hydroxy-2-methyl-1,2,3,4-tetrahydroisoquinolin-7-yl)amino) pyrimidin-4-yl)amino)-3-(dimethylphosphoryl)phenylsulfofluoridate or pharmaceutically acceptable salt thereof.

16. The compound according to claim 1 of formula

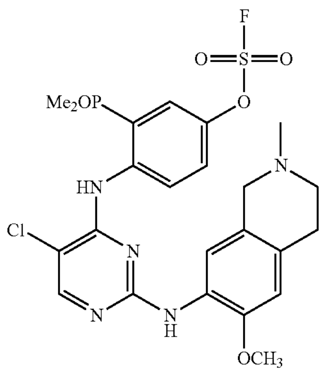

or a stereoisomer thereof, or a pharmaceutically acceptable salt thereof.

17. The compound according to claim 1 of formula

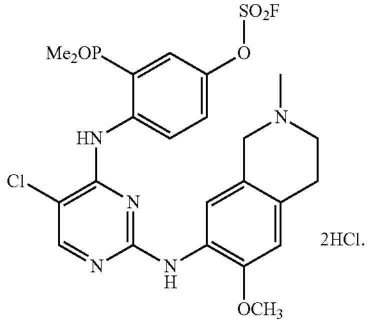

2HCl.

18. The compound of according to claim 1 formula

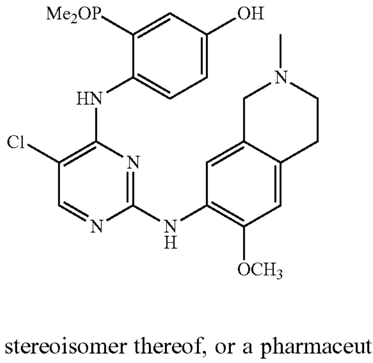

or a stereoisomer thereof, or a pharmaceutically acceptable salt thereof.

19. The compound according to claim 1 of formula

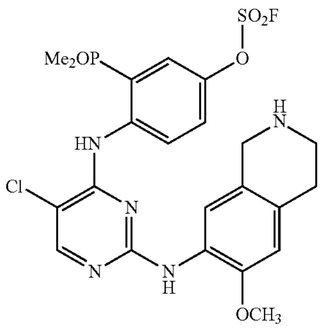

or a stereoisomer thereof, or a pharmaceutically acceptable salt thereof.

20. The compound according to claim 1 of formula

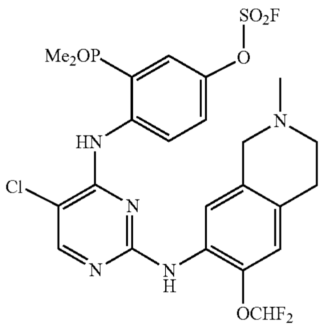

or a stereoisomer thereof, or a pharmaceutically acceptable salt thereof.

21. The compound according to claim 1 of

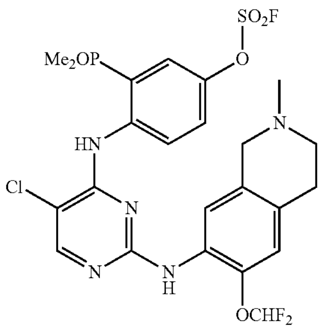

or a stereoisomer thereof, or a pharmaceutically acceptable salt thereof.

22. The compound according to claim 1 of formula

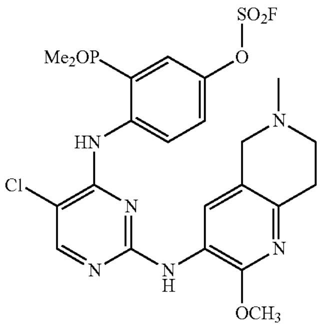

or a stereoisomer thereof, or a pharmaceutically acceptable salt thereof.

23. The compound according to claim 1 of formula

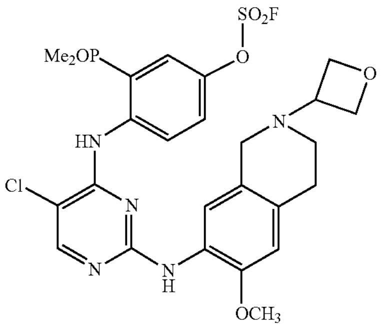

or a stereoisomer thereof, or a pharmaceutically acceptable salt thereof.

24. The compound according to claim 1 of formula

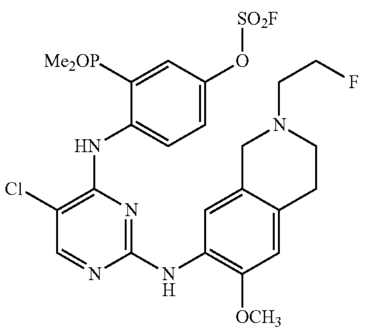

or a stereoisomer thereof, or a pharmaceutically acceptable salt thereof.

25. The compound according to claim 1 of formula

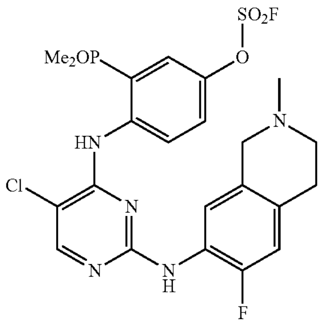

or a stereoisomer thereof, or a pharmaceutically acceptable salt thereof.

26. The compound according to claim 1 of formula

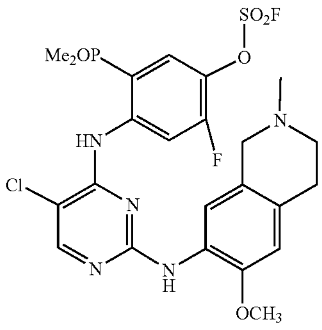

or a stereoisomer thereof, or a pharmaceutically acceptable salt thereof.

27. The compound according to claim 1 of formula

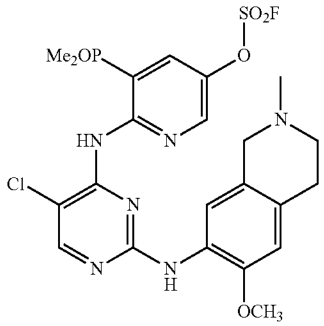

or a stereoisomer thereof, or a pharmaceutically acceptable salt thereof.

28. The compound according to claim 1 of formula

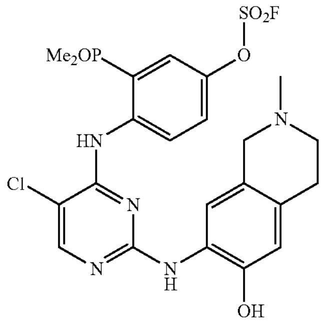

or a stereoisomer thereof, or a pharmaceutically acceptable salt thereof.

29. A pharmaceutical composition comprising an effective amount of a compound according to claim 1 and a pharmaceutically acceptable excipient.

30. The pharmaceutical composition according to claim 29, wherein the pharmaceutically acceptable excipient is a carrier or diluent.

* * * * *